(12) United States Patent
Kim et al.

(10) Patent No.: US 12,247,070 B2
(45) Date of Patent: Mar. 11, 2025

(54) USE OF ANTI-FAM19A5 ANTIBODIES FOR TREATING ATHEROSCLEROSIS

(71) Applicant: NEURACLE SCIENCE CO., LTD., Seoul (KR)

(72) Inventors: Bongcheol Kim, Seongnam-si (KR); Dong Sik Kim, Seoul (KR); Jae-Keun Lee, Seoul (KR); Juwon Shim, Seoul (KR)

(73) Assignee: NEURACLE SCIENCE CO., LTD., Seoul (KR)

( * ) Notice: Subject to any disclaimer, the term of this patent is extended or adjusted under 35 U.S.C. 154(b) by 856 days.

(21) Appl. No.: 17/418,681

(22) PCT Filed: Dec. 26, 2019

(86) PCT No.: PCT/IB2019/061377
§ 371 (c)(1),
(2) Date: Jun. 25, 2021

(87) PCT Pub. No.: WO2020/136603
PCT Pub. Date: Jul. 2, 2020

(65) Prior Publication Data
US 2022/0064277 A1   Mar. 3, 2022

Related U.S. Application Data

(60) Provisional application No. 62/785,569, filed on Dec. 27, 2018.

(51) Int. Cl.
C07K 16/24     (2006.01)
A61P 9/10      (2006.01)
A61K 39/00     (2006.01)

(52) U.S. Cl.
CPC ............... *C07K 16/24* (2013.01); *A61P 9/10* (2018.01); *A61K 2039/505* (2013.01); *C07K 2317/24* (2013.01); *C07K 2317/33* (2013.01); *C07K 2317/52* (2013.01); *C07K 2317/565* (2013.01); *C07K 2317/76* (2013.01)

(58) Field of Classification Search
CPC ............ C07K 16/24; C07K 2317/24; C07K 2317/33; C07K 2317/52; C07K 2317/565; C07K 2317/76; C07K 2317/92; C07K 2317/31; A61P 9/10; A61K 2039/505
See application file for complete search history.

(56) References Cited

U.S. PATENT DOCUMENTS

| | | |
|---|---|---|
| 4,044,126 A | 8/1977 | Cook et al. |
| 4,364,923 A | 12/1982 | Cook et al. |
| 4,414,209 A | 11/1983 | Cook et al. |
| 5,693,780 A | 12/1997 | Newman et al. |
| 5,709,874 A | 1/1998 | Hanson et al. |
| 5,759,542 A | 6/1998 | Gurewich |
| 5,840,674 A | 11/1998 | Yatvin et al. |
| 5,860,957 A | 1/1999 | Jacobsen et al. |
| 5,900,252 A | 5/1999 | Calanchi et al. |
| 5,948,433 A | 9/1999 | Burton et al. |
| 5,972,366 A | 10/1999 | Haynes et al. |
| 5,983,134 A | 11/1999 | Ostrow |
| 5,985,307 A | 11/1999 | Hanson et al. |
| 5,985,317 A | 11/1999 | Venkateshwaran et al. |
| 6,004,534 A | 12/1999 | Langer et al. |
| 6,010,715 A | 1/2000 | Wick et al. |
| 6,024,975 A | 2/2000 | D'Angelo et al. |
| 6,039,975 A | 3/2000 | Shah et al. |
| 6,048,736 A | 4/2000 | Kosak |
| 6,060,082 A | 5/2000 | Chen et al. |
| 6,071,495 A | 6/2000 | Unger et al. |
| 6,120,751 A | 9/2000 | Unger |
| 6,131,570 A | 10/2000 | Schuster et al. |
| 6,139,865 A | 10/2000 | Friend et al. |
| 6,167,301 A | 12/2000 | Flower et al. |
| 6,253,872 B1 | 7/2001 | Neumann |
| 6,256,533 B1 | 7/2001 | Yuzhakov et al. |
| 6,261,595 B1 | 7/2001 | Stanley et al. |
| 6,267,983 B1 | 7/2001 | Fujii et al. |
| 6,271,359 B1 | 8/2001 | Norris et al. |
| 6,274,552 B1 | 8/2001 | Tamarkin et al. |
| 6,316,652 B1 | 11/2001 | Steliou |
| 9,579,398 B2 | 2/2017 | Seong et al. |
| 10,640,557 B2 | 5/2020 | Seong et al. |
| 11,155,613 B2 * | 10/2021 | Kim ............ C07K 16/24 |
| 11,332,521 B2 * | 5/2022 | Kim ............ G01N 33/563 |

(Continued)

FOREIGN PATENT DOCUMENTS

WO    WO-9712622 A1    4/1997
WO    WO-9817815 A1    4/1998
(Continued)

OTHER PUBLICATIONS

Wang et al., Novel adipokine, FAM19A5, inhibits neointima formation after injury through sphingosine-1-phosphate receptor 2; 2018, Circulation, 138:48-63. (Year: 2018).*

Lee et al., Design and prediction of aptamers assisted by in silico methods; 2023, Biomedicines, 11, 356. (Year: 2023).*

An, Z., et al., "IgG2m4, an Engineered Antibody Isotype with Reduced Fc Function," Mabs 1(6):572-579, Taylor & Francis, United States (Nov.-Dec. 2009).

Bergheanu, S.C., et al., "Pathophysiology and Treatment of Atherosclerosis : Current View and Future Perspective on Lipoprotein Modification Treatment," Netherlands Heart Journal 25(4):231-242, Bohn Stafleu Van Loghum, Netherlands (Apr. 2017).

(Continued)

*Primary Examiner* — Daniel E Kolker
*Assistant Examiner* — James Ryland Melchior
(74) *Attorney, Agent, or Firm* — Sterne, Kessler, Goldstein & Fox P.L.L.C.

(57) ABSTRACT

The present disclosure relates to the pharmaceutical use of antagonists (e.g., an antibody or antigen-binding portion thereof) that specifically bind to FAM19A5 to treat an atherosclerosis in a subject in need thereof.

20 Claims, 10 Drawing Sheets
Specification includes a Sequence Listing.

(56) References Cited

U.S. PATENT DOCUMENTS

| | | | |
|---|---|---|---|
| 11,560,425 B2* | 1/2023 | Kim | A61P 35/00 |
| 11,618,783 B2* | 4/2023 | Kim | G01N 33/5058 |
| | | | 424/133.1 |
| 11,634,484 B2* | 4/2023 | Kim | A61P 25/02 |
| | | | 424/133.1 |
| 11,739,141 B2 | 8/2023 | Seong et al. | |
| 11,746,149 B2* | 9/2023 | Kim | C07K 16/24 |
| | | | 530/387.3 |
| 11,970,532 B2 | 4/2024 | Kim et al. | |
| 2004/0014194 A1 | 1/2004 | Beyer et al. | |
| 2012/0100140 A1 | 4/2012 | Reyes et al. | |
| 2014/0051591 A1 | 2/2014 | O'Donnell et al. | |
| 2020/0300870 A1 | 9/2020 | Seong et al. | |
| 2021/0347872 A1 | 11/2021 | Kim et al. | |
| 2022/0064277 A1 | 3/2022 | Kim et al. | |
| 2022/0073601 A1 | 3/2022 | Kim et al. | |
| 2023/0287096 A1 | 9/2023 | Kim et al. | |
| 2023/0348584 A1 | 11/2023 | Kim et al. | |

FOREIGN PATENT DOCUMENTS

| | | |
|---|---|---|
| WO | WO-9817816 A1 | 4/1998 |
| WO | WO-9818934 A1 | 5/1998 |
| WO | WO-9931251 A1 | 6/1999 |
| WO | WO-2017123556 A1 | 7/2017 |
| WO | WO-2017216559 A1 | 12/2017 |
| WO | WO-2018083538 A1 | 5/2018 |
| WO | WO-2020136603 A1 | 7/2020 |

OTHER PUBLICATIONS

Bird, R.E., et al., "Single-chain Antigen-binding Proteins," Science 242(4877):423-426, Association for the Advancement of Science, United States (Oct. 1988).

Bricogne, G., "[23] Bayesian Statistical Viewpoint on Structure Determination: Basic Concepts and Examples," Methods in Enzymology 276:361-423, Academic Press, United States (1997).

Bricogne, G., "Direct Phase Determination by Entropy Maximization and Likelihood Ranking: Status Report and Perspectives," Acta Crystallographica. Section D, Biological Crystallography 49(Pt1):37-60, Wiley-Blackwell, United States (Jan. 1993).

Champe, M., et al., "Monoclonal Antibodies that Block the Activity of Leukocyte Function—Associated Antigen 1 Recognize Three Discrete Epitopes in the Inserted Domain of CD11a," The Journal of Biological Chemistry 270 (3):1388-1394, Elsevier Inc. on behalf of American Society for Biochemistry and Molecular Biology, United States (Jan. 1995).

Chayen, N.E., "The Role of Oil in Macromolecular Crystallization," Structure 5(10):1269-1274, Cell Press, United States (Oct. 1997).

Cheung, R.C., et al., "Epitope-specific Antibody Response to the Surface Antigen of Duck Hepatitis B Virus in Infected Ducks," Virology 176(2):546-552, Academic Press, United States (1990).

Chothia, C. and Lesk, A.M., "Canonical Structures for the Hypervariable Regions of Immunoglobulins," Journal of Molecular Biology 196(4):901-917, Elsevier, Netherlands (Aug. 1987).

Cunningham, B.C. and Wells, J.A., "High-resolution Epitope Mapping of hGH-receptor Interactions by Alanine-scanning Mutagenesis," Science 244(4908):1081-1085, American Association for the Advancement of Science, United States (Jun. 1989).

Edelman, G.M., et al., "The Covalent Structure of an Entire gammaG Immunoglobulin Molecule," Proceedings of the National Academy of Sciences USA 63(1):78-85, National Academy of Sciences, United States (May 1969).

Giege, R., et al., "Crystallogenesis of biological macromolecules: facts and perspectives," Acta Crystallographica. Section D, Biological Crystallography 50(Pt4):339-350, Wiley-Blackwell, United States (Jul. 1994).

Harlow, E., et al., "Epitope mapping by competition assay," CSH Protoc 2006(2):pdb.prot4277, Cold Spring Harbor Laboratory Press, United States (2006).

Harmsen, M.M. and De Haard, H.J., "Properties, Production, and Applications of Camelid Single-Domain Antibody Fragments," Applied Microbiology and Biotechnology 77(1):13-22, Springer International, Germany (Nov. 2007).

Herrington, W., et al., "Epidemiology of Atherosclerosis and the Potential to Reduce the Global Burden of Atherothrombotic Disease," Circulation Research 118(4):535-546, Lippincott Williams & Wilkins, United States (Feb. 2016).

Huston, U.S., et al., "Protein Engineering of Antibody Binding Sites: Recovery of Specific Activity in an Anti-digoxin Single-chain Fv Analogue Produced in Escherichia Coli," Proceedings of the National Academy of Sciences of the United States of America 85(16):5879-5883, National Academy of Sciences, United States (Aug. 1988).

International Search Report and Written Opinion for International Application No. PCT/IB2019/061377, ISA/KR, Republic of Korea, mailed on Apr. 23, 2020, 9 pages.

Jefferis, R. and Lefranc, M.P., "Human Immunoglobulin Allotypes: Possible Implications for Immunogenicity," Mabs 1(4):332-338, Taylor & Francis, United States (Jul.-Aug. 2009).

Kabat, E.A. and Wu, T.T., "Attempts to Locate Complementarity-Determining Residues in the Variable Positions of Light and Heavy Chains," Annals of the New York Academy of Sciences 190:382-393, Blackwell, United States (Dec. 1971).

Kabat, E.A., et al., "Sequences of proteins of immunological interest," 5th Edition, NIH publication No. 91-3242, U.S. Department of Public Health and Human Services, National Institutes of Health, United States (1991).

Kirkland, T.N., et al., "Analysis of the Fine Specificity and Cross-reactivity of Monoclonal Anti-lipid A Antibodies," Journal of Microbiology 137(11):3614-3619, Microbiological Society of Korea, Korea (1986).

Kostelny, S.A., et al., "Formation of a Bispecific Antibody by the Use of Leucine Zippers," The Journal of Immunology 148(5):1547-1553, American Association of Immunologists, United States (Mar. 1992).

Lau, C., et al., "Chimeric Anti-CD14 IGG2/4 Hybrid Antibodies for Therapeutic Intervention in Pig and Human Models of Inflammation," Journal of Immunology 191(9):4769-4777, American Association of Immunologists, United States (Nov. 2013).

Lefranc, M.P., et al., "IMGT Unique Numbering for Immunoglobulin and T Cell Receptor Variable Domains and Ig Superfamily V-like Domains," Developmental and Comparative Immunology 27(1):55-77, Elsevier Science, United States (Jan. 2003).

Lonberg, N., et al., "Human Antibodies from Transgenic Animals," Nature Biotechnology 23(9):1117-1125, Nature Publishing Company, United States (Sep. 2005).

Lu, H. and Daugherty, A., "Recent Highlights of ATVB Atherosclerosis, " Arteriosclerosis, Thrombosis, and Vascular Biology 35(3):485-491, Lippincott Williams & Wilkins, United States (Mar. 2015).

McCafferty, J., et al., "Phage Antibodies: Filamentous Phage Displaying Antibody Variable Domains," Nature 348(6301):552-554, Nature Publishing Group, London (Dec. 1990).

McPherson, A., "Crystallization of Proteins From Polyethylene Glycol," The Journal of Biological Chemistry 251(20):6300-6303, Elsevier Inc. on behalf of American Society for Biochemistry and Molecular Biology, United States (Oct. 1976).

McPherson, A., "Current Approaches to Macromolecular Crystallization," European Journal of Biochemistry 189(1):1-23, Blackwell Science Ltd, England (Apr. 1990).

Moldenhauer, G., et al., "Identity of HML-1 Antigen on Intestinal Intraepithelial T Cells and of B-ly7 Antigen on Hairy Cell Leukaemia," Scandinavian Journal of Immunology 32(2):77-82, Blackwell Scientific Publications, England (1990).

Morel, G.A., et al., "Monoclonal Antibodies to Bovine Serum Albumin: Affinity and Specificity Determinations," Molecular Immunology 25(1):7-15, Pergamon Press, England (1988).

Morris, G.E., "Epitope Mapping by Chemical Fragmentation," Methods in Molecular Biology 66:121-127, Humana Press, United States (1996).

Roux, K.H., et al., "Comparisons of the Ability of Human IgG3 Hinge Mutants, IgM, IgE, and IgA2, to form Small Immune

(56) References Cited

OTHER PUBLICATIONS

Complexes: A Role for Flexibility and Geometry," The Journal of Immunology 161(8):4083-4090, American Association of Immunologists, United States (Oct. 1998).

Roversi, P., et al., "Modelling Prior Distributions of Atoms for Macromolecular Refinement and Completion," Acta Crystallographica. Section D, Biological Crystallography 56(Pt10):1316-1323, Wiley-Blackwell, United States (Oct. 2000).

Songsivilai, S. and Lachmann, P.J., "Bispecific Antibody: A Tool for Diagnosis and Treatment of Disease," Clinical and Experimental Immunology 79(3):315-321, Blackwell Scientific Publications, England (1990).

Stahli, C., et al., "Distinction of Epitopes by Monoclonal Antibodies," Methods in Enzymology 92:242-253, Academic Press, United States (1983).

Stroes, E.S., et al., "Statin-associated Muscle Symptoms: Impact on Statin Therapy-european Atherosclerosis Society Consensus Panel Statement on Assessment, Aetiology and Management," European Heart Journal 36(17):1012-1022, Oxford University Press, England (May 2015).

Tang, Y.T., et al., "TAFA: A Novel Secreted Family With Conserved Cysteine Residues and Restricted Expression in the Brain," Genomics 83(4):727-734, Academic Press, United States (Apr. 2004).

Vidarsson, G., et al., "IgG Subclasses and Allotypes: From Structure to Effector Functions," Frontiers in Immunology 5:520, Frontiers Research Foundation, Switzerland (Oct. 2014).

Wang, Y., et al., "Novel Adipokine, FAM19A5, Inhibits Neointima Formation After Injury Through Sphingosine-1-phosphate Receptor 2," Circulation, 138(1):48-63, Lippincott Williams & Wilkins, United States (Jul. 2018).

Ward, E.S., et al., "Binding Activities of a Repertoire of Single Immunoglobulin Variable Domains Secreted from *Escherichia coli*," Nature 341(6242):544-546, Nature Publishing Group, England (Oct. 1989).

\* cited by examiner

CD68  CD146

CD68  CD146

CD68

CD146

CD68

CD146

SEQUENCE LISTING

```
<160> NUMBER OF SEQ ID NOS: 273

<210> SEQ ID NO 1
<211> LENGTH: 132
<212> TYPE: PRT
<213> ORGANISM: Homo Sapiens

<400> SEQUENCE: 1

Met Ala Pro Ser Pro Arg Thr Gly Ser Arg Gln Asp Ala Thr Ala Leu
1               5                   10                  15

Pro Ser Met Ser Ser Thr Phe Trp Ala Phe Met Ile Leu Ala Ser Leu
                20                  25                  30

Leu Ile Ala Tyr Cys Ser Gln Leu Ala Ala Gly Thr Cys Glu Ile Val
            35                  40                  45

Thr Leu Asp Arg Asp Ser Ser Gln Pro Arg Arg Thr Ile Ala Arg Gln
        50                  55                  60

Thr Ala Arg Cys Ala Cys Arg Lys Gly Gln Ile Ala Gly Thr Thr Arg
65                  70                  75                  80

Ala Arg Pro Ala Cys Val Asp Ala Arg Ile Ile Lys Thr Lys Gln Trp
                85                  90                  95

Cys Asp Met Leu Pro Cys Leu Glu Gly Glu Gly Cys Asp Leu Leu Ile
                100                 105                 110

Asn Arg Ser Gly Trp Thr Cys Thr Gln Pro Gly Gly Arg Ile Lys Thr
```

```
              115                 120                 125

Thr Thr Val Ser
    130

<210> SEQ ID NO 2
<211> LENGTH: 125
<212> TYPE: PRT
<213> ORGANISM: Homo Sapiens

<400> SEQUENCE: 2

Met Gln Leu Leu Lys Ala Leu Trp Ala Leu Ala Gly Ala Ala Leu Cys
1               5                   10                  15

Cys Phe Leu Val Leu Val Ile His Ala Gln Phe Leu Lys Glu Gly Gln
            20                  25                  30

Leu Ala Ala Gly Thr Cys Glu Ile Val Thr Leu Asp Arg Asp Ser Ser
        35                  40                  45

Gln Pro Arg Arg Thr Ile Ala Arg Gln Thr Ala Arg Cys Ala Cys Arg
    50                  55                  60

Lys Gly Gln Ile Ala Gly Thr Thr Arg Ala Arg Pro Ala Cys Val Asp
65                  70                  75                  80

Ala Arg Ile Ile Lys Thr Lys Gln Trp Cys Asp Met Leu Pro Cys Leu
                85                  90                  95

Glu Gly Glu Gly Cys Asp Leu Leu Ile Asn Arg Ser Gly Trp Thr Cys
            100                 105                 110

Thr Gln Pro Gly Gly Arg Ile Lys Thr Thr Val Ser
        115                 120                 125

<210> SEQ ID NO 3
<211> LENGTH: 53
<212> TYPE: PRT
<213> ORGANISM: Homo Sapiens

<400> SEQUENCE: 3

Met Tyr His His Arg Glu Trp Pro Ala Arg Ile Ile Lys Thr Lys Gln
1               5                   10                  15

Trp Cys Asp Met Leu Pro Cys Leu Glu Gly Glu Gly Cys Asp Leu Leu
            20                  25                  30

Ile Asn Arg Ser Gly Trp Thr Cys Thr Gln Pro Gly Gly Arg Ile Lys
        35                  40                  45

Thr Thr Thr Val Ser
    50

<210> SEQ ID NO 4
<211> LENGTH: 1501
<212> TYPE: DNA
<213> ORGANISM: Homo Sapiens

<400> SEQUENCE: 4
ggcggcggag gatggcgcgc gcggggcccg cacgtggagg ccggcgcggg ggcgcgggca      60
gggccggctg ctgagacgcg ctgctgcccc ccgcgcgggc gccgcggctt caatggcgcc     120
atcgcccagg accggcagcc ggcaagatgc gaccgccctg cccagcatgt cctcaacttt     180
ctgggcgttc atgatcctgg ccagcctgct catcgcctac tgcagtcagc tggccgccgg     240
cacctgtgag attgtgacct ggaccgggga cagcagccag cctcggagga cgatcgcccg     300
gcagaccgcc cgctgtgcgt gtagaaaggg gcagatcgcc ggcaccacga gagcccggcc     360
cgcctgtgtg gacgcaagaa tcatcaagac caagcagtgg tgtgacatgc ttccgtgtct     420
```

```
ggaggggggaa ggctgcgact tgttaatcaa ccggtcaggc tggacgtgca cgcagcccgg      480
cgggaggata aagaccacca cggtctcctg acaaacacag cccctgaggg ggccccggga      540
gtggccttgg ctccctggag agcccacgtc tcagccacag ttctccactc gcctcggact      600
tcacccgttc tctgccgccc gcccactccg tttccctgtg gtccgtgaag gacggcctca      660
ggccttggca tcctgagctt cggtctgtcc agccgacccg aggaggccgg actcagacac      720
ataggcgggg ggcggcacct ggcatcagca atacgcagtc tgtgggagcc cggccgcgcc      780
cagcccccgc cgaccgtggc gttggccctg ctgtcctcag aggaggagga ggaggaggca      840
gctccggcag ccacagaagg ctgcagccca gcccgcctga cacgacgc ctgccccagg       900 ggactgtcag gcacagaagc ggcctcctcc cgtgccccag actgtccgaa ttgcttttat      960
tttcttatac tttcagtata ctccatagac caaagagcaa aatctatctg aacctggacg     1020
caccctcact gtcagggtcc ctggggtcgc ttgtgcgggc gggagggcaa tggtggcaga     1080
gacatgctgg tggccccggc ggagcggaga gggcggccgt ggtggaggcc tccacccccag    1140 gagcaccccg cacaccctcg gaggacgggc ttcggctgcg cggaggccgt ggcacacctg     1200
cgggaggcag cgacggcccc cacgcagacg ccgggaacgc aggccgcttt attcctctgt     1260
acttagatca acttgaccgt actaaaatcc ctttctgttt taaccagtta aacatgcctc     1320
ttctacagct ccattttga tagttggata atccagtatc tgccaagagc atgttgggtc     1380
tcccgtgact gctgcctcat cgataccccca tttagctcca gaaagcaaag aaaactcgag    1440
taacacttgt ttgaaagaga tcattaaatg tattttgcaa agcccaaaaa aaaaaaaaa     1500 a                                                                     1501

<210> SEQ ID NO 5
<211> LENGTH: 14
<212> TYPE: PRT
<213> ORGANISM: Artificial Sequence
<220> FEATURE:
<223> OTHER INFORMATION: Epitope F1

<400> SEQUENCE: 5

Gln Leu Ala Ala Gly Thr Cys Glu Ile Val Thr Leu Asp Arg
1               5                   10

<210> SEQ ID NO 6
<211> LENGTH: 20
<212> TYPE: PRT
<213> ORGANISM: Artificial Sequence
<220> FEATURE:
<223> OTHER INFORMATION: Epitope F2

<400> SEQUENCE: 6

Thr Leu Asp Arg Asp Ser Ser Gln Pro Arg Arg Thr Ile Ala Arg Gln
1               5                   10                  15

Thr Ala Arg Cys
            20

<210> SEQ ID NO 7
<211> LENGTH: 20
<212> TYPE: PRT
<213> ORGANISM: Artificial Sequence
<220> FEATURE:
<223> OTHER INFORMATION: Epitope F3

<400> SEQUENCE: 7

Thr Ala Arg Cys Ala Cys Arg Lys Gly Gln Ile Ala Gly Thr Thr Arg
1               5                   10                  15
```

Ala Arg Pro Ala
            20

<210> SEQ ID NO 8
<211> LENGTH: 20
<212> TYPE: PRT
<213> ORGANISM: Artificial Sequence
<220> FEATURE:
<223> OTHER INFORMATION: Epitope F4

<400> SEQUENCE: 8

Ala Arg Pro Ala Cys Val Asp Ala Arg Ile Ile Lys Thr Lys Gln Trp
1               5                   10                  15

Cys Asp Met Leu
            20

<210> SEQ ID NO 9
<211> LENGTH: 20
<212> TYPE: PRT
<213> ORGANISM: Artificial Sequence
<220> FEATURE:
<223> OTHER INFORMATION: Epitope F5

<400> SEQUENCE: 9

Cys Asp Met Leu Pro Cys Leu Glu Gly Glu Gly Cys Asp Leu Leu Ile
1               5                   10                  15

Asn Arg Ser Gly
            20

<210> SEQ ID NO 10
<211> LENGTH: 20
<212> TYPE: PRT
<213> ORGANISM: Artificial Sequence
<220> FEATURE:
<223> OTHER INFORMATION: Epitope F6

<400> SEQUENCE: 10

Asn Arg Ser Gly Trp Thr Cys Thr Gln Pro Gly Gly Arg Ile Lys Thr
1               5                   10                  15

Thr Thr Val Ser
            20

<210> SEQ ID NO 11
<211> LENGTH: 5
<212> TYPE: PRT
<213> ORGANISM: Artificial Sequence
<220> FEATURE:
<223> OTHER INFORMATION: 2-13 VH-CDR1

<400> SEQUENCE: 11

Ser His Gly Met Phe
1               5

<210> SEQ ID NO 12
<211> LENGTH: 17
<212> TYPE: PRT
<213> ORGANISM: Artificial Sequence
<220> FEATURE:
<223> OTHER INFORMATION: 2-13; 2-13D; 2-13D-37; 2-13D-37-1.5W-41;
      2-13D-37-3W-16 VH-CDR2

<400> SEQUENCE: 12

Glu Ile Thr Asn Asp Gly Ser Gly Thr Asn Tyr Gly Ser Ala Val Lys
1               5                   10                  15

Gly

<210> SEQ ID NO 13
<211> LENGTH: 20
<212> TYPE: PRT
<213> ORGANISM: Artificial Sequence
<220> FEATURE:
<223> OTHER INFORMATION: 2-13; 2-13D; 2-13D-37 VH-CDR3

<400> SEQUENCE: 13

Ser Thr Tyr Glu Cys Pro Gly Gly Phe Ser Cys Trp Gly Asp Thr Gly
1               5                   10                  15

Gln Ile Asp Ala
            20

<210> SEQ ID NO 14
<211> LENGTH: 5
<212> TYPE: PRT
<213> ORGANISM: Artificial Sequence
<220> FEATURE:
<223> OTHER INFORMATION: 3-2 VH-CDR1

<400> SEQUENCE: 14

Ser Phe Asn Met Phe
1               5

<210> SEQ ID NO 15
<211> LENGTH: 17
<212> TYPE: PRT
<213> ORGANISM: Artificial Sequence
<220> FEATURE:
<223> OTHER INFORMATION: 3-2 VH-CDR2

<400> SEQUENCE: 15

Gln Ile Ser Ser Ser Gly Ser Ser Thr Asn Tyr Ala Pro Ala Val Arg
1               5                   10                  15

Gly

<210> SEQ ID NO 16
<211> LENGTH: 24
<212> TYPE: PRT
<213> ORGANISM: Artificial Sequence
<220> FEATURE:
<223> OTHER INFORMATION: 3-2; 1-7A-IT; Low-PI; 1-30; 1-17; 1-32; 4-11;
      6-10 VH-CDR3

<400> SEQUENCE: 16

Ser Ser Tyr Asp Cys Pro Tyr Gly His Cys Ser Ser Gly Val Asp Ser
1               5                   10                  15

Ala Gly Glu Ile Asp Ala Asp Ala
            20

<210> SEQ ID NO 17
<211> LENGTH: 5
<212> TYPE: PRT
<213> ORGANISM: Artificial Sequence
<220> FEATURE:
<223> OTHER INFORMATION: 1-65; SS01-13; SS01-13-s5; S5-2.GKNG VH-CDR1

<400> SEQUENCE: 17

Ser Tyr Gln Met Gly
1               5

<210> SEQ ID NO 18
<211> LENGTH: 10

```
<212> TYPE: PRT
<213> ORGANISM: Artificial Sequence
<220> FEATURE:
<223> OTHER INFORMATION: 1-65; SS01-13 VH-CDR2

<400> SEQUENCE: 18

Val Ile Asn Lys Ser Gly Ser Asp Thr Ser
1               5                   10

<210> SEQ ID NO 19
<211> LENGTH: 13
<212> TYPE: PRT
<213> ORGANISM: Artificial Sequence
<220> FEATURE:
<223> OTHER INFORMATION: 1-65; SS01-13; SS01-13-s5; S5-2.GKNG VH-CDR3

<400> SEQUENCE: 19

Gly Ser Ala Ser Tyr Ile Thr Ala Ala Thr Ile Asp Ala
1               5                   10

<210> SEQ ID NO 20
<211> LENGTH: 8
<212> TYPE: PRT
<213> ORGANISM: Artificial Sequence
<220> FEATURE:
<223> OTHER INFORMATION: 1-28 VH-CDR1

<400> SEQUENCE: 20

Gly Phe Asp Phe Ser Asp Tyr Gly
1               5

<210> SEQ ID NO 21
<211> LENGTH: 8
<212> TYPE: PRT
<213> ORGANISM: Artificial Sequence
<220> FEATURE:
<223> OTHER INFORMATION: 1-28 VH-CDR2

<400> SEQUENCE: 21

Ile Arg Ser Asp Gly Ser Asn Pro
1               5

<210> SEQ ID NO 22
<211> LENGTH: 29
<212> TYPE: PRT
<213> ORGANISM: Artificial Sequence
<220> FEATURE:
<223> OTHER INFORMATION: 1-28 VH-CDR3

<400> SEQUENCE: 22

Ala Lys Asp Gly Asn Gly Tyr Cys Ala Leu Asp Ala Tyr Arg Ser Gly
1               5                   10                  15

Gly Tyr Ser Cys Gly Val Tyr Pro Gly Ser Ile Asp Ala
            20                  25

<210> SEQ ID NO 23
<211> LENGTH: 8
<212> TYPE: PRT
<213> ORGANISM: Artificial Sequence
<220> FEATURE:
<223> OTHER INFORMATION: 2-13 VL-CDR1

<400> SEQUENCE: 23

Ser Gly Gly Ser Tyr Ser Tyr Gly
1               5
```

```
<210> SEQ ID NO 24
<211> LENGTH: 7
<212> TYPE: PRT
<213> ORGANISM: Artificial Sequence
<220> FEATURE:
<223> OTHER INFORMATION: 2-13; 2-13D; 2-13D-37; 2-13D-37-1.5W-41;
      2-13D-37-3W-16 VL-CDR2

<400> SEQUENCE: 24

Trp Asp Asp Glu Arg Pro Ser
1               5

<210> SEQ ID NO 25
<211> LENGTH: 11
<212> TYPE: PRT
<213> ORGANISM: Artificial Sequence
<220> FEATURE:
<223> OTHER INFORMATION: 2-13; 2-13D; 2-13D-37; 2-13D-37-1.5W-41;
      2-13D-37-3W-16 VL-CDR3

<400> SEQUENCE: 25

Gly Thr Glu Asp Ile Ser Gly Thr Ala Gly Val
1               5                   10

<210> SEQ ID NO 26
<211> LENGTH: 13
<212> TYPE: PRT
<213> ORGANISM: Artificial Sequence
<220> FEATURE:
<223> OTHER INFORMATION: 3-2; 1-7A-IT; 1-17; 1-32; 4-11; 6-10 VL-CDR1

<400> SEQUENCE: 26

Ser Gly Gly Gly Ser Tyr Ala Gly Ser Tyr Tyr Tyr Gly
1               5                   10

<210> SEQ ID NO 27
<211> LENGTH: 7
<212> TYPE: PRT
<213> ORGANISM: Artificial Sequence
<220> FEATURE:
<223> OTHER INFORMATION: 3-2 VL-CDR2

<400> SEQUENCE: 27

Glu Ser Asn Lys Arg Pro Ser
1               5

<210> SEQ ID NO 28
<211> LENGTH: 10
<212> TYPE: PRT
<213> ORGANISM: Artificial Sequence
<220> FEATURE:
<223> OTHER INFORMATION: 3-2; 1-7A-IT VL-CDR3

<400> SEQUENCE: 28

Gly Ser Trp Asp Ser Ser Asn Gly Gly Ile
1               5                   10

<210> SEQ ID NO 29
<211> LENGTH: 11
<212> TYPE: PRT
<213> ORGANISM: Artificial Sequence
<220> FEATURE:
<223> OTHER INFORMATION: 1-65 VL-CDR1

<400> SEQUENCE: 29

Ser Gly Gly Gly Ser Ser Gly Tyr Gly Tyr Gly
1               5                   10
```

<210> SEQ ID NO 30
<211> LENGTH: 7
<212> TYPE: PRT
<213> ORGANISM: Artificial Sequence
<220> FEATURE:
<223> OTHER INFORMATION: 1-65 VL-CDR2

<400> SEQUENCE: 30

Trp Asn Asp Lys Arg Pro Ser
1               5

<210> SEQ ID NO 31
<211> LENGTH: 14
<212> TYPE: PRT
<213> ORGANISM: Artificial Sequence
<220> FEATURE:
<223> OTHER INFORMATION: 1-65; ss01-13; SS01-13-S5; S5-2.GKNG VL-CDR3

<400> SEQUENCE: 31

Gly Asn Asp Asp Tyr Ser Ser Asp Ser Gly Tyr Val Gly Val
1               5                   10

<210> SEQ ID NO 32
<211> LENGTH: 5
<212> TYPE: PRT
<213> ORGANISM: Artificial Sequence
<220> FEATURE:
<223> OTHER INFORMATION: 1-28 VL-CDR1

<400> SEQUENCE: 32

Gly Tyr Gly Tyr Gly
1               5

<210> SEQ ID NO 33
<211> LENGTH: 3
<212> TYPE: PRT
<213> ORGANISM: Artificial Sequence
<220> FEATURE:
<223> OTHER INFORMATION: 1-28 VL-CDR2

<400> SEQUENCE: 33

Gln Asn Asp
1

<210> SEQ ID NO 34
<211> LENGTH: 11
<212> TYPE: PRT
<213> ORGANISM: Artificial Sequence
<220> FEATURE:
<223> OTHER INFORMATION: 1-28 VL-CDR3

<400> SEQUENCE: 34

Gly Ser Glu Asp Ser Ser Thr Leu Ala Gly Ile
1               5                   10

<210> SEQ ID NO 35
<211> LENGTH: 129
<212> TYPE: PRT
<213> ORGANISM: Artificial Sequence
<220> FEATURE:
<223> OTHER INFORMATION: 2-13 Antibody VH

<400> SEQUENCE: 35

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser His

```
                    20                  25                  30
Gly Met Phe Trp Val Arg Gln Thr Pro Gly Lys Gly Leu Glu Tyr Val
                35                  40                  45

Ala Glu Ile Thr Asn Asp Gly Ser Gly Thr Asn Tyr Gly Ser Ala Val
            50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Phe Cys
                85                  90                  95

Ala Arg Ser Thr Tyr Glu Cys Pro Gly Gly Phe Ser Cys Trp Gly Asp
                100                 105                 110

Thr Gly Gln Ile Asp Ala Trp Gly His Gly Thr Glu Val Ile Val Ser
                115                 120                 125

Ser
```

<210> SEQ ID NO 36
<211> LENGTH: 131
<212> TYPE: PRT
<213> ORGANISM: Artificial Sequence
<220> FEATURE:
<223> OTHER INFORMATION: 3-2 Antibody VH

<400> SEQUENCE: 36

```
Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Phe
                20                  25                  30

Asn Met Phe Trp Val Arg Gln Ala Pro Gly Lys Gly Leu Glu Tyr Val
                35                  40                  45

Ala Gln Ile Ser Ser Ser Gly Ser Thr Asn Tyr Ala Pro Ala Val
            50                  55                  60

Arg Gly Arg Ala Thr Ile Ser Arg Asp Asn Gly Gln Ser Thr Val Arg
65                  70                  75                  80

Leu Gln Leu Asn Asn Pro Gly Ala Glu Asp Thr Gly Thr Tyr Tyr Cys
                85                  90                  95

Ala Lys Ser Ser Tyr Asp Cys Pro Tyr Gly His Cys Ser Ser Gly Val
                100                 105                 110

Asp Ser Ala Gly Glu Ile Asp Ala Trp Gly His Gly Thr Glu Val Ile
                115                 120                 125

Val Ser Ser
        130
```

<210> SEQ ID NO 37
<211> LENGTH: 122
<212> TYPE: PRT
<213> ORGANISM: Artificial Sequence
<220> FEATURE:
<223> OTHER INFORMATION: 1-65 Antibody VH

<400> SEQUENCE: 37

```
Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Tyr
                20                  25                  30

Gln Met Gly Trp Val Arg Gln Ala Pro Gly Lys Gly Leu Glu Trp Val
                35                  40                  45

Gly Val Ile Asn Lys Ser Gly Ser Asp Thr Ser Tyr Gly Ser Ala Val
```

```
                50                  55                  60
Lys Gly Arg Ala Thr Ile Ser Arg Asp Asn Gly Gln Ser Thr Val Arg
 65                  70                  75                  80

Leu Gln Leu Asn Asn Leu Arg Ala Glu Asp Thr Gly Thr Tyr Phe Cys
                 85                  90                  95

Ala Lys Gly Ser Ala Ser Tyr Ile Thr Ala Ala Thr Ile Asp Ala Trp
                100                 105                 110

Gly His Gly Thr Glu Val Ile Val Ser Ser
            115                 120

<210> SEQ ID NO 38
<211> LENGTH: 136
<212> TYPE: PRT
<213> ORGANISM: Artificial Sequence
<220> FEATURE:
<223> OTHER INFORMATION: 1-28 Antibody VH

<400> SEQUENCE: 38

Ala Val Thr Leu Asp Glu Ser Gly Gly Leu Gln Thr Pro Gly Gly
 1               5                  10                  15

Ala Leu Ser Leu Val Cys Lys Ala Ser Gly Phe Asp Phe Ser Asp Tyr
                 20                  25                  30

Gly Met Gly Trp Val Arg Gln Ala Pro Gly Lys Gly Leu Glu Trp Val
             35                  40                  45

Ala Ala Ile Arg Ser Asp Gly Ser Asn Pro Ser Tyr Gly Ser Ala Val
         50                  55                  60

Lys Gly Arg Ala Thr Ile Ser Lys Asp Asn Gly Arg Ser Thr Val Arg
 65                  70                  75                  80

Leu Gln Leu Asn Asn Leu Arg Ala Glu Asp Thr Ala Thr Tyr Tyr Cys
                 85                  90                  95

Ala Lys Asp Gly Asn Gly Tyr Cys Ala Leu Asp Ala Tyr Arg Ser Gly
                100                 105                 110

Gly Tyr Ser Cys Gly Val Tyr Pro Gly Ser Ile Asp Ala Trp Gly His
            115                 120                 125

Gly Thr Glu Val Ile Val Ser Ser
        130                 135

<210> SEQ ID NO 39
<211> LENGTH: 104
<212> TYPE: PRT
<213> ORGANISM: Artificial Sequence
<220> FEATURE:
<223> OTHER INFORMATION: 2-13 Antibody VL

<400> SEQUENCE: 39

Ala Leu Thr Gln Pro Ser Ser Val Ser Ala Asn Pro Gly Glu Thr Val
 1               5                  10                  15

Lys Ile Thr Cys Ser Gly Gly Ser Tyr Ser Tyr Gly Trp Phe Gln Gln
                 20                  25                  30

Lys Ser Pro Gly Ser Ala Leu Val Thr Val Ile Tyr Trp Asp Asp Glu
             35                  40                  45

Arg Pro Ser Asp Ile Pro Ser Arg Phe Ser Gly Ala Leu Ser Gly Ser
         50                  55                  60

Thr Asn Thr Leu Thr Ile Thr Gly Val Gln Ala Asp Asp Glu Ala Val
 65                  70                  75                  80

Tyr Phe Cys Gly Thr Glu Asp Ile Ser Gly Thr Ala Gly Val Phe Gly
                 85                  90                  95
```

```
Ala Gly Thr Thr Leu Thr Val Leu
            100
```

<210> SEQ ID NO 40
<211> LENGTH: 108
<212> TYPE: PRT
<213> ORGANISM: Artificial Sequence
<220> FEATURE:
<223> OTHER INFORMATION: 3-2 Antibody VL

<400> SEQUENCE: 40

```
Ala Leu Thr Gln Pro Ser Ser Val Ser Ala Asn Pro Gly Glu Thr Val
1               5                   10                  15

Lys Ile Thr Cys Ser Gly Gly Ser Tyr Ala Gly Ser Tyr Tyr Tyr
            20                  25                  30

Gly Trp Tyr Gln Gln Lys Ala Pro Gly Ser Ala Pro Val Thr Leu Ile
            35                  40                  45

Tyr Glu Ser Asn Lys Arg Pro Ser Asp Ile Pro Ser Arg Phe Ser Gly
        50                  55                  60

Ser Thr Ser Gly Ser Thr Ala Thr Leu Thr Ile Thr Gly Val Gln Ala
65                  70                  75                  80

Asp Asp Glu Ala Ile Tyr Tyr Cys Gly Ser Trp Asp Ser Ser Asn Gly
                85                  90                  95

Gly Ile Phe Gly Ala Gly Thr Thr Leu Thr Val Leu
            100                 105
```

<210> SEQ ID NO 41
<211> LENGTH: 110
<212> TYPE: PRT
<213> ORGANISM: Artificial Sequence
<220> FEATURE:
<223> OTHER INFORMATION: 1-65 Antibody VL

<400> SEQUENCE: 41

```
Ala Leu Thr Gln Pro Ser Ser Val Ser Ala Asn Pro Gly Glu Thr Val
1               5                   10                  15

Lys Ile Thr Cys Ser Gly Gly Gly Ser Gly Tyr Gly Tyr Gly Trp
            20                  25                  30

Tyr Gln Gln Lys Ser Pro Ser Ala Pro Leu Thr Val Ile Tyr Trp
            35                  40                  45

Asn Asp Lys Arg Pro Ser Asp Ile Pro Ser Arg Phe Ser Gly Ser Lys
        50                  55                  60

Ser Gly Ser Thr His Thr Leu Thr Ile Thr Gly Val Gln Ala Glu Asp
65                  70                  75                  80

Glu Ala Val Tyr Phe Cys Gly Asn Asp Asp Tyr Ser Ser Asp Ser Gly
                85                  90                  95

Tyr Val Gly Val Phe Gly Ala Gly Thr Thr Leu Thr Val Leu
            100                 105                 110
```

<210> SEQ ID NO 42
<211> LENGTH: 104
<212> TYPE: PRT
<213> ORGANISM: Artificial Sequence
<220> FEATURE:
<223> OTHER INFORMATION: 1-28 Antibody VL

<400> SEQUENCE: 42

```
Ala Leu Thr Gln Pro Ser Ser Val Ser Ala Asn Leu Glu Gly Thr Val
1               5                   10                  15

Glu Ile Thr Cys Ser Gly Ser Gly Tyr Gly Tyr Gly Trp Tyr Gln Gln
```

```
                 20                  25                  30
Lys Ser Pro Gly Ser Ala Pro Val Thr Val Ile Tyr Gln Asn Asp Lys
            35                  40                  45
Arg Pro Ser Asp Ile Pro Ser Arg Phe Ser Gly Ser Lys Ser Gly Ser
        50                  55                  60
Thr Gly Thr Leu Thr Ile Thr Gly Val Gln Val Glu Asp Glu Ala Val
    65                  70                  75                  80
Tyr Tyr Cys Gly Ser Glu Asp Ser Ser Thr Leu Ala Gly Ile Phe Gly
                    85                  90                  95
Ala Gly Thr Thr Leu Thr Val Leu
                100

<210> SEQ ID NO 43
<211> LENGTH: 387
<212> TYPE: DNA
<213> ORGANISM: Artificial Sequence
<220> FEATURE:
<223> OTHER INFORMATION: 2-13 Antibody VH

<400> SEQUENCE: 43
gccgtgacgt tggacgagtc cgggggcggc ctccagacgc ccggaggagc gctcagcctc      60
gtctgcaagg cctccgggtt caccttcagc agccatggca tgttctgggt gcgacagacg     120
cccggcaagg ggttggaata tgtcgctgaa attaccaatg atggtagtgg cacaaactac     180
gggtcggcgg tgaagggccg tgccaccatc tcgaggggaca acgggcagag cacagtgagg     240
ctgcagctga caaccctcag ggctgaggac accggcacct acttctgcgc cagatctact     300
tatgaatgtc ctggtggttt tagttgttgg ggtgatactg gtcaaataga cgcatggggc     360
cacgggaccg aagtcatcgt ctcctcc                                         387

<210> SEQ ID NO 44
<211> LENGTH: 393
<212> TYPE: DNA
<213> ORGANISM: Artificial Sequence
<220> FEATURE:
<223> OTHER INFORMATION: 3-2 Antibody VH

<400> SEQUENCE: 44
gccgtgacgt tggacgagtc cgggggcggc ctccagacgc ccggaggagc gctcagcctc      60
gtctgcaagg cctccgggtt caccttcagc agcttcaaca tgttctgggt gcgacaggcg     120
cccggcaagg ggctggaata cgtcgctcaa attagcagca gtggtagtag cacaaactac     180
gcacccgcgg tgaggggccg tgccaccatc tcgagggaca acgggcagag cacagtgagg     240
ctgcagctga acaaccccgg ggctgaagac accggcacct actactgcgc caaaagtagt     300
tatgactgtc cttacggtca ttgtagtagt ggtgttgata tgctggtga atcgacgca       360 tggggccacg ggaccgaagt catcgtctcc tcc                                  393

<210> SEQ ID NO 45
<211> LENGTH: 366
<212> TYPE: DNA
<213> ORGANISM: Artificial Sequence
<220> FEATURE:
<223> OTHER INFORMATION: 1-65 Antibody VH

<400> SEQUENCE: 45
gccgtgacgt tggacgagtc cgggggcggc ctccagacgc ccggaggagc gctcagcctc      60
gtctgcaagg cctccgggtt caccttcagc agctatcaga tgggctgggt gcgacaggcg     120
```

```
cccggcaagg ggctggaatg ggtcggtgtt attaacaaga gtggtagtga cacatcatac    180
gggtcggcgg tgaagggccg tgccaccatc tcgagggaca acgggcagag cacagtgagg    240
ctgcagctga acaacctcag ggctgaggac accggcacct acttctgcgc caaaggttct    300
gctagttata taactgctgc taccatcgac gcatggggcc acgggaccga agtcatcgtc    360
tcctcc                                                                366

<210> SEQ ID NO 46
<211> LENGTH: 408
<212> TYPE: DNA
<213> ORGANISM: Artificial Sequence
<220> FEATURE:
<223> OTHER INFORMATION: 1-28 Antibody VH

<400> SEQUENCE: 46
gccgtgacgt tggacgagtc cggggcggc ctccagacgc ccggaggagc gctcagcctc      60
gtctgcaagg cctccggtt cgacttcagc gattatggca tgggttgggt gcgacaggct    120
ccaggcaagg ggctggagtg ggttgctgct attagaagtg atggtagtaa cccatcatac    180
gggtcggcgg tgaagggccg tgccaccatc tcgaaggaca acgggcgaag cacagtgagg    240
ctgcagctga acaacctcag ggctgaggac accgccacct actactgcgc caaggatggt    300
aatggttact gtgctctcga tgcttatcgt agtggtggtt atagttgtgg tgtttatcct    360
ggtagcatcg acgcatgggg ccacgggacc gaagtcatcg tctcctcc                 408

<210> SEQ ID NO 47
<211> LENGTH: 312
<212> TYPE: DNA
<213> ORGANISM: Artificial Sequence
<220> FEATURE:
<223> OTHER INFORMATION: 2-13 Antibody VL

<400> SEQUENCE: 47
gccctgactc agccgtcctc ggtgtcagca aacccaggag aaaccgtcaa gataacctgc     60
tccgggggta gctatagcta tgctggttc cagcagaagt ctcctggcag tgcccttgtc    120
actgtgatct actgggatga tgagagaccc tcggacatcc cttcacgatt ctccggtgcc    180
ctatccggct ccacaaacac attaaccatc actgggtcc aagccgacga cgaggctgtc    240
tatttctgtg ggactgaaga catcagcggc actgctggtg tatttggggc cgggacaacc    300
ctgaccgtcc tg                                                        312

<210> SEQ ID NO 48
<211> LENGTH: 324
<212> TYPE: DNA
<213> ORGANISM: Artificial Sequence
<220> FEATURE:
<223> OTHER INFORMATION: 3-2 Antibody VL

<400> SEQUENCE: 48
gccctgactc agccgtcctc ggtgtcagca aacccaggag aaaccgtcaa gatcacctgc     60 tccggggtg gcagctatgc tggaagttac tattatggct ggtaccagca gaaggcacct    120
ggcagtgccc ctgtcactct gatctatgaa agcaacaaga gaccctcgga catcccttca    180
cgattctccg gttccacatc tggctccaca gccacactaa ccatcactgg ggtccaagcc    240
gatgacgagg ctatctatta ctgtgggagc tgggacagta gcaatggtgg tatatttggg    300
gccgggacaa ccctgaccgt ccta                                           324
```

<210> SEQ ID NO 49
<211> LENGTH: 331
<212> TYPE: DNA
<213> ORGANISM: Artificial Sequence
<220> FEATURE:
<223> OTHER INFORMATION: 1-65 Antibody VL

<400> SEQUENCE: 49

```
ggccctgact cagccgtcct cggtgtcagc aaaccctggg gaaactgtca agatcacctg      60
ctccggggggt ggtagcagtg ctatggttta tggctggtat cagcagaagt cacctagcag    120
tgcccctctc actgtgatct actggaacga caagagaccc tcggacatcc cttcacgatt    180
ctccggttcc aaatccggct ccacacacac attaaccatc actggggtcc aagccgagga    240
cgaggctgta tatttctgtg gaatgatga ctacagcagt gatagtggat atgtcggtgt      300
atttggggcc gggacaaccc tgaccgtcct a                                    331
```

<210> SEQ ID NO 50
<211> LENGTH: 312
<212> TYPE: DNA
<213> ORGANISM: Artificial Sequence
<220> FEATURE:
<223> OTHER INFORMATION: 1-28 Antibody VL

<400> SEQUENCE: 50

```
gccctgactc agccgtcctc ggtgtcagca aacctggaag gaaccgtcga gatcacctgc      60
tccgggagtg gctatggtta tggctggtat cagcagaagt ctcctggcag tgcccctgtc    120
actgtgatct atcagaacga caagagaccc tcggacatcc cttcacgatt ctccggttcc    180
aaatccggct ccacgggcac attaaccatc actggggtcc aagtcgagga cgaggctgtc    240
tattactgtg ggagtgaaga cagcagcact cttgctggta tatttggggc cgggacaacc    300
ctgaccgtcc ta                                                         312
```

<210> SEQ ID NO 51
<211> LENGTH: 100
<212> TYPE: PRT
<213> ORGANISM: Artificial Sequence
<220> FEATURE:
<223> OTHER INFORMATION: M3 mutant

<400> SEQUENCE: 51

```
Gln Phe Leu Lys Glu Gly Gln Leu Ala Ala Gly Thr Cys Glu Ile Val
1               5                   10                  15
Thr Leu Asp Arg Asp Ser Ser Gln Pro Arg Ile Glu Glu Arg Ser Gln
            20                  25                  30
Thr Ala Arg Cys Ala Cys Arg Lys Gly Gln Ile Ala Gly Thr Thr Arg
        35                  40                  45
Ala Arg Pro Ala Cys Val Asp Ala Arg Ile Ile Lys Thr Lys Gln Trp
    50                  55                  60
Cys Asp Met Leu Pro Cys Leu Glu Gly Glu Gly Cys Asp Leu Leu Ile
65                  70                  75                  80
Asn Arg Ser Gly Trp Thr Cys Thr Gln Pro Gly Gly Arg Ile Lys Thr
                85                  90                  95
Thr Thr Val Ser
            100
```

<210> SEQ ID NO 52
<211> LENGTH: 100
<212> TYPE: PRT
<213> ORGANISM: Artificial Sequence
<220> FEATURE:
<223> OTHER INFORMATION: M4 mutant

<400> SEQUENCE: 52

Gln Phe Leu Lys Glu Gly Gln Leu Ala Ala Gly Thr Cys Glu Ile Val
1               5                   10                  15

Thr Leu Asp Arg Asp Ser Ser Gln Pro Arg Arg Thr Ile Ala Arg Gln
            20                  25                  30

Thr Val Lys Cys Ser Cys Phe Pro Gly Gln Ile Ala Gly Thr Thr Arg
        35                  40                  45

Ala Arg Pro Ala Cys Val Asp Ala Arg Ile Ile Lys Thr Lys Gln Trp
    50                  55                  60

Cys Asp Met Leu Pro Cys Leu Glu Gly Glu Gly Cys Asp Leu Leu Ile
65                  70                  75                  80

Asn Arg Ser Gly Trp Thr Cys Thr Gln Pro Gly Gly Arg Ile Lys Thr
                85                  90                  95

Thr Thr Val Ser
            100

<210> SEQ ID NO 53
<211> LENGTH: 100
<212> TYPE: PRT
<213> ORGANISM: Artificial Sequence
<220> FEATURE:
<223> OTHER INFORMATION: M5 mutant

<400> SEQUENCE: 53

Gln Phe Leu Lys Glu Gly Gln Leu Ala Ala Gly Thr Cys Glu Ile Val
1               5                   10                  15

Thr Leu Asp Arg Asp Ser Ser Gln Pro Arg Arg Thr Ile Ala Arg Gln
            20                  25                  30

Thr Ala Arg Cys Ala Cys Arg Lys Gly Gln Ile Ala Gly Thr Thr Arg
        35                  40                  45

Asn Lys Pro Ser Cys Val Asp Ala Arg Ile Ile Lys Thr Lys Gln Trp
    50                  55                  60

Cys Asp Met Leu Pro Cys Leu Glu Gly Glu Gly Cys Asp Leu Leu Ile
65                  70                  75                  80

Asn Arg Ser Gly Trp Thr Cys Thr Gln Pro Gly Gly Arg Ile Lys Thr
                85                  90                  95

Thr Thr Val Ser
            100

<210> SEQ ID NO 54
<211> LENGTH: 100
<212> TYPE: PRT
<213> ORGANISM: Artificial Sequence
<220> FEATURE:
<223> OTHER INFORMATION: M6 mutant

<400> SEQUENCE: 54

Gln Phe Leu Lys Glu Gly Gln Leu Ala Ala Gly Thr Cys Glu Ile Val
1               5                   10                  15

Thr Leu Asp Arg Asp Ser Ser Gln Pro Arg Arg Thr Ile Ala Arg Gln
            20                  25                  30

Thr Ala Arg Cys Ala Cys Arg Lys Gly Gln Ile Ala Gly Thr Thr Arg
        35                  40                  45

Ala Arg Pro Ala Cys Val Asp Ala Arg Ile Ile Leu Gln Arg Trp Trp
    50                  55                  60

Cys Gln Met Glu Leu Cys Leu Glu Gly Glu Gly Cys Asp Leu Leu Ile
65                  70                  75                  80

Asn Arg Ser Gly Trp Thr Cys Thr Gln Pro Gly Gly Arg Ile Lys Thr
                85                  90                  95

Thr Thr Val Ser
            100

<210> SEQ ID NO 55
<211> LENGTH: 100
<212> TYPE: PRT
<213> ORGANISM: Artificial Sequence
<220> FEATURE:
<223> OTHER INFORMATION: M7 mutant

<400> SEQUENCE: 55

Gln Phe Leu Lys Glu Gly Gln Leu Ala Ala Gly Thr Cys Glu Ile Val
1               5                   10                  15

Thr Leu Asp Arg Asp Ser Ser Gln Pro Arg Arg Thr Ile Ala Arg Gln
            20                  25                  30

Thr Ala Arg Cys Ala Cys Arg Lys Gly Gln Ile Ala Gly Thr Thr Arg
        35                  40                  45

Ala Arg Pro Ala Cys Val Asp Ala Arg Ile Ile Lys Thr Lys Gln Trp
50                  55                  60

Cys Asp Met Leu Pro Cys Leu Glu Gly Glu Glu Cys Lys Thr Leu Pro
65                  70                  75                  80

Asp Asn Ser Gly Trp Thr Cys Thr Gln Pro Gly Gly Arg Ile Lys Thr
                85                  90                  95

Thr Thr Val Ser
            100

<210> SEQ ID NO 56
<211> LENGTH: 101
<212> TYPE: PRT
<213> ORGANISM: Artificial Sequence
<220> FEATURE:
<223> OTHER INFORMATION: M8 mutant

<400> SEQUENCE: 56

Gln Phe Leu Lys Glu Gly Gln Leu Ala Ala Gly Thr Cys Glu Ile Val
1               5                   10                  15

Thr Leu Asp Arg Asp Ser Ser Gln Pro Arg Arg Thr Ile Ala Arg Gln
            20                  25                  30

Thr Ala Arg Cys Ala Cys Arg Lys Gly Gln Ile Ala Gly Thr Thr Arg
        35                  40                  45

Ala Arg Pro Ala Cys Val Asp Ala Arg Ile Ile Lys Thr Lys Gln Trp
50                  55                  60

Cys Asp Met Leu Pro Cys Leu Glu Gly Glu Cys Asp Leu Leu Ile
65                  70                  75                  80

Asn Arg Ser Gly Trp Thr Cys Ser Cys Ser Ser Gly Asn Lys Ile Lys
                85                  90                  95

Thr Thr Thr Val Ser
            100

<210> SEQ ID NO 57
<211> LENGTH: 459
<212> TYPE: PRT
<213> ORGANISM: Artificial Sequence
<220> FEATURE:
<223> OTHER INFORMATION: 2-13 Antibody HC

<400> SEQUENCE: 57

```
Ala Val Thr Leu Asp Glu Ser Gly Gly Leu Gln Thr Pro Gly Gly
1               5                   10                  15
Ala Leu Ser Leu Val Cys Lys Ala Ser Gly Phe Thr Phe Ser Ser His
            20                  25                  30
Gly Met Phe Trp Val Arg Gln Thr Pro Gly Lys Gly Leu Glu Tyr Val
        35                  40                  45
Ala Glu Ile Thr Asn Asp Gly Ser Gly Thr Asn Tyr Gly Ser Ala Val
50                  55                  60
Lys Gly Arg Ala Thr Ile Ser Arg Asp Asn Gly Gln Ser Thr Val Arg
65                  70                  75                  80
Leu Gln Leu Asn Asn Leu Arg Ala Glu Asp Thr Gly Thr Tyr Phe Cys
                85                  90                  95
Ala Arg Ser Thr Tyr Glu Cys Pro Gly Gly Phe Ser Cys Trp Gly Asp
            100                 105                 110
Thr Gly Gln Ile Asp Ala Trp Gly His Gly Thr Glu Val Ile Val Ser
        115                 120                 125
Ser Ala Ser Thr Lys Gly Pro Ser Val Phe Pro Leu Ala Pro Ser Ser
130                 135                 140
Lys Ser Thr Ser Gly Gly Thr Ala Ala Leu Gly Cys Leu Val Lys Asp
145                 150                 155                 160
Tyr Phe Pro Glu Pro Val Thr Val Ser Trp Asn Ser Gly Ala Leu Thr
                165                 170                 175
Ser Gly Val His Thr Phe Pro Ala Val Leu Gln Ser Ser Gly Leu Tyr
            180                 185                 190
Ser Leu Ser Ser Val Val Thr Val Pro Ser Ser Ser Leu Gly Thr Gln
        195                 200                 205
Thr Tyr Ile Cys Asn Val Asn His Lys Pro Ser Asn Thr Lys Val Asp
210                 215                 220
Lys Lys Val Glu Pro Lys Ser Cys Asp Lys Thr His Thr Cys Pro Pro
225                 230                 235                 240
Cys Pro Ala Pro Glu Leu Leu Gly Gly Pro Ser Val Phe Leu Phe Pro
                245                 250                 255
Pro Lys Pro Lys Asp Thr Leu Met Ile Ser Arg Thr Pro Glu Val Thr
            260                 265                 270
Cys Val Val Val Asp Val Ser His Glu Asp Pro Glu Val Lys Phe Asn
        275                 280                 285
Trp Tyr Val Asp Gly Val Glu Val His Asn Ala Lys Thr Lys Pro Arg
290                 295                 300
Glu Glu Gln Tyr Asn Ser Thr Tyr Arg Val Val Ser Val Leu Thr Val
305                 310                 315                 320
Leu His Gln Asp Trp Leu Asn Gly Lys Glu Tyr Lys Cys Lys Val Ser
                325                 330                 335
Asn Lys Ala Leu Pro Ala Pro Ile Glu Lys Thr Ile Ser Lys Ala Lys
            340                 345                 350
Gly Gln Pro Arg Glu Pro Gln Val Tyr Thr Leu Pro Pro Ser Arg Glu
        355                 360                 365
Glu Met Thr Lys Asn Gln Val Ser Leu Thr Cys Leu Val Lys Gly Phe
370                 375                 380
Tyr Pro Ser Asp Ile Ala Val Glu Trp Glu Ser Asn Gly Gln Pro Glu
385                 390                 395                 400
Asn Asn Tyr Lys Thr Thr Pro Pro Val Leu Asp Ser Asp Gly Ser Phe
                405                 410                 415
```

Phe Leu Tyr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
        435                 440                 445

Thr Gln Lys Ser Leu Ser Leu Ser Pro Gly Lys
    450                 455

<210> SEQ ID NO 58
<211> LENGTH: 461
<212> TYPE: PRT
<213> ORGANISM: Artificial Sequence
<220> FEATURE:
<223> OTHER INFORMATION: 3-2 Antibody HC

<400> SEQUENCE: 58

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Phe
            20                  25                  30

Asn Met Phe Trp Val Arg Gln Ala Pro Gly Lys Gly Leu Glu Tyr Val
        35                  40                  45

Ala Gln Ile Ser Ser Ser Gly Ser Ser Thr Asn Tyr Ala Pro Ala Val
    50                  55                  60

Arg Gly Arg Ala Thr Ile Ser Arg Asp Asn Gly Gln Ser Thr Val Arg
65                  70                  75                  80

Leu Gln Leu Asn Asn Pro Gly Ala Glu Asp Thr Gly Thr Tyr Tyr Cys
                85                  90                  95

Ala Lys Ser Ser Tyr Asp Cys Pro Tyr Gly His Cys Ser Ser Gly Val
            100                 105                 110

Asp Ser Ala Gly Glu Ile Asp Ala Trp Gly His Gly Thr Glu Val Ile
        115                 120                 125

Val Ser Ser Ala Ser Thr Lys Gly Pro Ser Val Phe Pro Leu Ala Pro
    130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Gln Thr Tyr Ile Cys Asn Val Asn His Lys Pro Ser Asn Thr Lys
    210                 215                 220

Val Asp Lys Lys Val Glu Pro Lys Ser Cys Asp Lys Thr His Thr Cys
225                 230                 235                 240

Pro Pro Cys Pro Ala Pro Glu Leu Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Asn Ser Thr Tyr Arg Val Val Ser Val Leu
305                 310                 315                 320

```
Thr Val Leu His Gln Asp Trp Leu Asn Gly Lys Glu Tyr Lys Cys Lys
            325                 330                 335

Val Ser Asn Lys Ala Leu Pro Ala Pro Ile Glu Lys Thr Ile Ser Lys
        340                 345                 350

Ala Lys Gly Gln Pro Arg Glu Pro Gln Val Tyr Thr Leu Pro Pro Ser
    355                 360                 365

Arg Glu Glu Met Thr Lys Asn Gln Val Ser Leu Thr Cys Leu Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
    450                 455                 460

<210> SEQ ID NO 59
<211> LENGTH: 452
<212> TYPE: PRT
<213> ORGANISM: Artificial Sequence
<220> FEATURE:
<223> OTHER INFORMATION: 1-65 Antibody HC

<400> SEQUENCE: 59

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Tyr
            20                  25                  30

Gln Met Gly Trp Val Arg Gln Ala Pro Gly Lys Gly Leu Glu Trp Val
        35                  40                  45

Gly Val Ile Asn Lys Ser Gly Ser Asp Thr Ser Tyr Gly Ser Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Phe Cys
                85                  90                  95

Ala Lys Gly Ser Ala Ser Tyr Ile Thr Ala Ala Thr Ile Asp Ala Trp
            100                 105                 110

Gly His Gly Thr Glu Val Ile Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220
```

```
Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
        260                 265                 270

His Glu Asp Pro Glu Val Lys Phe Asn Trp Tyr Val Asp Gly Val Glu
    275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
        340                 345                 350

Val Tyr Thr Leu Pro Pro Ser Arg Glu Glu Met Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
    435                 440                 445

Ser Pro Gly Lys
    450

<210> SEQ ID NO 60
<211> LENGTH: 466
<212> TYPE: PRT
<213> ORGANISM: Artificial Sequence
<220> FEATURE:
<223> OTHER INFORMATION: 1-28 Antibody HC

<400> SEQUENCE: 60

Ala Val Thr Leu Asp Glu Ser Gly Gly Leu Gln Thr Pro Gly Gly
1               5                   10                  15

Ala Leu Ser Leu Val Cys Lys Ala Ser Gly Phe Asp Phe Ser Asp Tyr
                20                  25                  30

Gly Met Gly Trp Val Arg Gln Ala Pro Gly Lys Gly Leu Glu Trp Val
            35                  40                  45

Ala Ala Ile Arg Ser Asp Gly Ser Asn Pro Ser Tyr Gly Ser Ala Val
        50                  55                  60

Lys Gly Arg Ala Thr Ile Ser Lys Asp Asn Gly Arg Ser Thr Val Arg
65                  70                  75                  80

Leu Gln Leu Asn Asn Leu Arg Ala Glu Asp Thr Ala Thr Tyr Tyr Cys
                85                  90                  95

Ala Lys Asp Gly Asn Gly Tyr Cys Ala Leu Asp Ala Tyr Arg Ser Gly
            100                 105                 110

Gly Tyr Ser Cys Gly Val Tyr Pro Gly Ser Ile Asp Ala Trp Gly His
        115                 120                 125
```

Gly Thr Glu Val Ile Val Ser Ser Ala Ser Thr Lys Gly Pro Ser Val
        130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
            165                 170                 175

Trp Asn Ser Gly Ala Leu Thr Ser Gly Val His Thr Phe Pro Ala Val
        180                 185                 190

Leu Gln Ser Ser Gly Leu Tyr Ser Leu Ser Ser Val Val Thr Val Pro
    195                 200                 205

Ser Ser Ser Leu Gly Thr Gln Thr Tyr Ile Cys Asn Val Asn His Lys
210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
            245                 250                 255

Pro Ser Val Phe Leu Phe Pro Pro Lys Pro Lys Asp Thr Leu Met Ile
        260                 265                 270

Ser Arg Thr Pro Glu Val Thr Cys Val Val Val Asp Val Ser His Glu
    275                 280                 285

Asp Pro Glu Val Lys Phe Asn Trp Tyr Val Asp Gly Val Glu Val His
290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
            325                 330                 335

Glu Tyr Lys Cys Lys Val Ser Asn Lys Ala Leu Pro Ala Pro Ile Glu
        340                 345                 350

Lys Thr Ile Ser Lys Ala Lys Gly Gln Pro Arg Glu Pro Gln Val Tyr
    355                 360                 365

Thr Leu Pro Pro Ser Arg Glu Glu Met Thr Lys Asn Gln Val Ser Leu
370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
            405                 410                 415

Leu Asp Ser Asp Gly Ser Phe Phe Leu Tyr Ser Lys Leu Thr Val Asp
        420                 425                 430

Lys Ser Arg Trp Gln Gln Gly Asn Val Phe Ser Cys Ser Val Met His
    435                 440                 445

Glu Ala Leu His Asn His Tyr Thr Gln Lys Ser Leu Ser Leu Ser Pro
450                 455                 460

Gly Lys
465

<210> SEQ ID NO 61
<211> LENGTH: 211
<212> TYPE: PRT
<213> ORGANISM: Artificial Sequence
<220> FEATURE:
<223> OTHER INFORMATION: 2-13 Antibody LC

<400> SEQUENCE: 61

Ala Leu Thr Gln Pro Ser Ser Val Ser Ala Asn Pro Gly Glu Thr Val
1               5                   10                  15

```
Lys Ile Thr Cys Ser Gly Gly Ser Tyr Ser Tyr Gly Trp Phe Gln Gln
            20                  25                  30

Lys Ser Pro Gly Ser Ala Leu Val Thr Val Ile Tyr Trp Asp Asp Glu
            35                  40                  45

Arg Pro Ser Asp Ile Pro Ser Arg Phe Ser Gly Ala Leu Ser Gly Ser
        50                  55                  60

Thr Asn Thr Leu Thr Ile Thr Gly Val Gln Ala Asp Asp Glu Ala Val
65                  70                  75                  80

Tyr Phe Cys Gly Thr Glu Asp Ile Ser Gly Thr Ala Gly Val Phe Gly
                85                  90                  95

Ala Gly Thr Thr Leu Thr Val Leu Arg Ser Val Ala Ala Pro Ser Val
            100                 105                 110

Phe Ile Phe Pro Pro Ser Asp Glu Gln Leu Lys Ser Gly Thr Ala Ser
            115                 120                 125

Val Val Cys Leu Leu Asn Asn Phe Tyr Pro Arg Glu Ala Lys Val Gln
130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
            195                 200                 205

Gly Glu Cys
        210

<210> SEQ ID NO 62
<211> LENGTH: 215
<212> TYPE: PRT
<213> ORGANISM: Artificial Sequence
<220> FEATURE:
<223> OTHER INFORMATION: 3-2 Antibody LC

<400> SEQUENCE: 62

Ala Leu Thr Gln Pro Ser Ser Val Ser Ala Asn Pro Gly Glu Thr Val
1               5                   10                  15

Lys Ile Thr Cys Ser Gly Gly Gly Ser Tyr Ala Gly Ser Tyr Tyr Tyr
            20                  25                  30

Gly Trp Tyr Gln Gln Lys Ala Pro Gly Ser Ala Pro Val Thr Leu Ile
            35                  40                  45

Tyr Glu Ser Asn Lys Arg Pro Ser Asp Ile Pro Ser Arg Phe Ser Gly
        50                  55                  60

Ser Thr Ser Gly Ser Thr Ala Thr Leu Thr Ile Thr Gly Val Gln Ala
65                  70                  75                  80

Asp Asp Glu Ala Ile Tyr Tyr Cys Gly Ser Trp Asp Ser Ser Asn Gly
                85                  90                  95

Gly Ile Phe Gly Ala Gly Thr Thr Leu Thr Val Leu Arg Ser Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160
```

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 63
<211> LENGTH: 217
<212> TYPE: PRT
<213> ORGANISM: Artificial Sequence
<220> FEATURE:
<223> OTHER INFORMATION: 1-65 Antibody LC

<400> SEQUENCE: 63

Ala Leu Thr Gln Pro Ser Ser Val Ser Ala Asn Pro Gly Glu Thr Val
1               5                   10                  15

Lys Ile Thr Cys Ser Gly Gly Gly Ser Ser Gly Tyr Gly Tyr Gly Trp
            20                  25                  30

Tyr Gln Gln Lys Ser Pro Ser Ser Ala Pro Leu Thr Val Ile Tyr Trp
        35                  40                  45

Asn Asp Lys Arg Pro Ser Asp Ile Pro Ser Arg Phe Ser Gly Ser Lys
    50                  55                  60

Ser Gly Ser Thr His Thr Leu Thr Ile Thr Gly Val Gln Ala Glu Asp
65                  70                  75                  80

Glu Ala Val Tyr Phe Cys Gly Asn Asp Asp Tyr Ser Asp Ser Asp Gly
                85                  90                  95

Tyr Val Gly Val Phe Gly Ala Gly Thr Thr Leu Thr Val Leu Arg Ser
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 64
<211> LENGTH: 211
<212> TYPE: PRT
<213> ORGANISM: Artificial Sequence
<220> FEATURE:
<223> OTHER INFORMATION: 1-28 Antibody LC

<400> SEQUENCE: 64

Ala Leu Thr Gln Pro Ser Ser Val Ser Ala Asn Leu Glu Gly Thr Val
1               5                   10                  15

Glu Ile Thr Cys Ser Gly Ser Gly Tyr Gly Tyr Gly Trp Tyr Gln Gln

```
                    20                  25                  30
Lys Ser Pro Gly Ser Ala Pro Val Thr Val Ile Tyr Gln Asn Asp Lys
                35                  40                  45

Arg Pro Ser Asp Ile Pro Ser Arg Phe Ser Gly Ser Lys Ser Gly Ser
            50                  55                  60

Thr Gly Thr Leu Thr Ile Thr Gly Val Gln Val Glu Asp Glu Ala Val
65                  70                  75                  80

Tyr Tyr Cys Gly Ser Glu Asp Ser Ser Thr Leu Ala Gly Ile Phe Gly
                85                  90                  95

Ala Gly Thr Thr Leu Thr Val Leu Arg Ser Val Ala Ala Pro Ser Val
            100                 105                 110

Phe Ile Phe Pro Pro Ser Asp Glu Gln Leu Lys Ser Gly Thr Ala Ser
                115                 120                 125

Val Val Cys Leu Leu Asn Asn Phe Tyr Pro Arg Glu Ala Lys Val Gln
            130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
                195                 200                 205

Gly Glu Cys
    210

<210> SEQ ID NO 65
<211> LENGTH: 5
<212> TYPE: PRT
<213> ORGANISM: Artificial Sequence
<220> FEATURE:
<223> OTHER INFORMATION: EP1 Epitope

<400> SEQUENCE: 65

Ile Val Thr Leu Asp
1               5

<210> SEQ ID NO 66
<211> LENGTH: 5
<212> TYPE: PRT
<213> ORGANISM: Artificial Sequence
<220> FEATURE:
<223> OTHER INFORMATION: EP2 Epitope

<400> SEQUENCE: 66

Asp Ser Ser Gln Pro
1               5

<210> SEQ ID NO 67
<211> LENGTH: 5
<212> TYPE: PRT
<213> ORGANISM: Artificial Sequence
<220> FEATURE:
<223> OTHER INFORMATION: EP3 Epitope

<400> SEQUENCE: 67

Arg Thr Ile Ala Arg
1               5

<210> SEQ ID NO 68
```

```
<211> LENGTH: 7
<212> TYPE: PRT
<213> ORGANISM: Artificial Sequence
<220> FEATURE:
<223> OTHER INFORMATION: EP4 Epitope

<400> SEQUENCE: 68

Ala Arg Cys Ala Cys Arg Lys
1               5

<210> SEQ ID NO 69
<211> LENGTH: 4
<212> TYPE: PRT
<213> ORGANISM: Artificial Sequence
<220> FEATURE:
<223> OTHER INFORMATION: EP5 Epitope

<400> SEQUENCE: 69

Ala Arg Pro Ala
1

<210> SEQ ID NO 70
<211> LENGTH: 9
<212> TYPE: PRT
<213> ORGANISM: Artificial Sequence
<220> FEATURE:
<223> OTHER INFORMATION: EP6 Epitope

<400> SEQUENCE: 70

Lys Thr Lys Gln Trp Cys Asp Met Leu
1               5

<210> SEQ ID NO 71
<211> LENGTH: 8
<212> TYPE: PRT
<213> ORGANISM: Artificial Sequence
<220> FEATURE:
<223> OTHER INFORMATION: EP7 Epitope

<400> SEQUENCE: 71

Gly Cys Asp Leu Leu Ile Asn Arg
1               5

<210> SEQ ID NO 72
<211> LENGTH: 8
<212> TYPE: PRT
<213> ORGANISM: Artificial Sequence
<220> FEATURE:
<223> OTHER INFORMATION: EP8 Epitope

<400> SEQUENCE: 72

Thr Cys Thr Gln Pro Gly Gly Arg
1               5

<210> SEQ ID NO 73
<211> LENGTH: 20
<212> TYPE: PRT
<213> ORGANISM: Artificial Sequence
<220> FEATURE:
<223> OTHER INFORMATION: F2-01-BSA (#1)

<400> SEQUENCE: 73

Thr Ala Asp Arg Asp Ser Ser Gln Pro Arg Arg Thr Ile Ala Arg Gln
1               5                   10                  15

Thr Ala Arg Cys
            20
```

<210> SEQ ID NO 74
<211> LENGTH: 20
<212> TYPE: PRT
<213> ORGANISM: Artificial Sequence
<220> FEATURE:
<223> OTHER INFORMATION: F2-02-BSA (#2)

<400> SEQUENCE: 74

Thr Leu Ala Arg Asp Ser Ser Gln Pro Arg Arg Thr Ile Ala Arg Gln
1               5                   10                  15

Thr Ala Arg Cys
            20

<210> SEQ ID NO 75
<211> LENGTH: 20
<212> TYPE: PRT
<213> ORGANISM: Artificial Sequence
<220> FEATURE:
<223> OTHER INFORMATION: F2-03-BSA (#3)

<400> SEQUENCE: 75

Thr Leu Asp Arg Ala Ser Ser Gln Pro Arg Arg Thr Ile Ala Arg Gln
1               5                   10                  15

Thr Ala Arg Cys
            20

<210> SEQ ID NO 76
<211> LENGTH: 20
<212> TYPE: PRT
<213> ORGANISM: Artificial Sequence
<220> FEATURE:
<223> OTHER INFORMATION: F2-04-BSA (#4)

<400> SEQUENCE: 76

Thr Leu Asp Arg Asp Ala Ser Gln Pro Arg Arg Thr Ile Ala Arg Gln
1               5                   10                  15

Thr Ala Arg Cys
            20

<210> SEQ ID NO 77
<211> LENGTH: 20
<212> TYPE: PRT
<213> ORGANISM: Artificial Sequence
<220> FEATURE:
<223> OTHER INFORMATION: F2-05-BSA (#5)

<400> SEQUENCE: 77

Thr Leu Asp Arg Asp Ser Ala Gln Pro Arg Arg Thr Ile Ala Arg Gln
1               5                   10                  15

Thr Ala Arg Cys
            20

<210> SEQ ID NO 78
<211> LENGTH: 20
<212> TYPE: PRT
<213> ORGANISM: Artificial Sequence
<220> FEATURE:
<223> OTHER INFORMATION: F2-06-BSA (#6)

<400> SEQUENCE: 78

Thr Leu Asp Arg Asp Ser Ser Ala Pro Arg Arg Thr Ile Ala Arg Gln
1               5                   10                  15

Thr Ala Arg Cys
            20

<210> SEQ ID NO 79
<211> LENGTH: 20
<212> TYPE: PRT
<213> ORGANISM: Artificial Sequence
<220> FEATURE:
<223> OTHER INFORMATION: F2-07-BSA (#7)

<400> SEQUENCE: 79

Thr Leu Asp Arg Asp Ser Ser Gln Ala Arg Arg Thr Ile Ala Arg Gln
1               5                   10                  15

Thr Ala Arg Cys
            20

<210> SEQ ID NO 80
<211> LENGTH: 20
<212> TYPE: PRT
<213> ORGANISM: Artificial Sequence
<220> FEATURE:
<223> OTHER INFORMATION: F2-08-BSA (#8)

<400> SEQUENCE: 80

Thr Leu Asp Arg Asp Ser Ser Gln Pro Arg Ala Thr Ile Ala Arg Gln
1               5                   10                  15

Thr Ala Arg Cys
            20

<210> SEQ ID NO 81
<211> LENGTH: 20
<212> TYPE: PRT
<213> ORGANISM: Artificial Sequence
<220> FEATURE:
<223> OTHER INFORMATION: F2-09-BSA (#9)

<400> SEQUENCE: 81

Thr Leu Asp Arg Asp Ser Ser Gln Pro Arg Arg Ala Ile Ala Arg Gln
1               5                   10                  15

Thr Ala Arg Cys
            20

<210> SEQ ID NO 82
<211> LENGTH: 20
<212> TYPE: PRT
<213> ORGANISM: Artificial Sequence
<220> FEATURE:
<223> OTHER INFORMATION: F2-10-BSA (#10)

<400> SEQUENCE: 82

Thr Leu Asp Arg Asp Ser Ser Gln Pro Arg Arg Thr Ala Ala Arg Gln
1               5                   10                  15

Thr Ala Arg Cys
            20

<210> SEQ ID NO 83
<211> LENGTH: 20
<212> TYPE: PRT
<213> ORGANISM: Artificial Sequence
<220> FEATURE:
<223> OTHER INFORMATION: F2-11-BSA (#11)

<400> SEQUENCE: 83

Thr Leu Asp Arg Asp Ser Ser Gln Pro Arg Arg Thr Ile Arg Arg Gln
1               5                   10                  15

Thr Ala Arg Cys

20

<210> SEQ ID NO 84
<211> LENGTH: 20
<212> TYPE: PRT
<213> ORGANISM: Artificial Sequence
<220> FEATURE:
<223> OTHER INFORMATION: F2-12-BSA (#12)

<400> SEQUENCE: 84

Thr Leu Asp Arg Asp Ser Ser Gln Pro Arg Arg Thr Ile Ala Ala Gln
1               5                   10                  15

Thr Ala Arg Cys
            20

<210> SEQ ID NO 85
<211> LENGTH: 20
<212> TYPE: PRT
<213> ORGANISM: Artificial Sequence
<220> FEATURE:
<223> OTHER INFORMATION: F2-12-BSA (#13)

<400> SEQUENCE: 85

Thr Leu Asp Arg Asp Ser Ser Gln Pro Arg Arg Thr Ile Ala Arg Gln
1               5                   10                  15

Thr Val Arg Cys
            20

<210> SEQ ID NO 86
<211> LENGTH: 100
<212> TYPE: PRT
<213> ORGANISM: Artificial Sequence
<220> FEATURE:
<223> OTHER INFORMATION: Wild-type FAM19A5 Isoform 2 (without signal
      peptide)

<400> SEQUENCE: 86

Gln Phe Leu Lys Glu Gly Gln Leu Ala Ala Gly Thr Cys Glu Ile Val
1               5                   10                  15

Thr Leu Asp Arg Asp Ser Ser Gln Pro Arg Arg Thr Ile Ala Arg Gln
                20                  25                  30

Thr Ala Arg Cys Ala Cys Arg Lys Gly Gln Ile Ala Gly Thr Thr Arg
            35                  40                  45

Ala Arg Pro Ala Cys Val Asp Ala Arg Ile Ile Lys Thr Lys Gln Trp
        50                  55                  60

Cys Asp Met Leu Pro Cys Leu Glu Gly Glu Gly Cys Asp Leu Leu Ile
65                  70                  75                  80

Asn Arg Ser Gly Trp Thr Cys Thr Gln Pro Gly Gly Arg Ile Lys Thr
                85                  90                  95

Thr Thr Val Ser
            100

<210> SEQ ID NO 87
<211> LENGTH: 100
<212> TYPE: PRT
<213> ORGANISM: Artificial Sequence
<220> FEATURE:
<223> OTHER INFORMATION: M1 mutant

<400> SEQUENCE: 87

Gln Phe Leu Lys Glu Gly Gln Leu Ala Ala Gly Thr Cys Glu Val Ile
1               5                   10                  15

Ala Ala His Arg Asp Ser Ser Gln Pro Arg Arg Thr Ile Ala Arg Gln
            20                  25                  30

Thr Ala Arg Cys Ala Cys Arg Lys Gly Gln Ile Ala Gly Thr Thr Arg
        35                  40                  45

Ala Arg Pro Ala Cys Val Asp Ala Arg Ile Ile Lys Thr Lys Gln Trp
    50                  55                  60

Cys Asp Met Leu Pro Cys Leu Glu Gly Glu Gly Cys Asp Leu Leu Ile
65                  70                  75                  80

Asn Arg Ser Gly Trp Thr Cys Thr Gln Pro Gly Gly Arg Ile Lys Thr
                85                  90                  95

Thr Thr Val Ser
            100

<210> SEQ ID NO 88
<211> LENGTH: 100
<212> TYPE: PRT
<213> ORGANISM: Artificial Sequence
<220> FEATURE:
<223> OTHER INFORMATION: M2 mutant

<400> SEQUENCE: 88

Gln Phe Leu Lys Glu Gly Gln Leu Ala Ala Gly Thr Cys Glu Ile Val
1               5                   10                  15

Thr Leu Asp Arg Cys Cys Asn Lys Asn Arg Arg Thr Ile Ala Arg Gln
            20                  25                  30

Thr Ala Arg Cys Ala Cys Arg Lys Gly Gln Ile Ala Gly Thr Thr Arg
        35                  40                  45

Ala Arg Pro Ala Cys Val Asp Ala Arg Ile Ile Lys Thr Lys Gln Trp
    50                  55                  60

Cys Asp Met Leu Pro Cys Leu Glu Gly Glu Gly Cys Asp Leu Leu Ile
65                  70                  75                  80

Asn Arg Ser Gly Trp Thr Cys Thr Gln Pro Gly Gly Arg Ile Lys Thr
                85                  90                  95

Thr Thr Val Ser
            100

<210> SEQ ID NO 89
<211> LENGTH: 5
<212> TYPE: PRT
<213> ORGANISM: Artificial Sequence
<220> FEATURE:
<223> OTHER INFORMATION: P2-C12 VH CDR1

<400> SEQUENCE: 89

Thr Tyr Ala Val Thr
1               5

<210> SEQ ID NO 90
<211> LENGTH: 16
<212> TYPE: PRT
<213> ORGANISM: Artificial Sequence
<220> FEATURE:
<223> OTHER INFORMATION: P2-C12 VH CDR2

<400> SEQUENCE: 90

Tyr Ile Asn Trp Arg Gly Gly Thr Ser Tyr Ala Asn Trp Ala Lys Gly
1               5                   10                  15

<210> SEQ ID NO 91
<211> LENGTH: 15
<212> TYPE: PRT

```
<213> ORGANISM: Artificial Sequence
<220> FEATURE:
<223> OTHER INFORMATION: P2-C12 VH CDR3

<400> SEQUENCE: 91

Asp Ala Ser Ser Gly Ala Ala Phe Gly Ser Tyr Gly Met Asp Pro
1               5                   10                  15

<210> SEQ ID NO 92
<211> LENGTH: 11
<212> TYPE: PRT
<213> ORGANISM: Artificial Sequence
<220> FEATURE:
<223> OTHER INFORMATION: P2-C12 VL CDR1

<400> SEQUENCE: 92

Gln Ala Ser Gln Ser Ile Ser Ser Tyr Leu Ser
1               5                   10

<210> SEQ ID NO 93
<211> LENGTH: 7
<212> TYPE: PRT
<213> ORGANISM: Artificial Sequence
<220> FEATURE:
<223> OTHER INFORMATION: P2-C12 VL CDR2

<400> SEQUENCE: 93

Glu Ala Ser Lys Leu Ala Ser
1               5

<210> SEQ ID NO 94
<211> LENGTH: 12
<212> TYPE: PRT
<213> ORGANISM: Artificial Sequence
<220> FEATURE:
<223> OTHER INFORMATION: P2-C12 VL CDR3

<400> SEQUENCE: 94

Gln Gln Gly Tyr Ser Ser Thr Asn Val Trp Asn Ala
1               5                   10

<210> SEQ ID NO 95
<211> LENGTH: 6
<212> TYPE: PRT
<213> ORGANISM: Artificial Sequence
<220> FEATURE:
<223> OTHER INFORMATION: 13B4 VH CDR1

<400> SEQUENCE: 95

Ser Ser Asn Trp Trp Ser
1               5

<210> SEQ ID NO 96
<211> LENGTH: 16
<212> TYPE: PRT
<213> ORGANISM: Artificial Sequence
<220> FEATURE:
<223> OTHER INFORMATION: 13B4 VH CDR2

<400> SEQUENCE: 96

Glu Ile Tyr His Gly Gly Thr Thr Asn Tyr Asn Pro Ser Leu Lys Gly
1               5                   10                  15

<210> SEQ ID NO 97
<211> LENGTH: 9
<212> TYPE: PRT
<213> ORGANISM: Artificial Sequence
```

```
<220> FEATURE:
<223> OTHER INFORMATION: 13B4 VH CDR3

<400> SEQUENCE: 97

Trp Gln Leu Val Gly Gly Leu Asp Val
1               5

<210> SEQ ID NO 98
<211> LENGTH: 11
<212> TYPE: PRT
<213> ORGANISM: Artificial Sequence
<220> FEATURE:
<223> OTHER INFORMATION: 13B4 VL CDR1

<400> SEQUENCE: 98

Ser Gly Asp Lys Leu Gly Asn Val Tyr Ala Ser
1               5                   10

<210> SEQ ID NO 99
<211> LENGTH: 7
<212> TYPE: PRT
<213> ORGANISM: Artificial Sequence
<220> FEATURE:
<223> OTHER INFORMATION: 13B4 VL CDR2

<400> SEQUENCE: 99

Gln Asp Asn Lys Arg Pro Ser
1               5

<210> SEQ ID NO 100
<211> LENGTH: 9
<212> TYPE: PRT
<213> ORGANISM: Artificial Sequence
<220> FEATURE:
<223> OTHER INFORMATION: 13B4 VL CDR3

<400> SEQUENCE: 100

Gln Ala Trp Asp Ser Ser Thr Ala Val
1               5

<210> SEQ ID NO 101
<211> LENGTH: 5
<212> TYPE: PRT
<213> ORGANISM: Artificial Sequence
<220> FEATURE:
<223> OTHER INFORMATION: 13F7 VH CDR1

<400> SEQUENCE: 101

Gly Tyr Ser Trp Thr
1               5

<210> SEQ ID NO 102
<211> LENGTH: 16
<212> TYPE: PRT
<213> ORGANISM: Artificial Sequence
<220> FEATURE:
<223> OTHER INFORMATION: 13F7 VH CDR2

<400> SEQUENCE: 102

Glu Ile Ser His Phe Gly Ser Ala Asn Tyr Asn Pro Ser Leu Lys Ser
1               5                   10                  15

<210> SEQ ID NO 103
<211> LENGTH: 15
<212> TYPE: PRT
<213> ORGANISM: Artificial Sequence
<220> FEATURE:
```

```
<223> OTHER INFORMATION: 13F7 VH CDR3

<400> SEQUENCE: 103

Ala Leu Arg Gly Thr Tyr Ser Arg Phe Tyr Tyr Gly Met Asp Val
1               5                   10                  15

<210> SEQ ID NO 104
<211> LENGTH: 16
<212> TYPE: PRT
<213> ORGANISM: Artificial Sequence
<220> FEATURE:
<223> OTHER INFORMATION: 13F7 VL CDR1

<400> SEQUENCE: 104

Arg Ser Ser Gln Ser Leu Leu His Ser Asn Gly Tyr Asn Tyr Leu Asp
1               5                   10                  15

<210> SEQ ID NO 105
<211> LENGTH: 7
<212> TYPE: PRT
<213> ORGANISM: Artificial Sequence
<220> FEATURE:
<223> OTHER INFORMATION: 13F7 VL CDR2

<400> SEQUENCE: 105

Leu Gly Ser Asn Arg Ala Ser
1               5

<210> SEQ ID NO 106
<211> LENGTH: 9
<212> TYPE: PRT
<213> ORGANISM: Artificial Sequence
<220> FEATURE:
<223> OTHER INFORMATION: 13F7 VL CDR3

<400> SEQUENCE: 106

Met Gln Ala Arg Gln Thr Pro Leu Thr
1               5

<210> SEQ ID NO 107
<211> LENGTH: 5
<212> TYPE: PRT
<213> ORGANISM: Artificial Sequence
<220> FEATURE:
<223> OTHER INFORMATION: 15A9 VH CDR1

<400> SEQUENCE: 107

Ser Tyr Tyr Trp Ser
1               5

<210> SEQ ID NO 108
<211> LENGTH: 16
<212> TYPE: PRT
<213> ORGANISM: Artificial Sequence
<220> FEATURE:
<223> OTHER INFORMATION: 15A9 VH CDR2

<400> SEQUENCE: 108

Tyr Ile Tyr Pro Ser Gly Ser Thr Asn Tyr Asn Pro Ser Leu Lys Ser
1               5                   10                  15

<210> SEQ ID NO 109
<211> LENGTH: 12
<212> TYPE: PRT
<213> ORGANISM: Artificial Sequence
<220> FEATURE:
<223> OTHER INFORMATION: 15A9 VH CDR3
```

```
<400> SEQUENCE: 109

Val Asn Pro Phe Gly Tyr Tyr Tyr Ala Met Asp Val
1               5                   10

<210> SEQ ID NO 110
<211> LENGTH: 11
<212> TYPE: PRT
<213> ORGANISM: Artificial Sequence
<220> FEATURE:
<223> OTHER INFORMATION: 15A9 VL CDR1

<400> SEQUENCE: 110

Arg Ala Ser Gln Ser Ile Ser Thr Ser Leu Asn
1               5                   10

<210> SEQ ID NO 111
<211> LENGTH: 7
<212> TYPE: PRT
<213> ORGANISM: Artificial Sequence
<220> FEATURE:
<223> OTHER INFORMATION: 15A9 VL CDR2

<400> SEQUENCE: 111

Gly Ala Ser Thr Leu Gln Ser
1               5

<210> SEQ ID NO 112
<211> LENGTH: 9
<212> TYPE: PRT
<213> ORGANISM: Artificial Sequence
<220> FEATURE:
<223> OTHER INFORMATION: 15A9 VL CDR3

<400> SEQUENCE: 112

Gln Glu Ser Ala Ser Ile Pro Arg Thr
1               5

<210> SEQ ID NO 113
<211> LENGTH: 5
<212> TYPE: PRT
<213> ORGANISM: Artificial Sequence
<220> FEATURE:
<223> OTHER INFORMATION: P1-A03 VH CDR1

<400> SEQUENCE: 113

Ser Asp Tyr Met Ser
1               5

<210> SEQ ID NO 114
<211> LENGTH: 16
<212> TYPE: PRT
<213> ORGANISM: Artificial Sequence
<220> FEATURE:
<223> OTHER INFORMATION: P1-A03 VH CDR2

<400> SEQUENCE: 114

Ile Ile Tyr Pro Ser Thr Thr Thr Tyr Tyr Ala Ser Trp Ala Lys Gly
1               5                   10                  15

<210> SEQ ID NO 115
<211> LENGTH: 10
<212> TYPE: PRT
<213> ORGANISM: Artificial Sequence
<220> FEATURE:
<223> OTHER INFORMATION: P1-A03 VH CDR3
```

```
<400> SEQUENCE: 115

Gly Ser Asn Trp Ser Ser Gly Met Asn Leu
1               5                   10

<210> SEQ ID NO 116
<211> LENGTH: 11
<212> TYPE: PRT
<213> ORGANISM: Artificial Sequence
<220> FEATURE:
<223> OTHER INFORMATION: P1-A03 VL CDR1

<400> SEQUENCE: 116

Leu Ala Ser Glu Asp Ile Tyr Ser Gly Ile Ser
1               5                   10

<210> SEQ ID NO 117
<211> LENGTH: 7
<212> TYPE: PRT
<213> ORGANISM: Artificial Sequence
<220> FEATURE:
<223> OTHER INFORMATION: P1-A03 VL CDR2

<400> SEQUENCE: 117

Gly Ala Ser Asn Leu Glu Ser
1               5

<210> SEQ ID NO 118
<211> LENGTH: 12
<212> TYPE: PRT
<213> ORGANISM: Artificial Sequence
<220> FEATURE:
<223> OTHER INFORMATION: P1-A03 VL CDR3

<400> SEQUENCE: 118

Leu Gly Gly Tyr Ser Tyr Ser Ser Thr Gly Leu Thr
1               5                   10

<210> SEQ ID NO 119
<211> LENGTH: 5
<212> TYPE: PRT
<213> ORGANISM: Artificial Sequence
<220> FEATURE:
<223> OTHER INFORMATION: P1-A08 VH CDR1

<400> SEQUENCE: 119

Thr Tyr Tyr Met Ser
1               5

<210> SEQ ID NO 120
<211> LENGTH: 16
<212> TYPE: PRT
<213> ORGANISM: Artificial Sequence
<220> FEATURE:
<223> OTHER INFORMATION: P1-A08 VH CDR2

<400> SEQUENCE: 120

Ile Val Tyr Pro Ser Gly Thr Thr Tyr Tyr Ala Asn Trp Ala Lys Gly
1               5                   10                  15

<210> SEQ ID NO 121
<211> LENGTH: 8
<212> TYPE: PRT
<213> ORGANISM: Artificial Sequence
<220> FEATURE:
<223> OTHER INFORMATION: P1-A08 VH CDR3

<400> SEQUENCE: 121
```

Gly Asp Ser Phe Gly Tyr Gly Leu
1               5

<210> SEQ ID NO 122
<211> LENGTH: 11
<212> TYPE: PRT
<213> ORGANISM: Artificial Sequence
<220> FEATURE:
<223> OTHER INFORMATION: P1-A08 VL CDR1

<400> SEQUENCE: 122

Thr Ala Asp Thr Leu Ser Arg Ser Tyr Ala Ser
1               5                   10

<210> SEQ ID NO 123
<211> LENGTH: 7
<212> TYPE: PRT
<213> ORGANISM: Artificial Sequence
<220> FEATURE:
<223> OTHER INFORMATION: P1-A08 VL CDR2

<400> SEQUENCE: 123

Arg Asp Thr Ser Arg Pro Ser
1               5

<210> SEQ ID NO 124
<211> LENGTH: 13
<212> TYPE: PRT
<213> ORGANISM: Artificial Sequence
<220> FEATURE:
<223> OTHER INFORMATION: P1-A08 VL CDR3

<400> SEQUENCE: 124

Ala Thr Ser Asp Gly Ser Gly Ser Asn Tyr Gln Tyr Val
1               5                   10

<210> SEQ ID NO 125
<211> LENGTH: 5
<212> TYPE: PRT
<213> ORGANISM: Artificial Sequence
<220> FEATURE:
<223> OTHER INFORMATION: P1-F02 VH CDR1

<400> SEQUENCE: 125

Asn Tyr Tyr Met Gly
1               5

<210> SEQ ID NO 126
<211> LENGTH: 16
<212> TYPE: PRT
<213> ORGANISM: Artificial Sequence
<220> FEATURE:
<223> OTHER INFORMATION: P1-F02 VH CDR2

<400> SEQUENCE: 126

Ile Ile Tyr Ala Ser Gly Ser Thr Tyr Tyr Ala Ser Trp Ala Lys Gly
1               5                   10                  15

<210> SEQ ID NO 127
<211> LENGTH: 17
<212> TYPE: PRT
<213> ORGANISM: Artificial Sequence
<220> FEATURE:
<223> OTHER INFORMATION: P1-F02 VH CDR3

<400> SEQUENCE: 127

Ile Asp Ile Gly Val Gly Asp Tyr Gly Trp Ala Tyr Asp Arg Leu Asp
1               5                   10                  15

Leu

<210> SEQ ID NO 128
<211> LENGTH: 11
<212> TYPE: PRT
<213> ORGANISM: Artificial Sequence
<220> FEATURE:
<223> OTHER INFORMATION: P1-F02 VL CDR1

<400> SEQUENCE: 128

Leu Ala Ser Glu Asp Ile Tyr Ser Gly Ile Ser
1               5                   10

<210> SEQ ID NO 129
<211> LENGTH: 7
<212> TYPE: PRT
<213> ORGANISM: Artificial Sequence
<220> FEATURE:
<223> OTHER INFORMATION: P1-F02 VL CDR2

<400> SEQUENCE: 129

Gly Ala Ser Asn Leu Glu Ser
1               5

<210> SEQ ID NO 130
<211> LENGTH: 10
<212> TYPE: PRT
<213> ORGANISM: Artificial Sequence
<220> FEATURE:
<223> OTHER INFORMATION: P1-F02 VL CDR3

<400> SEQUENCE: 130

Leu Gly Gly Tyr Ser Tyr Ser Ser Ile Thr
1               5                   10

<210> SEQ ID NO 131
<211> LENGTH: 5
<212> TYPE: PRT
<213> ORGANISM: Artificial Sequence
<220> FEATURE:
<223> OTHER INFORMATION: P2-A01 VH CDR1

<400> SEQUENCE: 131

Gly Tyr Tyr Met Ser
1               5

<210> SEQ ID NO 132
<211> LENGTH: 16
<212> TYPE: PRT
<213> ORGANISM: Artificial Sequence
<220> FEATURE:
<223> OTHER INFORMATION: P2-A01 VH CDR2

<400> SEQUENCE: 132

Ile Ile Tyr Pro Ser Gly Ser Thr Asp Tyr Ala Ser Trp Ala Lys Gly
1               5                   10                  15

<210> SEQ ID NO 133
<211> LENGTH: 15
<212> TYPE: PRT
<213> ORGANISM: Artificial Sequence
<220> FEATURE:
<223> OTHER INFORMATION: P2-A01 VH CDR3

<400> SEQUENCE: 133

Val Ala Gly Tyr Val Gly Tyr Gly Tyr Glu Thr Phe Phe Asp Ile
1               5                   10                  15

<210> SEQ ID NO 134
<211> LENGTH: 11
<212> TYPE: PRT
<213> ORGANISM: Artificial Sequence
<220> FEATURE:
<223> OTHER INFORMATION: P2-A01 VL CDR1

<400> SEQUENCE: 134

Leu Ala Ser Glu Asp Ile Tyr Ser Gly Ile Ser
1               5                   10

<210> SEQ ID NO 135
<211> LENGTH: 7
<212> TYPE: PRT
<213> ORGANISM: Artificial Sequence
<220> FEATURE:
<223> OTHER INFORMATION: P2-A01 VL CDR2

<400> SEQUENCE: 135

Gly Ala Ser Asn Leu Glu Ser
1               5

<210> SEQ ID NO 136
<211> LENGTH: 14
<212> TYPE: PRT
<213> ORGANISM: Artificial Sequence
<220> FEATURE:
<223> OTHER INFORMATION: P2-A01 VL CDR3

<400> SEQUENCE: 136

Leu Gly Gly Val Thr Tyr Ser Ser Thr Gly Thr His Leu Thr
1               5                   10

<210> SEQ ID NO 137
<211> LENGTH: 5
<212> TYPE: PRT
<213> ORGANISM: Artificial Sequence
<220> FEATURE:
<223> OTHER INFORMATION: P2-A03 VH CDR1

<400> SEQUENCE: 137

Asn Tyr Asp Met Ser
1               5

<210> SEQ ID NO 138
<211> LENGTH: 16
<212> TYPE: PRT
<213> ORGANISM: Artificial Sequence
<220> FEATURE:
<223> OTHER INFORMATION: P2-A03 VH CDR2

<400> SEQUENCE: 138

Phe Met Asp Thr Asp Gly Ser Ala Tyr Tyr Ala Thr Trp Ala Lys Gly
1               5                   10                  15

<210> SEQ ID NO 139
<211> LENGTH: 11
<212> TYPE: PRT
<213> ORGANISM: Artificial Sequence
<220> FEATURE:
<223> OTHER INFORMATION: P2-A03 VH CDR3

<400> SEQUENCE: 139

-continued

Arg Gly Ser Ser Tyr Tyr Gly Gly Ile Asp Ile
1               5                   10

<210> SEQ ID NO 140
<211> LENGTH: 11
<212> TYPE: PRT
<213> ORGANISM: Artificial Sequence
<220> FEATURE:
<223> OTHER INFORMATION: P2-A03 VL CDR1

<400> SEQUENCE: 140

Gln Ala Ser Gln Ser Ile Gly Gly Asn Leu Ala
1               5                   10

<210> SEQ ID NO 141
<211> LENGTH: 7
<212> TYPE: PRT
<213> ORGANISM: Artificial Sequence
<220> FEATURE:
<223> OTHER INFORMATION: P2-A03 VL CDR2

<400> SEQUENCE: 141

Arg Ala Ser Thr Leu Ala Ser
1               5

<210> SEQ ID NO 142
<211> LENGTH: 14
<212> TYPE: PRT
<213> ORGANISM: Artificial Sequence
<220> FEATURE:
<223> OTHER INFORMATION: P2-A03a VL CDR3

<400> SEQUENCE: 142

Gln Ser Pro Ala Tyr Asp Pro Ala Ala Tyr Val Gly Asn Ala
1               5                   10

<210> SEQ ID NO 143
<211> LENGTH: 5
<212> TYPE: PRT
<213> ORGANISM: Artificial Sequence
<220> FEATURE:
<223> OTHER INFORMATION: P2-F07 VH CDR1

<400> SEQUENCE: 143

Ser Tyr Tyr Met Asn
1               5

<210> SEQ ID NO 144
<211> LENGTH: 16
<212> TYPE: PRT
<213> ORGANISM: Artificial Sequence
<220> FEATURE:
<223> OTHER INFORMATION: P2-F07 VH CDR2

<400> SEQUENCE: 144

Ile Ile Tyr Pro Ser Gly Thr Thr Tyr Tyr Ala Gly Trp Ala Lys Gly
1               5                   10                  15

<210> SEQ ID NO 145
<211> LENGTH: 8
<212> TYPE: PRT
<213> ORGANISM: Artificial Sequence
<220> FEATURE:
<223> OTHER INFORMATION: P2-F07 VH CDR3

<400> SEQUENCE: 145

Thr Val Ser Gly Tyr Phe Asp Ile

<210> SEQ ID NO 146
<211> LENGTH: 11
<212> TYPE: PRT
<213> ORGANISM: Artificial Sequence
<220> FEATURE:
<223> OTHER INFORMATION: P2-F07 VL CDR1

<400> SEQUENCE: 146

Leu Ala Ser Glu Asp Ile Tyr Ser Ala Leu Ala
1               5                   10

<210> SEQ ID NO 147
<211> LENGTH: 7
<212> TYPE: PRT
<213> ORGANISM: Artificial Sequence
<220> FEATURE:
<223> OTHER INFORMATION: P2-F07 VL CDR2

<400> SEQUENCE: 147

Gly Thr Ser Asn Leu Glu Ser
1               5

<210> SEQ ID NO 148
<211> LENGTH: 9
<212> TYPE: PRT
<213> ORGANISM: Artificial Sequence
<220> FEATURE:
<223> OTHER INFORMATION: P2-F07 VL CDR3

<400> SEQUENCE: 148

Gln Gly Tyr Ser Ser Tyr Pro Leu Thr
1               5

<210> SEQ ID NO 149
<211> LENGTH: 5
<212> TYPE: PRT
<213> ORGANISM: Artificial Sequence
<220> FEATURE:
<223> OTHER INFORMATION: P2-F11 VH CDR1

<400> SEQUENCE: 149

Ser Tyr Gly Val Ser
1               5

<210> SEQ ID NO 150
<211> LENGTH: 16
<212> TYPE: PRT
<213> ORGANISM: Artificial Sequence
<220> FEATURE:
<223> OTHER INFORMATION: P2-F11 VH CDR2

<400> SEQUENCE: 150

Tyr Ile Ala Asn Asn Tyr Asn Pro His Tyr Ala Ser Trp Ala Lys Gly
1               5                   10                  15

<210> SEQ ID NO 151
<211> LENGTH: 7
<212> TYPE: PRT
<213> ORGANISM: Artificial Sequence
<220> FEATURE:
<223> OTHER INFORMATION: P2-F11 VH CDR3

<400> SEQUENCE: 151

Asp Asn Tyr Gly Met Asp Pro
1               5

<210> SEQ ID NO 152
<211> LENGTH: 13
<212> TYPE: PRT
<213> ORGANISM: Artificial Sequence
<220> FEATURE:
<223> OTHER INFORMATION: P2-F11 VL CDR1

<400> SEQUENCE: 152

Gln Ala Ser Gln Ser Val Tyr Asn Asn Lys Asn Leu Ala
1               5                   10

<210> SEQ ID NO 153
<211> LENGTH: 7
<212> TYPE: PRT
<213> ORGANISM: Artificial Sequence
<220> FEATURE:
<223> OTHER INFORMATION: P2-F11 VL CDR2

<400> SEQUENCE: 153

Ala Ala Ser Thr Leu Ala Ser
1               5

<210> SEQ ID NO 154
<211> LENGTH: 13
<212> TYPE: PRT
<213> ORGANISM: Artificial Sequence
<220> FEATURE:
<223> OTHER INFORMATION: P2-F11 VL CDR3

<400> SEQUENCE: 154

Gln Gly Glu Phe Ser Cys Ser Ser Ala Asp Cys Asn Ala
1               5                   10

<210> SEQ ID NO 155
<211> LENGTH: 121
<212> TYPE: PRT
<213> ORGANISM: Artificial Sequence
<220> FEATURE:
<223> OTHER INFORMATION: P2-C12 VH

<400> SEQUENCE: 155

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Thr Tyr Ala
            20                  25                  30

Val Thr Trp Val Arg Gln Ala Pro Gly Lys Gly Leu Glu Trp Ile Gly
        35                  40                  45

Tyr Ile Asn Trp Arg Gly Gly Thr Ser Tyr Ala Asn Trp Ala Lys Gly
    50                  55                  60

Arg Phe Thr Ile Ser Lys Thr Ser Ser Thr Val Asp Leu Lys Met
65                  70                  75                  80

Thr Ser Pro Thr Thr Glu Asp Thr Ala Thr Tyr Phe Cys Ala Arg Asp
                85                  90                  95

Ala Ser Ser Gly Ala Ala Phe Gly Ser Tyr Gly Met Asp Pro Trp Gly
            100                 105                 110

Pro Gly Thr Leu Val Thr Val Ser Ser
        115                 120

<210> SEQ ID NO 156
<211> LENGTH: 118
<212> TYPE: PRT
<213> ORGANISM: Artificial Sequence

```
<220> FEATURE:
<223> OTHER INFORMATION: 13B4 VH

<400> SEQUENCE: 156

Gln Val Gln Leu Gln Glu Ser Gly Pro Gly Leu Val Lys Pro Ser Gly
1               5                   10                  15

Thr Leu Ser Leu Asn Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Gly Gly Thr Thr Asn Tyr Asn Pro Ser Leu
    50                  55                  60

Lys Gly Arg Val Thr Met Ser Val Asp Lys Thr Lys Asn Gln Phe Ser
65                  70                  75                  80

Leu Arg Leu Ser Ser Val Thr Ala Val Asp Thr Ala Val Tyr Tyr Cys
                85                  90                  95

Ala Arg Trp Gln Leu Val Gly Gly Leu Asp Val Trp Gly Gln Gly Thr
            100                 105                 110

Thr Val Thr Val Ser Ser
        115

<210> SEQ ID NO 157
<211> LENGTH: 123
<212> TYPE: PRT
<213> ORGANISM: Artificial Sequence
<220> FEATURE:
<223> OTHER INFORMATION: 13F7 VH

<400> SEQUENCE: 157

Gln Val Gln Leu Gln Glu Trp Gly Ala Gly Leu Leu Lys Pro Ser Glu
1               5                   10                  15

Thr Leu Ser Leu Thr Cys Ala Ile Asn Ala Glu Ser Phe Asn Gly Tyr
            20                  25                  30

Ser Trp Thr Trp Ile Arg Gln Pro Pro Gly Lys Gly Leu Glu Trp Ile
        35                  40                  45

Gly Glu Ile Ser His Phe Gly Ser Ala Asn Tyr Asn Pro Ser Leu Lys
    50                  55                  60

Ser Arg Ala Thr Ile Ser Ala Asp Lys Ser Lys Asn Gln Phe Ser Leu
65                  70                  75                  80

Lys Leu Thr Ser Val Thr Ala Val Asp Thr Ala Val Tyr Tyr Cys Ala
                85                  90                  95

Arg Ala Leu Arg Gly Thr Tyr Ser Arg Phe Tyr Tyr Gly Met Asp Val
            100                 105                 110

Trp Gly Gln Gly Thr Thr Val Thr Val Ser Ser
        115                 120

<210> SEQ ID NO 158
<211> LENGTH: 120
<212> TYPE: PRT
<213> ORGANISM: Artificial Sequence
<220> FEATURE:
<223> OTHER INFORMATION: 15A9 VH

<400> SEQUENCE: 158

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30
```

```
Tyr Trp Ser Trp Ile Arg Gln Pro Pro Gly Lys Gly Leu Glu Trp Ile
            35                  40                  45

Gly Tyr Ile Tyr Pro Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Asn Leu Lys Ser Val Thr Ala Val Asp Thr Ala Val Tyr Tyr Cys Ala
                85                  90                  95

Arg Val Asn Pro Phe Gly Tyr Tyr Tyr Ala Met Asp Val Trp Gly Gln
                100                 105                 110

Gly Thr Thr Val Thr Val Ser Ser
        115                 120
```

<210> SEQ ID NO 159
<211> LENGTH: 116
<212> TYPE: PRT
<213> ORGANISM: Artificial Sequence
<220> FEATURE:
<223> OTHER INFORMATION: P1-A03 VH

<400> SEQUENCE: 159

```
Gln Ser Val Glu Glu Ser Gly Gly Arg Leu Val Thr Pro Gly Thr Pro
 1               5                  10                  15

Leu Thr Leu Thr Cys Thr Val Ser Gly Phe Ser Leu Ser Ser Asp Tyr
                20                  25                  30

Met Ser Trp Val Arg Gln Ala Pro Gly Glu Gly Leu Glu Trp Ile Gly
            35                  40                  45

Ile Ile Tyr Pro Ser Thr Thr Thr Tyr Tyr Ala Ser Trp Ala Lys Gly
 50                  55                  60

Arg Phe Thr Ile Ser Lys Thr Ser Ser Thr Thr Val Glu Leu Lys Met
 65                  70                  75                  80

Thr Ser Leu Thr Thr Glu Asp Thr Ala Thr Tyr Phe Cys Ala Arg Gly
                85                  90                  95

Ser Asn Trp Ser Ser Gly Met Asn Leu Trp Gly Pro Gly Thr Leu Val
                100                 105                 110

Thr Val Ser Ser
        115
```

<210> SEQ ID NO 160
<211> LENGTH: 113
<212> TYPE: PRT
<213> ORGANISM: Artificial Sequence
<220> FEATURE:
<223> OTHER INFORMATION: P1-A08 VH

<400> SEQUENCE: 160

```
Gln Ser Leu Glu Glu Ser Gly Gly Arg Leu Val Thr Pro Gly Thr Pro
 1               5                  10                  15

Leu Thr Leu Thr Cys Thr Ala Ser Gly Phe Ser Leu Ser Thr Tyr Tyr
                20                  25                  30

Met Ser Trp Val Arg Gln Ala Pro Gly Lys Gly Leu Glu Trp Ile Gly
            35                  40                  45

Ile Val Tyr Pro Ser Gly Thr Thr Tyr Tyr Ala Asn Trp Ala Lys Gly
 50                  55                  60

Arg Phe Thr Ile Ser Ala Ser Thr Val Asp Leu Met Ile Thr
 65                  70                  75                  80

Ser Pro Thr Thr Glu Asp Thr Ala Thr Tyr Phe Cys Ala Arg Gly Asp
                85                  90                  95
```

-continued

Ser Phe Gly Tyr Gly Leu Trp Gly Pro Gly Thr Leu Val Thr Val Ser
            100                 105                 110
Ser

<210> SEQ ID NO 161
<211> LENGTH: 122
<212> TYPE: PRT
<213> ORGANISM: Artificial Sequence
<220> FEATURE:
<223> OTHER INFORMATION: P1-F02 VH

<400> SEQUENCE: 161

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Asn Tyr Tyr
            20                  25                  30

Met Gly Trp Val Arg Gln Ala Pro Gly Glu Gly Leu Glu Trp Ile Gly
        35                  40                  45

Ile Ile Tyr Ala Ser Gly Ser Thr Tyr Tyr Ala Ser Trp Ala Lys Gly
    50                  55                  60

Arg Phe Thr Ile Ser Lys Thr Ser Thr Thr Val Asp Leu Lys Met Thr
65                  70                  75                  80

Ser Leu Thr Thr Glu Asp Thr Ala Thr Tyr Phe Cys Ala Arg Ile Asp
                85                  90                  95

Ile Gly Val Gly Asp Tyr Gly Trp Ala Tyr Asp Arg Leu Asp Leu Trp
            100                 105                 110

Gly Gln Gly Thr Leu Val Thr Val Ser Ser
        115                 120

<210> SEQ ID NO 162
<211> LENGTH: 121
<212> TYPE: PRT
<213> ORGANISM: Artificial Sequence
<220> FEATURE:
<223> OTHER INFORMATION: P2-A01 VH

<400> SEQUENCE: 162

Gln Glu Gln Leu Val Glu Ser Gly Gly Arg Leu Val Thr Pro Gly Thr
1               5                   10                  15

Pro Leu Thr Leu Ser Cys Thr Ala Ser Gly Phe Phe Leu Ser Gly Tyr
            20                  25                  30

Tyr Met Ser Trp Val Arg Gln Ala Pro Gly Lys Gly Leu Glu Trp Ile
        35                  40                  45

Gly Ile Ile Tyr Pro Ser Gly Ser Thr Asp Tyr Ala Ser Trp Ala Lys
    50                  55                  60

Gly Arg Phe Thr Ile Ser Lys Thr Ser Thr Thr Val Asp Leu Lys Ile
65                  70                  75                  80

Thr Thr Pro Thr Thr Glu Asp Thr Ala Thr Tyr Phe Cys Ala Arg Val
                85                  90                  95

Ala Gly Tyr Val Gly Tyr Gly Tyr Glu Thr Phe Phe Asp Ile Trp Gly
            100                 105                 110

Pro Gly Thr Leu Val Thr Val Ser Leu
        115                 120

<210> SEQ ID NO 163
<211> LENGTH: 116
<212> TYPE: PRT
<213> ORGANISM: Artificial Sequence

<220> FEATURE:
<223> OTHER INFORMATION: P2-A03 VH

<400> SEQUENCE: 163

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Asn Asn Tyr Asp
            20                  25                  30

Met Ser Trp Val Arg Gln Ala Pro Gly Lys Gly Leu Glu Tyr Ile Gly
        35                  40                  45

Phe Met Asp Thr Asp Gly Ser Ala Tyr Tyr Ala Thr Trp Ala Lys Gly
    50                  55                  60

Arg Phe Thr Ile Ser Arg Thr Ser Thr Thr Val Asp Leu Lys Met Thr
65                  70                  75                  80

Ser Pro Thr Thr Glu Asp Thr Ala Thr Tyr Phe Cys Ala Arg Arg Gly
                85                  90                  95

Ser Ser Tyr Tyr Gly Gly Ile Asp Ile Trp Gly Pro Gly Thr Pro Val
            100                 105                 110

Thr Val Ser Leu
        115

<210> SEQ ID NO 164
<211> LENGTH: 113
<212> TYPE: PRT
<213> ORGANISM: Artificial Sequence
<220> FEATURE:
<223> OTHER INFORMATION: P2-F07 VH

<400> SEQUENCE: 164

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Tyr
            20                  25                  30

Met Asn Trp Val Arg Gln Ala Pro Gly Lys Gly Leu Glu Trp Ile Gly
        35                  40                  45

Ile Ile Tyr Pro Ser Gly Thr Thr Tyr Tyr Ala Gly Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Ser Glu Asp Thr Ala Thr Tyr Phe Cys Ala Arg Thr Val
                85                  90                  95

Ser Gly Tyr Phe Asp Ile Trp Gly Pro Gly Thr Leu Val Thr Val Ser
            100                 105                 110

Leu

<210> SEQ ID NO 165
<211> LENGTH: 114
<212> TYPE: PRT
<213> ORGANISM: Artificial Sequence
<220> FEATURE:
<223> OTHER INFORMATION: P2-F11 VH

<400> SEQUENCE: 165

Gln Glu Gln Leu Val Glu Ser Gly Gly Arg Leu Val Thr Pro Gly Thr
1               5                   10                  15

Thr Leu Thr Leu Thr Cys Thr Val Ser Gly Phe Ser Leu Ser Ser Tyr
            20                  25                  30

Gly Val Ser Trp Val Arg Gln Ala Pro Gly Lys Gly Leu Glu Trp Ile

```
                35                  40                  45
Gly Tyr Ile Ala Asn Asn Tyr Asn Pro His Tyr Ala Ser Trp Ala Lys
 50                  55                  60

Gly Arg Phe Thr Ile Ser Lys Thr Ser Thr Thr Val Asp Leu Lys
 65                  70                  75                  80

Met Thr Ser Leu Thr Thr Glu Asp Thr Ala Thr Tyr Phe Cys Ala Arg
                 85                  90                  95

Asp Asn Tyr Gly Met Asp Pro Trp Gly Pro Gly Thr Leu Val Thr Val
                100                 105                 110

Ser Ser

<210> SEQ ID NO 166
<211> LENGTH: 110
<212> TYPE: PRT
<213> ORGANISM: Artificial Sequence
<220> FEATURE:
<223> OTHER INFORMATION: P2-C12 VL

<400> SEQUENCE: 166

Glu Leu Asp Met Thr Gln Thr Pro Ser Ser Val Ser Ala Ala Val Gly
 1               5                  10                  15

Gly Thr Val Thr Ile Lys Cys Gln Ala Ser Gln Ser Ile Ser Ser Tyr
                 20                  25                  30

Leu Ser Trp Tyr Gln Gln Lys Pro Gly Gln Pro Pro Lys Leu Leu Ile
             35                  40                  45

Tyr Glu Ala Ser Lys Leu Ala Ser Gly Val Pro Ser Arg Phe Ser Gly
 50                  55                  60

Ser Gly Tyr Gly Thr Glu Phe Thr Leu Thr Ile Ser Asp Leu Glu Cys
 65                  70                  75                  80

Ala Asp Ala Ala Thr Tyr Tyr Cys Gln Gln Gly Tyr Ser Ser Thr Asn
                 85                  90                  95

Val Trp Asn Ala Phe Gly Gly Gly Thr Asn Val Glu Ile Lys
                100                 105                 110

<210> SEQ ID NO 167
<211> LENGTH: 106
<212> TYPE: PRT
<213> ORGANISM: Artificial Sequence
<220> FEATURE:
<223> OTHER INFORMATION: 13B4 VL

<400> SEQUENCE: 167

Ser Tyr Glu Leu Thr Gln Pro Leu Ser Val Ser Val Ser Pro Gly Gln
 1               5                  10                  15

Thr Ala Ser Ile Thr Cys Ser Gly Asp Lys Leu Gly Asn Val Tyr Ala
                 20                  25                  30

Ser Trp Tyr Gln Gln Lys Pro Gly Gln Ser Pro Thr Leu Val Ile Tyr
             35                  40                  45

Gln Asp Asn Lys Arg Pro Ser Gly Ile Pro Glu Arg Phe Ser Gly Ser
 50                  55                  60

Asn Ser Gly Lys Thr Ala Thr Leu Thr Ile Ser Gly Thr Gln Ala Leu
 65                  70                  75                  80

Asp Glu Ala Asp Tyr Tyr Cys Gln Ala Trp Asp Ser Ser Thr Ala Val
                 85                  90                  95

Phe Gly Gly Gly Thr Lys Leu Thr Val Leu
                100                 105
```

<210> SEQ ID NO 168
<211> LENGTH: 112
<212> TYPE: PRT
<213> ORGANISM: Artificial Sequence
<220> FEATURE:
<223> OTHER INFORMATION: 13F7 VL

<400> SEQUENCE: 168

```
Asp Ile Val Met Thr Gln Thr Pro Leu Ser Leu Pro Val Ala Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Val Gln Lys Pro Gly Gln Pro
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Arg Gln Thr Pro Leu Thr Phe Gly Gly Gly Thr Lys Val Glu Ile Lys
            100                 105                 110
```

<210> SEQ ID NO 169
<211> LENGTH: 107
<212> TYPE: PRT
<213> ORGANISM: Artificial Sequence
<220> FEATURE:
<223> OTHER INFORMATION: 15A9 VL

<400> SEQUENCE: 169

```
Asp Ile Gln Met Thr Gln Ser Pro Ser Ser Leu Ser Ala Ser Val Gly
1               5                   10                  15

Asp Arg Ile Thr Ile Ser Cys Arg Ala Ser Gln Ser Ile Ser Thr Ser
            20                  25                  30

Leu Asn Trp Tyr Gln Gln Thr Pro Gly Lys Ala Pro Arg Leu Leu Ile
        35                  40                  45

Tyr Gly Ala Ser Thr Leu Gln Ser Gly Val Pro Ser Arg Phe Ser Gly
    50                  55                  60

Gly Ser Gly Thr Asp Phe Ser Leu Thr Ile Thr Ser Leu Gln Pro
65                  70                  75                  80

Glu Asp Phe Ala Thr Tyr Tyr Cys Gln Glu Ser Ala Ser Ile Pro Arg
                85                  90                  95

Thr Phe Gly Gln Gly Thr Lys Leu Asp Ile Lys
            100                 105
```

<210> SEQ ID NO 170
<211> LENGTH: 110
<212> TYPE: PRT
<213> ORGANISM: Artificial Sequence
<220> FEATURE:
<223> OTHER INFORMATION: P1-A03 VL

<400> SEQUENCE: 170

```
Glu Leu Val Met Thr Gln Thr Pro Pro Ser Leu Ser Ala Ser Val Gly
1               5                   10                  15

Glu Thr Val Arg Ile Arg Cys Leu Ala Ser Glu Asp Ile Tyr Ser Gly
            20                  25                  30

Ile Ser Trp Tyr Gln Gln Lys Pro Glu Lys Pro Pro Thr Leu Leu Ile
        35                  40                  45
```

```
Ser Gly Ala Ser Asn Leu Glu Ser Gly Val Pro Pro Arg Phe Ser Gly
    50                  55                  60

Ser Gly Ser Gly Thr Asp Tyr Thr Leu Thr Ile Gly Gly Val Gln Ala
65              70                  75                  80

Glu Asp Ala Ala Thr Tyr Tyr Cys Leu Gly Gly Tyr Ser Tyr Ser Ser
                85                  90                  95

Thr Gly Leu Thr Phe Gly Ala Gly Thr Asn Val Glu Ile Lys
            100                 105                 110
```

<210> SEQ ID NO 171
<211> LENGTH: 110
<212> TYPE: PRT
<213> ORGANISM: Artificial Sequence
<220> FEATURE:
<223> OTHER INFORMATION: P1-A08 VL

<400> SEQUENCE: 171

```
Glu Leu Val Leu Thr Gln Ser Pro Ser Val Gln Val Asn Leu Gly Gln
1               5                   10                  15

Thr Val Ser Leu Thr Cys Thr Ala Asp Thr Leu Ser Arg Ser Tyr Ala
            20                  25                  30

Ser Trp Tyr Gln Gln Lys Pro Gly Gln Ala Pro Val Leu Leu Ile Tyr
        35                  40                  45

Arg Asp Thr Ser Arg Pro Ser Gly Val Pro Asp Arg Phe Ser Gly Ser
    50                  55                  60

Ser Ser Gly Asn Thr Ala Thr Leu Thr Ile Ser Gly Ala Gln Ala Gly
65              70                  75                  80

Asp Glu Ala Asp Tyr Tyr Cys Ala Thr Ser Asp Gly Ser Gly Ser Asn
                85                  90                  95

Tyr Gln Tyr Val Phe Gly Gly Gly Thr Gln Leu Thr Val Thr
            100                 105                 110
```

<210> SEQ ID NO 172
<211> LENGTH: 108
<212> TYPE: PRT
<213> ORGANISM: Artificial Sequence
<220> FEATURE:
<223> OTHER INFORMATION: P1-F02 VL

<400> SEQUENCE: 172

```
Glu Leu Asp Met Thr Gln Thr Pro Pro Ser Leu Ser Ala Ser Val Gly
1               5                   10                  15

Glu Thr Val Arg Ile Arg Cys Leu Ala Ser Glu Asp Ile Tyr Ser Gly
            20                  25                  30

Ile Ser Trp Tyr Gln Gln Lys Pro Gly Lys Pro Pro Thr Leu Leu Ile
        35                  40                  45

Tyr Gly Ala Ser Asn Leu Glu Ser Gly Val Pro Pro Arg Phe Ser Gly
    50                  55                  60

Ser Gly Ser Gly Thr Asp Tyr Thr Leu Thr Ile Gly Gly Val Gln Ala
65              70                  75                  80

Glu Asp Ala Ala Thr Tyr Tyr Cys Leu Gly Gly Tyr Ser Tyr Ser Ser
                85                  90                  95

Ile Thr Phe Gly Ala Gly Thr Asn Val Glu Ile Lys
            100                 105
```

<210> SEQ ID NO 173
<211> LENGTH: 112
<212> TYPE: PRT

<213> ORGANISM: Artificial Sequence
<220> FEATURE:
<223> OTHER INFORMATION: P2-A01 VL

<400> SEQUENCE: 173

Glu Leu Val Met Thr Gln Thr Pro Pro Ser Leu Ser Ala Ser Val Gly
1               5                   10                  15

Glu Thr Val Arg Ile Arg Cys Leu Ala Ser Glu Asp Ile Tyr Ser Gly
            20                  25                  30

Ile Ser Trp Tyr Gln Gln Lys Pro Gly Lys Pro Thr Leu Leu Ile
        35                  40                  45

Tyr Gly Ala Ser Asn Leu Glu Ser Gly Val Pro Pro Arg Phe Ser Gly
    50                  55                  60

Ser Gly Ser Gly Ser Asp Tyr Thr Leu Thr Ile Gly Gly Val Gln Ala
65              70                  75                  80

Glu Asp Ala Ala Thr Tyr Tyr Cys Leu Gly Gly Val Thr Tyr Ser Ser
                85                  90                  95

Thr Gly Thr His Leu Thr Phe Gly Ala Gly Thr Asn Val Glu Ile Lys
            100                 105                 110

<210> SEQ ID NO 174
<211> LENGTH: 112
<212> TYPE: PRT
<213> ORGANISM: Artificial Sequence
<220> FEATURE:
<223> OTHER INFORMATION: P2-A03 VL

<400> SEQUENCE: 174

Glu Leu Asp Leu Thr Gln Thr Pro Ala Ser Val Ser Glu Pro Val Gly
1               5                   10                  15

Gly Thr Val Thr Ile Lys Cys Gln Ala Ser Gln Ser Ile Gly Gly Asn
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Pro Ser Arg Phe Lys Gly
    50                  55                  60

Ser Gly Ser Gly Thr Asp Phe Thr Leu Thr Ile Ser Asp Leu Glu Cys
65              70                  75                  80

Ala Asp Ala Ala Thr Tyr Tyr Cys Gln Ser Pro Ala Tyr Asp Pro Ala
                85                  90                  95

Ala Tyr Val Gly Asn Ala Phe Gly Gly Gly Thr Glu Leu Glu Ile Leu
            100                 105                 110

<210> SEQ ID NO 175
<211> LENGTH: 107
<212> TYPE: PRT
<213> ORGANISM: Artificial Sequence
<220> FEATURE:
<223> OTHER INFORMATION: P2-F07 VL

<400> SEQUENCE: 175

Glu Leu Asp Leu Thr Gln Thr Pro Pro Ser Leu Ser Ala Ser Val Gly
1               5                   10                  15

Gly Thr Val Thr Ile Asn Cys Leu Ala Ser Glu Asp Ile Tyr Ser Ala
            20                  25                  30

Leu Ala Trp Tyr Gln Gln Lys Pro Gly Lys Pro Pro Thr Leu Leu Ile
        35                  40                  45

Ser Gly Thr Ser Asn Leu Glu Ser Gly Val Pro Pro Arg Phe Ser Gly
    50                  55                  60

Ser Gly Ser Gly Thr Asp Tyr Thr Leu Thr Ile Gly Val Gln Ala
65                  70                  75                  80

Glu Asp Ala Ala Thr Tyr Phe Cys Gln Gly Tyr Ser Ser Tyr Pro Leu
                85                  90                  95

Thr Phe Gly Ala Gly Thr Asn Val Glu Ile Lys
            100                 105

<210> SEQ ID NO 176
<211> LENGTH: 113
<212> TYPE: PRT
<213> ORGANISM: Artificial Sequence
<220> FEATURE:
<223> OTHER INFORMATION: P2-F11 VL

<400> SEQUENCE: 176

Glu Leu Asp Leu Thr Gln Thr Pro Ser Ser Val Ser Ala Ala Val Gly
1               5                   10                  15

Gly Thr Val Thr Ile Asn Cys Gln Ala Ser Gln Ser Val Tyr Asn Asn
            20                  25                  30

Lys Asn Leu Ala Trp Tyr Gln Gln Lys Pro Gly Gln Pro Pro Lys Leu
        35                  40                  45

Leu Ile Tyr Ala Ala Ser Thr Leu Ala Ser Gly Val Ser Ser Arg Phe
    50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Tyr Cys Gln Gly Glu Phe Ser Cys
                85                  90                  95

Ser Ser Ala Asp Cys Asn Ala Phe Gly Gly Gly Thr Glu Leu Glu Ile
                100                 105                 110

Leu

<210> SEQ ID NO 177
<211> LENGTH: 363
<212> TYPE: DNA
<213> ORGANISM: Artificial Sequence
<220> FEATURE:
<223> OTHER INFORMATION: P2-C12 VH

<400> SEQUENCE: 177
cagtcgctgg aggagtccgg gggtcgcctg gtcacgcctg ggacacccct gacactcacc     60
tgcaccgtct ctggattctc cctcagtacc tatgcagtga cctgggtccg ccaggctcca    120
gggaaggggc tggaatggat cggatacatt aattggcgtg gtgggacatc ctacgcgaac    180
tgggcgaaag ccgattcac catctccaaa acctcgtcga ccacggtgga tctgaaaatg    240
accagtccga caaccgagga cacgccacc tatttctgtg ccagagatgc tagtagtggt    300
gctgcttttg ggtcttacgg catggacccc tggggcccag gaccctcgt caccgtctct    360 tca                                                                  363

<210> SEQ ID NO 178
<211> LENGTH: 330
<212> TYPE: DNA
<213> ORGANISM: Artificial Sequence
<220> FEATURE:
<223> OTHER INFORMATION: P2-C12 VL

<400> SEQUENCE: 178
gagctcgata tgacccagac tccatcctcc gtgtctgcag ctgtgggagg cacagtcacc     60

```
atcaagtgcc aggccagtca gagcattagt agctactat cctggtatca gcagaaacca    120
gggcagcctc ccaagctcct gatctatgaa gcatccaaac tggcctctgg ggtcccatcg    180
cggttcagcg gcagtggata tgggacagag ttcactctca ccatcagcga cctggagtgt    240
gccgatgctg ccacttacta ctgtcaacag ggttatagta gtactaatgt ttggaatgct    300
ttcggcggag gcaccaatgt ggaaatcaaa                                      330
```

```
<210> SEQ ID NO 179
<211> LENGTH: 451
<212> TYPE: PRT
<213> ORGANISM: Artificial Sequence
<220> FEATURE:
<223> OTHER INFORMATION: P2-C12 HC

<400> SEQUENCE: 179
```

```
Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Thr Tyr Ala
            20                  25                  30

Val Thr Trp Val Arg Gln Ala Pro Gly Lys Gly Leu Glu Trp Ile Gly
        35                  40                  45

Tyr Ile Asn Trp Arg Gly Gly Thr Ser Tyr Ala Asn Trp Ala Lys Gly
    50                  55                  60

Arg Phe Thr Ile Ser Lys Thr Ser Thr Thr Val Asp Leu Lys Met
65                  70                  75                  80

Thr Ser Pro Thr Thr Glu Asp Thr Ala Thr Tyr Phe Cys Ala Arg Asp
                85                  90                  95

Ala Ser Ser Gly Ala Ala Phe Gly Ser Tyr Gly Met Asp Pro Trp Gly
            100                 105                 110

Pro Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320
```

```
Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 180
<211> LENGTH: 448
<212> TYPE: PRT
<213> ORGANISM: Artificial Sequence
<220> FEATURE:
<223> OTHER INFORMATION: 13B4 HC

<400> SEQUENCE: 180

Gln Val Gln Leu Gln Glu Ser Gly Pro Gly Leu Val Lys Pro Ser Gly
1               5                   10                  15

Thr Leu Ser Leu Asn Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Gly Gly Thr Thr Asn Tyr Asn Pro Ser Leu
    50                  55                  60

Lys Gly Arg Val Thr Met Ser Val Asp Lys Thr Lys Asn Gln Phe Ser
65                  70                  75                  80

Leu Arg Leu Ser Ser Val Thr Ala Val Asp Thr Ala Val Tyr Tyr Cys
                85                  90                  95

Ala Arg Trp Gln Leu Val Gly Gly Leu Asp Val Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220
```

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 181
<211> LENGTH: 453
<212> TYPE: PRT
<213> ORGANISM: Artificial Sequence
<220> FEATURE:
<223> OTHER INFORMATION: 13F7 HC

<400> SEQUENCE: 181

Gln Val Gln Leu Gln Glu Trp Gly Ala Gly Leu Leu Lys Pro Ser Glu
1               5                   10                  15

Thr Leu Ser Leu Thr Cys Ala Ile Asn Ala Glu Ser Phe Asn Gly Tyr
            20                  25                  30

Ser Trp Thr Trp Ile Arg Gln Thr Pro Gly Lys Gly Leu Glu Trp Ile
        35                  40                  45

Gly Glu Ile Ser His Phe Gly Ser Ala Asn Tyr Asn Pro Ser Leu Lys
    50                  55                  60

Ser Arg Ala Thr Ile Ser Ala Asp Lys Ser Lys Asn Gln Phe Ser Leu
65                  70                  75                  80

Lys Leu Thr Ser Val Thr Ala Val Asp Thr Ala Val Tyr Tyr Cys Ala
                85                  90                  95

Arg Ala Leu Arg Gly Thr Tyr Ser Arg Phe Tyr Tyr Gly Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

```
Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys
    450

<210> SEQ ID NO 182
<211> LENGTH: 450
<212> TYPE: PRT
<213> ORGANISM: Artificial Sequence
<220> FEATURE:
<223> OTHER INFORMATION: 15A9 HC

<400> SEQUENCE: 182

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45
```

```
Gly Tyr Ile Tyr Pro Ser Gly Ser Thr Asn Tyr Asn Pro Ser Leu Lys
             50                  55                  60

Ser Arg Val Thr Ile Ser Val Asp Thr Ser Lys Asn Gln Phe Ser Leu
 65                  70                  75                  80

Asn Leu Lys Ser Val Thr Ala Val Asp Thr Ala Val Tyr Tyr Cys Ala
                 85                  90                  95

Arg Val Asn Pro Phe Gly Tyr Tyr Ala Met Asp Val Trp Gly Gln
                100                 105                 110

Gly Thr Thr Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450
```

```
<210> SEQ ID NO 183
<211> LENGTH: 446
<212> TYPE: PRT
<213> ORGANISM: Artificial Sequence
<220> FEATURE:
<223> OTHER INFORMATION: P1-A03 HC

<400> SEQUENCE: 183

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Asp Tyr
            20                  25                  30

Met Ser Trp Val Arg Gln Ala Pro Gly Glu Gly Leu Glu Trp Ile Gly
        35                  40                  45

Ile Ile Tyr Pro Ser Thr Thr Thr Tyr Tyr Ala Ser Trp Ala Lys Gly
50                  55                  60

Arg Phe Thr Ile Ser Lys Thr Ser Ser Thr Val Glu Leu Lys Met
65                  70                  75                  80

Thr Ser Leu Thr Thr Glu Asp Thr Ala Thr Tyr Phe Cys Ala Arg Gly
                85                  90                  95

Ser Asn Trp Ser Ser Gly Met Asn Leu Trp Gly Pro Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365
```

```
Lys Gly Phe Tyr Pro Ser Asp Ile Ala Val Glu Trp Glu Ser Asn Gly
            370                 375                 380

Gln Pro Glu Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445
```

<210> SEQ ID NO 184
<211> LENGTH: 443
<212> TYPE: PRT
<213> ORGANISM: Artificial Sequence
<220> FEATURE:
<223> OTHER INFORMATION: P1-A08 HC

<400> SEQUENCE: 184

```
Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Thr Tyr Tyr
                20                  25                  30

Met Ser Trp Val Arg Gln Ala Pro Gly Lys Gly Leu Glu Trp Ile Gly
            35                  40                  45

Ile Val Tyr Pro Ser Gly Thr Thr Tyr Tyr Ala Asn Trp Ala Lys Gly
        50                  55                  60

Arg Phe Thr Ile Ser Thr Ala Ser Thr Thr Val Asp Leu Met Ile Thr
65                  70                  75                  80

Ser Pro Thr Thr Glu Asp Thr Ala Thr Tyr Phe Cys Ala Arg Gly Asp
                85                  90                  95

Ser Phe Gly Tyr Gly Leu Trp Gly Pro Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285
```

```
Glu Glu Gln Tyr Asn Ser Thr Tyr Arg Val Val Ser Val Leu Thr Val
    290                 295                 300
Leu His Gln Asp Trp Leu Asn Gly Lys Glu Tyr Lys Cys Lys Val Ser
305                 310                 315                 320
Asn Lys Ala Leu Pro Ala Pro Ile Glu Lys Thr Ile Ser Lys Ala Lys
                325                 330                 335
Gly Gln Pro Arg Glu Pro Gln Val Tyr Thr Leu Pro Pro Ser Arg Glu
                340                 345                 350
Glu Met Thr Lys Asn Gln Val Ser Leu Thr Cys Leu Val Lys Gly Phe
                355                 360                 365
Tyr Pro Ser Asp Ile Ala Val Glu Trp Glu Ser Asn Gly Gln Pro Glu
370                 375                 380
Asn Asn Tyr Lys Thr Thr Pro Pro Val Leu Asp Ser Asp Gly Ser Phe
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
                420                 425                 430
Thr Gln Lys Ser Leu Ser Leu Ser Pro Gly Lys
                435                 440

<210> SEQ ID NO 185
<211> LENGTH: 452
<212> TYPE: PRT
<213> ORGANISM: Artificial Sequence
<220> FEATURE:
<223> OTHER INFORMATION: P1-F02 HC

<400> SEQUENCE: 185

Gln Ser Leu Glu Glu Ser Gly Gly Arg Leu Val Thr Pro Gly Thr Pro
1               5                   10                  15
Leu Thr Leu Thr Cys Thr Ala Ser Gly Phe Ser Leu Ser Asn Tyr Tyr
                20                  25                  30
Met Gly Trp Val Arg Gln Ala Pro Gly Glu Gly Leu Glu Trp Ile Gly
                35                  40                  45
Ile Ile Tyr Ala Ser Gly Ser Thr Tyr Tyr Ala Ser Trp Ala Lys Gly
            50                  55                  60
Arg Phe Thr Ile Ser Lys Thr Ser Thr Val Asp Leu Lys Met Thr
65                  70                  75              80
Ser Leu Thr Thr Glu Asp Thr Ala Thr Tyr Phe Cys Ala Arg Ile Asp
                85                  90                  95
Ile Gly Val Gly Asp Tyr Gly Trp Ala Tyr Asp Arg Leu Asp Leu Trp
                100                 105                 110
Gly Gln Gly Thr Leu Val Thr Val Ser Ser Ala Ser Thr Lys Gly Pro
                115                 120                 125
Ser Val Phe Pro Leu Ala Pro Ser Ser Lys Ser Thr Ser Gly Gly Thr
130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
                180                 185                 190
Val Pro Ser Ser Ser Leu Gly Thr Gln Thr Tyr Ile Cys Asn Val Asn
                195                 200                 205
```

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
                275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Glu Glu Met Thr Lys Asn Gln Val
                355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly Lys
    450

<210> SEQ ID NO 186
<211> LENGTH: 451
<212> TYPE: PRT
<213> ORGANISM: Artificial Sequence
<220> FEATURE:
<223> OTHER INFORMATION: P2-A01 HC

<400> SEQUENCE: 186

Gln Glu Gln Leu Val Glu Ser Gly Gly Arg Leu Val Thr Pro Gly Thr
1               5                   10                  15

Pro Leu Thr Leu Ser Cys Thr Ala Ser Gly Phe Phe Leu Ser Gly Tyr
                20                  25                  30

Tyr Met Ser Trp Val Arg Gln Ala Pro Gly Lys Gly Leu Glu Trp Ile
            35                  40                  45

Gly Ile Ile Tyr Pro Ser Gly Ser Thr Asp Tyr Ala Ser Trp Ala Lys
        50                  55                  60

Gly Arg Phe Thr Ile Ser Lys Thr Ser Thr Thr Val Asp Leu Lys Ile
65                  70                  75                  80

Thr Thr Pro Thr Thr Glu Asp Thr Ala Thr Tyr Phe Cys Ala Arg Val
                85                  90                  95

Ala Gly Tyr Val Gly Tyr Gly Tyr Glu Thr Phe Phe Asp Ile Trp Gly
                100                 105                 110

```
Pro Gly Thr Leu Val Thr Val Ser Leu Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 187
<211> LENGTH: 446
<212> TYPE: PRT
<213> ORGANISM: Artificial Sequence
<220> FEATURE:
<223> OTHER INFORMATION: P2-A03 HC

<400> SEQUENCE: 187

Gln Ser Val Glu Glu Ser Gly Gly Arg Leu Val Thr Pro Gly Thr Pro
1               5                   10                  15
```

-continued

```
Leu Thr Leu Thr Cys Thr Val Ser Gly Phe Ser Leu Asn Asn Tyr Asp
         20                  25                  30

Met Ser Trp Val Arg Gln Ala Pro Gly Lys Gly Leu Glu Tyr Ile Gly
         35                  40                  45

Phe Met Asp Thr Asp Gly Ser Ala Tyr Tyr Ala Thr Trp Ala Lys Gly
         50                  55                  60

Arg Phe Thr Ile Ser Arg Thr Ser Thr Thr Val Asp Leu Lys Met Thr
 65              70                  75                  80

Ser Pro Thr Thr Glu Asp Thr Ala Thr Tyr Phe Cys Ala Arg Arg Gly
                 85                  90                  95

Ser Ser Tyr Tyr Gly Gly Ile Asp Ile Trp Gly Pro Gly Thr Pro Val
             100                 105                 110

Thr Val Ser Leu Ala Ser Thr Lys Gly Pro Ser Val Phe Pro Leu Ala
         115                 120                 125

Pro Ser Ser Lys Ser Thr Ser Gly Gly Thr Ala Ala Leu Gly Cys Leu
         130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                 165                 170                 175

Gly Leu Tyr Ser Leu Ser Ser Val Val Thr Val Pro Ser Ser Ser Leu
             180                 185                 190

Gly Thr Gln Thr Tyr Ile Cys Asn Val Asn His Lys Pro Ser Asn Thr
         195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                 245                 250                 255

Glu Val Thr Cys Val Val Val Asp Val Ser His Glu Asp Pro Glu Val
             260                 265                 270

Lys Phe Asn Trp Tyr Val Asp Gly Val Glu Val His Asn Ala Lys Thr
         275                 280                 285

Lys Pro Arg Glu Glu Gln Tyr Asn Ser Thr Tyr Arg Val Val Ser Val
         290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                 325                 330                 335

Lys Ala Lys Gly Gln Pro Arg Glu Pro Gln Val Tyr Thr Leu Pro Pro
             340                 345                 350

Ser Arg Glu Glu Met Thr Lys Asn Gln Val Ser Leu Thr Cys Leu Val
         355                 360                 365

Lys Gly Phe Tyr Pro Ser Asp Ile Ala Val Glu Trp Glu Ser Asn Gly
         370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                 405                 410                 415

Gln Gln Gly Asn Val Phe Ser Cys Ser Val Met His Glu Ala Leu His
             420                 425                 430

Asn His Tyr Thr Gln Lys Ser Leu Ser Leu Ser Pro Gly Lys
```

-continued

```
             435                 440                 445

<210> SEQ ID NO 188
<211> LENGTH: 443
<212> TYPE: PRT
<213> ORGANISM: Artificial Sequence
<220> FEATURE:
<223> OTHER INFORMATION: P2-F07 HC

<400> SEQUENCE: 188

Gln Ser Leu Glu Glu Ser Gly Gly Arg Leu Val Thr Pro Gly Thr Pro
1               5                  10                  15

Leu Thr Leu Thr Cys Thr Ala Ser Gly Phe Ser Leu Ser Ser Tyr Tyr
            20                  25                  30

Met Asn Trp Val Arg Gln Ala Pro Gly Lys Gly Leu Glu Trp Ile Gly
        35                  40                  45

Ile Ile Tyr Pro Ser Gly Thr Thr Tyr Tyr Ala Gly Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Ser Glu Asp Thr Ala Thr Tyr Phe Cys Ala Arg Thr Val
                85                  90                  95

Ser Gly Tyr Phe Asp Ile Trp Gly Pro Gly Thr Leu Val Thr Val Ser
            100                 105                 110

Leu Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
```

```
            355                 360                 365
Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 189
<211> LENGTH: 444
<212> TYPE: PRT
<213> ORGANISM: Artificial Sequence
<220> FEATURE:
<223> OTHER INFORMATION: P2-F11 HC

<400> SEQUENCE: 189

Gln Glu Gln Leu Val Glu Ser Gly Gly Arg Leu Val Thr Pro Gly Thr
1               5                   10                  15

Thr Leu Thr Leu Thr Cys Thr Val Ser Gly Phe Ser Leu Ser Ser Tyr
            20                  25                  30

Gly Val Ser Trp Val Arg Gln Ala Pro Gly Lys Gly Leu Glu Trp Ile
        35                  40                  45

Gly Tyr Ile Ala Asn Asn Tyr Asn Pro His Tyr Ala Ser Trp Ala Lys
    50                  55                  60

Gly Arg Phe Thr Ile Ser Lys Thr Ser Thr Thr Val Asp Leu Lys
65                  70                  75                  80

Met Thr Ser Leu Thr Thr Glu Asp Thr Ala Thr Tyr Phe Cys Ala Arg
                85                  90                  95

Asp Asn Tyr Gly Met Asp Pro Trp Gly Pro Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
```

```
              275                 280                 285
Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
                340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
                370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys
                435                 440

<210> SEQ ID NO 190
<211> LENGTH: 217
<212> TYPE: PRT
<213> ORGANISM: Artificial Sequence
<220> FEATURE:
<223> OTHER INFORMATION: P2-C12 LC

<400> SEQUENCE: 190

Glu Leu Asp Met Thr Gln Thr Pro Ser Ser Val Ser Ala Ala Val Gly
1               5                   10                  15

Gly Thr Val Thr Ile Lys Cys Gln Ala Ser Gln Ser Ile Ser Ser Tyr
                20                  25                  30

Leu Ser Trp Tyr Gln Gln Lys Pro Gly Gln Pro Pro Lys Leu Leu Ile
                35                  40                  45

Tyr Glu Ala Ser Lys Leu Ala Ser Gly Val Pro Ser Arg Phe Ser Gly
50                  55                  60

Ser Gly Tyr Gly Thr Glu Phe Thr Leu Thr Ile Ser Asp Leu Glu Cys
65                  70                  75                  80

Ala Asp Ala Ala Thr Tyr Tyr Cys Gln Gln Gly Tyr Ser Ser Thr Asn
                85                  90                  95

Val Trp Asn Ala Phe Gly Gly Gly Thr Asn Val Glu Ile Lys Arg Ser
                100                 105                 110

Val Ala Ala Pro Ser Val Phe Ile Phe Pro Pro Ser Asp Glu Gln Leu
                115                 120                 125

Lys Ser Gly Thr Ala Ser Val Val Cys Leu Leu Asn Asn Phe Tyr Pro
                130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
                180                 185                 190

Lys Val Tyr Ala Cys Glu Val Thr His Gln Gly Leu Ser Ser Pro Val
```

Thr Lys Ser Phe Asn Arg Gly Glu Cys
    210             215

<210> SEQ ID NO 191
<211> LENGTH: 213
<212> TYPE: PRT
<213> ORGANISM: Artificial Sequence
<220> FEATURE:
<223> OTHER INFORMATION: 13B4 LC

<400> SEQUENCE: 191

Ser Tyr Glu Leu Thr Gln Pro Leu Ser Val Ser Val Ser Pro Gly Gln
1               5                   10                  15

Thr Ala Ser Ile Thr Cys Ser Gly Asp Lys Leu Gly Asn Val Tyr Ala
            20                  25                  30

Ser Trp Tyr Gln Gln Lys Pro Gly Gln Ser Pro Thr Leu Val Ile Tyr
        35                  40                  45

Gln Asp Asn Lys Arg Pro Ser Gly Ile Pro Glu Arg Phe Ser Gly Ser
    50                  55                  60

Asn Ser Gly Lys Thr Ala Thr Leu Thr Ile Ser Gly Thr Gln Ala Leu
65                  70                  75                  80

Asp Glu Ala Asp Tyr Tyr Cys Gln Ala Trp Asp Ser Ser Thr Ala Val
                85                  90                  95

Phe Gly Gly Gly Thr Lys Leu Thr Val Leu Arg Ser Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 192
<211> LENGTH: 219
<212> TYPE: PRT
<213> ORGANISM: Artificial Sequence
<220> FEATURE:
<223> OTHER INFORMATION: 13F7 LC

<400> SEQUENCE: 192

Asp Ile Val Met Thr Gln Thr Pro Leu Ser Leu Pro Val Ala Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Val Gln Lys Pro Gly Gln Pro
        35                  40                  45

Pro Gln Leu Leu Ile Tyr Leu Gly Ser Asn Arg Ala Ser Gly Val Pro
    50                  55                  60

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Arg Gln Thr Pro Leu Thr Phe Gly Gly Gly Thr Lys Val Glu Ile Lys
            100                 105                 110

Arg Ser Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 193
<211> LENGTH: 214
<212> TYPE: PRT
<213> ORGANISM: Artificial Sequence
<220> FEATURE:
<223> OTHER INFORMATION: 15A9 LC

<400> SEQUENCE: 193

Asp Ile Gln Met Thr Gln Ser Pro Ser Ser Leu Ser Ala Ser Val Gly
 1               5                  10                  15

Asp Arg Ile Thr Ile Ser Cys Arg Ala Ser Gln Ser Ile Ser Thr Ser
             20                  25                  30

Leu Asn Trp Tyr Gln Gln Thr Pro Gly Lys Ala Pro Arg Leu Leu Ile
         35                  40                  45

Tyr Gly Ala Ser Thr Leu Gln Ser Gly Val Pro Ser Arg Phe Ser Gly
 50                  55                  60

Gly Gly Ser Gly Thr Asp Phe Ser Leu Thr Ile Thr Ser Leu Gln Pro
 65                  70                  75                  80

Glu Asp Phe Ala Thr Tyr Tyr Cys Gln Glu Ser Ala Ser Ile Pro Arg
                 85                  90                  95

Thr Phe Gly Gln Gly Thr Lys Leu Asp Ile Lys Arg Ser Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys
    210
```

<210> SEQ ID NO 194
<211> LENGTH: 217
<212> TYPE: PRT
<213> ORGANISM: Artificial Sequence
<220> FEATURE:
<223> OTHER INFORMATION: P1-A03 LC

<400> SEQUENCE: 194

```
Glu Leu Val Met Thr Gln Thr Pro Pro Ser Leu Ser Ala Ser Val Gly
1               5                   10                  15

Glu Thr Val Arg Ile Arg Cys Leu Ala Ser Glu Asp Ile Tyr Ser Gly
            20                  25                  30

Ile Ser Trp Tyr Gln Gln Lys Pro Glu Lys Pro Thr Leu Leu Ile
        35                  40                  45

Ser Gly Ala Ser Asn Leu Glu Ser Gly Val Pro Pro Arg Phe Ser Gly
    50                  55                  60

Ser Gly Ser Gly Thr Asp Tyr Thr Leu Thr Ile Gly Gly Val Gln Ala
65                  70                  75                  80

Glu Asp Ala Ala Thr Tyr Tyr Cys Leu Gly Gly Tyr Tyr Ser Ser
                85                  90                  95

Thr Gly Leu Thr Phe Gly Ala Gly Thr Asn Val Glu Ile Lys Arg Ser
                100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 195
<211> LENGTH: 217
<212> TYPE: PRT
<213> ORGANISM: Artificial Sequence
<220> FEATURE:
<223> OTHER INFORMATION: P1-A08 LC

<400> SEQUENCE: 195

```
Glu Leu Val Leu Thr Gln Ser Pro Ser Val Gln Val Asn Leu Gly Gln
1               5                   10                  15

Thr Val Ser Leu Thr Cys Thr Ala Asp Thr Leu Ser Arg Ser Tyr Ala
            20                  25                  30

Ser Trp Tyr Gln Gln Lys Pro Gly Gln Ala Pro Val Leu Leu Ile Tyr
        35                  40                  45

Arg Asp Thr Ser Arg Pro Ser Gly Val Pro Asp Arg Phe Ser Gly Ser
    50                  55                  60

Ser Ser Gly Asn Thr Ala Thr Leu Thr Ile Ser Gly Ala Gln Ala Gly
65                  70                  75                  80
```

Asp Glu Ala Asp Tyr Tyr Cys Ala Thr Ser Asp Gly Ser Gly Ser Asn
            85                  90                  95

Tyr Gln Tyr Val Phe Gly Gly Gly Thr Gln Leu Thr Val Thr Arg Ser
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
            165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
            195                 200                 205

Thr Lys Ser Phe Asn Arg Gly Glu Cys
            210                 215

<210> SEQ ID NO 196
<211> LENGTH: 215
<212> TYPE: PRT
<213> ORGANISM: Artificial Sequence
<220> FEATURE:
<223> OTHER INFORMATION: P1-F02 LC

<400> SEQUENCE: 196

Glu Leu Asp Met Thr Gln Thr Pro Pro Ser Leu Ser Ala Ser Val Gly
1               5                   10                  15

Glu Thr Val Arg Ile Arg Cys Leu Ala Ser Glu Asp Ile Tyr Ser Gly
            20                  25                  30

Ile Ser Trp Tyr Gln Gln Lys Pro Gly Lys Pro Pro Thr Leu Leu Ile
            35                  40                  45

Tyr Gly Ala Ser Asn Leu Glu Ser Gly Val Pro Pro Arg Phe Ser Gly
50                  55                  60

Ser Gly Ser Gly Thr Asp Tyr Thr Leu Thr Ile Gly Gly Val Gln Ala
65                  70                  75                  80

Glu Asp Ala Ala Thr Tyr Tyr Cys Leu Gly Gly Tyr Ser Tyr Ser Ser
            85                  90                  95

Ile Thr Phe Gly Ala Gly Thr Asn Val Glu Ile Lys Arg Ser Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
210                 215

<210> SEQ ID NO 197
<211> LENGTH: 219
<212> TYPE: PRT
<213> ORGANISM: Artificial Sequence
<220> FEATURE:
<223> OTHER INFORMATION: P2-A01 LC

<400> SEQUENCE: 197

```
Glu Leu Val Met Thr Gln Thr Pro Ser Leu Ser Ala Ser Val Gly
1               5                   10                  15

Glu Thr Val Arg Ile Arg Cys Leu Ala Ser Glu Asp Ile Tyr Ser Gly
                20                  25                  30

Ile Ser Trp Tyr Gln Gln Lys Pro Gly Lys Pro Thr Leu Leu Ile
        35                  40                  45

Tyr Gly Ala Ser Asn Leu Glu Ser Gly Val Pro Arg Phe Ser Gly
    50                  55                  60

Ser Gly Ser Gly Ser Asp Tyr Thr Leu Thr Ile Gly Gly Val Gln Ala
65                  70                  75                  80

Glu Asp Ala Ala Thr Tyr Tyr Cys Leu Gly Gly Val Thr Tyr Ser Ser
                85                  90                  95

Thr Gly Thr His Leu Thr Phe Gly Ala Gly Thr Asn Val Glu Ile Lys
                100                 105                 110

Arg Ser Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215
```

<210> SEQ ID NO 198
<211> LENGTH: 219
<212> TYPE: PRT
<213> ORGANISM: Artificial Sequence
<220> FEATURE:
<223> OTHER INFORMATION: P2-A03 LC

<400> SEQUENCE: 198

```
Glu Leu Asp Leu Thr Gln Thr Pro Ala Ser Val Ser Glu Pro Val Gly
1               5                   10                  15

Gly Thr Val Thr Ile Lys Cys Gln Ala Ser Gln Ser Ile Gly Gly Asn
                20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Pro Ser Arg Phe Lys Gly
    50                  55                  60

Ser Gly Ser Gly Thr Asp Phe Thr Leu Thr Ile Ser Asp Leu Glu Cys
65                  70                  75                  80

Ala Asp Ala Ala Thr Tyr Tyr Cys Gln Ser Pro Ala Tyr Asp Pro Ala
```

```
                    85                  90                  95
Ala Tyr Val Gly Asn Ala Phe Gly Gly Gly Thr Glu Leu Glu Ile Leu
            100                 105                 110

Arg Ser Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 199
<211> LENGTH: 214
<212> TYPE: PRT
<213> ORGANISM: Artificial Sequence
<220> FEATURE:
<223> OTHER INFORMATION: P2-F07 LC

<400> SEQUENCE: 199

Glu Leu Asp Leu Thr Gln Thr Pro Pro Ser Leu Ser Ala Ser Val Gly
1               5                  10                  15

Gly Thr Val Thr Ile Asn Cys Leu Ala Ser Glu Asp Ile Tyr Ser Ala
            20                  25                  30

Leu Ala Trp Tyr Gln Gln Lys Pro Gly Lys Pro Thr Leu Leu Ile
            35                  40                  45

Ser Gly Thr Ser Asn Leu Glu Ser Gly Val Pro Pro Arg Phe Ser Gly
        50                  55                  60

Ser Gly Ser Gly Thr Asp Tyr Thr Leu Thr Ile Gly Gly Val Gln Ala
65                  70                  75                  80

Glu Asp Ala Ala Thr Tyr Phe Cys Gln Gly Tyr Ser Ser Tyr Pro Leu
                85                  90                  95

Thr Phe Gly Ala Gly Thr Asn Val Glu Ile Lys Arg Ser Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210
```

```
<210> SEQ ID NO 200
<211> LENGTH: 220
<212> TYPE: PRT
<213> ORGANISM: Artificial Sequence
<220> FEATURE:
<223> OTHER INFORMATION: P2-F11 LC

<400> SEQUENCE: 200

Glu Leu Asp Leu Thr Gln Thr Pro Ser Ser Val Ser Ala Ala Val Gly
1               5                   10                  15

Gly Thr Val Thr Ile Asn Cys Gln Ala Ser Gln Ser Val Tyr Asn Asn
            20                  25                  30

Lys Asn Leu Ala Trp Tyr Gln Gln Lys Pro Gly Gln Pro Pro Lys Leu
        35                  40                  45

Leu Ile Tyr Ala Ala Ser Thr Leu Ala Ser Gly Val Ser Ser Arg Phe
    50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Tyr Cys Gln Gly Glu Phe Ser Cys
                85                  90                  95

Ser Ser Ala Asp Cys Asn Ala Phe Gly Gly Gly Thr Glu Leu Glu Ile
            100                 105                 110

Leu Arg Ser Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 201
<211> LENGTH: 251
<212> TYPE: PRT
<213> ORGANISM: Artificial Sequence
<220> FEATURE:
<223> OTHER INFORMATION: 3-2 scFv

<400> SEQUENCE: 201

Ala Leu Thr Gln Pro Ser Ser Val Ser Ala Asn Pro Gly Glu Thr Val
1               5                   10                  15

Lys Ile Thr Cys Ser Gly Gly Gly Ser Tyr Ala Gly Ser Tyr Tyr Tyr
            20                  25                  30

Gly Trp Tyr Gln Gln Lys Ala Pro Gly Ser Ala Pro Val Thr Leu Ile
        35                  40                  45

Tyr Glu Ser Asn Lys Arg Pro Ser Asp Ile Pro Ser Arg Phe Ser Gly
    50                  55                  60

Ser Thr Ser Gly Ser Thr Ala Thr Leu Thr Ile Thr Gly Val Gln Ala
65                  70                  75                  80

Asp Asp Glu Ala Ile Tyr Tyr Cys Gly Ser Trp Asp Ser Ser Asn Gly
                85                  90                  95
```

```
Gly Ile Phe Gly Ala Gly Thr Thr Leu Thr Val Leu Ser Gly Gly Gly
                100                 105                 110

Gly Ser Ser Gly Gly Gly Ser Ala Val Thr Leu Asp Glu Ser Gly
        115                 120                 125

Gly Gly Leu Gln Thr Pro Gly Gly Ala Leu Ser Leu Val Cys Lys Ala
        130                 135                 140

Ser Gly Phe Thr Phe Ser Ser Phe Asn Met Phe Trp Val Arg Gln Ala
145                 150                 155                 160

Pro Gly Lys Gly Leu Glu Tyr Val Ala Gln Ile Ser Ser Ser Gly Ser
                165                 170                 175

Ser Thr Asn Tyr Ala Pro Ala Val Arg Gly Arg Ala Thr Ile Ser Arg
            180                 185                 190

Asp Asn Gly Gln Ser Thr Val Arg Leu Gln Leu Asn Asn Pro Gly Ala
            195                 200                 205

Glu Asp Thr Gly Thr Tyr Tyr Cys Ala Lys Ser Ser Tyr Asp Cys Pro
        210                 215                 220

Tyr Gly His Cys Ser Ser Gly Val Asp Ser Ala Gly Glu Ile Asp Ala
225                 230                 235                 240

Trp Gly His Gly Thr Glu Val Ile Val Ser Ser
                245                 250
```

<210> SEQ ID NO 202
<211> LENGTH: 244
<212> TYPE: PRT
<213> ORGANISM: Artificial Sequence
<220> FEATURE:
<223> OTHER INFORMATION: 1-65 scFv

<400> SEQUENCE: 202

```
Ala Leu Thr Gln Pro Ser Ser Val Ser Ala Asn Pro Gly Glu Thr Val
1               5                   10                  15

Lys Ile Thr Cys Ser Gly Gly Ser Ser Gly Tyr Gly Tyr Gly Trp
                20                  25                  30

Tyr Gln Gln Lys Ser Pro Ser Ser Ala Pro Leu Thr Val Ile Tyr Trp
            35                  40                  45

Asn Asp Lys Arg Pro Ser Asp Ile Pro Ser Arg Phe Ser Gly Ser Lys
        50                  55                  60

Ser Gly Ser Thr His Thr Leu Thr Ile Thr Gly Val Gln Ala Glu Asp
65                  70                  75                  80

Glu Ala Val Tyr Phe Cys Gly Asn Asp Asp Tyr Ser Ser Asp Ser Gly
                85                  90                  95

Tyr Val Gly Val Phe Gly Ala Gly Thr Thr Leu Thr Val Leu Ser Gly
                100                 105                 110

Gly Gly Gly Ser Ser Gly Gly Gly Ser Ala Val Thr Leu Asp Glu
            115                 120                 125

Ser Gly Gly Gly Leu Gln Thr Pro Gly Gly Ala Leu Ser Leu Val Cys
        130                 135                 140

Lys Ala Ser Gly Phe Thr Phe Ser Ser Tyr Gln Met Gly Trp Val Arg
145                 150                 155                 160

Gln Ala Pro Gly Lys Gly Leu Glu Trp Val Gly Val Ile Asn Lys Ser
                165                 170                 175

Gly Ser Asp Thr Ser Tyr Gly Ser Ala Val Lys Gly Arg Ala Thr Ile
            180                 185                 190

Ser Arg Asp Asn Gly Gln Ser Thr Val Arg Leu Gln Leu Asn Asn Leu
        195                 200                 205
```

```
Arg Ala Glu Asp Thr Gly Thr Tyr Phe Cys Ala Lys Gly Ser Ala Ser
    210                 215                 220

Tyr Ile Thr Ala Ala Thr Ile Asp Ala Trp Gly His Gly Thr Glu Val
225                 230                 235                 240

Ile Val Ser Ser
```

<210> SEQ ID NO 203
<211> LENGTH: 245
<212> TYPE: PRT
<213> ORGANISM: Artificial Sequence
<220> FEATURE:
<223> OTHER INFORMATION: 2-13 scFv

<400> SEQUENCE: 203

```
Ala Leu Thr Gln Pro Ser Ser Val Ser Ala Asn Pro Gly Glu Thr Val
1               5                   10                  15

Lys Ile Thr Cys Ser Gly Gly Ser Tyr Ser Tyr Gly Trp Phe Gln Gln
            20                  25                  30

Lys Ser Pro Gly Ser Ala Leu Val Thr Val Ile Tyr Trp Asp Asp Glu
        35                  40                  45

Arg Pro Ser Asp Ile Pro Ser Arg Phe Ser Gly Ala Leu Ser Gly Ser
    50                  55                  60

Thr Asn Thr Leu Thr Ile Thr Gly Val Gln Ala Asp Asp Glu Ala Val
65                  70                  75                  80

Tyr Phe Cys Gly Thr Glu Asp Ile Ser Gly Thr Ala Gly Val Phe Gly
                85                  90                  95

Ala Gly Thr Thr Leu Thr Val Leu Ser Gly Gly Gly Ser Ser Gly
            100                 105                 110

Gly Gly Gly Ser Ala Val Thr Leu Asp Glu Ser Gly Gly Leu Gln
        115                 120                 125

Thr Pro Gly Gly Ala Leu Ser Leu Val Cys Lys Ala Ser Gly Phe Thr
    130                 135                 140

Phe Ser Ser His Gly Met Phe Trp Val Arg Gln Thr Pro Gly Lys Gly
145                 150                 155                 160

Leu Glu Tyr Val Ala Glu Ile Thr Asn Asp Gly Ser Gly Thr Asn Tyr
                165                 170                 175

Gly Ser Ala Val Lys Gly Arg Ala Thr Ile Ser Arg Asp Asn Gly Gln
            180                 185                 190

Ser Thr Val Arg Leu Gln Leu Asn Asn Leu Arg Ala Glu Asp Thr Gly
        195                 200                 205

Thr Tyr Phe Cys Ala Arg Ser Thr Tyr Glu Cys Pro Gly Gly Phe Ser
    210                 215                 220

Cys Trp Gly Asp Thr Gly Gln Ile Asp Ala Trp Gly His Gly Thr Glu
225                 230                 235                 240

Val Ile Val Ser Ser
                245
```

<210> SEQ ID NO 204
<211> LENGTH: 753
<212> TYPE: DNA
<213> ORGANISM: Artificial Sequence
<220> FEATURE:
<223> OTHER INFORMATION: 3-2 scFv

<400> SEQUENCE: 204

```
gcattgactc agccctcttc cgtgagtgct aatccaggtg aaacagtaaa aataacttgc      60
agtgggggag ggtcttacgc aggatcttat tattatggat ggtaccagca aaaagcccct     120
```

```
gggtctgcac cagtcactct gatatacgag agcaataaac gcccttccga catccccagc    180
cgcttttctg gttctacctc tggcagtact gctaccttga ctattaccgg ggtccaggct    240
gacgacgaag ccatttatta ttgtggaagt tgggattcaa gcacggggg tatattcggc     300 gctggtacta cccttaccgt gctgtccggt ggggtggga gcagtggagg tggaggaagt     360
gctgtaactc ttgatgaaag cggggagggg ctgcaaaccc ctggcggggc cttgtccttg    420
gtttgtaagg cttccggatt tactttctca agttttaata tgttttgggt gcgacaggcc    480
ccagggaaag ggttggaata tgttgcacag atctccagct caggttcatc caccaattat    540
gcacctgccg tccgagggag ggctacaatt tctaggaca acgggcagtc aactgtacgg     600
ttgcagctta caatcccgg agcagaagat acaggtacct attactgtgc taagagttca    660
tacgactgtc cctatggtca ctgttcctca ggtgttgact ccgcagggga gatagatgct    720
tgggggcatg ggaccgaagt gattgtgtca tct                                753

<210> SEQ ID NO 205
<211> LENGTH: 732
<212> TYPE: DNA
<213> ORGANISM: Artificial Sequence
<220> FEATURE:
<223> OTHER INFORMATION: 1-65 scFv

<400> SEQUENCE: 205
gccttgacac aaccctcatc agtatctgct aaccccggcg aaacagttaa ataacatgc     60 tcaggaggtg gttcatctgg ctatggatat gggtggtatc aacagaaatc accaagttcc    120
gcccccttga ccgtgattta ttggaatgat aagcgcccct cagacattcc cagtcgcttc    180
tcaggcagta atcaggctc aacccatact cttactatca ccggtgtcca agcagaagat    240
gaagccgtgt attttgtgg aatgatgac tattccagcg attctggcta tgtaggagtg     300
ttcggtgccg gtactaccct cacagtattg agtggtggtg gcggaagttc aggtggtggt    360
ggaagcgctg tcactttgga tgaatcaggt ggaggcctcc aaaccccagg tggcgcactc    420
agtctcgtat gtaaagcctc tggtttcact ttcagctcat atcaaatggg atgggtgcgg    480
caggctcccg gcaagggggtt ggagtgggtc ggtgttatca acaagagcgg ctctgatact    540
agctatggaa gcgcagtcaa ggggagagct actataagca gggataatgg caaagtacc    600 gtcaggcttc aattgaacaa tctcagggct gaggatacag gaacctactt ctgcgccaaa    660
gggtcagcat cttatatcac agcagctacc attgacgcat ggggacatgg cacagaggtc    720 attgttttcca gt                                                      732

<210> SEQ ID NO 206
<211> LENGTH: 735
<212> TYPE: DNA
<213> ORGANISM: Artificial Sequence
<220> FEATURE:
<223> OTHER INFORMATION: 2-13 scFv

<400> SEQUENCE: 206
gctctgacac aaccaagctc tgtcagtgca aatccaggag agaccgttaa atcacttgc     60 agcggaggct cttattccta cggatggttc agcaaaaaa gtcctggttc agccctcgtt    120
actgtcatct actgggacga cgagcgccct agcgatattc ctagtagatt ctcaggggct    180
cttagcggct ccactaatac tttgaccatt actggagtac aggctgatga cgaagcagtt    240
tacttctgtg gcaccgaaga tataagcgga actgcagggg tatttggggc tggtacaaca    300
```

-continued

```
ctcacagtgc tctccggggg gggcgggagc tcaggaggcg gcggatcagc tgtaaccctg    360
gacgaatctg gtgggggct tcaaacaccc ggaggagccc tctccctcgt atgcaaagct    420
tcaggattca ccttctcttc acatggaatg ttctgggtaa ggcagacacc tggcaaggg    480 cttgaatatg tagctgagat cactaatgac ggtagcggta caaactatgg gtctgctgtg    540
aaaggccggg ctacaataag tcgagacaat ggacaaagta ccgttagact ccagctcaac    600
aacctgcgag ctgaggacac aggcacttac ttttgtgcac gcagtactta cgagtgtcca    660
ggtggatttt catgttgggg agataccgga cagatcgacg cttgggggca cggcaccgag    720
gtcattgtaa gtagc                                                     735
```

<210> SEQ ID NO 207
<211> LENGTH: 12
<212> TYPE: PRT
<213> ORGANISM: Artificial Sequence
<220> FEATURE:
<223> OTHER INFORMATION: Linker

<400> SEQUENCE: 207

Ser Gly Gly Gly Gly Ser Ser Gly Gly Gly Gly Ser
1               5                   10

<210> SEQ ID NO 208
<211> LENGTH: 11
<212> TYPE: PRT
<213> ORGANISM: Artificial Sequence
<220> FEATURE:
<223> OTHER INFORMATION: SS01-13 VL CDR1

<400> SEQUENCE: 208

Ser Gly Gly Ala Ser Ser Gly Tyr Gly Tyr Gly
1               5                   10

<210> SEQ ID NO 209
<211> LENGTH: 7
<212> TYPE: PRT
<213> ORGANISM: Artificial Sequence
<220> FEATURE:
<223> OTHER INFORMATION: SS01-13 VL CDR2

<400> SEQUENCE: 209

Lys Asp Asp Glu Arg Pro Ser
1               5

<210> SEQ ID NO 210
<211> LENGTH: 14
<212> TYPE: PRT
<213> ORGANISM: Artificial Sequence
<220> FEATURE:
<223> OTHER INFORMATION: SS01-13 VL CDR3

<400> SEQUENCE: 210

Gly Asn Asp Asp Tyr Ser Ser Asp Ser Gly Tyr Val Gly Val
1               5                   10

<210> SEQ ID NO 211
<211> LENGTH: 122
<212> TYPE: PRT
<213> ORGANISM: Artificial Sequence
<220> FEATURE:
<223> OTHER INFORMATION: SS01-13 VH

<400> SEQUENCE: 211

Ala Val Thr Leu Asp Glu Ser Gly Gly Gly Leu Gln Thr Pro Gly Gly

-continued

```
1               5                   10                  15
Ala Leu Ser Leu Ser Cys Lys Ala Ser Gly Phe Thr Phe Ser Ser Tyr
            20                  25                  30

Gln Met Gly Trp Val Arg Gln Ala Pro Gly Lys Gly Leu Glu Trp Val
            35                  40                  45

Gly Val Ile Asn Lys Ser Gly Ser Asp Thr Ser Tyr Gly Ser Ala Val
            50                  55                  60

Lys Gly Arg Ala Thr Ile Ser Arg Asp Asn Gly Gln Ser Thr Leu Tyr
65                  70                  75                  80

Leu Gln Met Asn Asn Leu Arg Ala Glu Asp Thr Ala Val Tyr Phe Cys
                    85                  90                  95

Ala Lys Gly Ser Ala Ser Tyr Ile Thr Ala Ala Thr Ile Asp Ala Trp
                    100                 105                 110

Gly His Gly Thr Glu Val Ile Val Ser Ser
                    115                 120
```

<210> SEQ ID NO 212
<211> LENGTH: 109
<212> TYPE: PRT
<213> ORGANISM: Artificial Sequence
<220> FEATURE:
<223> OTHER INFORMATION: SS01-13 VL

<400> SEQUENCE: 212

```
Ala Leu Thr Gln Pro Ser Ser Val Ser Ala Asn Pro Gly Glu Thr Val
1               5                   10                  15

Arg Ile Thr Cys Ser Gly Gly Ala Ser Ser Gly Tyr Tyr Gly Trp
            20                  25                  30

Tyr Gln Gln Lys Pro Ser Ser Ala Pro Leu Thr Val Ile Tyr Lys Asp
            35                  40                  45

Asp Glu Arg Pro Ser Asp Ile Pro Ser Arg Phe Ser Gly Ser Ser Ser
            50                  55                  60

Gly Ser Thr His Thr Leu Thr Ile Thr Gly Val Gln Ala Glu Asp Glu
65                  70                  75                  80

Ala Val Tyr Phe Cys Gly Asn Asp Asp Tyr Ser Ser Asp Ser Gly Tyr
                    85                  90                  95

Val Gly Val Phe Gly Ala Gly Thr Thr Leu Thr Val Leu
                    100                 105
```

<210> SEQ ID NO 213
<211> LENGTH: 7
<212> TYPE: PRT
<213> ORGANISM: Artificial Sequence
<220> FEATURE:
<223> OTHER INFORMATION: SS01-13 and S5-2.GKNG Abs VL-CDR2

<400> SEQUENCE: 213

```
Lys Asp Ser Glu Arg Pro Ser
1               5
```

<210> SEQ ID NO 214
<211> LENGTH: 122
<212> TYPE: PRT
<213> ORGANISM: Artificial Sequence
<220> FEATURE:
<223> OTHER INFORMATION: SS01-13-S5 Ab VH

<400> SEQUENCE: 214

```
Ala Val Thr Leu Asp Glu Ser Gly Gly Gly Leu Gln Thr Pro Gly Gly
1               5                   10                  15
```

```
Ala Leu Arg Leu Ser Cys Lys Ala Ser Gly Phe Thr Phe Ser Ser Tyr
            20                  25                  30

Gln Met Gly Trp Val Arg Gln Ala Pro Gly Lys Gly Leu Glu Trp Val
        35                  40                  45

Ser Ala Ile Asn Lys Ser Gly Ser Asp Thr Ser Tyr Gly Ser Ala Val
 50                  55                  60

Lys Gly Arg Ala Thr Ile Ser Arg Asp Asn Gly Gln Ser Thr Leu Tyr
65                   70                  75                  80

Leu Gln Met Asn Ser Leu Arg Ala Glu Asp Thr Ala Val Tyr Phe Cys
                85                  90                  95

Ala Lys Gly Ser Ala Ser Tyr Ile Thr Ala Ala Thr Ile Asp Ala Trp
            100                 105                 110

Gly His Gly Thr Glu Val Ile Val Ser Ser
            115                 120
```

```
<210> SEQ ID NO 215
<211> LENGTH: 109
<212> TYPE: PRT
<213> ORGANISM: Artificial Sequence
<220> FEATURE:
<223> OTHER INFORMATION: SS01-13-S5; S5-2.GKNG Abs VL

<400> SEQUENCE: 215

Ala Leu Thr Gln Pro Ser Ser Val Ser Ala Asn Pro Gly Glu Thr Ala
1               5                   10                  15

Arg Ile Thr Cys Ser Gly Gly Ala Ser Ser Gly Tyr Gly Tyr Gly Trp
            20                  25                  30

Tyr Gln Gln Lys Pro Ser Ser Ala Pro Leu Thr Val Ile Tyr Lys Asp
            35                  40                  45

Ser Glu Arg Pro Ser Asp Ile Pro Ser Arg Phe Ser Gly Ser Ser Ser
 50                  55                  60

Gly Ser Thr His Thr Leu Thr Ile Ser Gly Val Gln Ala Glu Asp Glu
65                   70                  75                  80

Ala Val Tyr Phe Cys Gly Asn Asp Asp Tyr Ser Ser Asp Ser Gly Tyr
                85                  90                  95

Val Gly Val Phe Gly Ala Gly Thr Thr Leu Thr Val Leu
            100                 105
```

```
<210> SEQ ID NO 216
<211> LENGTH: 366
<212> TYPE: PRT
<213> ORGANISM: Artificial Sequence
<220> FEATURE:
<223> OTHER INFORMATION: SS01-13-S5 Ab VH (nucleic acid)

<400> SEQUENCE: 216

Gly Cys Cys Gly Thr Gly Ala Cys Gly Thr Thr Gly Gly Ala Cys Gly
1               5                   10                  15

Ala Gly Thr Cys Cys Gly Gly Gly Cys Gly Gly Cys Cys Thr
            20                  25                  30

Cys Cys Ala Gly Ala Cys Gly Cys Cys Gly Gly Ala Gly Gly Ala
            35                  40                  45

Gly Cys Gly Cys Thr Cys Cys Gly Cys Cys Thr Cys Thr Cys Thr Thr
            50                  55                  60

Gly Cys Ala Ala Gly Gly Cys Cys Thr Cys Gly Gly Gly Thr
65                   70                  75                  80

Cys Ala Cys Cys Thr Thr Cys Ala Gly Cys Ala Gly Cys Thr Ala Thr
```

```
                    85                  90                  95
Cys Ala Gly Ala Thr Gly Gly Cys Thr Gly Gly Thr Gly Cys
                100                 105                 110
Gly Ala Cys Ala Gly Gly Cys Gly Cys Cys Gly Gly Cys Ala Ala
                115                 120                 125
Gly Gly Gly Gly Cys Thr Gly Gly Ala Ala Thr Gly Gly Thr Cys
            130                 135                 140
Ala Gly Cys Gly Cys Gly Ala Thr Thr Ala Ala Thr Ala Ala Gly Ala
145                 150                 155                 160
Gly Cys Gly Gly Thr Ala Gly Thr Gly Ala Cys Ala Cys Ala Thr Cys
                165                 170                 175
Ala Thr Ala Cys Gly Gly Thr Cys Gly Gly Cys Gly Gly Thr Gly
                180                 185                 190
Ala Ala Gly Gly Gly Cys Cys Gly Thr Gly Cys Ala Cys Cys Ala
                195                 200                 205
Thr Cys Thr Cys Gly Ala Gly Gly Ala Cys Ala Ala Cys Gly Gly
                210                 215                 220
Gly Cys Ala Gly Ala Gly Cys Ala Cys Ala Cys Thr Gly Thr Ala Cys
225                 230                 235                 240
Cys Thr Gly Cys Ala Gly Ala Thr Gly Ala Ala Cys Ala Gly Cys Cys
                245                 250                 255
Thr Cys Ala Gly Gly Cys Thr Gly Ala Gly Gly Ala Cys Ala Cys
                260                 265                 270
Cys Gly Cys Thr Gly Thr Thr Thr Ala Cys Thr Ala Cys Thr Gly Cys
                275                 280                 285
Gly Cys Cys Ala Ala Ala Gly Gly Thr Thr Cys Thr Gly Cys Thr Ala
            290                 295                 300
Gly Thr Thr Ala Cys Ala Thr Ala Ala Cys Thr Gly Cys Thr Gly Cys
305                 310                 315                 320
Thr Ala Cys Cys Ala Thr Cys Gly Ala Cys Gly Cys Ala Thr Gly Gly
                325                 330                 335
Gly Gly Cys Cys Ala Cys Gly Gly Gly Ala Cys Cys Gly Ala Ala Gly
                340                 345                 350
Thr Cys Ala Thr Cys Gly Thr Cys Thr Cys Cys Thr Cys Cys
                355                 360                 365

<210> SEQ ID NO 217
<211> LENGTH: 327
<212> TYPE: PRT
<213> ORGANISM: Artificial Sequence
<220> FEATURE:
<223> OTHER INFORMATION: SS01-13-S5; S5-2.GKNG Ab VL (nucleic acid)

<400> SEQUENCE: 217

Gly Cys Cys Cys Thr Gly Ala Cys Thr Cys Ala Gly Cys Cys Gly Thr
1               5                   10                  15
Cys Cys Thr Cys Gly Gly Thr Gly Thr Cys Ala Gly Cys Ala Ala Ala
                20                  25                  30
Cys Cys Cys Thr Gly Gly Gly Gly Ala Ala Ala Cys Thr Gly Cys Gly
            35                  40                  45
Cys Gly Thr Ala Thr Cys Ala Cys Cys Thr Gly Cys Thr Cys Cys Gly
        50                  55                  60
Gly Thr Gly Gly Thr Gly Cys Thr Ala Gly Cys Ala Gly Thr Gly Gly
65                  70                  75                  80
Cys Thr Ala Thr Gly Gly Thr Thr Ala Thr Gly Gly Cys Thr Gly Gly
```

```
                85                  90                  95
Thr Ala Thr Cys Ala Gly Cys Ala Gly Ala Ala Gly Cys Cys Thr Ala
            100                 105                 110
Gly Cys Ala Gly Thr Gly Cys Cys Cys Thr Cys Thr Cys Ala Cys
            115                 120                 125
Thr Gly Thr Gly Ala Thr Cys Thr Ala Cys Ala Ala Ala Gly Ala Cys
            130                 135                 140
Thr Cys Thr Gly Ala Ala Ala Gly Ala Cys Cys Thr Cys Gly Gly
145                 150                 155                 160
Ala Cys Ala Thr Cys Cys Cys Thr Thr Cys Ala Cys Gly Ala Thr Thr
            165                 170                 175
Cys Thr Cys Cys Gly Gly Thr Thr Cys Cys Thr Cys Thr Thr Cys Cys
            180                 185                 190
Gly Gly Cys Thr Cys Cys Ala Cys Ala Cys Ala Cys Ala Cys Ala Thr
            195                 200                 205
Thr Ala Ala Cys Cys Ala Thr Cys Ala Gly Cys Gly Gly Gly Gly Thr
            210                 215                 220
Cys Cys Ala Ala Gly Cys Cys Gly Ala Gly Ala Cys Gly Ala Gly
225                 230                 235                 240
Gly Cys Thr Gly Thr Ala Thr Ala Thr Thr Cys Thr Gly Thr Gly
            245                 250                 255
Gly Gly Ala Ala Thr Gly Ala Thr Gly Ala Cys Thr Ala Cys Ala Gly
            260                 265                 270
Cys Ala Gly Thr Gly Ala Thr Ala Gly Thr Gly Ala Thr Ala Thr
            275                 280                 285
Gly Thr Cys Gly Gly Thr Gly Thr Ala Thr Thr Thr Gly Gly Gly Gly
            290                 295                 300
Cys Cys Gly Gly Gly Ala Cys Ala Ala Cys Cys Cys Thr Gly Ala Cys
305                 310                 315                 320
Cys Gly Thr Cys Cys Thr Ala
            325

<210> SEQ ID NO 218
<211> LENGTH: 10
<212> TYPE: PRT
<213> ORGANISM: Artificial Sequence
<220> FEATURE:
<223> OTHER INFORMATION: 1-7A-IT VH-CDR1

<400> SEQUENCE: 218

Gly Phe Thr Phe Ser Ser Phe Asn Met Phe
1               5                   10

<210> SEQ ID NO 219
<211> LENGTH: 17
<212> TYPE: PRT
<213> ORGANISM: Artificial Sequence
<220> FEATURE:
<223> OTHER INFORMATION: 1-7A-IT VH-CDR2

<400> SEQUENCE: 219

Gln Ile Ser Ser Ser Gly Ser Ser Thr Asn Tyr Ala Pro Ala Val Lys
1               5                   10                  15
Gly

<210> SEQ ID NO 220
<211> LENGTH: 10
<212> TYPE: PRT
```

```
<213> ORGANISM: Artificial Sequence
<220> FEATURE:
<223> OTHER INFORMATION: Low-PI; 1-30; 1-17; 1-32; 4-11; 6-10 VH-CDR1

<400> SEQUENCE: 220

Gly Phe Asp Phe Glu Ser Phe Asn Met Phe
1               5                   10

<210> SEQ ID NO 221
<211> LENGTH: 17
<212> TYPE: PRT
<213> ORGANISM: Artificial Sequence
<220> FEATURE:
<223> OTHER INFORMATION: Low-PI; 1-30; 1-17; 1-32; 4-11; 6-10 VH-CDR2

<400> SEQUENCE: 221

Gln Ile Ser Ser Ser Glu Glu Asp Glu Asn Tyr Ala Pro Ala Val Lys
1               5                   10                  15

Gly

<210> SEQ ID NO 222
<211> LENGTH: 10
<212> TYPE: PRT
<213> ORGANISM: Artificial Sequence
<220> FEATURE:
<223> OTHER INFORMATION: 2-13D VH-CDR1

<400> SEQUENCE: 222

Gly Phe Thr Phe Ser Ser His Gly Met Phe
1               5                   10

<210> SEQ ID NO 223
<211> LENGTH: 10
<212> TYPE: PRT
<213> ORGANISM: Artificial Sequence
<220> FEATURE:
<223> OTHER INFORMATION: 2-13D-37; 2-13D-37-1.5W-41; 2-13D-37-3W-16
      VH-CDR1

<400> SEQUENCE: 223

Gly Phe Asp Phe Ser Ser His Gly Met Phe
1               5                   10

<210> SEQ ID NO 224
<211> LENGTH: 7
<212> TYPE: PRT
<213> ORGANISM: Artificial Sequence
<220> FEATURE:
<223> OTHER INFORMATION: 1-7A-IT VH-CDR2

<400> SEQUENCE: 224

Glu Asn Asn Lys Arg Pro Ser
1               5

<210> SEQ ID NO 225
<211> LENGTH: 13
<212> TYPE: PRT
<213> ORGANISM: Artificial Sequence
<220> FEATURE:
<223> OTHER INFORMATION: Low-PI; 1-30 VL-CDR1

<400> SEQUENCE: 225

Ser Gly Gly Gly Ser Glu Glu Glu Gln Tyr Tyr Tyr Gly
1               5                   10

<210> SEQ ID NO 226
```

```
<211> LENGTH: 7
<212> TYPE: PRT
<213> ORGANISM: Artificial Sequence
<220> FEATURE:
<223> OTHER INFORMATION: Low-PI VH-CDR2

<400> SEQUENCE: 226

Glu Asp Glu Glu Arg Pro Ser
1               5

<210> SEQ ID NO 227
<211> LENGTH: 10
<212> TYPE: PRT
<213> ORGANISM: Artificial Sequence
<220> FEATURE:
<223> OTHER INFORMATION: Low-PI; 1-30; 1-17; 1-32 VL-CDR3

<400> SEQUENCE: 227

Gly Ser Trp Asp Ser Glu Asp Glu Asp His
1               5                   10

<210> SEQ ID NO 228
<211> LENGTH: 7
<212> TYPE: PRT
<213> ORGANISM: Artificial Sequence
<220> FEATURE:
<223> OTHER INFORMATION: 1-30; 1-32 VL-CDR2

<400> SEQUENCE: 228

Gln Asp Glu Glu Arg Pro Ser
1               5

<210> SEQ ID NO 229
<211> LENGTH: 7
<212> TYPE: PRT
<213> ORGANISM: Artificial Sequence
<220> FEATURE:
<223> OTHER INFORMATION: 1-17 VL-CDR2

<400> SEQUENCE: 229

Glu Asp Glu Gln Arg Pro Ser
1               5

<210> SEQ ID NO 230
<211> LENGTH: 7
<212> TYPE: PRT
<213> ORGANISM: Artificial Sequence
<220> FEATURE:
<223> OTHER INFORMATION: 4-11 Ab VL-CDR2

<400> SEQUENCE: 230

Glu Asp His Glu Arg Pro Ser
1               5

<210> SEQ ID NO 231
<211> LENGTH: 10
<212> TYPE: PRT
<213> ORGANISM: Artificial Sequence
<220> FEATURE:
<223> OTHER INFORMATION: 4-11 VL-CDR3

<400> SEQUENCE: 231

Gly Ser Trp Asp Ser Ser Asp Glu Asp His
1               5                   10

<210> SEQ ID NO 232
<211> LENGTH: 7
```

```
<212> TYPE: PRT
<213> ORGANISM: Artificial Sequence
<220> FEATURE:
<223> OTHER INFORMATION: 6-10 VL-CDR2

<400> SEQUENCE: 232

Gln Asp Leu Leu Arg Pro Ser
1               5

<210> SEQ ID NO 233
<211> LENGTH: 10
<212> TYPE: PRT
<213> ORGANISM: Artificial Sequence
<220> FEATURE:
<223> OTHER INFORMATION: 6-10 VL-CDR3

<400> SEQUENCE: 233

Gly Ser Trp Asp Ser Leu Ser Ser Ser His
1               5                   10

<210> SEQ ID NO 234
<211> LENGTH: 131
<212> TYPE: PRT
<213> ORGANISM: Artificial Sequence
<220> FEATURE:
<223> OTHER INFORMATION: 1-7A-IT VH

<400> SEQUENCE: 234

Ala Val Thr Leu Asp Glu Ser Gly Gly Gly Leu Gln Thr Pro Gly Gly
1               5                   10                  15

Ala Leu Arg Leu Ser Cys Lys Ala Ser Gly Phe Thr Phe Ser Ser Phe
            20                  25                  30

Asn Met Phe Trp Val Arg Gln Ala Pro Gly Lys Gly Leu Glu Tyr Val
        35                  40                  45

Ser Gln Ile Ser Ser Ser Gly Ser Ser Thr Asn Tyr Ala Pro Ala Val
    50                  55                  60

Lys Gly Arg Ala Thr Ile Ser Arg Asp Asn Gly Gln Ser Thr Leu Tyr
65                  70                  75                  80

Leu Gln Met Asn Ser Leu Arg Ala Glu Asp Thr Gly Thr Tyr Tyr Cys
                85                  90                  95

Ala Lys Ser Ser Tyr Asp Cys Pro Tyr Gly His Cys Ser Ser Gly Val
            100                 105                 110

Asp Ser Ala Gly Glu Ile Asp Ala Trp Gly His Gly Thr Glu Val Ile
        115                 120                 125

Val Ser Ser
    130

<210> SEQ ID NO 235
<211> LENGTH: 131
<212> TYPE: PRT
<213> ORGANISM: Artificial Sequence
<220> FEATURE:
<223> OTHER INFORMATION: Low-PI; 1-30; 1-17; 1-32; 4-11; 6-10 VH

<400> SEQUENCE: 235

Ala Val Thr Leu Asp Glu Ser Gly Gly Gly Leu Gln Thr Pro Gly Gly
1               5                   10                  15

Ala Leu Arg Leu Ser Cys Lys Ala Ser Gly Phe Asp Phe Glu Ser Phe
            20                  25                  30

Asn Met Phe Trp Val Arg Gln Ala Pro Gly Lys Gly Leu Glu Tyr Val
        35                  40                  45
```

Ser Gln Ile Ser Ser Ser Glu Asp Glu Asn Tyr Ala Pro Ala Val
    50              55                  60

Lys Gly Arg Ala Thr Ile Ser Arg Asp Asn Gly Gln Ser Thr Leu Tyr
 65                  70                  75                  80

Leu Gln Met Asn Ser Leu Arg Ala Glu Asp Thr Gly Thr Tyr Tyr Cys
                 85                  90                  95

Ala Lys Ser Ser Tyr Asp Cys Pro Tyr Gly His Cys Ser Ser Gly Val
            100                 105                 110

Asp Ser Ala Gly Glu Ile Asp Ala Trp Gly His Gly Thr Glu Val Ile
            115                 120                 125

Val Ser Ser
    130

<210> SEQ ID NO 236
<211> LENGTH: 129
<212> TYPE: PRT
<213> ORGANISM: Artificial Sequence
<220> FEATURE:
<223> OTHER INFORMATION: 2-13D VH

<400> SEQUENCE: 236

Ala Val Thr Leu Asp Glu Ser Gly Gly Gly Leu Gln Thr Pro Gly Gly
 1               5                  10                  15

Ala Leu Arg Leu Ser Cys Ser Ala Ser Gly Phe Thr Phe Ser Ser His
                 20                  25                  30

Gly Met Phe Trp Val Arg Gln Ala Pro Gly Lys Gly Leu Glu Tyr Val
             35                  40                  45

Ser Glu Ile Thr Asn Asp Gly Ser Gly Thr Asn Tyr Gly Ser Ala Val
    50                  55                  60

Lys Gly Arg Ala Thr Ile Ser Arg Asp Asn Gly Gln Ser Thr Leu Tyr
 65                  70                  75                  80

Leu Gln Met Asn Ser Leu Arg Ala Glu Asp Thr Gly Thr Tyr Phe Cys
                 85                  90                  95

Ala Arg Ser Thr Tyr Glu Cys Pro Gly Gly Phe Ser Cys Trp Gly Asp
            100                 105                 110

Thr Gly Gln Ile Asp Ala Trp Gly His Gly Thr Glu Val Ile Val Ser
            115                 120                 125

Ser

<210> SEQ ID NO 237
<211> LENGTH: 129
<212> TYPE: PRT
<213> ORGANISM: Artificial Sequence
<220> FEATURE:
<223> OTHER INFORMATION: 2-13D-37-1.5W-41 VH

<400> SEQUENCE: 237

Ala Val Thr Leu Asp Glu Ser Gly Gly Gly Leu Gln Thr Pro Gly Gly
 1               5                  10                  15

Ala Leu Arg Leu Ser Cys Ser Ala Ser Gly Phe Asp Phe Ser Ser His
                 20                  25                  30

Gly Met Phe Trp Val Arg Gln Ala Pro Gly Lys Gly Leu Glu Tyr Val
             35                  40                  45

Ser Glu Ile Thr Asn Asp Gly Ser Gly Thr Asn Tyr Gly Ser Ala Val
    50                  55                  60

Lys Gly Arg Ala Thr Ile Ser Arg Asp Asn Gly Gln Ser Thr Leu Tyr
 65                  70                  75                  80

Leu Gln Met Asn Ser Leu Arg Ala Glu Asp Thr Gly Thr Tyr Phe Cys
                85                  90                  95

Ala Arg Ser Ser Tyr Val Cys Pro Gly Gly Phe Ser Cys Trp Gly Asp
            100                 105                 110

Thr Gly Gln Ile Asp Ala Trp Gly His Gly Thr Glu Val Ile Val Ser
        115                 120                 125

Ser

<210> SEQ ID NO 238
<211> LENGTH: 107
<212> TYPE: PRT
<213> ORGANISM: Artificial Sequence
<220> FEATURE:
<223> OTHER INFORMATION: 1-7A-IT VL

<400> SEQUENCE: 238

Ala Leu Thr Gln Pro Ser Ser Val Ser Ala Asn Pro Gly Glu Thr Val
1               5                   10                  15

Lys Ile Thr Cys Ser Gly Gly Ser Tyr Ala Gly Ser Tyr Tyr Tyr
            20                  25                  30

Gly Trp Tyr Gln Gln Lys Pro Gly Ser Ala Pro Val Thr Leu Ile Tyr
        35                  40                  45

Glu Asn Asn Lys Arg Pro Ser Asp Ile Pro Ser Arg Phe Ser Gly Ser
    50                  55                  60

Thr Ser Gly Ser Thr Ala Thr Leu Thr Ile Thr Gly Val Gln Ala Gly
65                  70                  75                  80

Asp Glu Ala Asp Tyr Tyr Cys Gly Ser Trp Asp Ser Ser Asn Gly Gly
                85                  90                  95

Ile Phe Gly Ala Gly Thr Thr Leu Thr Val Leu
            100                 105

<210> SEQ ID NO 239
<211> LENGTH: 107
<212> TYPE: PRT
<213> ORGANISM: Artificial Sequence
<220> FEATURE:
<223> OTHER INFORMATION: Low-PI VL

<400> SEQUENCE: 239

Ala Leu Thr Gln Pro Ser Ser Val Ser Ala Asn Pro Gly Glu Thr Val
1               5                   10                  15

Lys Ile Thr Cys Ser Gly Gly Ser Glu Glu Glu Gln Tyr Tyr Tyr
            20                  25                  30

Gly Trp Tyr Gln Gln Lys Pro Gly Ser Ala Pro Val Thr Leu Ile Tyr
        35                  40                  45

Glu Asp Glu Glu Arg Pro Ser Asp Ile Pro Ser Arg Phe Ser Gly Ser
    50                  55                  60

Thr Ser Gly Ser Thr Ala Thr Leu Thr Ile Thr Gly Val Gln Ala Gly
65                  70                  75                  80

Asp Glu Ala Asp Tyr Tyr Cys Gly Ser Trp Asp Ser Glu Asp Glu Asp
                85                  90                  95

His Phe Gly Ala Gly Thr Thr Leu Thr Val Leu
            100                 105

<210> SEQ ID NO 240
<211> LENGTH: 107
<212> TYPE: PRT
<213> ORGANISM: Artificial Sequence
<220> FEATURE:

<223> OTHER INFORMATION: 1-30 VL

<400> SEQUENCE: 240

Ala Leu Thr Gln Pro Ser Ser Val Ser Ala Asn Pro Gly Glu Thr Val
1               5                   10                  15

Lys Ile Thr Cys Ser Gly Gly Ser Glu Glu Glu Gln Tyr Tyr Tyr
            20                  25                  30

Gly Trp Tyr Gln Gln Lys Pro Gly Ser Ala Pro Val Thr Leu Ile Tyr
            35                  40                  45

Gln Asp Glu Glu Arg Pro Ser Asp Ile Pro Ser Arg Phe Ser Gly Ser
        50                  55                  60

Thr Ser Gly Ser Thr Ala Thr Leu Thr Ile Thr Gly Val Gln Ala Gly
65                  70                  75                  80

Asp Glu Ala Asp Tyr Tyr Cys Gly Ser Trp Asp Ser Glu Asp Glu Asp
                85                  90                  95

His Phe Gly Ala Gly Thr Thr Leu Thr Val Leu
            100                 105

<210> SEQ ID NO 241
<211> LENGTH: 107
<212> TYPE: PRT
<213> ORGANISM: Artificial Sequence
<220> FEATURE:
<223> OTHER INFORMATION: 1-17 VL

<400> SEQUENCE: 241

Ala Leu Thr Gln Pro Ser Ser Val Ser Ala Asn Pro Gly Glu Thr Val
1               5                   10                  15

Lys Ile Thr Cys Ser Gly Gly Ser Tyr Ala Gly Ser Tyr Tyr Tyr
            20                  25                  30

Gly Trp Tyr Gln Gln Lys Pro Gly Ser Ala Pro Val Thr Leu Ile Tyr
            35                  40                  45

Glu Asp Glu Gln Arg Pro Ser Asp Ile Pro Ser Arg Phe Ser Gly Ser
        50                  55                  60

Thr Ser Gly Ser Thr Ala Thr Leu Thr Ile Thr Gly Val Gln Ala Gly
65                  70                  75                  80

Asp Glu Ala Asp Tyr Tyr Cys Gly Ser Trp Asp Ser Glu Asp Glu Asp
                85                  90                  95

His Phe Gly Ala Gly Thr Thr Leu Thr Val Leu
            100                 105

<210> SEQ ID NO 242
<211> LENGTH: 107
<212> TYPE: PRT
<213> ORGANISM: Artificial Sequence
<220> FEATURE:
<223> OTHER INFORMATION: 1-32 VL

<400> SEQUENCE: 242

Ala Leu Thr Gln Pro Ser Ser Val Ser Ala Asn Pro Gly Glu Thr Val
1               5                   10                  15

Lys Ile Thr Cys Ser Gly Gly Ser Tyr Ala Gly Ser Tyr Tyr Tyr
            20                  25                  30

Gly Trp Tyr Gln Gln Lys Pro Gly Ser Ala Pro Val Thr Leu Ile Tyr
            35                  40                  45

Gln Asp Glu Glu Arg Pro Ser Asp Ile Pro Ser Arg Phe Ser Gly Ser
        50                  55                  60

Thr Ser Gly Ser Thr Ala Thr Leu Thr Ile Thr Gly Val Gln Ala Gly

```
                65                  70                  75                  80
Asp Glu Ala Asp Tyr Tyr Cys Gly Ser Trp Asp Ser Glu Asp
                    85                  90                  95

His Phe Gly Ala Gly Thr Thr Leu Thr Val Leu
                100                 105

<210> SEQ ID NO 243
<211> LENGTH: 107
<212> TYPE: PRT
<213> ORGANISM: Artificial Sequence
<220> FEATURE:
<223> OTHER INFORMATION: 4-11 VL

<400> SEQUENCE: 243

Ala Leu Thr Gln Pro Ser Ser Val Ser Ala Asn Pro Gly Glu Thr Val
1               5                   10                  15

Lys Ile Thr Cys Ser Gly Gly Ser Tyr Ala Gly Ser Tyr Tyr Tyr
                20                  25                  30

Gly Trp Tyr Gln Gln Lys Pro Gly Ser Ala Pro Val Thr Leu Ile Tyr
            35                  40                  45

Glu Asp His Glu Arg Pro Ser Asp Ile Pro Ser Arg Phe Ser Gly Ser
50                  55                  60

Thr Ser Gly Ser Thr Ala Thr Leu Thr Ile Thr Gly Val Gln Ala Gly
65                  70                  75                  80

Asp Glu Ala Asp Tyr Tyr Cys Gly Ser Trp Asp Ser Asp Glu Asp
                85                  90                  95

His Phe Gly Ala Gly Thr Thr Leu Thr Val Leu
                100                 105

<210> SEQ ID NO 244
<211> LENGTH: 107
<212> TYPE: PRT
<213> ORGANISM: Artificial Sequence
<220> FEATURE:
<223> OTHER INFORMATION: 6-10 VL

<400> SEQUENCE: 244

Ala Leu Thr Gln Pro Ser Ser Val Ser Ala Asn Pro Gly Glu Thr Val
1               5                   10                  15

Lys Ile Thr Cys Ser Gly Gly Ser Tyr Ala Gly Ser Tyr Tyr Tyr
                20                  25                  30

Gly Trp Tyr Gln Gln Lys Pro Gly Ser Ala Pro Val Thr Leu Ile Tyr
            35                  40                  45

Gln Asp Leu Leu Arg Pro Ser Asp Ile Pro Ser Arg Phe Ser Gly Ser
50                  55                  60

Thr Ser Gly Ser Thr Ala Thr Leu Thr Ile Thr Gly Val Gln Ala Gly
65                  70                  75                  80

Asp Glu Ala Asp Tyr Tyr Cys Gly Ser Trp Asp Ser Leu Ser Ser Ser
                85                  90                  95

His Phe Gly Ala Gly Thr Thr Leu Thr Val Leu
                100                 105

<210> SEQ ID NO 245
<211> LENGTH: 103
<212> TYPE: PRT
<213> ORGANISM: Artificial Sequence
<220> FEATURE:
<223> OTHER INFORMATION: 2-13D; 2-13D-37-1.5W-41; 2-13D-37-3W-16 VL

<400> SEQUENCE: 245
```

```
Ala Leu Thr Gln Pro Ser Ser Val Ser Ala Asn Pro Gly Glu Thr Ala
1               5                   10                  15

Lys Ile Thr Cys Ser Gly Gly Val Tyr Ser Tyr Gly Trp Phe Gln Gln
                20                  25                  30

Lys Pro Gly Ser Ala Leu Val Thr Val Ile Tyr Trp Asp Asp Glu Arg
            35                  40                  45

Pro Ser Asp Ile Pro Ser Arg Phe Ser Gly Ala Leu Ser Gly Ser Thr
        50                  55                  60

Asn Thr Leu Thr Ile Thr Gly Val Gln Ala Glu Asp Glu Ala Asp Tyr
65                  70                  75                  80

Tyr Cys Gly Thr Glu Asp Ile Ser Gly Thr Ala Gly Val Phe Gly Ala
                85                  90                  95

Gly Thr Thr Leu Thr Val Leu
                100
```

<210> SEQ ID NO 246
<211> LENGTH: 20
<212> TYPE: PRT
<213> ORGANISM: Artificial Sequence
<220> FEATURE:
<223> OTHER INFORMATION: 2-13D-37-1.5W-41 VH-CDR3

<400> SEQUENCE: 246

```
Ser Ser Tyr Val Cys Pro Gly Gly Phe Ser Cys Trp Gly Asp Thr Gly
1               5                   10                  15

Gln Ile Asp Ala
            20
```

<210> SEQ ID NO 247
<211> LENGTH: 20
<212> TYPE: PRT
<213> ORGANISM: Artificial Sequence
<220> FEATURE:
<223> OTHER INFORMATION: 2-13D-37-3W-16 VH-CDR3

<400> SEQUENCE: 247

```
Ser Asn Tyr Ala Cys Pro Gly Gly Phe Ser Cys Trp Gly Asp Thr Gly
1               5                   10                  15

Gln Ile Asp Ala
            20
```

<210> SEQ ID NO 248
<211> LENGTH: 8
<212> TYPE: PRT
<213> ORGANISM: Artificial Sequence
<220> FEATURE:
<223> OTHER INFORMATION: 2-13D; 2-13D-37-1.5W-41; 2-13D-37-3W-16 VL-CDR1

<400> SEQUENCE: 248

```
Ser Gly Gly Val Tyr Ser Tyr Gly
1               5
```

<210> SEQ ID NO 249
<211> LENGTH: 122
<212> TYPE: PRT
<213> ORGANISM: Artificial Sequence
<220> FEATURE:
<223> OTHER INFORMATION: S5-2.GKNG VH

<400> SEQUENCE: 249

```
Ala Val Thr Leu Asp Glu Ser Gly Gly Gly Leu Gln Thr Pro Gly Gly
1               5                   10                  15
```

```
Ala Leu Arg Leu Ser Cys Lys Ala Ser Gly Phe Thr Phe Ser Ser Tyr
            20                  25                  30

Gln Met Gly Trp Val Arg Gln Ala Pro Gly Lys Gly Leu Glu Trp Val
        35                  40                  45

Ser Ala Ile Asn Lys Gly Gly Ser Asp Thr Ser Tyr Gly Ser Ala Val
 50                  55                  60

Lys Gly Arg Ala Thr Ile Ser Arg Asp Asn Gly Gln Ser Thr Leu Tyr
 65                  70                  75                  80

Leu Gln Met Asn Ser Leu Arg Ala Glu Asp Thr Ala Val Tyr Phe Cys
                85                  90                  95

Ala Lys Gly Ser Ala Ser Tyr Ile Thr Ala Ala Thr Ile Asp Ala Trp
            100                 105                 110

Gly His Gly Thr Glu Val Ile Val Ser Ser
            115                 120
```

<210> SEQ ID NO 250
<211> LENGTH: 129
<212> TYPE: PRT
<213> ORGANISM: Artificial Sequence
<220> FEATURE:
<223> OTHER INFORMATION: 2-13D-37 VH

<400> SEQUENCE: 250

```
Ala Val Thr Leu Asp Glu Ser Gly Gly Gly Leu Gln Thr Pro Gly Gly
 1               5                  10                  15

Ala Leu Arg Leu Ser Cys Ser Ala Ser Gly Phe Asp Phe Ser Ser His
            20                  25                  30

Gly Met Phe Trp Val Arg Gln Ala Pro Gly Lys Gly Leu Glu Tyr Val
        35                  40                  45

Ser Glu Ile Thr Asn Asp Gly Ser Gly Thr Asn Tyr Gly Ser Ala Val
 50                  55                  60

Lys Gly Arg Ala Thr Ile Ser Arg Asp Asn Gly Gln Ser Thr Leu Tyr
 65                  70                  75                  80

Leu Gln Met Asn Ser Leu Arg Ala Glu Asp Thr Gly Thr Tyr Phe Cys
                85                  90                  95

Ala Arg Ser Thr Tyr Glu Cys Pro Gly Phe Ser Cys Trp Gly Asp
            100                 105                 110

Thr Gly Gln Ile Asp Ala Trp Gly His Gly Thr Glu Val Ile Val Ser
            115                 120                 125

Ser
```

<210> SEQ ID NO 251
<211> LENGTH: 129
<212> TYPE: PRT
<213> ORGANISM: Artificial Sequence
<220> FEATURE:
<223> OTHER INFORMATION: 2-13D-37-3W-16 VH

<400> SEQUENCE: 251

```
Ala Val Thr Leu Asp Glu Ser Gly Gly Gly Leu Gln Thr Pro Gly Gly
 1               5                  10                  15

Ala Leu Arg Leu Ser Cys Ser Ala Ser Gly Phe Asp Phe Ser Ser His
            20                  25                  30

Gly Met Phe Trp Val Arg Gln Ala Pro Gly Lys Gly Leu Glu Tyr Val
        35                  40                  45

Ser Glu Ile Thr Asn Asp Gly Ser Gly Thr Asn Tyr Gly Ser Ala Val
 50                  55                  60
```

-continued

Lys Gly Arg Ala Thr Ile Ser Arg Asp Asn Gly Gln Ser Thr Leu Tyr
65                  70                  75                  80

Leu Gln Met Asn Ser Leu Arg Ala Glu Asp Thr Gly Thr Tyr Phe Cys
            85                  90                  95

Ala Arg Ser Asn Tyr Ala Cys Pro Gly Gly Phe Ser Cys Trp Gly Asp
        100                 105                 110

Thr Gly Gln Ile Asp Ala Trp Gly His Gly Thr Glu Val Ile Val Ser
    115                 120                 125

Ser

<210> SEQ ID NO 252
<211> LENGTH: 10
<212> TYPE: PRT
<213> ORGANISM: Artificial Sequence
<220> FEATURE:
<223> OTHER INFORMATION: SS01-13 VH-CDR2

<400> SEQUENCE: 252

Ala Ile Asn Lys Ser Gly Ser Asp Thr Ser
1               5                   10

<210> SEQ ID NO 253
<211> LENGTH: 10
<212> TYPE: PRT
<213> ORGANISM: Artificial Sequence
<220> FEATURE:
<223> OTHER INFORMATION: S5-2.GKNG VH-CDR2

<400> SEQUENCE: 253

Ala Ile Asn Lys Gly Gly Ser Asp Thr Ser
1               5                   10

<210> SEQ ID NO 254
<211> LENGTH: 393
<212> TYPE: DNA
<213> ORGANISM: Artificial Sequence
<220> FEATURE:
<223> OTHER INFORMATION: 1-7A-IT VH

<400> SEQUENCE: 254
gccgtgacgt tggatgaatc cgggggcggc ctccagacgc ccggaggagc gctccgcctc    60
agctgcaagg cctctgggtt caccttcagc agcttcaaca tgttctgggt gcgacaggcg   120
cccggcaagg gctggaata cgtctcgcag attagcagca gtggtagtag cacaaactac   180
gcacccgcgg tgaaaggccg tgccaccatc tcgaggga cgggcagag cacactgtat   240
ctgcagatga acagcctgcg cgctgaagac accggcacct actactgcgc caaaagtagt   300
tatgactgtc cttacggtca ttgtagtagt ggtgttgata tgctggtga atcgacgca   360
tggggccacg ggaccgaagt catcgtctcc tcc                               393

<210> SEQ ID NO 255
<211> LENGTH: 393
<212> TYPE: DNA
<213> ORGANISM: Artificial Sequence
<220> FEATURE:
<223> OTHER INFORMATION: Low-PI VH

<400> SEQUENCE: 255
gccgtgacgt tggatgaatc cgggggcggc ctccagacgc ccggaggagc gctccgcctc    60
agctgcaagg cctctgggtt caccttcagc agcttcaaca tgttctgggt gcgacaggcg   120

```
cccggcaagg ggctggaata cgtctcgcag attagcagca gtggtagtag cacaaactac    180
gcacccgcgg tgaaaggccg tgccaccatc tcgagggaca cgggcagag cacactgtat     240 ctgcagatga acagcctgcg cgctgaagac accggcacct actactgcgc caaaagtagt    300
tatgactgtc cttacggtca ttgtagtagt ggtgttgata gtgctggtga gatcgacgca    360
tggggccacg ggaccgaagt catcgtctcc tcc                                 393
```

<210> SEQ ID NO 256
<211> LENGTH: 393
<212> TYPE: DNA
<213> ORGANISM: Artificial Sequence
<220> FEATURE:
<223> OTHER INFORMATION: 1-30; 1-17; 1-32; 4-11; 6-10 VH

<400> SEQUENCE: 256

```
gccgtgacgt tggatgaatc cgggggcggc ctccagacgc ccggaggagc gctccgcctc    60
agctgcaagg cctctggctt tgattttgaa agcttcaaca tgttctgggt gcgacaggcg    120
cccggcaagg ggctggaata cgtctcgcag attagcagca gtgaagaaga tgaaaactac    180
gcacccgcgg tgaaaggccg tgccaccatc tcgagggaca cgggcagag cacactgtat     240 ctgcagatga acagcctgcg cgctgaagac accggcacct actactgcgc caaaagtagt    300
tatgactgtc cttacggtca ttgtagtagt ggtgttgata gtgctggtga gatcgacgca    360
tggggccacg ggaccgaagt catcgtctcc tcc                                 393
```

<210> SEQ ID NO 257
<211> LENGTH: 387
<212> TYPE: PRT
<213> ORGANISM: Artificial Sequence
<220> FEATURE:
<223> OTHER INFORMATION: 2-13D VH

<400> SEQUENCE: 257

```
Gly Cys Cys Gly Thr Gly Ala Cys Gly Thr Gly Gly Ala Cys Gly
1               5                   10                  15

Ala Gly Thr Cys Cys Gly Gly Gly Gly Cys Gly Gly Cys Cys Thr
            20                  25                  30

Cys Cys Ala Gly Ala Cys Gly Cys Cys Gly Gly Ala Gly Gly Ala
        35                  40                  45

Gly Cys Gly Cys Thr Cys Cys Gly Cys Cys Thr Cys Ala Gly Cys Thr
    50                  55                  60

Gly Cys Ala Gly Cys Gly Cys Thr Cys Cys Gly Gly Cys Thr Thr
65                  70                  75                  80

Cys Ala Cys Cys Thr Thr Cys Ala Gly Cys Ala Gly Cys Thr Ala Thr
                85                  90                  95

Gly Gly Cys Ala Thr Gly Thr Thr Cys Thr Gly Gly Thr Gly Cys
            100                 105                 110

Gly Ala Cys Ala Gly Gly Cys Gly Cys Cys Cys Gly Gly Cys Ala Ala
        115                 120                 125

Gly Gly Gly Gly Thr Thr Gly Gly Ala Ala Thr Ala Thr Gly Thr Cys
    130                 135                 140

Thr Cys Gly Gly Ala Gly Ala Thr Thr Ala Cys Cys Ala Ala Thr Gly
145                 150                 155                 160

Ala Thr Gly Gly Thr Ala Gly Thr Gly Gly Cys Ala Cys Ala Ala Ala
                165                 170                 175

Cys Thr Ala Cys Gly Gly Gly Thr Cys Gly Gly Cys Gly Thr Gly
            180                 185                 190
```

```
Ala Ala Gly Gly Gly Cys Cys Gly Thr Gly Cys Cys Ala Cys Cys Ala
            195                 200                 205
Thr Cys Thr Cys Gly Ala Gly Gly Ala Cys Ala Ala Cys Gly Gly
        210                 215                 220
Gly Cys Ala Gly Ala Gly Cys Ala Cys Ala Cys Thr Gly Thr Ala Thr
225                 230                 235                 240
Cys Thr Gly Cys Ala Gly Ala Thr Gly Ala Cys Ala Gly Cys Cys
            245                 250                 255
Thr Cys Ala Gly Gly Cys Thr Gly Ala Gly Gly Ala Cys Ala Cys
            260                 265                 270
Cys Gly Gly Cys Ala Cys Cys Thr Ala Cys Thr Thr Cys Thr Gly Cys
            275                 280                 285
Gly Cys Cys Ala Gly Ala Thr Cys Thr Ala Cys Thr Thr Ala Thr Gly
            290                 295                 300
Ala Ala Thr Gly Thr Cys Cys Thr Gly Gly Thr Gly Gly Thr Thr
305                 310                 315                 320
Thr Ala Gly Thr Thr Gly Thr Gly Gly Gly Thr Gly Ala Thr
                325                 330                 335
Ala Cys Thr Gly Gly Thr Cys Ala Ala Ala Thr Ala Gly Ala Cys Gly
            340                 345                 350
Cys Ala Thr Gly Gly Cys Cys Ala Cys Gly Gly Gly Ala Cys
        355                 360                 365
Cys Gly Ala Ala Gly Thr Cys Ala Thr Cys Gly Thr Cys Thr Cys Cys
            370                 375                 380
Thr Cys Cys
385

<210> SEQ ID NO 258
<211> LENGTH: 387
<212> TYPE: PRT
<213> ORGANISM: Artificial Sequence
<220> FEATURE:
<223> OTHER INFORMATION: 2-13D-37-1.5W-41 VH

<400> SEQUENCE: 258

Gly Cys Cys Gly Thr Gly Ala Cys Gly Thr Thr Gly Gly Ala Cys Gly
1               5                   10                  15
Ala Gly Thr Cys Cys Gly Gly Gly Gly Cys Gly Gly Cys Cys Thr
            20                  25                  30
Cys Cys Ala Gly Ala Cys Gly Cys Cys Gly Gly Ala Gly Ala
        35                  40                  45
Gly Cys Gly Cys Thr Cys Cys Gly Cys Thr Thr Ala Gly Cys Thr
    50                  55                  60
Gly Cys Ala Gly Cys Gly Cys Thr Cys Gly Gly Gly Thr Thr
65                  70                  75                  80
Cys Gly Ala Thr Thr Cys Ala Gly Cys Ala Gly Cys Cys Ala Thr
                85                  90                  95
Gly Gly Cys Ala Thr Gly Thr Cys Thr Gly Gly Thr Gly Cys
            100                 105                 110
Gly Ala Cys Ala Gly Gly Cys Cys Cys Cys Gly Gly Cys Ala Ala
            115                 120                 125
Gly Gly Gly Gly Thr Thr Gly Gly Ala Ala Thr Ala Thr Gly Thr Cys
            130                 135                 140
Thr Cys Gly Gly Ala Gly Ala Thr Thr Ala Cys Cys Ala Ala Thr Gly
145                 150                 155                 160
```

Ala Thr Gly Gly Thr Ala Gly Thr Gly Gly Cys Ala Cys Ala Ala Ala
                165                 170                 175

Cys Thr Ala Cys Gly Gly Thr Cys Gly Gly Cys Gly Gly Thr Gly
            180                 185                 190

Ala Ala Gly Gly Gly Cys Cys Gly Thr Gly Cys Cys Ala Cys Cys Ala
            195                 200                 205

Thr Cys Thr Cys Gly Ala Gly Gly Ala Cys Ala Ala Cys Gly Gly
        210                 215                 220

Gly Cys Ala Gly Ala Gly Cys Ala Cys Ala Cys Thr Gly Thr Ala Thr
225                 230                 235                 240

Cys Thr Gly Cys Ala Gly Ala Thr Gly Ala Ala Cys Ala Gly Cys Cys
            245                 250                 255

Thr Cys Ala Gly Gly Cys Thr Gly Ala Gly Gly Ala Cys Ala Cys
        260                 265                 270

Cys Gly Gly Cys Ala Cys Cys Thr Ala Cys Thr Thr Cys Thr Gly Cys
            275                 280                 285

Gly Cys Cys Ala Gly Ala Thr Cys Thr Thr Cys Thr Thr Ala Thr Gly
290                 295                 300

Thr Thr Thr Gly Thr Cys Cys Gly Gly Thr Gly Gly Thr Thr Thr
305                 310                 315                 320

Thr Ala Gly Thr Thr Gly Thr Thr Gly Gly Gly Gly Thr Gly Ala Thr
            325                 330                 335

Ala Cys Thr Gly Gly Thr Cys Ala Ala Ala Thr Ala Gly Ala Cys Gly
            340                 345                 350

Cys Ala Thr Gly Gly Gly Gly Cys Cys Ala Cys Gly Gly Gly Ala Cys
            355                 360                 365

Cys Gly Ala Ala Gly Thr Cys Ala Thr Cys Gly Thr Cys Thr Cys Cys
        370                 375                 380

Thr Cys Cys
385

<210> SEQ ID NO 259
<211> LENGTH: 387
<212> TYPE: PRT
<213> ORGANISM: Artificial Sequence
<220> FEATURE:
<223> OTHER INFORMATION: 2-13D-37-3W-16 VH

<400> SEQUENCE: 259

Gly Cys Cys Gly Thr Gly Ala Cys Gly Thr Thr Gly Gly Ala Cys Gly
1               5                   10                  15

Ala Gly Thr Cys Cys Gly Gly Gly Gly Cys Gly Gly Cys Cys Thr
            20                  25                  30

Cys Cys Ala Gly Ala Cys Gly Cys Cys Gly Gly Ala Gly Gly Ala
        35                  40                  45

Gly Cys Gly Cys Thr Cys Cys Gly Cys Cys Thr Thr Ala Gly Cys Thr
        50                  55                  60

Gly Cys Ala Gly Cys Gly Cys Cys Thr Cys Gly Gly Thr Thr
65                  70                  75                  80

Cys Gly Ala Thr Thr Cys Ala Gly Cys Ala Gly Cys Cys Ala Thr
        85                  90                  95

Gly Gly Cys Ala Thr Gly Thr Cys Thr Gly Gly Gly Thr Gly Cys
            100                 105                 110

Gly Ala Cys Ala Gly Gly Cys Gly Cys Cys Gly Gly Cys Ala Ala
        115                 120                 125

```
Gly Gly Gly Gly Thr Gly Ala Ala Thr Ala Thr Gly Thr Cys
        130                 135                 140

Thr Cys Gly Gly Ala Gly Ala Thr Ala Cys Cys Ala Ala Thr Gly
145                 150                 155                 160

Ala Thr Gly Gly Thr Ala Gly Thr Gly Gly Cys Ala Cys Ala Ala
            165                 170                 175

Cys Thr Ala Cys Gly Gly Thr Cys Gly Gly Cys Gly Gly Thr Gly
            180                 185                 190

Ala Ala Gly Gly Gly Cys Cys Gly Thr Gly Cys Ala Cys Cys Ala
            195                 200                 205

Thr Cys Thr Cys Gly Ala Gly Gly Ala Cys Ala Ala Cys Gly Gly
            210                 215                 220

Gly Cys Ala Gly Ala Gly Cys Ala Cys Ala C

Ala Ala Gly Cys Cys Thr Gly Cys Ala Gly Thr Cys Cys Cys
            100                 105                 110

Thr Thr Gly Thr Cys Ala Cys Thr Gly Thr Gly Ala Thr Cys Thr Ala
            115                 120                 125

Cys Thr Gly Gly Gly Ala Thr Gly Ala Thr Gly Ala Gly Ala Gly Ala
            130                 135                 140

Cys Cys Cys Thr Cys Gly Gly Ala Cys Thr Cys Cys Thr Thr
145                 150                 155                 160

Cys Ala Cys Gly Ala Thr Thr Cys Thr Cys Cys Gly Gly Thr Gly Cys
            165                 170                 175

Cys Cys Thr Ala Thr Cys Cys Gly Gly Cys Thr Cys Cys Ala Cys Ala
            180                 185                 190

Ala Ala Cys Ala Cys Ala Thr Thr Ala Ala Cys Ala Thr Cys Ala
            195                 200                 205

Cys Thr Gly Gly Gly Thr Cys Cys Ala Ala Gly Cys Cys Gly Ala
            210                 215                 220

Ala Gly Ala Cys Gly Ala Gly Gly Cys Thr Gly Ala Thr Thr Ala Thr
225                 230                 235                 240

Thr Ala Thr Thr Gly Thr Gly Gly Ala Cys Thr Gly Ala Ala Gly
            245                 250                 255

Ala Cys Ala Thr Cys Ala Gly Cys Gly Gly Cys Ala Cys Thr Gly Cys
            260                 265                 270

Thr Gly Gly Thr Gly Thr Ala Thr Thr Thr Gly Gly Gly Cys Cys
            275                 280                 285

Gly Gly Gly Ala Cys Ala Ala Cys Cys Cys Thr Gly Ala Cys Cys Gly
            290                 295                 300

Thr Cys Cys Thr Gly
305

<210> SEQ ID NO 261
<211> LENGTH: 321
<212> TYPE: PRT
<213> ORGANISM: Artificial Sequence
<220> FEATURE:
<223> OTHER INFORMATION: 1-7A-IT VL

<400> SEQUENCE: 261

Gly Cys Cys Cys Thr Gly Ala Cys Thr Cys Ala Gly Cys Cys Gly Thr
1               5                   10                  15

Cys Cys Thr Cys Gly Gly Thr Gly Thr Cys Ala Gly Cys Ala Ala Ala
            20                  25                  30

Cys Cys Cys Ala Gly Gly Ala Gly Ala Ala Cys Cys Gly Thr Cys
            35                  40                  45

Ala Ala Gly Ala Thr Cys Ala Cys Cys Thr Gly Cys Thr Cys Cys Gly
            50                  55                  60

Gly Gly Gly Gly Thr Gly Cys Ala Gly Cys Thr Ala Thr Gly Cys
65                  70                  75                  80

Thr Gly Gly Ala Ala Gly Thr Thr Ala Cys Thr Ala Thr Ala Thr
            85                  90                  95

Gly Gly Cys Thr Gly Gly Thr Ala Thr Cys Ala Gly Cys Ala Gly Ala
            100                 105                 110

Ala Gly Cys Cys Thr Gly Gly Cys Ala Gly Thr Gly Cys Cys Cys Cys
            115                 120                 125

Thr Gly Thr Cys Ala Cys Thr Cys Thr Gly Ala Thr Cys Thr Ala Thr
            130                 135                 140

Gly Ala Ala Ala Ala Cys Ala Ala Cys Ala Gly Ala Gly Ala Cys
145                 150                 155                 160

Cys Cys Thr Cys Gly Gly Ala Cys Ala Thr Cys Cys Thr Thr Cys
                165                 170                 175

Ala Cys Gly Ala Thr Thr Cys Thr Cys Cys Gly Gly Thr Cys Cys
                180                 185                 190

Ala Cys Ala Thr Cys Thr Gly Gly Cys Thr Cys Cys Ala Cys Ala Gly
            195                 200                 205

Cys Cys Ala Cys Ala Cys Thr Ala Ala Cys Cys Ala Thr Cys Ala Cys
210                 215                 220

Thr Gly Gly Gly Thr Cys Cys Ala Ala Gly Cys Cys Gly Gly Cys
225                 230                 235                 240

Gly Ala Cys Gly Ala Gly Gly Cys Thr Gly Ala Thr Thr Ala Thr Thr
            245                 250                 255

Ala Cys Thr Gly Thr Gly Gly Ala Gly Cys Thr Gly Gly Gly Ala
            260                 265                 270

Cys Ala Gly Thr Ala Gly Cys Ala Ala Thr Gly Gly Thr Gly Gly Thr
            275                 280                 285

Ala Thr Ala Thr Thr Thr Gly Gly Gly Cys Cys Gly Gly Gly Ala
            290                 295                 300

Cys Ala Ala Cys Cys Cys Thr Gly Ala Cys Cys Gly Thr Cys Cys Thr
305                 310                 315                 320

Ala

<210> SEQ ID NO 262
<211> LENGTH: 321
<212> TYPE: PRT
<213> ORGANISM: Artificial Sequence
<220> FEATURE:
<223> OTHER INFORMATION: Low-PI VL

<400> SEQUENCE: 262

Gly Cys Cys Cys Thr Gly Ala Cys Thr Cys Ala Gly Cys Cys Gly Thr
1               5                   10                  15

Cys Cys Thr Cys Gly Gly Thr Gly Thr Cys Ala Gly Cys Ala Ala Ala
                20                  25                  30

Cys Cys Cys Ala Gly Gly Ala Gly Ala Ala Cys Cys Gly Thr Cys
            35                  40                  45

Ala Ala Gly Ala Thr Cys Ala Cys Thr Gly Cys Thr Cys Cys Gly
            50                  55                  60

Gly Gly Gly Gly Thr Gly Gly Cys Ala Gly Cys Thr Ala Thr Gly Cys
65                  70                  75                  80

Thr Gly Gly Ala Ala Gly Thr Thr Ala Cys Thr Ala Thr Ala Thr
                85                  90                  95

Gly Gly Cys Thr Gly Gly Thr Ala Cys Ala Gly Cys Ala Gly Ala
            100                 105                 110

Ala Gly Cys Cys Thr Gly Gly Cys Ala Gly Gly Cys Cys Cys Cys
            115                 120                 125

Thr Gly Thr Cys Ala Cys Thr Cys Thr Gly Ala Thr Cys Thr Ala Thr
130                 135                 140

Gly Ala Ala Ala Ala Cys Ala Ala Cys Ala Ala Gly Ala Gly Ala Cys
145                 150                 155                 160

Cys Cys Thr Cys Gly Gly Ala Cys Ala Thr Cys Cys Thr Thr Cys
                165                 170                 175

Ala Cys Gly Ala Thr Cys Thr Cys Cys Gly Gly Thr Cys Cys
                180                 185                 190

Ala Cys Ala Thr Cys Thr Gly Gly Cys Thr Cys Ala Cys Ala Gly
            195                 200                 205

Cys Cys Ala Cys Ala Cys Thr Ala Ala Cys Cys Ala Thr Cys Ala Cys
            210                 215                 220

Thr Gly Gly Gly Gly Thr Cys Cys Ala Ala Gly Cys Cys Gly Gly Cys
225                 230                 235                 240

Gly Ala Cys Gly Ala Gly Gly Cys Thr Gly Ala Thr Thr Ala Thr Thr
                245                 250                 255

Ala Cys Thr Gly Thr Gly Gly Gly Ala Gly Cys Thr Gly Gly Gly Ala
            260                 265                 270

Cys Ala Gly Thr Ala Gly Cys Ala Ala Thr G

```
                    210                 215                 220

Thr Gly Gly Gly Thr Cys Cys Ala Ala Gly Cys Cys Gly Cys
225                 230                 235                 240

Gly Ala Cys Gly Ala Gly Gly Cys Thr Gly Ala Thr Ala Thr Thr
            245                 250                 255

Ala Cys Thr Gly Thr Gly Gly Ala Gly Cys Thr Gly Gly Ala
        260                 265                 270

Cys Ala Gly Thr Gly Ala Ala Gly Ala Thr Gly Ala Ala Gly Ala Thr
            275                 280                 285

Cys Ala Thr Thr Thr Thr Gly Gly Gly Cys Gly Gly Gly Ala
        290                 295                 300

Cys Ala Ala Cys Cys Cys Thr Gly Ala Cys Cys Gly Thr Cys Cys Thr
305                 310                 315                 320

Ala
```

<210> SEQ ID NO 264
<211> LENGTH: 321
<212> TYPE: PRT
<213> ORGANISM: Artificial Sequence
<220> FEATURE:
<223> OTHER INFORMATION: 1-17 VL

<400> SEQUENCE: 264

```
Gly Cys Cys Cys Thr Gly Ala Cys Thr Cys Ala Gly Cys Cys Gly Thr
1               5                   10                  15

Cys Cys Thr Cys Gly Gly Thr Gly Thr Cys Ala Gly Cys Ala Ala Ala
                20                  25                  30

Cys Cys Cys Ala Gly Gly Ala Gly Ala Ala Ala Cys Cys Gly Thr Cys
            35                  40                  45

Ala Ala Gly Ala Thr Cys Ala Cys Cys Thr Gly Cys Thr Cys Cys Gly
        50                  55                  60

Gly Gly Gly Gly Thr Gly Gly Cys Ala Gly Cys Thr Ala Thr Gly Cys
65                  70                  75                  80

Thr Gly Gly Ala Ala Gly Thr Thr Ala Cys Thr Ala Thr Ala Thr
                85                  90                  95

Gly Gly Cys Thr Gly Gly Thr Ala Thr Cys Ala Gly Cys Ala Gly Ala
            100                 105                 110

Ala Gly Cys Cys Thr Gly Gly Cys Ala Gly Thr Gly Cys Cys Cys Cys
        115                 120                 125

Thr Gly Thr Cys Ala Cys Thr Cys Thr Gly Ala Thr Cys Thr Ala Thr
    130                 135                 140

Gly Ala Ala Gly Ala Thr Gly Ala Ala Cys Ala Gly Ala Gly Ala Cys
145                 150                 155                 160

Cys Cys Thr Cys Gly Gly Ala Cys Ala Thr Cys Cys Cys Thr Thr Cys
                165                 170                 175

Ala Cys Gly Ala Thr Thr Cys Thr Cys Cys Gly Gly Thr Thr Cys Cys
            180                 185                 190

Ala Cys Ala Thr Cys Thr Gly Gly Cys Thr Cys Cys Ala Cys Ala Gly
        195                 200                 205

Cys Cys Ala Cys Ala Cys Thr Ala Ala Cys Cys Ala Thr Cys Ala Cys
    210                 215                 220

Thr Gly Gly Gly Gly Thr Cys Cys Ala Ala Gly Cys Cys Gly Gly Cys
225                 230                 235                 240

Gly Ala Cys Gly Ala Gly Gly Cys Thr Gly Ala Thr Thr Ala Thr Thr
                245                 250                 255
```

Ala Cys Thr Gly Thr Gly Gly Ala Gly Cys Thr Gly Gly Ala
        260                 265                 270

Cys Ala Gly Thr Gly Ala Ala Gly Ala Thr Gly Ala Ala Gly Ala Thr
        275                 280                 285

Cys Ala Thr Thr Thr Thr Gly Gly Gly Cys Cys Gly Gly Gly Ala
        290                 295                 300

Cys Ala Ala Cys Cys Cys Thr Gly Ala Cys Cys Gly Thr Cys Thr
305                 310                 315                 320

Ala

<210> SEQ ID NO 265
<211> LENGTH: 321
<212> TYPE: PRT
<213> ORGANISM: Artificial Sequence
<220> FEATURE:
<223> OTHER INFORMATION: 1-32 VL

<400> SEQUENCE: 265

Gly Cys Cys Cys Thr Gly Ala Cys Thr Cys Ala Gly Cys Cys Gly Thr
1               5                   10                  15

Cys Cys Thr Cys Gly Gly Thr Gly Thr Cys Ala Gly Cys Ala Ala Ala
            20                  25                  30

Cys Cys Cys Ala Gly Gly Ala Gly Ala Ala Cys Cys Gly Thr Cys
        35                  40                  45

Ala Ala Gly Ala Thr Cys Ala Cys Thr Gly Cys Thr Cys Cys Gly
    50                  55                  60

Gly Gly Gly Gly Thr Ala Gly Cys Ala Gly Thr Ala Thr Gly Cys
65                  70                  75                  80

Thr Gly Gly Ala Ala Gly Thr Thr Ala Cys Thr Ala Thr Ala Thr
            85                  90                  95

Gly Gly Cys Thr Gly Gly Thr Ala Cys Ala Gly Cys Ala Gly Ala
            100                 105                 110

Ala Gly Cys Cys Thr Gly Gly Cys Ala Gly Thr Gly Cys Cys Cys Cys
        115                 120                 125

Thr Gly Thr Cys Ala Cys Thr Cys Thr Gly Ala Thr Cys Th

```
Cys Ala Thr Thr Thr Gly Gly Gly Cys Cys Gly Gly Ala
            290             295             300

Cys Ala Ala Cys Cys Cys Thr Gly Ala Cys Cys Gly Thr Cys Cys Thr
305                 310                 315                 320

Ala
```

<210> SEQ ID NO 266
<211> LENGTH: 321
<212> TYPE: PRT
<213> ORGANISM: Artificial Sequence
<220> FEATURE:
<223> OTHER INFORMATION: 4-11 VL

<400> SEQUENCE: 266

```
Gly Cys Cys Cys Thr Gly Ala Cys Thr Cys Ala Gly Cys Cys Gly Thr
1               5                   10                  15

Cys Cys Thr Cys Gly Gly Thr Gly Thr Cys Ala Gly Cys Ala Ala Ala
                20                  25                  30

Cys Cys Cys Ala Gly Gly Ala Gly Ala Ala Cys Cys Gly Thr Cys
                35                  40                  45

Ala Ala Gly Ala Thr Cys Ala Cys Thr Gly Cys Thr Cys Cys Gly
            50                  55                  60

Gly Gly Gly Gly Thr Gly Gly Cys Ala Gly Cys Thr Ala Thr Gly Cys
65                  70                  75                  80

Thr Gly Gly Ala Ala Gly Thr Thr Ala Cys Thr Ala Thr Ala Thr
                85                  90                  95

Gly Gly Cys Thr Gly Gly Thr Ala Thr Cys Ala Gly Cys Ala Gly Ala
                100                 105                 110

Ala Gly Cys Cys Thr Gly Gly Cys Ala Gly Thr Gly Cys Cys Cys Cys
            115                 120                 125

Thr Gly Thr Cys Ala Cys Thr Cys Thr Gly Ala Thr Cys Thr Ala Thr
            130                 135                 140

Gly Ala Ala Gly Ala Cys Cys Ala Cys Gly Ala Gly Ala Gly Ala Cys
145                 150                 155                 160

Cys Cys Thr Cys Gly Gly Ala Cys Ala Thr Cys Cys

<210> SEQ ID NO 267
<211> LENGTH: 321
<212> TYPE: PRT
<213> ORGANISM: Artificial Sequence
<220> FEATURE:
<223> OTHER INFORMATION: 6-10 VL

<400> SEQUENCE: 267

```
Gly Cys Cys Cys Thr Gly Ala Cys Thr Cys Ala Gly Cys Cys Gly Thr
1               5                   10                  15

Cys Cys Thr Cys Gly Gly Thr Gly Thr Cys Ala Gly Cys Ala Ala Ala
            20                  25                  30

Cys Cys Cys Ala Gly Gly Ala Gly Ala Ala Cys Cys Gly Thr Cys
        35                  40                  45

Ala Ala Gly Ala Thr Cys Ala Cys Cys Thr Gly Cys Thr Cys Cys Gly
    50                  55                  60

Gly Gly Gly Gly Thr Gly Cys Ala Gly Cys Thr Ala Thr Gly Cys
65                  70                  75                  80

Thr Gly Gly Ala Ala Gly Thr Thr Ala Cys Thr Ala Thr Ala Thr
                85                  90                  95

Gly Gly Cys Thr Gly Gly Thr Ala Thr Cys Ala Gly Cys Ala Gly Ala
            100                 105                 110

Ala Gly Cys Cys Thr Gly Gly Cys Ala Gly Thr Gly Cys Cys Cys
    115                 120                 125

Thr Gly Thr Cys Ala Cys Thr Cys Thr Gly Ala Thr Cys Thr Ala Thr
130                 135                 140

Cys Ala Gly Gly Ala Thr Cys Thr Gly Cys Thr Gly Ala Gly Ala Cys
145                 150                 155                 160

Cys Cys Thr Cys Gly Gly Ala Cys Ala Thr Cys Cys Thr Thr Cys
            165                 170                 175

Ala Cys Gly Ala Thr Thr Cys Thr Cys Cys Gly Gly Thr Thr Cys Cys
            180                 185                 190

Ala Cys Ala Thr Cys Thr Gly Gly C

<223> OTHER INFORMATION: 2-13D; 2-13-37; 2-13D-37-1.5W-41;
2-13D-37-3W-16 VL

<400> SEQUENCE: 268

```
Gly Cys Cys Cys Thr Gly Ala Cys Thr Cys Ala Gly Cys Cys Gly Thr
1               5                   10                  15

Cys Cys Thr Cys Gly Gly Thr Gly Thr Cys Ala Gly Cys Ala Ala Ala
            20                  25                  30

Cys Cys Cys Ala Gly Gly Ala Gly Ala Ala Cys Cys Gly Cys Gly
            35                  40                  45

Ala Ala Gly Ala Thr Ala Ala Cys Cys Thr Gly Cys Thr Cys Cys Gly
        50                  55                  60

Gly Gly Gly Gly Thr Gly Thr Gly Ala Thr Ala Gly Cys Thr Ala
65              70                  75                  80

Thr Gly Gly Cys Thr Gly Gly Thr Thr Cys Cys Ala Gly Cys Ala Gly
            85                  90                  95

Ala Ala Gly Cys Cys Thr Gly Gly Cys Ala Gly Thr Gly Cys Cys Cys
        100                 105                 110

Thr Thr Gly Thr Cys Ala Cys Thr Gly Thr Cys Ala Thr Cys Thr Ala
        115                 120                 125

Cys Thr Gly Gly Gly Ala Thr Gly Ala Thr Ala Gly Ala Gly Ala
        130                 135                 140

Cys Cys Cys Thr Cys Gly Gly Ala Cys Ala Cys Cys Cys Thr Thr
145                 150                 155                 160

Cys Ala Cys Gly Ala Thr Thr Cys Thr Cys Cys Gly Gly Thr Gly Cys
            165                 170                 175

Cys Cys Thr Ala Thr Cys Cys Gly Gly Cys Thr Cys Ala Cys Ala
            180                 185                 190

Ala Ala Cys Ala Cys Ala Thr Thr Ala Ala Cys Ala Thr Cys Ala
        195                 200                 205

Cys Thr Gly Gly Gly Thr Cys Cys Ala Ala Gly Cys Cys Gly Ala
        210                 215                 220

Ala Gly Ala Cys Gly Ala Gly Gly Cys Thr Gly Ala Thr Ala Thr
225                 230                 235                 240

Thr Ala Thr Thr Gly Thr Gly Gly Ala Cys Thr Gly Ala Ala Gly
            245                 250                 255

Ala Cys Ala Thr Cys Ala Gly Cys Gly Gly Cys Ala Cys Thr Gly Cys
            260                 265                 270

Thr Gly Gly Thr Gly Thr Ala Thr Thr Thr Gly Gly Gly Cys Cys
            275                 280                 285

Gly Gly Gly Ala Cys Ala Ala Cys Cys Thr Gly Ala Cys Cys Gly
        290                 295                 300

Thr Cys Cys Thr Gly
305
```

<210> SEQ ID NO 269
<211> LENGTH: 366
<212> TYPE: PRT
<213> ORGANISM: Artificial Sequence
<220> FEATURE:
<223> OTHER INFORMATION: S5-2.GKNG VH

<400> SEQUENCE: 269

```
Gly Cys Cys Gly Thr Gly Ala Cys Gly Thr Thr Gly Gly Ala Cys Gly
1               5                   10                  15

Ala Gly Thr Cys Cys Gly Gly Gly Gly Gly Cys Gly Gly Cys Cys Thr
```

```
            20                  25                  30
Cys Cys Ala Gly Ala Gly Cys Cys Gly Gly Ala Gly Gly Ala
        35                  40                  45
Gly Cys Gly Cys Thr Cys Cys Gly Cys Cys Thr Cys Thr Thr
    50                  55                  60
Gly Cys Ala Ala Gly Gly Cys Cys Thr Cys Gly Gly Thr Thr
65                  70                  75                  80
Cys Ala Cys Cys Thr Thr Cys Ala Gly Cys Ala Gly Cys Thr Ala Thr
                85                  90                  95
Cys Ala Gly Ala Thr Gly Gly Gly Cys Thr Gly Gly Thr Gly Cys
                100                 105                 110
Gly Ala Cys Ala Gly Gly Cys Gly Cys Cys Gly Gly Cys Ala Ala
            115                 120                 125
Gly Gly Gly Gly Cys Thr Gly Gly Ala Ala Thr Gly Gly Thr Cys
            130                 135                 140
Ala Gly Cys Gly Cys Gly Ala Thr Thr Ala Ala Thr Ala Ala Gly Gly
145                 150                 155                 160
Gly Cys Gly Gly Thr Ala Gly Thr Gly Ala Cys Ala Cys Ala Thr Cys
                165                 170                 175
Ala Thr Ala Cys Gly Gly Gly Thr Cys Gly Gly Cys Gly Gly Thr Gly
                180                 185                 190
Ala Ala Gly Gly Gly Cys Cys Gly Thr Gly Cys Cys Ala Cys Cys Ala
            195                 200                 205
Thr Cys Thr Cys Gly Ala Gly Gly Ala Cys Ala Ala Cys Gly

```
                    20                  25                  30
Cys Cys Cys Thr Gly Gly Gly Ala Ala Cys Thr Gly Cys Gly
                35                  40                  45
Cys Gly Thr Ala Thr Cys Ala Cys Cys Thr Gly Cys Thr Cys Gly
            50                  55                  60
Gly Thr Gly Gly Thr Gly Cys Thr Ala Gly Cys Ala Gly Thr Gly Gly
65                  70                  75                  80
Cys Thr Ala Thr Gly Gly Thr Thr Ala Thr Gly Cys Thr Gly Gly
                85                  90                  95
Thr Ala Thr Cys Ala Gly Cys Ala Gly Ala Ala Gly Cys Cys Thr Ala

```
                50                  55                  60
Gly Cys Ala Ala Gly Cys Thr Cys Gly Gly Thr Thr
65                  70                  75                  80
Cys Ala Cys Cys Thr Thr Cys Ala Gly Cys Ala Gly Cys Thr Ala Thr
                    85                  90                  95
Cys Ala Gly Ala Thr Gly Gly Cys Thr Gly Gly Thr Gly Cys
                100                 105                 110
Gly Ala Cys Ala Gly Gly Cys Gly Cys Cys Gly Gly Cys Ala Ala
            115                 120                 125
Gly Gly Gly Gly Cys Thr Gly Gly Ala Ala Thr Gly Gly Thr Cys
        130                 135                 140
Gly Gly Thr Gly Thr Thr Ala Thr Thr Ala Ala Cys Ala Ala Gly Thr
145                 150                 155                 160
Cys Thr Gly Gly Thr Ala Gly Thr Gly Ala Cys Ala Cys Ala Thr Cys
                165                 170                 175
Ala Thr Ala Cys Gly Gly Gly Thr Cys Gly Gly Cys Gly Gly Thr Gly
                180                 185                 190
Ala Ala Gly Gly Gly Cys Cys Gly Thr Gly Cys Cys Ala Cys Cys Ala
            195                 200                 205
Thr Cys Thr Cys Gly Ala Gly Gly Ala Cys Ala Ala Cys Gly Gly
        210                 215                 220
Gly Cys Ala Gly Ala Gly Cys Ala Cys Ala Gly Thr Gly Thr Ala Cys
225                 230                 235                 240
Cys Thr Gly Cys Ala Gly Ala Thr Gly Ala Ala Cys Ala Ala Cys Cys
                245                 250                 255
Thr Cys Ala Gly Gly Cys Thr Gly Ala Gly Gly Ala Cys Ala Cys
                260                 265                 270
Cys Gly Cys Thr Gly Thr Thr Thr Ala Cys Thr Thr Cys Thr Gly Cys
            275                 280                 285
Gly Cys Cys Ala Ala Gly Gly Thr Thr Cys Thr Gly Cys Thr Ala
290                 295                 300
Gly Thr Thr Ala Cys Ala Thr Ala Ala Cys Thr Gly Cys Thr Gly Cys
305                 310                 315                 320
Thr Ala Cys Cys Ala Thr Cys Gly Ala Cys Gly Cys Ala Thr Gly Gly
                325                 330                 335
Gly Gly Cys Cys Ala Cys Gly Gly Ala Cys Cys Gly Ala Ala Gly
            340                 345                 350
Thr Cys Ala Thr Cys Gly Thr Cys Thr Cys Cys Thr Cys Cys
        355                 360                 365
```

<210> SEQ ID NO 272
<211> LENGTH: 327
<212> TYPE: PRT
<213> ORGANISM: Artificial Sequence
<220> FEATURE:
<223> OTHER INFORMATION: SS01-13 VL

<400> SEQUENCE: 272

```
Gly Cys Cys Cys Thr Gly Ala Cys Thr Cys Ala Gly Cys Cys Gly Thr
1                   5                   10                  15
Cys Cys Thr Cys Gly Gly Thr Gly Thr Cys Ala Gly Cys Ala Ala Ala
                20                  25                  30
Cys Cys Cys Thr Gly Gly Gly Gly Ala Ala Ala Cys Thr Gly Thr Thr
            35                  40                  45
Cys Gly Thr Ala Thr Cys Ala Cys Cys Thr Gly Cys Thr Cys Gly Gly
```

```
                50                  55                  60
Gly Gly Gly Gly Thr Gly Cys Thr Ala Gly Cys Ala Gly Thr Gly Gly
65                  70                  75                  80

Cys Thr Ala Thr Gly Gly Thr Thr Ala Thr Gly Gly Cys Thr Gly Gly
                85                  90                  95

Thr Ala Thr Cys Ala Gly Cys Ala Gly Ala Ala Gly Cys Cys Thr Ala
                    100                 105                 110

Gly Cys Ala Gly Thr Gly Cys Cys Cys Thr Cys Thr Cys Ala Cys
            115                 120                 125

Thr Gly Thr Gly Ala Thr Cys Thr Ala Cys Ala Ala Gly Ala Cys
        130                 135                 140

Gly Ala Cys Gly Ala Ala Gly Ala Cys Cys Thr Cys Gly Gly
145                 150                 155                 160

Ala Cys Ala Thr Cys Cys Cys Thr Thr Cys Ala Cys Gly Ala Thr Thr
                    165                 170                 175

Cys Thr Cys Cys Gly Gly Thr Thr Cys Cys Thr Cys Thr Cys
                180                 185                 190

Gly Gly Cys Thr Cys Cys Ala Cys Ala Cys Ala Cys Ala Thr
            195                 200                 205

Thr Ala Ala Cys Cys Ala Thr Cys Ala Cys Thr Gly Gly Gly Thr
210                 215                 220

Cys Cys Ala Ala Gly Cys Gly Ala Gly Ala Cys Gly Ala Gly
225                 230                 235                 240

Gly Cys Thr Gly Thr Ala Thr Ala Thr Thr Cys Thr Gly Thr Gly
            245                 250                 255

Gly Gly Ala Ala Thr Gly Ala Thr Gly Ala Cys Thr Ala Cys Ala Gly
                260                 265                 270

Cys Ala Gly Thr Gly Ala Thr Ala Gly Thr Gly Ala Thr Ala Thr
            275                 280                 285

Gly Thr Cys Gly Gly Thr Gly Thr Ala Thr Thr Gly Gly Gly Gly
                290                 295                 300

Cys Cys Gly Gly Gly Ala Cys Ala Ala Cys Cys Thr Gly Ala Cys
305                 310                 315                 320

Cys Gly Thr Cys Cys Thr Ala
                325

<210> SEQ ID NO 273
<211> LENGTH: 387
<212> TYPE: PRT
<213> ORGANISM: Artificial Sequence
<220> FEATURE:
<223> OTHER INFORMATION: 2-13D-37 VH

<400> SEQUENCE: 273

Gly Cys Cys Gly Thr Gly Ala Cys Gly Thr Thr Gly Gly Ala Cys Gly
1               5                   10                  15

Ala Gly Thr Cys Cys Gly Gly Gly Gly Cys Gly Gly Cys Cys Thr
                20                  25                  30

Cys Cys Ala Gly Ala Cys Gly Cys Cys Gly Gly Ala Gly Ala
            35                  40                  45

Gly Cys Gly Cys Thr Cys Cys Gly Cys Thr Ala Gly Cys Thr
        50                  55                  60

Gly Cys Ala Gly Cys Gly Cys Cys Thr Cys Gly Gly Gly Thr
65                  70                  75                  80

Cys Gly Ala Thr Thr Thr Cys Ala Gly Cys Ala Gly Cys Cys Ala Thr
```

-continued

```
                85                  90                  95
Gly Gly Cys Ala Thr Gly Thr Thr Cys Thr Gly Gly Thr Gly Cys
            100                 105                 110
Gly Ala Cys Ala Gly Gly Cys Gly Cys Cys Gly Gly Cys Ala Ala
            115                 120                 125
Gly Gly Gly Gly Thr Thr Gly Gly Ala Ala Thr Ala Thr Gly Thr Cys
    130                 135                 140
Thr Cys Gly Gly Ala Gly Ala Thr Thr Ala Cys Cys Ala Ala Thr Gly
145                 150                 155                 160
Ala Thr Gly Gly Thr Ala Gly Thr Gly Gly Cys Ala Cys Ala Ala Ala
                165                 170                 175
Cys Thr Ala Cys Gly Gly Gly Thr Cys Gly Gly Cys Gly Gly Thr Gly
                180                 185                 190
Ala Ala Gly Gly Gly Cys Cys Gly Thr Gly Cys Cys Ala Cys Cys Ala
            195                 200                 205
Thr Cys Thr Cys Gly Ala Gly Gly Gly Ala Cys Ala Ala Cys Gly Gly
            210                 215                 220
Gly Cys Ala Gly Ala Gly Cys Ala Cys Ala Cys Thr Gly Thr Ala Thr
225                 230                 235                 240
Cys Thr Gly Cys Ala Gly Ala Thr Gly Ala Ala Cys Ala Gly Cys Cys
                245                 250                 255
Thr Cys Ala Gly Gly Cys Thr Gly Ala Gly Gly Ala Cys Ala Cys
            260                 265                 270
Cys Gly Gly Cys Ala Cys Cys Thr Ala Cys Thr Thr Cys Thr Gly Cys
            275                 280                 285
Gly Cys Cys Ala Gly Ala Thr Cys Thr Ala Cys Thr Ala Thr Gly
    290                 295                 300
Ala Ala Thr Gly Thr Cys Cys Thr Gly Gly Thr Gly Gly Thr Thr Thr
305                 310                 315                 320
Thr Ala Gly Thr Thr Gly Thr Cys Gly Gly Gly Thr Gly Ala Thr
                325                 330                 335
Ala Cys Thr Gly Gly Thr Cys Ala Ala Ala Thr Ala Gly Ala Cys Gly
            340                 345                 350
Cys Ala Thr Gly Gly Gly Gly Cys Cys Ala Cys Gly Gly Gly Ala Cys
    355                 360                 365
Cys Gly Ala Ala Gly Thr Cys Ala Thr Cys Gly Thr Cys Thr Cys Cys
    370                 375                 380
Thr Cys Cys
385
```

USE OF ANTI-FAM19A5 ANTIBODIES FOR TREATING ATHEROSCLEROSIS

CROSS-REFERENCE TO RELATED APPLICATIONS

This PCT application claims the priority benefit of U.S. Provisional Application No. 62/785,569, filed Dec. 27, 2018, which is incorporated herein by reference in its entirety.

REFERENCE TO SEQUENCE LISTING SUBMITTED ELECTRONICALLY

The content of the electronically submitted sequence listing in ASCII text file (Name: 3763_015PC01_SeqListing_ST25.txt; Size: 262,323 bytes; and Date of Creation: Dec. 26, 2019) filed with the application is incorporated herein by reference in its entirety.

FIELD OF THE DISCLOSURE

The present disclosure provides methods for the treatment of atherosclerosis in a subject (e.g., a human) using antagonists against family with sequence similarity 19, member A5 (FAM19A5) (e.g., anti-FAM19A5 antibody) or a composition comprising such antagonists.

BACKGROUND OF THE DISCLOSURE

Atherosclerosis is a disease characterized by the narrowing of blood vessels (e.g., artery) due to the accumulation of lipid-laden macrophages, resulting in lesion or plaque formation. Lu, H., et al., *Arterioscler Thromb Vasc Biol* 35(3): 485-491 (2015). Initially, there are usually no symptoms, but if left untreated, atherosclerosis can lead to coronary artery disease, stroke, peripheral artery disease, or kidney problems, depending on the arteries affected.

Atherosclerosis generally starts when a person is young and worsens with age. By the age of 65, almost all people are affected to some degree. Current treatment options generally include diet, exercise, and medications, such as agents that lower cholesterol (e.g., statins), that regulate blood pressure (e.g., antihypertensive drugs), and/or that decrease clotting (e.g., aspirin). Bergheanu, S. C., et al., *Neth Heart J* 25(4): 231-242 (2017). In severe cases, more invasive procedures may be necessary (e.g., percutaneous coronary intervention, coronary artery bypass graft, or carotid endarterectomy). Despite such treatment options, atherosclerosis remains the number one cause of death and disability in the developed world. Herrington, W., et al., *Circ Res* 118(4):535-46 (2016). Moreover, many of the available treatment options can have undesirable side effects. Stroes, E. S., et al., *Eur Heart J* 36(17):1012-22 (2015).

Accordingly, there remains a need for more effective and comprehensive treatment options for atherosclerosis.

BRIEF SUMMARY OF THE DISCLOSURE

Provided herein is a method of increasing a phagocytosis of low density lipoprotein (LDL) by macrophages in a subject in need thereof, comprising administering to the subject an antagonist against a family with sequence similarity 19, member A5 (FAM19A5) protein (FAM19A5 antagonist).

In some embodiments, the phagocytosis of LDL by macrophages is increased by at least about 5%, at least about 10%, at least about 20%, at least about 30%, at least about 40%, at least about 50%, at least about 60%, at least about 70%, at least about 80%, or at least about 90% or more, compared to a reference (e.g., corresponding value in a subject that did not receive the FAM19A5 antagonist or corresponding value in the subject prior to administering the FAM19A5 antagonist). In certain embodiments, the increase in phagocytosis of LDL by macrophages occurs at an atherosclerotic lesion. In further embodiments, the LDL comprises oxidized LDL. In some embodiments, the atherosclerotic lesion site is in a blood vessel. In certain embodiments, the blood vessel comprises an artery, vein, capillaries, or combinations thereof. In some embodiments, the artery is an aorta.

Also disclosed herein is a method of increasing a migration and/or accumulation of macrophages at an atherosclerotic lesion site in a subject in need thereof, comprising administering to the subject an antagonist against a family with sequence similarity 19, member A5 (FAM19A5) protein (FAM19A5 antagonist).

In some embodiments, the migration and/or accumulation of macrophages at an atherosclerotic lesion site is increased by at least about 5%, at least about 10%, at least about 20%, at least about 30%, at least about 40%, at least about 50%, at least about 60%, at least about 70%, at least about 80%, or at least about 90% or more, compared to a reference (e.g., corresponding value in a subject that did not receive the FAM19A5 antagonist or corresponding value in the subject prior to administering the FAM19A5 antagonist). In further embodiments, the increased migration and/or accumulation of macrophages at an atherosclerotic lesion site is associated with a decrease in a low density lipoprotein (LDL) level in the subject.

Present disclosure provides a method of reducing a low density lipoprotein (LDL) level in a subject in need thereof, comprising administering to the subject an antagonist against a family with sequence similarity 19, member A5 (FAM19A5) protein (FAM19A5 antagonist). In some embodiments, the LDL level in the subject is reduced by at least about 5%, at least about 10%, at least about 20%, at least about 30%, at least about 40%, at least about 50%, at least about 60%, at least about 70%, at least about 80%, or at least about 90% or more, compared to a reference (e.g., corresponding value in a subject that did not receive the FAM19A5 antagonist or corresponding value in the subject prior to administering the FAM19A5 antagonist).

In some embodiments, a subject disclosed herein (e.g., treated with a FAM19A5 antagonist) exhibits one or more of the following properties: (i) an increased phagocytosis of LDL by macrophages; (ii) an increased migration and/or accumulation of macrophages to an atherosclerotic lesion site; and (iii) a reduced LDL level.

Provided herein is a method of treating an atherosclerosis in a subject in need thereof, comprising administering to the subject an antagonist against a family with sequence similarity 19, member A5 (FAM19A5) protein (FAM19A5 antagonist).

In some embodiments, the atherosclerosis is associated with a disease comprising coronary heart disease (CHD), carotid artery disease, peripheral artery disease, chronic kidney disease, stroke, retinal artery occlusion, abdominal pain caused by intestinal damage, peritonitis, or combinations thereof. In certain embodiments, the atherosclerosis is associated with a high fat and/or high cholesterol (hypercholesterolemic) diet. In further embodiments, the atherosclerosis is associated with an increased total cholesterol level, increased triglyceride level, increased LDL level, decreased HDL level, increased number and/or retention of oxo-LDL-induced foam cells within a plaque, or combinations thereof, compared to a subject without atherosclerosis (e.g., a healthy subject).

In some embodiments, administering a FAM19A5 antagonist (e.g., anti-FAM19A5 antibody) reduces a low density lipoprotein (LDL) level in the subject by at least about 5%, at least about 10%, at least about 20%, at least about 30%, at least about 40%, at least about 50%, at least about 60%, at least about 70%, at least about 80%, or at least about 90% or more, compared to a reference (e.g., corresponding value in a subject that did not receive the FAM19A5 antagonist or corresponding value in the subject prior to administering the FAM19A5 antagonist).

In some embodiments, administering a FAM19A5 antagonist increases a migration and/or accumulation of macrophages at an atherosclerotic lesion site in an aorta of a subject by at least about 5%, at least about 10%, at least about 20%, at least about 30%, at least about 40%, at least about 50%, at least about 60%, at least about 70%, at least about 80%, or at least about 90% or more, compared to a reference (e.g., corresponding value in a subject that did not receive the FAM19A5 antagonist or corresponding value in the subject prior to administering the FAM19A5 antagonist).

In some embodiments, administering a FAM19A5 antagonist increases a phagocytosis of LDL by macrophages by at least about 5%, at least about 10%, at least about 20%, at least about 30%, at least about 40%, at least about 50%, at least about 60%, at least about 70%, at least about 80%, or at least about 90% or more, compared to a reference (e.g., corresponding value in a subject that did not receive the FAM19A5 antagonist or corresponding value in the subject prior to administering the FAM19A5 antagonist). In certain embodiments, the increase in phagocytosis of LDL by macrophages occurs at an atherosclerotic lesion site in a blood vessel. In some embodiments, the LDL comprises oxidized LDL. In certain embodiments, the blood vessel comprises an artery, vein, capillaries, or combinations thereof. In some embodiments, the artery is an aorta.

In some embodiments, the FAM19A5 antagonist is an antisense oligonucleotide, siRNA, shRNA, miRNA, dsRNA targeting FAM19A5, aptamer, PNA, or a vector including the same.

In some embodiments, the FAM19A5 antagonist is an antibody, or an antigen-binding portion thereof, that specifically binds to the FAM19A5 protein ("anti-FAM19A5 antibody"). In certain embodiments, wherein the anti-FAM19A5 antibody exhibits a property selected from: (a) binds to soluble human FAM19A5 with a $K_D$ of 10 nM or less as measured by enzyme-linked immunosorbent assay (ELISA); (b) binds to membrane bound human FAM19A5 with a $K_D$ of 10 nM or less as measured by ELISA; and (c) both (a) and (b).

In some embodiments, the anti-FAM19A5 antibody cross-competes for binding to a human FAM19A5 epitope with a reference antibody, wherein the reference antibody is selected from the group consisting of the antibodies in TABLES 2-5. In certain embodiments, the reference antibody comprises heavy chain CDR1, CDR2, and CDR3 and light chain CDR1, CDR2, and CDR3, wherein the heavy chain CDR1 comprises the amino acid sequence set forth as SEQ ID NO: 14, the heavy chain CDR2 comprises the amino acid sequence set forth as SEQ ID NO: 15, the heavy chain CDR3 comprises the amino acid sequence set forth as SEQ ID NO: 16, the light chain CDR1 comprises the amino acid sequence set forth as SEQ ID NO: 26, the light chain CDR2 comprises the amino acid sequence set forth as SEQ ID NO: 27, and the light chain CDR3 comprises the amino acid sequence set forth as SEQ ID NO: 28.

In some embodiments, the anti-FAM19A5 antibody specifically binds to the same FAM19A5 epitope as a reference antibody, wherein the reference antibody is selected from the group consisting of TABLES 2-5. In certain embodiments, the reference antibody comprises heavy chain CDR1, CDR2, and CDR3 and light chain CDR1, CDR2, and CDR3, wherein the heavy chain CDR1 comprises the amino acid sequence set forth as SEQ ID NO: 14, the heavy chain CDR2 comprises the amino acid sequence set forth as SEQ ID NO: 15, the heavy chain CDR3 comprises the amino acid sequence set forth as SEQ ID NO: 16, the light chain CDR1 comprises the amino acid sequence set forth as SEQ ID NO: 26, the light chain CDR2 comprises the amino acid sequence set forth as SEQ ID NO: 27, and the light chain CDR3 comprises the amino acid sequence set forth as SEQ ID NO: 28.

In some embodiments, the anti-FAM19A5 antibody specifically binds to at least one FAM19A5 epitope, which is SEQ ID NO: 6 or SEQ ID NO: 9.

In some embodiments, the anti-FAM19A5 antibody comprises a heavy chain CDR1, CDR2, and CDR3, and a light chain CDR1, CDR2, and CDR3, (i) wherein the heavy chain CDR1 comprises a CDR1 selected from the group consisting of CDR1s in TABLE 2; (ii) wherein the heavy chain CDR2 comprises a CDR2 selected from the group consisting of CDR2s in TABLE 2; (iii) wherein the heavy chain CDR3 comprises a CDR3 selected from the group consisting of CDR3s in TABLE 2; (iv) wherein the light chain CDR1 comprises a CDR1 selected from the group consisting of CDR1s in TABLE 3; (v) wherein the light chain CDR2 comprises a CDR2 selected from the group consisting of CDR2s in TABLE 3; and/or (vi) wherein the light chain CDR3 comprises a CDR3 selected from the group consisting of CDR3s in TABLE 3.

In some embodiments, the anti-FAM19A5 antibody comprises a heavy chain CDR1, CDR2, and CDR3, and a light chain CDR1, CDR2, and CDR3, (i) wherein the heavy chain CDR1 comprises the amino acid sequence set forth as SEQ ID NO: 14; (ii) wherein the heavy chain CDR2 comprises the amino acid sequence set forth as SEQ ID NO: 15; (iii) wherein the heavy chain CDR3 comprises the amino acid sequence set forth as SEQ ID NO: 16; (iv) wherein the light chain CDR1 comprises the amino acid sequence set forth as SEQ ID NO: 26; (v) wherein the light chain CDR2 comprises the amino acid sequence set forth as SEQ ID NO: 27; and/or (vi) wherein the light chain CDR3 comprises the amino acid sequence set forth as SEQ ID NO: 28.

In some embodiments, the anti-FAM19A5 antibody comprises a heavy chain CDR1, CDR2, and CDR3, and a light chain CDR1, CDR2, and CDR3, wherein the heavy chain CDR1, CDR2, and CDR3 comprises the amino acid sequence set forth as SEQ ID NOs: 14, 15, and 16, respectively, and the light chain CDR1, CDR2, and CDR3 comprises the amino acid sequence set forth as SEQ ID NOs: 26, 27, and 28, respectively.

In some embodiments, the anti-FAM19A5 antibody comprises a heavy chain variable region (VH) and a light chain variable region (VL), wherein the VH comprises the amino acid sequence set forth as SEQ ID NO: 36.

In some embodiments, the anti-FAM19A5 antibody comprises a heavy chain variable region (VH) and a light chain variable region (VL), wherein the VH comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NO: 36. In certain embodiments, the anti-FAM19A5 antibody comprises a heavy chain variable region (VH) and a light chain variable region (VL), wherein the VL comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NO: 40.

In some embodiments, the anti-FAM19A5 antibody comprises a heavy chain variable region (VH) and a light chain variable region (VL), (i) wherein the VH comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NO: 36; and (ii) wherein the VL comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NO: 40.

In some embodiments, the anti-FAM19A5 antibody comprises a Fab, Fab', F(ab')2, Fv, or single chain Fv (scFv). In certain embodiments, the anti-FAM19A5 antibody is selected from the group consisting of an IgG1, an IgG2, an IgG3, an IgG4, and a variant thereof. In some embodiments, the anti-FAM19A5 antibody is an IgG2, an IgG4, or a combination thereof. In further embodiments, the anti-FAM19A5 antibody comprises an IgG2/IgG4 isotype antibody. In some embodiments, the anti-FAM19A5 antibody comprises a constant region without the Fc function. In some embodiments, the anti-FAM19A5 antibody is a chimeric antibody, a human antibody, or a humanized antibody.

In some embodiments, the FAM19A5 antagonist is linked to a molecule having a second binding moiety, thereby forming a bispecific molecule. In some embodiments, the FAM19A5 antagonist is linked to an agent, thereby forming an immunoconjugate.

In some embodiments, methods disclosed herein further comprise administering a therapeutic agent.

In some embodiments, the FAM19A5 antagonist disclosed herein is formulated with a pharmaceutically acceptable carrier. In some embodiments, the FAM19A5 antagonist is administered intravenously, subcutaneously, intramuscularly, orally, intravitreally, intrathecally, or combinations thereof.

In some embodiments, the subject being treated with the present disclosure is a human.

In some embodiments, methods disclosed herein further comprise administering a cholesterol lowering agent. In certain embodiments, the cholesterol lowering agent is administered subsequent to or concurrently with the FAM19A5 antagonist.

BRIEF DESCRIPTION OF THE DRAWINGS

FIG. 3A show expression in normal mice (i.e., regular diet). FIG. 3B show expression in hypercholesterolemic mice treated with a human IgG control antibody. FIGS. 3C and 3D show expression in mice treated with anti-FAM19A5 antibody at two different concentrations, 5 mg/kg and 10 mg/kg, respectively. Images shown are at 100× magnification.

FIG. 4A shows the phagocytic uptake of the PHRODO™ Green $E.$ $coli$ BioParticles over a course of 22 hours in BV2 cells treated with one of the following: (i) human Fc alone ("1"), (ii) human FAM19A5-Fc protein alone ("2"), or (iii) human FAM19A5-Fc protein in combination with varying concentrations (25 µg/mL ("6"), 12.5 µg/mL ("5"), 6.25 µg/mL ("4"), or 3.125 µg/mL ("3")) of anti-FAM19A5 antibody. Data are shown as mean±S.D. FIG. 4B provides representative immunofluorescence images of BV2 cells treated with one of the following: (i) human Fc alone (left panel), (ii) human FAM19A5-Fc protein alone (center panel), or (iii) human FAM19A5-Fc protein in combination with anti-FAM19A5 antibody (25 µg/mL) (right panel).

FIG. 6A provides representative histogram plots for each of the different treatment groups (value provided in the upper right quandrant represents the percentage of BMDMs that are positive for PHRODO™ expression). FIG. 6B provides a table summarizing the results from three independent experiments. The different BMDM treatment groups shown in FIGS. 6A and 6B include the following: (A1) mouse BMDMs only, (A2) mouse BMDMs+apoptotic thymocytes, (A3) mouse BMDMs+apoptotic thymocytes+control Fc (0.4 µM), (A4) mouse BMDMs+apoptotic thymocytes+control Fc (0.8 µM), (A5) mouse BMDMs+apoptotic thymocytes+FAM19A5-Fc (0.4 µM) and (A6) mouse BMDMs+apoptotic thymocytes+FAM19A5-Fc (0.8 µM).

FIG. 7A provides representative histogram plots for each of the different treatment groups (value provided in the upper right quandrant represents the percentage of BMDMs that are positive for PHRODO™ expression). FIG. 7B provides a table summarizing the results from three independent experiments. The different BMDM treatment groups shown in FIGS. 7A and 7B include the following: (B1) mouse BMDMs+apoptotic thymocytes+FAM19A5-Fc (0.8 μM)+hIgG1 control antibody (25 nM), (B2) mouse BMDMs+apoptotic thymocytes+FAM19A5-Fc (0.8 μM)+hIgG1 control antibody (50 nM), (B3) mouse BMDMs+apoptotic thymocytes+FAM19A5-Fc (0.8 μM)+ "3-2" anti-FAM19A5 antibody (25 nM), (B4) mouse BMDMs+apoptotic thymocytes+FAM19A5-Fc (0.8 μM)+ "3-2" anti-FAM19A5 antibody (50 nM), (B5) mouse BMDMs+apoptotic thymocytes+FAM19A5-Fc (0.8 μM)+ "1-65" anti-FAM19A5 antibody (25 nM), and (B6) mouse BMDMs+apoptotic thymocytes+FAM19A5-Fc (0.8 μM)+ "1-65" anti-FAM19A5 antibody (50 nM).

DETAILED DESCRIPTION OF THE DISCLOSURE

Figure 1:
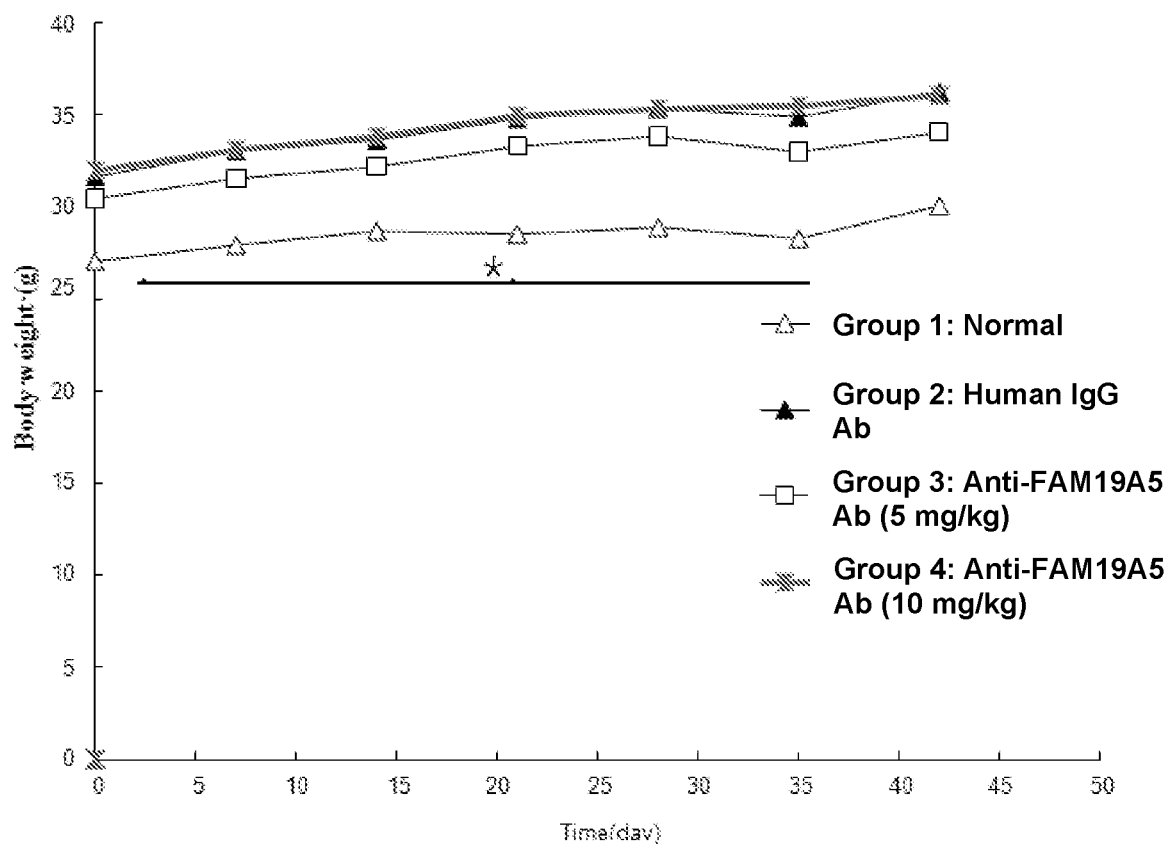
FIG. 1 shows the effect of anti-FAM19A5 antibody on the body weight of hypercholesterolemic mice. The mice were treated with either human IgG control antibody (Group 2, black triangle) or anti-FAM19A5 antibody at two different concentrations, 5 mg/kg (Group 3, open square) or 10 mg/kg (Group 4). Normal mice (i.e., regular diet; Group 1, open triangle) were used as a control. Body weight was measured at 7 different time points over a course of about 42 days.

To facilitate an understanding of the disclosure disclosed herein, a number of terms and phrases are defined. Additional definitions are set forth throughout the detailed description.

I. Definitions

Throughout this disclosure, the term "a" or "an" entity refers to one or more of that entity; for example, "an antibody," is understood to represent one or more antibodies. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systéme International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "about" is used herein to mean approximately, roughly, around, or in the regions of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower).

As used herein, the term "atherosclerosis," "atherosclerotic plaque," "plaque," or "atheroma" refers to the accumulation of one or more of lipids, cholesterol, collagen, and macrophages on the walls of a blood vessel. In some embodiments, such accumulation can result from an inflammatory process involving interaction among modified lipoproteins, monocyte-derived macrophages, T cells, and normal cellular elements of blood vessel walls. This inflammatory process can lead to the development of complex lesions or plaques along the walls of a blood vessel, resulting in the narrowing of the blood vessel lumen.

Non-limiting examples of risk factors for atherosclerosis can include hypertension, diabetes, hypercholesterolemia, elevated plasma low density lipoprotein (LDL) and triglycerides, smoking, obesity, family history, unhealthy diet, and combinations thereof.

As used herein, the term "HDL" refers to high-density lipoproteins.

As used herein, the term "LDL" refers to low-density lipoproteins. In some embodiments, LDL is oxidized ("oxidized LDL").

As used herein, the term "VLDL" refers to very low density lipoproteins.

The term "hypercholesterolemia," as used herein, refers to a condition characterized by very high levels of total cholesterol in the blood (e.g., atherosclerosis). "Total cholesterol" refers to the sum of all the major plasma lipoproteins (e.g., LDL, HDL, and VLDL) present in plasma.

In some embodiments, hypercholesterolemia is associated with a total cholesterol level of at least about 200 mg/dL, at least about 210 mg/dL, at least about 220 mg/dL, at least about 230 mg/dL, at least about 240 mg/dL, at least about 250 mg/dL, at least about 260 mg/dL, at least about 270 mg/dL, at least about 280 mg/dL, at least about 290 mg/dL or more. In certain embodiments, hypercholesterolemia is associated with a total cholesterol level of about 240 mg/dL or more.

In some embodiments, a hypercholesterolemic subject has an elevated LDL level in the blood. In certain embodiments, the LDL level in a hypercholesterolemic subject is at least about 130 mg/dL, at least about 140 mg/dL, at least about 150 mg/dL, at least about 160 mg/dL, at least about 170 mg/dL, at least about 180 mg/dL, at least about 190 mg/dL, at least about 200 mg/dL or more. In some embodiments, the LDL level in a hypercholesterolemic subject is about 160 mg/dL or more. In certain embodiments, the LDL level in a hypercholesterolemic subject is about 190 mg/dL or more.

In some embodiments, a hypercholesterolemic subject has an elevated triglyceride level in the blood. In some embodiments, the triglyceride level in a hypercholesterolemic subject is at least about 150 mg/dL, at least about 175 mg/dL, at least about 200 mg/dL, at least about 225 mg/dL, at least about 250 mg/dL, at least about 275 mg/dL, at least about 300 mg/dL, at least about 325 mg/dL, at least about 350 mg/dL, at least about 375 mg/dL, at least about 400 mg/dL, at least about 425 mg/dL, at least about 450 mg/dL, at least about 475 mg/dL, at least about 500 mg/dL, at least about 525 mg/dL, at least about 550 mg/dL, at least about 575 mg/dL, at least about 600 mg/dL, at least about 625 mg/dL, at least about 650 mg/dL or more. In certain embodiments, the triglyceride level in a hypercholesterolemic subject is about 150 mg/dL or more. In other embodiments, the triglyceride level in a hypercholesterolemic subject is about 200 mg/dL or more. In further embodiments, the triglyceride level in a hypercholesterolemic subject is about 500 mg/dL or more.

In some embodiments, a hypercholesterolemic subject has a reduced HDL level in the blood. In certain embodiments, the HDL level in a hypercholesterolemic subject is less than about 50 mg/dL, less than about 45 mg/dL, less than about 40 mg/dL, less than about 30 mg/dL, less than about 20 mg/dL, less than about 10 mg/dL, or less than about 5 mg/dL.

As used herein, the term "foam cells" refers to a type of macrophage that localize to fatty deposits on blood vessel walls, where they ingest low-density lipoproteins (e.g., oxidized LDL) and become laden with lipids, giving them a foamy appearance. These cells secrete various substances involved in plaque growth and their death promotes inflammation, thereby contributing to cardiovascular diseases. The accumulation of foam cells within the blood vessels can lead to formation of fatty streaks, which are the early atherosclerotic lesions.

The terms "treat," "treating," and "treatment," as used herein, refer to any type of intervention or process performed on, or administering an active agent to, the subject with the objective of reversing, alleviating, ameliorating, inhibiting, or slowing down or preventing the progression, development, severity or recurrence of a symptom, complication, condition or biochemical indicia associated with a disease. Treatment can be of a subject having a disease or a subject who does not have a disease (e.g., for prophylaxis).

As used herein, "administering" refers to the physical introduction of a therapeutic agent or a composition comprising a therapeutic agent to a subject, using any of the various methods and delivery systems known to those skilled in the art. The different routes of administration for antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravitreal, intravenous, intraperitoneal, intramuscular, intraarterial, intrathecal, intralymphatic, intralesional, intracapsular, intraorbital, intracardiac, intradermal, transtracheal, pulmonary, subcutaneous, subcuticular, intraarticular, subcapsular, subarachnoid, intraventricle, intravitreal, epidural, and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

The term "therapeutically effective amount" as used herein refers to an amount of a drug, alone or in combination with another therapeutic agent, effective to "treat" a disease or disorder in a subject or reduce the risk, potential, possibility or occurrence of a disease or disorder (e.g., atherosclerosis). A "therapeutically effective amount" includes an amount of a drug or a therapeutic agent that provides some improvement or benefit to a subject having or at risk of having a disease or disorder (e.g., atherosclerosis). Thus, a "therapeutically effective" amount is an amount that reduces the risk, potential, possibility or occurrence of a disease or provides disorder or some alleviation, mitigation, and/or reduces at least one indicator (e.g., increased inflammation or plaque formation), and/or decrease in at least one clinical symptom of a disease or disorder.

As used herein, the term "subject" includes any human or non-human animal. The term "non-human animal" includes all vertebrates, e.g., mammals and non-mammals, such as non-human primates, sheep, dog, cow, chickens, amphibians, reptiles, etc.

The term "family with sequence similarity 19, member A5" or "FAM19A5" refers to a protein that belongs to the TAFA family (also known as FAM19 family) of five highly homologous proteins. Tang T. Y. et al., *Genomics* 83(4):727-34 (2004). These proteins contain conserved cysteine residues at fixed positions, and are distantly related to macrophage inflammatory protein 1-alpha (MIP-1-alpha), a member of the CC-chemokine family. The TAFA proteins are expressed in specific regions of the brain and the spinal cord. These proteins are believed to be generated and secreted by adult neural stem cells in neurogenesis processes. FAM19A5 is also known as TAFA5 or Chemokine-like protein TAFA-5.

FAM19A5 is believed to be important for the development, differentiation, formation of a complete central nervous system. FAM19A5 also plays a significant role in the pathogenesis of many central nervous system damage and/or degenerative brain diseases (e.g., Huntington's disease, Parkinson's disease, Alzheimer's disease, cerebrospinal damage, strokes, and brain tumors). Upon damage to the central nervous system, neural stem cells produce FAM19A5, which induces the differentiation of normal astrocytes into reactive astrocytes. These reactive astrocytes (along with microglia) can express a wide array of ECMs (e.g., proteoglycans) and induce the formation of glial scars, which can surround the damaged region of the central nervous system like a net and prevent the regeneration of the neurons. Antagonists against FAM19A5 (e.g., anti-FAM19A5 antibody) can be used in the prevention and/or treatment of central nervous system injuries and/or diseases. See U.S. Pat. No. 9,579,398.

However, for certain diseases, particularly those associated with blood vessel abnormalities, a recent study has suggested that FAM19A5 antagonists may not be a viable treatment option. Wang et al., *Circulation* 138(1):48-63 (2018). Wang et al. showed that the adipose tissues of normal, healthy individuals produce FAM19A5, which signals through sphingosine-1-phosphate receptor 2 (S1PR2) to suppress the proliferation and migration of vascular smooth muscle cells (VSMCs) and to attenuate postinjury neointima formation. However, in obese individuals, there is a significant decrease in FAM19A5 expression (both mRNA and protein) in the adipose tissues. Wang et al. concludes that this decrease in FAM19A5 activity is responsible for the accelerated development of cardiovascular diseases observed in many obese individuals.

In humans, the gene encoding FAM19A5 is located on chromosome 22. There are three human FAM19A5 (UniProt: Q7Z5A7) isoforms, which are believed to be produced by alternative splicing: isoform 1 (UniProt: Q7Z5A7-1), which consists of 132 amino acids; isoform 2 (UniProt: Q7Z5A7-2), which consists of 125 amino acids; and isoform 3 (UniProt: Q7Z5A7-3), which consists of 53 amino acids. Human FAM19A5 protein is believed to exist as both membrane bound and soluble (secreted) forms. Isoform 1 is believed to be a membrane protein with one transmembrane region. Isoform 2, which was reported in Tang T. Y. et al., *Genomics* 83(4):727-34 (2004) as a secreted protein (soluble), contains a signal peptide at amino acid positions 1-25. Isoform 3 is predicted based on EST data. Below are the amino acid sequences of the three known human FAM19A5 isoforms.

(I) Isoform 1 (UniProt: Q7Z5A7-1, transmembrane protein): this isoform has been chosen as the canonical sequence.

```
                                            (SEQ ID NO: 1)
MAPSPRTGSR QDATALPSMS STFWAFMILA SLLIAYCSQL

AAGTCEIVTL DRDSSQPRRT IARQTARCAC RKGQIAGTTR

ARPACVDARI IKTKQWCDML PCLEGEGCDL LINRSGWTCT

QPGGRIKTTT VS
```

(II) Isoform 2 (UniProt: Q7Z5A7-2, soluble protein):

```
                                            (SEQ ID NO: 2)
MQLLKALWAL AGAALCCFLV LVIHAQFLKE GQLAAGTCEI

VTLDRDSSQP RRTIARQTAR CACRKGQIAG TTRARPACVD

ARIIKTKQWC DMLPCLEGEG CDLLINRSGW TCTQPGGRIK

TTTVS
```

(III) Isoform 3 (UniProt: Q7Z5A7-3):

```
                                            (SEQ ID NO: 3)
MYHHREWPAR IIKTKQWCDM LPCLEGEGCD LLINRSGWTC

TQPGGRIKTT TVS
```

The term "FAM19A5" includes any variants or isoforms of FAM19A5 which are naturally expressed by cells. Accordingly, antibodies described herein can cross-react with different isoforms in the same species (e.g., different isoforms of human FAM19A5), or cross-react with FAM19A5 from species other than human (e.g., mouse FAM19A5). Alternatively, the antibodies can be specific for human FAM19A5 and cannot exhibit any cross-reactivity with other species. FAM19A5, or any variants and isoforms thereof, can either be isolated from cells or tissues which naturally express them or be recombinantly produced. The polynucleotide encoding human FAM19A5 has the GenBank Accession No. BC039396 and the following sequence:

TABLE 1A

Polynucleotide sequence of human FAM19A5

Polynucleotide sequence (SEQ ID NO: 4)

| | |
|---|---|
| FAM19A5 (GenBank Accession No. BC039396) | ggcggcggag gatggcgcgc gcggggcccg cacgtggagg ccggcgcggg ggcgcgggca gggccggctg ctgagacgcg ctgctgcccc ccgcgcgggc gccgcggctt caatggcgcc atcgcccagg accggcagcc ggcaagatgc gaccgccctg cccagcatgt cctcaacttt ctgggcgttc atgatcctgg ccagcctgct catcgcctac tgcagtcagc tggccgccgg cacctgtgag attgtgacct tggaccggga cagcagccag cctcggagga cgatcgcccg gcagaccgcc cgctgtgcgt gtagaaaggg gcagatcgcc ggcaccacga gagcccggcc cgcctgtgtg gacgcaagaa tcatcaagac caagcagtgg tgtgacatgc ttccgtgtct ggaggggggaa ggctgcgact tgttaatcaa ccggtcaggc tggacgtgca cgcagcccgg cgggaggata aagaccacca cggtctcctg acaaacacag cccctgaggg ggccccggga gtggccttgg ctccctggag agcccacgtc tcagccacag ttctccactc gcctcggact tcacccgttc tctgccgccc gcccactccg tttccctgtg gtccgtgaag gacggcctca ggccttggca tcctgagctt cggtctgtcc agccgacccg aggaggccgg actcagacac ataggcgggg ggcggcacct ggcatcagca atacgcagtc tgtgggagcc cggccgcgcc cagcccccgc cgaccgtggc gttggccctg ctgtcctcag aggaggagga ggaggaggca gctccggcag ccacagaagg ctgcagccca gcccgcctga gacacgacgc ctgcccagg ggactgtcag gcacagaagc ggcctcctcc cgtgcccag actgtccgaa ttgcttttat tttcttatac tttcagtata ctccatagac caaagagcaa aatctatctg aacctggacg cacctcact gtcagggtcc ctggggtcgc ttgtgcgggc gggaggggcaa tggtggcaga gacatgctgg tggcccggc ggagcggaga gggcggccgt ggtggaggcc tccaccccag gagcacccg cacaccctcg gaggacgggc ttcggctgcg cggaggccgt ggcacacctg cggggaggcag cgacggcccc cacgcagacg ccgggaacgc aggccgcttt attcctctgt acttagatca acttgaccgt actaaaatcc ctttctgttt taaccagtta aacatgcctc ttctacagct ccatttttga tagttggata atccagtatc tgccaaagagc atgttgggtc tcccgtgact gctgcctcat cgatacccca tttagctcca gaaagcaaag aaaactcgag taacacttgt ttgaaagaga tcattaaatg tatttttgcaa agcccaaaaa aaaaaaaaaa a |

The term "antagonist against a FAM19A5 protein" refers to all antagonists that suppress and/or neutralize the expression and/or activity of the FAM19A5 protein. Such antagonist can be a peptide, nucleic acid, or a compound. More specifically, the antagonist can be an antisense-oligonucleotide, siRNA, shRNA, miRNA, dsRNA, aptamer, PNA (peptide nucleic acid) targeting FAM19A5, or a vector including the same. In some embodiments, the antagonist can be an antibody, or an antigen-binding portion thereof, that specifically binds to the FAM19A5 protein.

The terms "antibody" and "antibodies" are terms of art and can be used interchangeably herein and refer to a molecule with an antigen binding site that specifically binds an antigen. The terms as used herein include whole antibodies and any antigen binding fragments (i.e., "antigen-binding portions") or single chains thereof. An "antibody" refers, in one embodiment, to a glycoprotein comprising at least two heavy (H) chains and two light (L) chains interconnected by disulfide bonds, or an antigen-binding portion thereof. In another embodiment, an "antibody" refers to a single chain antibody comprising a single variable domain, e.g., VHH domain. Each heavy chain is comprised of a heavy chain variable region (abbreviated herein as VH) and a heavy chain constant region. In certain naturally-occurring antibodies, the heavy chain constant region is comprised of three domains, CH1, CH2 and CH3. In certain naturally-occurring antibodies, each light chain is comprised of a light chain variable region (abbreviated herein as VL) and a light chain constant region. The light chain constant region is comprised of one domain, CL.

The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "Kabat numbering" and like terms are recognized in the art and refer to a system of numbering amino acid residues in the heavy and light chain variable regions of an antibody, or an antigen-binding portion thereof. In certain aspects, the CDRs of an antibody can be determined according to the Kabat numbering system (see, e.g., Kabat E A & Wu T T (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein have been determined according to the Kabat numbering scheme.

The phrases "amino acid position numbering as in Kabat," "Kabat position," and grammatical variants thereof refer to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FW or CDR of the variable domain. For example, a heavy chain variable domain can include a single amino acid insert (residue 52a according to Kabat) after residue 52 of H2 and inserted residues (e.g., residues 82a, 82b, and 82c, etc. according to Kabat) after heavy chain FW residue 82. See TABLE 1B.

TABLE 1B

| Loop | Kabat | AbM | Chothia |
|---|---|---|---|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 . . . 34 |
| | (Kabat Numbering) | | |
| H1 | H31-H35 | H26-H35 | H26-H32 |
| | (Chothia Numbering) | | |
| H2 | H50-H65 | H50-H58 | H52-H56 |
| H3 | H95-H102 | H95-H102 | H95-H102 |

The Kabat numbering of residues can be determined for a given antibody by alignment at regions of homology of the sequence of the antibody with a "standard" Kabat numbered sequence. Chothia refers instead to the location of the structural loops (Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

IMGT (ImMunoGeneTics) also provides a numbering system for the immunoglobulin variable regions, including the CDRs. See, e.g., Lefranc, M. P. et al., Dev. Comp. Immunol. 27: 55-77(2003), which is herein incorporated by reference. The IMGT numbering system was based on an alignment of more than 5,000 sequences, structural data, and characterization of hypervariable loops and allows for easy comparison of the variable and CDR regions for all species. According to the IMGT numbering schema VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97.

For all heavy chain constant region amino acid positions discussed in the present disclosure, numbering is according to the EU index first described in Edelman et al., 1969, Proc. Natl. Acad. Sci. USA 63(1):78-85, describing the amino acid sequence of myeloma protein EU, which is the first human IgG1 sequenced. The EU index of Edelman et al. is also set forth in Kabat et al., 1991, Sequences of Proteins of Immunological Interest, 5th Ed., United States Public Health Service, National Institutes of Health, Bethesda. Thus, the phrases "EU index as set forth in Kabat" or "EU index of Kabat" and "position . . . according to the EU index as set forth in Kabat," and grammatical variants thereof refer to the residue numbering system based on the human IgG1 EU antibody of Edelman et al. as set forth in Kabat 1991.

The numbering system used for the variable domains (both heavy chain and light chain) and light chain constant region amino acid sequence is that set forth in Kabat 1991.

Antibodies can be of any type (e.g., IgG, IgE, IgM, IgD, IgA, or IgY), any class (e.g., IgD, IgG2, IgG3, IgG4, IgA1, or IgA2), or any subclass (e.g., IgG1, IgG2, IgG3, and IgG4 in humans; and IgG1, IgG2a, IgG2b, and IgG3 in mice) of immunoglobulin molecule. Immunoglobulins, e.g., IgG1, exist in several allotypes, which differ from each other in at most a few amino acids. An antibody disclosed herein can be from any of the commonly known isotypes, classes, subclasses, or allotypes. In certain embodiments, the antibodies described herein are of the IgG1, IgG2, IgG3, or IgG4 subclass or any hybrid thereof. In certain embodiments, the antibodies are of the human IgG1 subclass or the human IgG2 or human IgG4 subclass.

"Antibody" includes, by way of example, both naturally-occurring and non-naturally-occurring antibodies; monoclonal and polyclonal antibodies; chimeric and humanized antibodies; human and non-human antibodies; wholly synthetic antibodies; single chain antibodies; monospecific antibodies; multispecific antibodies (including bispecific antibodies); tetrameric antibodies comprising two heavy chain and two light chain molecules; an antibody light chain monomer; an antibody heavy chain monomer; an antibody light chain dimer, an antibody heavy chain dimer; an antibody light chain-antibody heavy chain pair; intrabodies; heteroconjugate antibodies; monovalent antibodies; camelized antibodies; affybodies; anti-idiotypic (anti-Id) antibodies (including, e.g., anti-anti-Id antibodies), and single-domain antibodies (sdAbs), which include binding molecules consisting of a single monomeric variable antibody domain that are fully capable of antigen binding (e.g., a VH domain or a VL domain). Harmen M. M. and Haard H. J. *Appl Microbiol Biotechnol.* 77(1): 13-22 (2007)).

The term "antigen-binding portion" of an antibody, as used herein, refers to one or more fragments of an antibody that retain the ability to specifically bind to an antigen (e.g., human FAM19A5). Such "fragments" are, for example between about 8 and about 1500 amino acids in length, suitably between about 8 and about 745 amino acids in length, suitably about 8 to about 300, for example about 8 to about 200 amino acids, or about 10 to about 50 or 100 amino acids in length. It has been shown that the antigen-binding function of an antibody can be performed by fragments of a full-length antibody. Examples of binding fragments encompassed within the term "antigen-binding portion" of an antibody, e.g., an anti-FAM19A5 antibody described herein, include (i) a Fab fragment, a monovalent fragment consisting of the VL, VH, CL, and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, and disulfide-linked Fvs (sdFv); (v) a dAb fragment (Ward et al., (1989) Nature 341:544-546), which consists of a VH domain; and (vi) an isolated complementarity determining region (CDR) or (vii) a combination of two or more isolated CDRs which can optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)); see, e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

As used herein, the terms "variable region" and "variable domain" are used interchangeably and are common in the art. The variable region typically refers to a portion of an antibody, generally, a portion of a light or heavy chain, typically about the amino-terminal 110 to 120 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR).

Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

As used herein, the term "heavy chain" (HC) when used in reference to an antibody can refer to any distinct type, e.g., alpha ($\alpha$), delta ($\delta$), epsilon ($\epsilon$), gamma ($\gamma$) and mu ($\mu$), based on the amino acid sequence of the constant domain, which give rise to IgA, IgD, IgE, IgG and IgM classes of antibodies, respectively, including subclasses of IgG, e.g., IgG1, IgG2, IgG3 and IgG4.

As used herein, the term "light chain" (LC) when used in reference to an antibody can refer to any distinct type, e.g., kappa ($\kappa$) or lambda ($\lambda$) based on the amino acid sequence of the constant domains. Light chain amino acid sequences are well known in the art. In specific embodiments, the light chain is a human light chain.

The terms "VL" and "VL domain" are used interchangeably to refer to the light chain variable region of an antibody.

The terms "VH" and "VH domain" are used interchangeably to refer to the heavy chain variable region of an antibody.

As used herein, the terms "constant region" and "constant domain" are interchangeable and have its meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

An "Fc region" (fragment crystallizable region) or "Fc domain" or "Fc" refers to the C— terminal region of the heavy chain of an antibody that mediates the binding of the immunoglobulin to host tissues or factors, including binding to Fc receptors located on various cells of the immune system (e.g., effector cells) or to the first component (C1q) of the classical complement system. Thus, a Fc region comprises the constant region of an antibody excluding the first constant region immunoglobulin domain (e.g., CH1 or CL). In IgG, IgA and IgD antibody isotypes, the Fc region comprises two identical protein fragments, derived from the second (CH2) and third (CH3) constant domains of the antibody's two heavy chains; IgM and IgE Fc regions comprise three heavy chain constant domains (CH domains 2-4) in each polypeptide chain. For IgG, the Fc region comprises immunoglobulin domains Cγ2 and Cγ3 and the hinge between Cγ1 and Cγ2. Although the boundaries of the Fc region of an immunoglobulin heavy chain might vary, the human IgG heavy chain Fc region is usually defined to stretch from an amino acid residue at position C226 or P230 (or amino acid between these two amino acids) to the carboxy-terminus of the heavy chain, wherein the numbering is according to the EU index as in Kabat. The CH2 domain of a human IgG Fc region extends from about amino acid 231 to about amino acid 340, whereas the CH3 domain is positioned on C-terminal side of a Cm domain in a Fc region, i.e., it extends from about amino acid 341 to about amino acid 447 of an IgG. As used herein, the Fc region can be a native sequence Fc, including any allotypic variant, or a variant Fc (e.g., a non-naturally-occurring Fc). Fc can also refer to this region in isolation or in the context of a Fc-comprising protein polypeptide such as a "binding protein comprising a Fc region," also referred to as an "Fc fusion protein" (e.g., an antibody or immunoadhesion).

A "native sequence Fc region" or "native sequence Fc" comprises an amino acid sequence that is identical to the amino acid sequence of a Fc region found in nature. Native sequence human Fc regions include a native sequence human IgG1 Fc region; native sequence human IgG2 Fc region; native sequence human IgG3 Fc region; and native sequence human IgG4 Fc region as well as naturally-occurring variants thereof. Native sequence Fc includes the various allotypes of Fcs (see, e.g., Jefferis et al. (2009) *mAbs* 1:1; Vidarsson G. et al. *Front Immunol.* 5:520 (published online Oct. 20, 2014)).

An "Fc receptor" or "FcR" is a receptor that binds to the Fc region of an immunoglobulin. FcRs that bind to an IgG antibody comprise receptors of the FcγR family, including allelic variants and alternatively spliced forms of these receptors. The FcγR family consists of three activating (FcγRI, FcγRIII, and FcγRIV in mice; FcγRIA, FcγRIIA, and FcγRIIIA in humans) and one inhibitory (FcγRIIB) receptor. Human IgG1 binds to most human Fc receptors and elicits the strongest Fc effector functions. It is considered equivalent to murine IgG2a with respect to the types of activating Fc receptors that it binds to. Conversely, human IgG4 elicits the least Fc effector functions. Vidarsson G. et al. *Front Immunol.* 5:520 (published online Oct. 20, 2014).

The constant region can be manipulated, e.g., by recombinant technology, to eliminate one or more effector functions. An "effector function" refers to the interaction of an antibody Fc region with a Fc receptor or ligand, or a biochemical event that results therefrom. Exemplary "effector functions" include C1q binding, complement dependent cytotoxicity (CDC), Fc receptor binding, FcγR-mediated effector functions such as ADCC and antibody dependent cell-mediated phagocytosis (ADCP), and down regulation of a cell surface receptor (e.g., the B cell receptor; BCR). Such effector functions generally require the Fc region to be combined with a binding domain (e.g., an antibody variable domain). Accordingly, the term "a constant region without the Fc function" include constant regions with reduced or without one or more effector functions mediated by Fc region.

Effector functions of an antibody can be reduced or avoided by different approaches. Effector functions of an antibody can be reduced or avoided by using antibody fragments lacking the Fc region (e.g., such as a Fab, F(ab')2, single chain Fv (scFv), or a sdAb consisting of a monomeric VH or VL domain). Alternatively, the so-called aglycosylated antibodies can be generated by removing sugars that are linked to particular residues in the Fc region to reduce the effector functions of an antibody while retaining other valuable attributes of the Fc region (e.g., prolonged half-life and heterodimerization). Aglycosylated antibodies can be generated by, for example, deleting or altering the residue the sugar is attached to, removing the sugars enzymatically, producing the antibody in cells cultured in the presence of a glycosylation inhibitor, or by expressing the antibody in cells unable to glycosylate proteins (e.g., bacterial host cells). See, e.g., U.S. Pub. No. 20120100140. Another approach is to employ Fc regions from an IgG subclass that have reduced effector function, for example, IgG2 and IgG4 antibodies are characterized by having lower levels of Fc effector functions than IgG1 and IgG3. The residues most proximal to the hinge region in the CH2 domain of the Fc part are responsible for effector functions of antibodies as it contains a largely overlapping binding site for C1q (complement) and IgG-Fc receptors (FcγR) on effector cells of the innate immune system. Vidarsson G. et al. *Front Immunol.* 5:520 (published online Oct. 20, 2014). Accordingly, antibodies with reduced or without Fc effector functions can be prepared by generating, e.g., a chimeric Fc region which comprises a CH2 domain from an IgG antibody of the IgG4 isotype and a CH3 domain from an IgG antibody of the IgG1 isotype, or a chimeric Fc region which comprises hinge region from IgG2 and CH2 region from IgG4 (see, e.g., Lau C. et al. *J. Immunol.* 191:4769-4777 (2013)), or a Fc region with mutations that result in altered Fc effector functions, e.g., reduced or no Fc functions. Such Fc regions with mutations are known in the art. See, e.g., U.S. Pub. No. 20120100140 and U.S. and PCT applications cited therein and An et al. *mAbs* 1:6, 572-579 (2009); the disclosure of which are incorporated by reference to their entirety.

A "hinge", "hinge domain" or "hinge region" or "antibody hinge region" refers to the domain of a heavy chain constant region that joins the CH1 domain to the CH2 domain and includes the upper, middle, and lower portions of the hinge (Roux et al. *J Immunol.* 1998 161:4083). The hinge provides varying levels of flexibility between the binding and effector regions of an antibody and also provides sites for intermolecular disulfide bonding between the two heavy chain constant regions. As used herein, a hinge starts at Glu216 and ends at Gly237 for all IgG isotypes (Roux et al., 1998 *J Immunol* 161:4083). The sequences of wild-type IgG1, IgG2, IgG3 and IgG4 hinges are known in the art. See, e.g., Kabat E A et al., (1991) Sequences of Proteins of Immunological Interest, Fifth Edition, U.S. Department of Health and Human Services, NIH Publication No. 91-3242; Vidarsson G. et al. *Front Immunol.* 5:520 (published online Oct. 20, 2014).

The term "CH1 domain" refers to the heavy chain constant region linking the variable domain to the hinge in a heavy chain constant domain. As used herein, a CH1 domain starts at A118 and ends at V215. The term "CH1 domain" includes wildtype CH1 domains, as well as naturally existing variants thereof (e.g., allotypes). CH1 domain sequences of IgG1, IgG2, IgG3, and IgG4 (including wildtype and allotypes) are known in the art. See, e.g., Kabat E A et al, (1991) supra and Vidarsson G. et al. *Front Immunol.* 5:520 (published online Oct. 20, 2014). Exemplary CH1 domains include CH1 domains with mutations that modify a biological activity of an antibody, e.g., half-life, e.g., described in U.S. Pub. No. 20120100140 and U.S. patents and publications and PCT publications cited therein.

The term "CH2 domain" refers to the heavy chain constant region linking the hinge to the CH3 domain in a heavy chain constant domain. As used herein, a CH2 domain starts at P238 and ends at K340. The term "CH2 domain" includes wildtype CH2 domains, as well as naturally existing variants thereof (e.g., allotypes). CH2 domain sequences of IgG1, IgG2, IgG3, and IgG4 (including wildtype and allotypes) are known in the art. See, e.g., Kabat E A et al., (1991) supra and Vidarsson G. et al. *Front Immunol.* 5:520 (published online Oct. 20, 2014). Exemplary CH2 domains include CH2 domains with mutations that modify a biological activity of an antibody, e.g., half-life and/or reduced Fc effector function, e.g., described in U.S. Pub. No. 20120100140 and U.S. patents and publications and PCT publications cited therein.

The term "CH3 domain" refers to the heavy chain constant region that is C-terminal to the CH2 domain in a heavy chain constant domain. As used herein, a CH3 domain starts at G341 and ends at K447. The term "CH3 domain" includes wildtype CH3 domains, as well as naturally existing variants thereof (e.g., allotypes). CH3 domain sequences of IgG1, IgG2, IgG3, and IgG4 (including wildtype and allotypes) are known in the art. See, e.g., Kabat E A et al., (1991) supra and Vidarsson G. et al. *Front Immunol.* 5:520 (published online Oct. 20, 2014). Exemplary CH3 domains include CH3 domains with mutations that modify a biological activity of an antibody, e.g., half-life, e.g., described in U.S. Pub. No. 20120100140 and U.S. patents and publications and PCT publications cited therein.

As used herein, "isotype" refers to the antibody class (e.g., IgG1, IgG2, IgG3, IgG4, IgM, IgA1, IgA2, IgD, and IgE antibody) that is encoded by the heavy chain constant region genes.

"Allotype" refers to naturally-occurring variants within a specific isotype group, which variants differ in a few amino acids (see, e.g., Jefferis et al. (2009) *mAbs* 1:1). Antibodies described herein can be of any allotype. Allotypes of IgG1, IgG2, IgG3, and IgG4 are known in the art. See, e.g., Kabat E A et al., (1991) supra; Vidarsson G. et al. *Front Immunol.* 5:520 (published online Oct. 20, 2014); and Lefranc M P, *mAbs* 1:4, 1-7(2009).

The phrases "an antibody recognizing an antigen" and "an antibody specific for an antigen" are used interchangeably herein with the term "an antibody which binds specifically to an antigen."

An "isolated antibody," as used herein, is intended to refer to an antibody which is substantially free of other antibodies having different antigenic specificities (e.g., an isolated antibody that specifically binds to FAM19A5 is substantially free of antibodies that specifically bind antigens other than FAM19A5). An isolated antibody that specifically binds to an epitope of FAM19A5 can, however, have cross-reactivity to other FAM19A5 proteins from different species.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$ and is expressed as a molar concentration (M), whereas $K_A$ is calculated from the quotient of $k_{on}/k_{off}$. $k_{on}$ refers to the association rate constant of, e.g., an antibody to an antigen, and $k_{off}$ refers to the dissociation of, e.g., an antibody to an antigen. The $k_{on}$ and $k_{off}$ can be determined by techniques known to one of ordinary skill in the art, such as immunoassays (e.g., enzyme-linked immunosorbent assay (ELISA)), BIACORE™ or kinetic exclusion assay)(KINEXA®).

As used herein, the terms "specifically binds," "specifically recognizes," "specific binding," "selective binding," and "selectively binds," are analogous terms in the context of antibodies and refer to molecules (e.g., antibodies) that bind to an antigen (e.g., epitope or immune complex) as such binding is understood by one skilled in the art. For example, a molecule that specifically binds to an antigen can bind to other peptides or polypeptides, generally with lower affinity as determined by, e.g., immunoassays, BIACORE™, KINEXA® 3000 instrument (Sapidyne Instruments, Boise, Id.), or other assays known in the art. In a specific embodiment, molecules that specifically bind to an antigen bind to the antigen with a $K_A$ that is at least 2 logs, 2.5 logs, 3 logs, 4 logs or greater than the $K_A$ when the molecules bind to another antigen.

Antibodies typically bind specifically to their cognate antigen with high affinity, reflected by a dissociation constant ($K_D$) of $10^{-5}$ to $10^{-11}$ M or less. Any $K_D$ greater than about $10^{-4}$ M is generally considered to indicate nonspecific binding. As used herein, an antibody that "binds specifically" to an antigen refers to an antibody that binds to the antigen and substantially identical antigens with high affinity, which means having a $K_D$ of $10^{-7}$ M or less, preferably $10^{-8}$ M or less, even more preferably $10^{-9}$ M or less, and most preferably between $10^{-8}$ M and $10^{-10}$ M or less, when determined by, e.g., immunoassays (e.g., ELISA) or surface plasmon resonance (SPR) technology in a BIACORE™ 2000 instrument using the predetermined antigen, but does not bind with high affinity to unrelated antigens.

As used herein, the term "antigen" refers to any natural or synthetic immunogenic substance, such as a protein, peptide, or hapten. An antigen can be FAM19A5 or a fragment thereof.

As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). Epitopes formed from contiguous amino acids are typically, but not always, retained on exposure to denaturing solvents, whereas epitopes formed by tertiary folding are typically lost on treatment with denaturing solvents. An epitope typically includes at least 1, 2, 3, 4, 5, 6, 7, 8, 9, 10, 11, 12, 13, 14, 15, or 20 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides from (e.g., from FAM19A5) are tested for reactivity with a given antibody (e.g., anti-FAM19A5 antibody). Methods of determining spatial conformation of epitopes include techniques in the art and those described herein, for example, x-ray crystallography, 2-dimensional nuclear magnetic resonance and HDX-MS (see, e.g., Epitope Mapping Protocols in Methods in Molecular Biology, Vol. 66, G. E. Morris, Ed. (1996)).

In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization can be accomplished using any of the known methods in the art (e.g., Giege R et al., (1994) *Acta Crystallogr D Biol Crystallogr* 50(Pt 4): 339-350; McPherson A (1990) *Eur J Biochem* 189: 1-23; Chayen N E (1997) *Structure* 5: 1269-1274; McPherson A (1976) *J Biol Chem* 251: 6300-6303). Antibody:antigen crystals can be studied using well known X-ray diffraction techniques and can be refined using computer software such as X-PLOR (Yale University, 1992, distributed by Molecular Simulations, Inc.; see, e.g., *Meth Enzymol* (1985) volumes 114 & 115, eds Wyckoff H W et al.; U.S. 2004/0014194), and BUSTER (Bricogne G (1993) *Acta Crystallogr D Biol Crystallogr* 49(Pt 1): 37-60; Bricogne G (1997) *Meth Enzymol* 276A: 361-423, ed Carter C W; Roversi P et al., (2000) *Acta Crystallogr D Biol Crystallogr* 56(Pt 10): 1316-1323). Mutagenesis mapping studies can be accomplished using any method known to one of skill in the art. See, e.g., Champe M et al., (1995) *J Biol Chem* 270: 1388-1394 and Cunningham B C & Wells J A (1989) *Science* 244: 1081-1085 for a description of mutagenesis techniques, including alanine scanning mutagenesis techniques.

The term "epitope mapping" refers to the process of identification of the molecular determinants for antibody-antigen recognition.

The term "binds to the same epitope" with reference to two or more antibodies means that the antibodies bind to the same segment of amino acid residues, as determined by a given method. Techniques for determining whether antibodies bind to the "same epitope on FAM19A5" with the antibodies described herein include, for example, epitope mapping methods, such as, x-ray analyses of crystals of antigen: antibody complexes which provides atomic resolution of the epitope and hydrogen/deuterium exchange mass spectrometry (HDX-MS). Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. Antibodies having the same VH and VL or the same CDR1, 2 and 3 sequences are expected to bind to the same epitope.

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, can be determined using known competition experiments. In certain embodiments, an antibody competes with, and inhibits binding of another antibody to a target by at least 10%, 20%, 30%, 40%, 50%, 60%, 70%, 80%, 90% or 100%. The level of inhibition or competition can be different depending on which antibody is the "blocking antibody" (i.e., the cold antibody that is incubated first with the target). Competition assays can be conducted as described, for example, in Ed Harlow and David Lane, Cold Spring Harb Protoc; 2006; doi: 10.1101/pdb.prot4277 or in Chapter 11 of "Using Antibodies" by Ed Harlow and David Lane, Cold Spring Harbor Laboratory Press, Cold Spring Harbor, N.Y., USA 1999. Competing antibodies bind to the same epitope, an overlapping epitope or to adjacent epitopes (e.g., as evidenced by steric hindrance).

Other competitive binding assays include: solid phase direct or indirect radioimmunoassay (MA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, Antibodies: A Laboratory Manual, Cold Spring Harbor Press (1988)); solid phase direct label MA using 1-125 label (see Morel et al., *Mol. Immunol.* 25(1):7 (1988)); solid phase direct biotin-avidin EIA (Cheung et al., *Virology* 176:546 (1990)); and direct labeled MA. (Moldenhauer et al., *Scand. J. Immunol.* 32:77 (1990)).

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

The term "monoclonal antibody," as used herein, refers to an antibody that displays a single binding specificity and affinity for a particular epitope or a composition of antibodies in which all antibodies display a single binding specificity and affinity for a particular epitope. Accordingly, the term "human monoclonal antibody" refers to an antibody or antibody composition that display(s) a single binding specificity and which has variable and optional constant regions derived from human germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations which occur, for example, during antibody maturation. As known in the art (see, e.g., Lonberg (2005) *Nature Biotech.* 23(9): 1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid molecules that encode the light chain and heavy chain immunoglobulin polypeptides in response to an antigen cannot have sequence identity with the original nucleic acid molecules, but instead will be substantially identical or similar (i.e., have at least 80% identity).

A "human" antibody (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The antibodies described herein can include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. The terms "human" antibodies and "fully human" antibodies are used synonymously.

A "humanized" antibody refers to an antibody in which some, most or all of the amino acids outside the CDR domains of a non-human antibody are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

The term "cross-reacts," as used herein, refers to the ability of an antibody described herein to bind to FAM19A5 from a different species. For example, an antibody described herein that binds human FAM19A5 can also bind another species of FAM19A5 (e.g., mouse FAM19A5). As used herein, cross-reactivity can be measured by detecting a specific reactivity with purified antigen in binding assays (e.g., SPR, ELISA) or binding to, or otherwise functionally interacting with, cells physiologically expressing FAM19A5. Methods for determining cross-reactivity include standard binding assays as described herein, for example, by BIACORE™ surface plasmon resonance (SPR) analysis using a BIACORE™ 2000 SPR instrument (Biacore AB, Uppsala, Sweden), or flow cytometric techniques.

The term "naturally-occurring" as applied to an object herein refers to the fact that an object can be found in nature. For example, a polypeptide or polynucleotide sequence that is present in an organism (including viruses) that can be isolated from a source in nature and which has not been intentionally modified by man in the laboratory is naturally-occurring.

A "polypeptide" refers to a chain comprising at least two consecutively linked amino acid residues, with no upper limit on the length of the chain. One or more amino acid residues in the protein can contain a modification such as, but not limited to, glycosylation, phosphorylation or disulfide bond formation. A "protein" can comprise one or more polypeptides.

The term "nucleic acid molecule," as used herein, is intended to include DNA molecules and RNA molecules. A nucleic acid molecule can be single-stranded or double-stranded, and can be cDNA.

The term "vector," as used herein, is intended to refer to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" can be used interchangeably as the plasmid is the most commonly used form of vector. However, also included are other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell that comprises a nucleic acid that is not naturally present in the cell, and can be a cell into which a recombinant expression vector has been introduced. It should be understood that such terms are intended to refer not only to the particular subject cell but to the progeny of such a cell. Because certain modifications can occur in succeeding generations due to either mutation or environmental influences, such progeny cannot, in fact, be identical to the parent cell, but are still included within the scope of the term "host cell" as used herein.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

The term "therapeutically effective amount" as used herein refers to an amount of a drug, alone or in combination with another therapeutic agent, effective to "treat" a disease or disorder in a subject or reduce the risk, potential, possibility or occurrence of a disease or disorder (e.g., atherosclerosis). A "therapeutically effective amount" includes an amount of a drug or a therapeutic agent (e.g., anti-FAM19A5 antibodies disclosed herein) that provides some improvement or benefit to a subject having or at risk of having a disease or disorder (e.g., atherosclerosis). Thus, a "therapeutically effective" amount is an amount that reduces the risk, potential, possibility, or occurrence of a disease or disorder or provides some alleviation, mitigation, and/or reduces at least one indicator, and/or decrease in at least one clinical symptom of a disease or disorder (e.g., atherosclerosis).

II. Methods of Treating Atherosclerosis

Disclosed herein are methods of treating a cardiovascular condition in a subject in need thereof. More specifically, the methods disclosed herein can be used to treat an atherosclerosis, including diseases and disorders associated with atherosclerosis. Non-limiting examples of such diseases and disorders include coronary artery disease, stroke, peripheral artery disease, kidney impairment, retinal artery occlusion, abdominal pain caused by intestinal damage, and peritonitis, or combinations thereof. As described infra, atherosclerosis is generally associated with abnormal levels of lipoproteins in the plasma. In certain embodiments, the term "lipoprotein" comprises total cholesterol, LDL, HDL, triglyceride, or combinations thereof. Abnormal levels of such lipoproteins can cause accumulation of lipid-laden macrophages (also known as foam cells), resulting in lesion or plaque build-up along blood vessel wall. Accordingly, the present disclosure also provides methods of modulating (i.e., decreasing or increasing) the levels of one or more lipoproteins in a subject in need thereof (e.g., having atherosclerosis). Also provided herein are methods for reducing a number of foam cells (e.g., ox-LDL-induced foam cells) and/or retention of foam cells within a plaque in a subject in need thereof.

In some embodiments, methods disclosed herein comprise administering to the subject an antagonist against FAM19A5 protein ("FAM19A5 antagonist"). In some embodiments, the FAM19A5 antagonist is an antisense oligonucleotide, siRNA, shRNA, miRNA, dsRNA targeting FAM19A5, aptamer, PNA, or a vector including the same. In other embodiments, the FAM19A5 antagonist is an antibody, or an antigen-binding portion thereof, that specifically binds to the FAM19A5 protein ("an anti-FAM19A5 antibody"), a polynucleotide encoding the anti-FAM19A5 antibody, or a vector comprising the polynucleotide thereof. In some embodiments, the anti-FAM19A5 antibody binds to FAM19A5 protein and reduces FAM19A5 activity.

Subjects that can be treated with the methods disclosed herein (e.g., having atherosclerosis) can exhibit one or more of the following properties: (i) an increased total cholesterol level, (ii) an increased triglyceride level, (iii) an increased LDL level, (iv) a reduced HDL level, (v) increased number of foam cells and/or retention of foam cells in a plaque, (vi) or combinations thereof, compared to a subject who does not have atherosclerosis (e.g., a healthy subject).

Accordingly, not being bound by any single theory, a FAM19A5 antagonist disclosed herein (e.g., anti-FAM19A5 antibody) can treat atherosclerosis by reducing, alleviating, and/or reversing one or more of the properties described above. In some embodiments, a FAM19A5 antagonist is capable of neutralizing a FAM19A5 protein, e.g., a FAM19A5 neutralizing agent. In other embodiments, a FAM19A5 antagonist is an anti-FAM19A5 antibody. In some embodiments, the anti-FAM19A5 antibody is a neutralizing antibody.

In some embodiments, a FAM19A5 antagonist disclosed herein can reduce a total cholesterol level in a subject in need thereof. In certain embodiments, the total cholesterol level in the subject is reduced by at least about 5%, at least about 10%, at least about 20%, at least about 30%, at least about 40%, at least about 50%, at least about 60%, at least about 70%, at least about 80%, or at least about 90% or more, compared to a reference (e.g., corresponding value in a subject that did not receive the FAM19A5 antagonist or corresponding value in the subject prior to administering the FAM19A5 antagonist).

In some embodiments, a FAM19A5 antagonist disclosed herein can reduce a triglyceride level in a subject in need thereof. In certain embodiments, the triglyceride level in the subject is reduced by at least about 5%, at least about 10%, at least about 20%, at least about 30%, at least about 40%, at least about 50%, at least about 60%, at least about 70%, at least about 80%, or at least about 90% or more, compared to a reference (e.g., corresponding value in a subject that did not receive the FAM19A5 antagonist or corresponding value in the subject prior to administering the FAM19A5 antagonist).

In some embodiments, a FAM19A5 antagonist disclosed herein can reduce a low density lipoprotein (LDL) level in a subject in need thereof. In certain embodiments, the LDL level in the subject is reduced by at least about 5%, at least about 10%, at least about 20%, at least about 30%, at least about 40%, at least about 50%, at least about 60%, at least about 70%, at least about 80%, or at least about 90% or more, compared to a reference (e.g., corresponding value in a subject that did not receive the FAM19A5 antagonist or corresponding value in the subject prior to administering the FAM19A5 antagonist).

In some embodiments, a FAM19A5 antagonist disclosed herein can increase a high density lipoprotein (HDL) level in a subject in need thereof. In certain embodiments, the HDL level in the subject is increased by at least about 5%, at least about 10%, at least about 20%, at least about 30%, at least about 40%, at least about 50%, at least about 60%, at least about 70%, at least about 80%, or at least about 90% or more, compared to a reference (e.g., corresponding value in a subject that did not receive the FAM19A5 antagonist or corresponding value in the subject prior to administering the FAM19A5 antagonist).

In some embodiments, a FAM19A5 antagonist disclosed herein (e.g., anti-FAM19A5 antibody) can increase the migration and/or accumulation of macrophages to an atherosclerotic lesion site in a subject in need thereof. In certain embodiments, the migration and/or accumulation of macrophages at an atherosclerotic lesion site is increased by at least about 5%, at least about 10%, at least about 20%, at least about 30%, at least about 40%, at least about 50%, at least about 60%, at least about 70%, at least about 80%, or at least about 90% or more, compared to a reference (e.g., corresponding value in a subject that did not receive the FAM19A5 antagonist or corresponding value in the subject prior to administering the FAM19A5 antagonist).

In some embodiments, a FAM19A5 antagonist can increase the phagocytosis of low density lipoprotein (LDL) by macrophages (or other cells with phagocytic abilities, e.g., dendritic cells) in a subject in need thereof. In certain embodiments, the phagocytosis of LDL by macrophages is increased by at least about 5%, at least about 10%, at least about 20%, at least about 30%, at least about 40%, at least about 50%, at least about 60%, at least about 70%, at least about 80%, or at least about 90% or more, compared to a reference (e.g., corresponding value in a subject that did not receive the FAM19A5 antagonist or corresponding value in the subject prior to administering the FAM19A5 antagonist).

Without wishing to be bound by any particular mechanism or theory, in some embodiments, (i) the increase in the migration and/or accumulation of macrophages at an atherosclerotic lesion site and/or (ii) the increase in the phagocytosis of LDL by the macrophages can reduce the level of LDL in the blood, and thereby treat atherosclerosis (or diseases or disorders associated with atherosclerosis). In some embodiments, the macrophages are lipid-laden macrophages (also known as foam cells).

In some embodiments, a FAM19A5 antagonist disclosed herein can induce a normalization of a blood vessel in a subject in need thereof. In certain embodiments, blood vessel normalization comprises (i) increased number of blood vessels, (ii) improved connectivity of blood vessels, (iii) decreased blood vessel permeability, (iv) increased blood flow rate, or (v) any combinations thereof. In certain embodiments, normalization of a blood vessel is associated with reduced plaque build-up within the walls of the blood vessels.

As used herein, the term "blood vessel" refers to any of the vessels through which blood circulates in the body. The term "vessel" refers to any channel for carrying a fluid, such as an artery or vein. In some embodiments, a blood vessel comprises an artery, vein, or capillary. In certain embodiments, a blood vessel comprises an aorta.

As described infra, if not properly treated, atherosclerosis can lead to other cardiovascular diseases and disorders. Accordingly, in some embodiments, atherosclerosis that can be treated with the present methods is associated with a disease comprising coronary heart disease (CHD), carotid artery disease, peripheral artery disease, chronic kidney disease, stroke, retinal artery occlusion, abdominal pain caused by intestinal damage, and peritonitis, or combinations thereof. In some embodiments, the atherosclerosis is associated with a high fat and/or high cholesterol (hypercholesterolemic) diet. In certain embodiments, a high fat and/or high cholesterol diet comprises a total fat concentration of at least about 20%, at least about 25%, at least about 30%, at least about 35%, at least about 40%, at least about 45%, at least about 50%, at least about 55%, at least about 60%, at least about 65%, at least about 70%, at least about 75%, at least about 80% or more. In some embodiments, a high fat and/or high cholesterol diet comprises a total fat concentration of about 42%. In other embodiments, the atherosclerosis is associated with an increased total cholesterol level, increased triglyceride level, increased LDL level, decreased HDL level, increased number and/or retention of oxo-LDL-induced foam cells within a plaque, or combinations thereof, compared to a subject without atherosclerosis (e.g., a healthy subject).

In some embodiments, the term "reference," as used herein, refers to a corresponding subject (e.g., having atherosclerosis) who did not receive a composition disclosed herein (e.g., FAM19A5 antagonist, e.g., anti-FAM19A5 antibody). The term "reference" can also refer to a same subject (e.g., having atherosclerosis) but prior to the administration of a composition disclosed herein. In certain embodiments, the term "reference" refers to an average of a population of subjects (e.g., having atherosclerosis).

In some embodiments, subject that can be treated with the present methods is a nonhuman animal, such as a rat or a mouse. In other embodiments, subject that can be treated with the methods disclosed herein is a human.

In some embodiments, a FAM19A5 antagonist (e.g., anti-FAM19A5 antibody), a bispecific molecule, or an immunoconjugate, or a composition thereof disclosed herein, is delivered to a subject via intravenous administration. Non-limiting examples of other administration route include subcutaneously, intramuscularly, orally, intravitreally, intrathecally, or combinations thereof.

For administration of a FAM19A5 antagonist, or a composition thereof, disclosed herein (e.g., anti-FAM19A5 antibody), dosage ranges from about 0.0001 to 100 mg/kg.

In some embodiments, a FAM19A5 antagonist, or a composition thereof, can be administered in combination with one or more additional agent (e.g., therapeutic agent) for treating atherosclerosis. Non-limiting examples of such additional agent include (i) a cholesterol lowering agent, (ii) anti-platelet agent, (iii) beta-blocker, (iv) angiotensin-converting enzyme (ACE) inhibitor, (v) calcium channel blockers, (vi) diabetes drug, or (vii) combinations thereof.

In some embodiments, a cholesterol lowering agent comprises a statin (e.g., atorvastatin (LIPITOR®), fluvastatin (LESCOL®), lovastatin, pitavastatin (LIVAL®), pravastatin (PRAVACHOL®), rosuvastatin calcium (CRESTOR®), and simvastatin (ZOCOR®). In other embodiments, a cholesterol lowering agent comprises a PCSK9 inhibitor (e.g., alirocumab (PRALUENT®) and evolocumab (REPATHA®).

In some embodiments, an anti-platelet agent comprises acetylsalicyclic acid or aspirin (ASPIRIN®, ASAPHEN®, ENTROPHEN®, NOVASEN®), clopidogrel (PLAVIX®), prasugrel (EFFIENT®), or ticagrelor (BRILINTA®).

In some embodiments, a beta blocker comprises acebutolol (SECTRAL®), atenolol (TENORMIN®), bisoprolol (ZEBETA®), metoprolol (LOPRESSOR® and TOPROL-XL®), nadolol (CORGARD®), nebivolol (BYSTOLIC®), or propranolol (INDERAL LA® and INNOPRAN XL®).

In some embodiments, an ACE inhibitor comprises benazepril (LOTENSIN®, LOTENSIN HCT®), captopril) (CAPOTEN®), enalapril (VASOTEC®), fosinopril (MONOPRIL®), lisinopril (PRINIVIL®, ZESTRIL®), moexipril (UNIVASC®), perindopril (ACEON®), quinapril (ACCUPRIL®), ramipril (ALTACE®), or trandolapril (MAVIK®).

In some embodiments, a calcium channel blocker comprises amlodipine (NORVASC), diltiazem (CARDIZEM®, TIAZAC®), felodipine, isradipine, nicardipine, nifedipine (ADALAT CC®, AFEDITAB CR®, PROCARDIA®), nisoldipine (SULAR®), or verapamil (CALAN®, VERELAN®).

In some embodiments, a diabetes drug comprises metformin (GLUCOPHAGE®, GLUMETZA®), sulfonylureas (DIABETA®, GLYNASE®, GLUCOTROL®, AMARYL®), meglitindies (PRANDIN®, STARLIX®), thiazolidinediones (AVANDIA®, ACTOS®), DPP-4 inhibitors (JANUVIA®, ONGLYZA®, TRADJENTA®), GLP-1 receptor agonists (BYETTA®, VICTOZA®), SGLT2 inhibitors (INVOKANA®, FARXIGA®), or insulin therapy.

Other currently available treatment options that can be used in combination with FAM19A5 antagonist, or a composition thereof, include, but are not limited to, surgery (e.g., coronary artery bypass graft, or carotid endarterectomy) and controlling modifiable risk factors (e.g., exercise, healthy diet, stopping tobacco use).

III. FAM19A5 Antagonists

In some embodiments, a FAM19A5 antagonist useful for the present disclosure is an antisense oligonucleotide, siRNA, shRNA, miRNA, dsRNA, aptamer, PNA (peptide nucleic acid) that specifically targets FAM19A5, or a vector including the same. In other embodiments, a FAM19A5 antagonist is an antibody, or an antigen-binding portion thereof, that specifically binds to the FAM19A5 protein ("anti-FAM19A5 antibody"), a polynucleotide encoding the anti-FAM19A5 antibody, or a vector comprising the polynucleotide thereof.

Antibodies that are useful in the methods disclosed herein include monoclonal antibodies, which are characterized by particular functional features or properties. For example, the antibodies specifically bind human FAM19A5, including soluble FAM19A5 and membrane bound FAM19A5. In addition to binding specifically to soluble and/or membrane bound human FAM19A5, the antibodies described herein also (a) binds to soluble human FAM19A5 with a $K_D$ of 10 nM or less; (b) binds to membrane bound human FAM19A5 with a $K_D$ of 10 nM or less; or both (a) and (b).

In some embodiments, the anti-FAM19A5 antibody or antigen binding portion thereof specifically binds to soluble human FAM19A5 or membrane-bound human with high affinity, for example, with a $K_D$ of $10^{-7}$ M or less, $10^{-8}$ M (10 nM) or less, $10^{-9}$ M (1 nM) or less, $10^{-10}$ M (0.1 nM) or less, $10^{-11}$ M or less, or $10^{-12}$ M or less, e.g., $10^{-12}$ M to $10^{-7}$ M, $10^{-11}$ M to $10^{-7}$ M, $10^{-10}$ M to $10^{-7}$ M, or $10^{-9}$M to $10^{-7}$M, e.g., $10^{-12}$ M, $5\times10^{-12}$M, $10^{-11}$M, $5\times10^{-11}$M, $10^{-10}$ M, $5\times10^{-10}$ M, $10^{-9}$ M, $5\times10^{-9}$ M, $10^{-8}$M, $5\times10^{-8}$ M, $10^{-7}$ M, or $5\times10^{-7}$ M. Standard assays to evaluate the binding ability of the antibody toward human FAM19A5 of various species are known in the art, including for example, ELISAs, Western blots, and RIAs. Suitable assays are described in detail in the Examples. The binding kinetics (e.g., binding affinity) of the antibodies also can be assessed by standard assays known in the art, such as by ELISA, BIACORE™ analysis, or KINEXA®.

In some embodiments, the anti-FAM19A5 antibody or antigen binding portion thereof binds to soluble human FAM19A5 with a $K_D$, e.g., as determined by ELISA, of $10^{-7}$M or less, $10^{-8}$ M (10 nM) or less, $10^{-9}$ M (1 nM) or less, $10^{-10}$ M or less, $10^{-12}$ M to $10^{-7}$ M, $10^{-11}$M to $10^{-7}$ M, $10^{-10}$ M to $10^{-7}$ M, $10^{-9}$ M to $10^{-7}$ M, or $10^{-8}$ M to $10^{-7}$ M. In some embodiments, the anti-FAM19A5 antibody or antigen binding portion thereof binds to soluble FAM19A5 with a $K_D$ of 10 nM or less, e.g., between 0.1 and 10 nM, between 0.1 and 5 nM, between 0.1 and 1 nM, between 0.5 and 10 nM, between 0.5 and 5 nM, between 0.5 and 1 nM, between 1 and 10 nM, between 1 and 5 nM, or between 5 and 10 nM. In some embodiments, the anti-FAM19A5 antibody or antigen binding portion thereof specifically binds to soluble human FAM19A5 with a $K_D$ of about 1 pM, 2 pM, 3 pM, 4 pM, 5 pM, 6 pM, 7 pM, 8 pM, 9 pM, 10 pM, 20 pM, 30 pM, 40 pM, 50 pM, 60 pM, 70 pM, 80 pM, 90 pM, 100 pM, 200 pM, 300 pM, 400 pM, 500 pM, 600 pM, 700 pM, 800 pM, or 900 pM, or about 1 nM, 2 nM, 3 nM, 4 nM, 5 nM, 6 nM, 7 nM, 8 nM, or 9 nM, or about 10 nM, 20 nM, 30 nM, 40 nM, 50 nM, 60 nM, 70 nM, 80 nM, or 90 nM, as determined by as determined by ELISA.

In some embodiments, the anti-FAM19A5 antibody or antigen binding portion thereof binds to membrane-bound human with a $K_D$, e.g., as determined by ELISA, of $10^{-7}$ M or less, $10^{-8}$M (10 nM) or less, $10^{-9}$ M (1 nM) or less, $10^{-10}$ M or less, $10^{-12}$ M to $10^{-7}$ M, $10^{-11}$ M to $10^{-7}$ M, $10^{-10}$ M to $10^{-7}$ M, $10^{-9}$ M to $10^{-7}$ M, or $10^{-8}$ M to $10^{-7}$ M. In certain embodiments, the anti-FAM19A5 antibody or antigen binding portion thereof specifically binds to membrane-bound human FAM19A5 with a $K_D$ of 10 nM or less as determined by ELISA, e.g., between 0.1 and 10 nM, between 0.1 and 5 nM, between 0.1 and 1 nM, between 0.5 and 10 nM, between 0.5 and 5 nM, between 0.5 and 1 nM, between 1 and 10 nM, between 1 and 5 nM, or between 5 and 10 nM. In some embodiments, the anti-FAM19A5 antibody or antigen binding portion thereof binds to membrane-bound human FAM19A5 with a $K_D$ of about 1 pM, 2 pM, 3 pM, 4 pM, 5 pM, 6 pM, 7 pM, 8 pM, 9 pM, 10 pM, 20 pM, 30 pM, 40 pM, 50 pM, 60 pM, 70 pM, 80 pM, 90 pM, 100 pM, 200 pM, 300 pM, 400 pM, 500 pM, 600 pM, 700 pM, 800 pM, or 900 pM, or about 1 nM, 2 nM, 3 nM, 4 nM, 5 nM, 6 nM, 7 nM, 8 nM, or 9 nM, or about 10 nM, 20 nM, 30 nM, 40 nM, 50 nM, 60 nM, 70 nM, 80 nM, or 90 nM, as determined by as determined by ELISA.

In certain embodiments, the anti-FAM19A5 antibody or antigen binding portion thereof that is useful in the methods disclosed herewith cross-competes for binding to (or inhibits binding of) a human FAM19A5 epitope with an anti-FAM19A5 antibody comprising CDRs or variable regions disclosed herein.

In certain embodiments, anti-FAM19A5 antibodies or antigen binding portions thereof inhibit binding of a reference antibody comprising heavy chain CDR1, CDR2, and CDR3, and light chain CDR1, CDR2, and CDR3, (i) wherein the heavy chain CDR1, CDR2, and CDR3 of the reference antibody comprise the amino acid sequence of SEQ ID NO: 11, SEQ ID NO: 12, and SEQ ID NO: 13, respectively, and light chain CDR1, CDR2, and CDR3 of the reference antibody comprise the amino acid sequence of SEQ ID NO: 23, SEQ ID NO: 24, and SEQ ID NO: 25; (ii) wherein the heavy chain CDR1 comprises the amino acid sequence of SEQ ID NO: 14, the heavy chain CDR2 comprises the amino acid sequence of SEQ ID NO: 15, and the heavy chain CDR3 comprises the amino acid sequence of SEQ ID NO: 16, the light chain CDR1 comprises the amino acid sequence of SEQ ID NO: 26, the light chain CDR2 comprises the amino acid sequence of SEQ ID NO: 27, and the light chain CDR3 comprises the amino acid sequence of SEQ ID NO: 28; (iii) wherein the heavy chain CDR1 comprises the amino acid sequence of SEQ ID NO: 17, the heavy chain CDR2 comprises the amino acid sequence of SEQ ID NO: 18, and the heavy chain CDR3 comprises the amino acid sequence of SEQ ID NO: 19, the light chain CDR1 comprises the amino acid sequence of SEQ ID NO: 29, the light chain CDR2 comprises the amino acid sequence of SEQ ID NO: 30, and the light chain CDR3 comprises the amino acid sequence of SEQ ID NO: 31; (iv) wherein the heavy chain CDR1 comprises the amino acid sequence of SEQ ID NO: 20, the heavy chain CDR2 comprises the amino acid sequence of SEQ ID NO: 21, the heavy chain CDR3 comprises the amino acid sequence of SEQ ID NO: 22, the light chain CDR1 comprises the amino acid sequence of SEQ ID NO: 32, the light chain CDR2 comprises the amino acid sequence of SEQ ID NO: 33, and the light chain CDR3 comprises the amino acid sequence of SEQ ID NO: 34; (v) wherein the heavy chain CDR1 comprises the amino acid sequence of SEQ ID NO: 89, the heavy chain CDR2 comprises the amino acid sequence of SEQ ID NO: 90, the heavy chain CDR3 comprises the amino acid sequence of SEQ ID NO: 91, the light chain CDR1 comprises the amino acid sequence of SEQ ID NO: 92, the light chain CDR2 comprises the amino acid sequence of SEQ ID NO: 93, and the light chain CDR3 comprises the amino acid sequence of SEQ ID NO: 94; (vi) wherein the heavy chain CDR1 comprises the amino acid sequence of SEQ ID NO: 95, the heavy chain CDR2 comprises the amino acid sequence of SEQ ID NO: 96, the heavy chain CDR3 comprises the amino acid sequence of SEQ ID NO:

97, the light chain CDR1 comprises the amino acid sequence of SEQ ID NO: 98, the light chain CDR2 comprises the amino acid sequence of SEQ ID NO: 99, and the light chain CDR3 comprises the amino acid sequence of SEQ ID NO: 100; (vii) wherein the heavy chain CDR1 comprises the amino acid sequence of SEQ ID NO: 101, the heavy chain CDR2 comprises the amino acid sequence of SEQ ID NO: 102, the heavy chain CDR3 comprises the amino acid sequence of SEQ ID NO: 103, the light chain CDR1 comprises the amino acid sequence of SEQ ID NO: 104, the light chain CDR2 comprises the amino acid sequence of SEQ ID NO: 105, and the light chain CDR3 comprises the amino acid sequence of SEQ ID NO: 106; (viii) wherein the heavy chain CDR1 comprises the amino acid sequence of SEQ ID NO: 107, the heavy chain CDR2 comprises the amino acid sequence of SEQ ID NO: 108, the heavy chain CDR3 comprises the amino acid sequence of SEQ ID NO: 109, the light chain CDR1 comprises the amino acid sequence of SEQ ID NO: 110, the light chain CDR2 comprises the amino acid sequence of SEQ ID NO: 111, and the light chain CDR3 comprises the amino acid sequence of SEQ ID NO: 112; (ix) wherein the heavy chain CDR1 comprises the amino acid sequence of SEQ ID NO: 113, the heavy chain CDR2 comprises the amino acid sequence of SEQ ID NO: 114, the heavy chain CDR3 comprises the amino acid sequence of SEQ ID NO: 115, the light chain CDR1 comprises the amino acid sequence of SEQ ID NO: 116, the light chain CDR2 comprises the amino acid sequence of SEQ ID NO: 117, and the light chain CDR3 comprises the amino acid sequence of SEQ ID NO: 118; (x) wherein the heavy chain CDR1 comprises the amino acid sequence of SEQ ID NO: 119, the heavy chain CDR2 comprises the amino acid sequence of SEQ ID NO: 120, the heavy chain CDR3 comprises the amino acid sequence of SEQ ID NO: 121, the light chain CDR1 comprises the amino acid sequence of SEQ ID NO: 122, the light chain CDR2 comprises the amino acid sequence of SEQ ID NO: 123, and the light chain CDR3 comprises the amino acid sequence of SEQ ID NO: 124; (xi) wherein the heavy chain CDR1 comprises the amino acid sequence of SEQ ID NO: 125, the heavy chain CDR2 comprises the amino acid sequence of SEQ ID NO: 126, the heavy chain CDR3 comprises the amino acid sequence of SEQ ID NO: 127, the light chain CDR1 comprises the amino acid sequence of SEQ ID NO: 128, the light chain CDR2 comprises the amino acid sequence of SEQ ID NO: 129, and the light chain CDR3 comprises the amino acid sequence of SEQ ID NO: 130; (xii) wherein the heavy chain CDR1 comprises the amino acid sequence of SEQ ID NO: 131, the heavy chain CDR2 comprises the amino acid sequence of SEQ ID NO: 132, the heavy chain CDR3 comprises the amino acid sequence of SEQ ID NO: 133, the light chain CDR1 comprises the amino acid sequence of SEQ ID NO: 134, the light chain CDR2 comprises the amino acid sequence of SEQ ID NO: 135, and the light chain CDR3 comprises the amino acid sequence of SEQ ID NO: 136; (xiii) wherein the heavy chain CDR1 comprises the amino acid sequence of SEQ ID NO: 137, the heavy chain CDR2 comprises the amino acid sequence of SEQ ID NO: 138, the heavy chain CDR3 comprises the amino acid sequence of SEQ ID NO: 139, the light chain CDR1 comprises the amino acid sequence of SEQ ID NO: 140, the light chain CDR2 comprises the amino acid sequence of SEQ ID NO: 141, and the light chain CDR3 comprises the amino acid sequence of SEQ ID NO: 142; (xiv) wherein the heavy chain CDR1 comprises the amino acid sequence of SEQ ID NO: 143, the heavy chain CDR2 comprises the amino acid sequence of SEQ ID NO: 144, the heavy chain CDR3 comprises the amino acid sequence of SEQ ID NO: 145, the light chain CDR1 comprises the amino acid sequence of SEQ ID NO: 146, the light chain CDR2 comprises the amino acid sequence of SEQ ID NO: 147, and the light chain CDR3 comprises the amino acid sequence of SEQ ID NO: 148; (xv) wherein the heavy chain CDR1 comprises the amino acid sequence of SEQ ID NO: 149, the heavy chain CDR2 comprises the amino acid sequence of SEQ ID NO: 150, the heavy chain CDR3 comprises the amino acid sequence of SEQ ID NO: 151, the light chain CDR1 comprises the amino acid sequence of SEQ ID NO: 152, the light chain CDR2 comprises the amino acid sequence of SEQ ID NO: 153, and the light chain CDR3 comprises the amino acid sequence of SEQ ID NO: 154; (xvi) wherein the heavy chain CDR1 comprises the amino acid sequence of SEQ ID NO: 17, the heavy chain CDR2 comprises the amino acid sequence of SEQ ID NO: 18, the heavy chain CDR3 comprises the amino acid sequence of SEQ ID NO: 19, the light chain CDR1 comprises the amino acid sequence of SEQ ID NO: 208, the light chain CDR2 comprises the amino acid sequence of SEQ ID NO: 209, and the light chain CDR3 comprises the amino acid sequence of SEQ ID NO: 210. In some aspects, the heavy chain CDR1, CDR2, and CDR3 of the reference antibody comprise a CDR1, CDR2, and CDR3 sequence as set forth in Table 2, respectively, and the light chain CDR1, CDR2, and CDR3 of the reference antibody comprise a CDR1, CDR2, and CDR3 sequence as set forth in Table 3, respectively.

In some embodiments, the reference antibody comprises (a) heavy and light chain variable region sequences comprising SEQ ID NOs: 35 and 39, respectively; (b) heavy and light chain variable region sequences comprising SEQ ID NOs: 36 and 40, respectively; (c) heavy and light chain variable region sequences comprising SEQ ID NOs: 37 and 41, respectively; (d) heavy and light chain variable region sequences comprising SEQ ID NOs: 38 and 42, respectively; (e) heavy and light chain variable region sequences comprising SEQ ID NOs: 155 and 166, respectively; (f) heavy and light chain variable region sequences comprising SEQ ID NOs: 156 and 167, respectively; (g) heavy and light chain variable region sequences comprising SEQ ID NOs: 157 and 168, respectively; (h) heavy and light chain variable region sequences comprising SEQ ID NOs: 158 and 169, respectively; (i) heavy and light chain variable region sequences comprising SEQ ID NOs: 159 and 170, respectively; (j) heavy and light chain variable region sequences comprising SEQ ID NOs: 160 and 171, respectively; (k) heavy and light chain variable region sequences comprising SEQ ID NOs: 161 and 172, respectively; (l) heavy and light chain variable region sequences comprising SEQ ID NOs: 162 and 173, respectively; (m) heavy and light chain variable region sequences comprising SEQ ID NOs: 163 and 174, respectively; (n) heavy and light chain variable region sequences comprising SEQ ID NOs: 164 and 175, respectively; (o) heavy and light chain variable region sequences comprising SEQ ID NOs: 165 and 176, respectively; (p) heavy and light chain variable region sequences comprising SEQ ID NOs: 211 and 212, respectively. In some aspects, the reference antibody comprises a heavy chain variable region (VH) and a light chain variable region (VL), wherein the VH comprises an amino acid sequence as set forth in Table 4, and the VL comprises an amino acid sequence as set forth in Table 5.

In certain embodiments, the anti-FAM19A5 antibody or antigen binding portion thereof inhibits binding of such a reference antibody to human FAM19A5 by at least 10%, 20%, 30%, 40%, 50%, 60%, 70%, 80%, or 90% or by 100%.

Competing antibodies bind to the same epitope, an overlapping epitope or to adjacent epitopes (e.g., as evidenced by steric hindrance). Whether two antibodies compete with each other for binding to a target can be determined using competition experiments known in the art such as RIA and EIA.

In certain embodiments, the anti-FAM19A5 antibody or antigen binding portions thereof bind to the same FAM19A5 epitope as a reference antibody disclosed herein comprising heavy chain CDR1, CDR2, and CDR3 and light chain CDR1, CDR2, and CDR3, (i) wherein the heavy chain CDR1 comprises the amino acid sequence of SEQ ID NO: 11, the heavy chain CDR2 comprises the amino acid sequence of SEQ ID NO: 12, the heavy chain CDR3 comprises the amino acid sequence of SEQ ID NO: 13, the light chain CDR1 comprises the amino acid sequence of SEQ ID NO: 23, the light chain CDR2 comprises the amino acid sequence of SEQ ID NO: 24, and the light chain CDR3 comprises the amino acid sequence of SEQ ID NO: 25; (ii) wherein the heavy chain CDR1 comprises the amino acid sequence of SEQ ID NO: 14, the heavy chain CDR2 comprises the amino acid sequence of SEQ ID NO: 15, the heavy chain CDR3 comprises the amino acid sequence of SEQ ID NO: 16, the light chain CDR1 comprises the amino acid sequence of SEQ ID NO: 26, the light chain CDR2 comprises the amino acid sequence of SEQ ID NO: 27, and the light chain CDR3 comprises the amino acid sequence of SEQ ID NO: 28; (iii) wherein the heavy chain CDR1 comprises the amino acid sequence of SEQ ID NO: 17, the heavy chain CDR2 comprises the amino acid sequence of SEQ ID NO: 18, the heavy chain CDR3 comprises the amino acid sequence of SEQ ID NO: 19, the light chain CDR1 comprises the amino acid sequence of SEQ ID NO: 29, the light chain CDR2 comprises the amino acid sequence of SEQ ID NO: 30, and the light chain CDR3 comprises the amino acid sequence of SEQ ID NO: 31; (iv) wherein the heavy chain CDR1 comprises the amino acid sequence of SEQ ID NO: 20, the heavy chain CDR2 comprises the amino acid sequence of SEQ ID NO: 21, the heavy chain CDR3 comprises the amino acid sequence of SEQ ID NO: 22, the light chain CDR1 comprises the amino acid sequence of SEQ ID NO: 32, the light chain CDR2 comprises the amino acid sequence of SEQ ID NO: 33, and the light chain CDR3 comprises the amino acid sequence of SEQ ID NO: 34; (v) wherein the heavy chain CDR1 comprises the amino acid sequence of SEQ ID NO: 89, the heavy chain CDR2 comprises the amino acid sequence of SEQ ID NO: 90, the heavy chain CDR3 comprises the amino acid sequence of SEQ ID NO: 91, the light chain CDR1 comprises the amino acid sequence of SEQ ID NO: 92, the light chain CDR2 comprises the amino acid sequence of SEQ ID NO: 93, and the light chain CDR3 comprises the amino acid sequence of SEQ ID NO: 94; (vi) wherein the heavy chain CDR1 comprises the amino acid sequence of SEQ ID NO: 95, the heavy chain CDR2 comprises the amino acid sequence of SEQ ID NO: 96, the heavy chain CDR3 comprises the amino acid sequence of SEQ ID NO: 97, the light chain CDR1 comprises the amino acid sequence of SEQ ID NO: 98, the light chain CDR2 comprises the amino acid sequence of SEQ ID NO: 99, and the light chain CDR3 comprises the amino acid sequence of SEQ ID NO: 100; (vii) wherein the heavy chain CDR1 comprises the amino acid sequence of SEQ ID NO: 101, the heavy chain CDR2 comprises the amino acid sequence of SEQ ID NO: 102, the heavy chain CDR3 comprises the amino acid sequence of SEQ ID NO: 103, the light chain CDR1 comprises the amino acid sequence of SEQ ID NO: 104, the light chain CDR2 comprises the amino acid sequence of SEQ ID NO: 105, and the light chain CDR3 comprises the amino acid sequence of SEQ ID NO: 106; (viii) wherein the heavy chain CDR1 comprises the amino acid sequence of SEQ ID NO: 107, the heavy chain CDR2 comprises the amino acid sequence of SEQ ID NO: 108, the heavy chain CDR3 comprises the amino acid sequence of SEQ ID NO: 109, the light chain CDR1 comprises the amino acid sequence of SEQ ID NO: 110, the light chain CDR2 comprises the amino acid sequence of SEQ ID NO: 111, and the light chain CDR3 comprises the amino acid sequence of SEQ ID NO: 112; (ix) wherein the heavy chain CDR1 comprises the amino acid sequence of SEQ ID NO: 113, the heavy chain CDR2 comprises the amino acid sequence of SEQ ID NO: 114, the heavy chain CDR3 comprises the amino acid sequence of SEQ ID NO: 115, the light chain CDR1 comprises the amino acid sequence of SEQ ID NO: 116, the light chain CDR2 comprises the amino acid sequence of SEQ ID NO: 117, and the light chain CDR3 comprises the amino acid sequence of SEQ ID NO: 118; (x) wherein the heavy chain CDR1 comprises the amino acid sequence of SEQ ID NO: 119, the heavy chain CDR2 comprises the amino acid sequence of SEQ ID NO: 120, the heavy chain CDR3 comprises the amino acid sequence of SEQ ID NO: 121, the light chain CDR1 comprises the amino acid sequence of SEQ ID NO: 122, the light chain CDR2 comprises the amino acid sequence of SEQ ID NO: 123, and the light chain CDR3 comprises the amino acid sequence of SEQ ID NO: 124; (xi) wherein the heavy chain CDR1 comprises the amino acid sequence of SEQ ID NO: 125, the heavy chain CDR2 comprises the amino acid sequence of SEQ ID NO: 126, the heavy chain CDR3 comprises the amino acid sequence of SEQ ID NO: 127, the light chain CDR1 comprises the amino acid sequence of SEQ ID NO: 128, the light chain CDR2 comprises the amino acid sequence of SEQ ID NO: 129, and the light chain CDR3 comprises the amino acid sequence of SEQ ID NO: 130; (xii) wherein the heavy chain CDR1 comprises the amino acid sequence of SEQ ID NO: 131, the heavy chain CDR2 comprises the amino acid sequence of SEQ ID NO: 132, the heavy chain CDR3 comprises the amino acid sequence of SEQ ID NO: 133, the light chain CDR1 comprises the amino acid sequence of SEQ ID NO: 134, the light chain CDR2 comprises the amino acid sequence of SEQ ID NO: 135, and the light chain CDR3 comprises the amino acid sequence of SEQ ID NO: 136; (xiii) wherein the heavy chain CDR1 comprises the amino acid sequence of SEQ ID NO: 137, the heavy chain CDR2 comprises the amino acid sequence of SEQ ID NO: 138, the heavy chain CDR3 comprises the amino acid sequence of SEQ ID NO: 139, the light chain CDR1 comprises the amino acid sequence of SEQ ID NO: 140, the light chain CDR2 comprises the amino acid sequence of SEQ ID NO: 141, and the light chain CDR3 comprises the amino acid sequence of SEQ ID NO: 142; (xiv) wherein the heavy chain CDR1 comprises the amino acid sequence of SEQ ID NO: 143, the heavy chain CDR2 comprises the amino acid sequence of SEQ ID NO: 144, the heavy chain CDR3 comprises the amino acid sequence of SEQ ID NO: 145, the light chain CDR1 comprises the amino acid sequence of SEQ ID NO: 146, the light chain CDR2 comprises the amino acid sequence of SEQ ID NO: 147, and the light chain CDR3 comprises the amino acid sequence of SEQ ID NO: 148; (xv) wherein the heavy chain CDR1 comprises the amino acid sequence of SEQ ID NO: 149, the heavy chain CDR2 comprises the amino acid sequence of SEQ ID NO: 150, the heavy chain CDR3 comprises the amino acid sequence of SEQ ID NO: 151, the light chain CDR1 comprises the amino acid sequence of SEQ ID NO: 152, the light chain CDR2 comprises the amino acid sequence of SEQ ID NO: 153, and the light chain CDR3 comprises the amino acid sequence of SEQ ID NO: 154; or (xvi) wherein the heavy chain CDR1 comprises the amino acid sequence of SEQ ID NO: 17, the heavy chain CDR2 comprises the amino acid sequence of SEQ ID NO: 18, the heavy chain CDR3 comprises the amino acid sequence of SEQ ID NO: 19, the light chain CDR1 comprises the amino acid sequence of SEQ ID NO: 208, the light chain CDR2 comprises the amino acid sequence of SEQ ID NO: 209, and the light chain CDR3 comprises the amino acid sequence of SEQ ID NO: 210. In some aspects, the heavy chain CDR1, CDR2, and CDR3 of the reference antibody comprise a CDR1, CDR2, and CDR3 sequence as set forth in Table 2, respectively, and the light chain CDR1, CDR2, and CDR3 of the reference antibody comprise a CDR1, CDR2, and CDR3 sequence as set forth in Table 3, respectively.

In some embodiments, the reference antibody comprises (a) heavy and light chain variable region sequences comprising SEQ ID NOs: 35 and 39, respectively; (b) heavy and light chain variable region sequences comprising SEQ ID NOs: 36 and 40, respectively; (c) heavy and light chain variable region sequences comprising SEQ ID NOs: 37 and 41, respectively; (d) heavy and light chain variable region sequences comprising SEQ ID NOs: 38 and 42, respectively; (e) heavy and light chain variable region sequences comprising SEQ ID NOs: 155 and 166, respectively; (f) heavy and light chain variable region sequences comprising SEQ ID NOs: 156 and 167, respectively; (g) heavy and light chain variable region sequences comprising SEQ ID NOs: 157 and 168, respectively; (h) heavy and light chain variable region sequences comprising SEQ ID NOs: 158 and 169, respectively; (i) heavy and light chain variable region sequences comprising SEQ ID NOs: 159 and 170, respectively; (j) heavy and light chain variable region sequences comprising SEQ ID NOs: 160 and 171, respectively; (k) heavy and light chain variable region sequences comprising SEQ ID NOs: 161 and 172, respectively; (l) heavy and light chain variable region sequences comprising SEQ ID NOs: 162 and 173, respectively; (m) heavy and light chain variable region sequences comprising SEQ ID NOs: 163 and 174, respectively; (n) heavy and light chain variable region sequences comprising SEQ ID NOs: 164 and 175, respectively; (o) heavy and light chain variable region sequences comprising SEQ ID NOs: 165 and 176, respectively; (p) heavy and light chain variable region sequences comprising SEQ ID NOs: 211 and 212, respectively. In some aspects, the reference antibody comprises a heavy chain variable region (VH) and a light chain variable region (VL), wherein the VH comprises an amino acid sequence as set forth in Table 4, and the VL comprises an amino acid sequence as set forth in Table 5.

Techniques for determining whether two antibodies bind to the same epitope include, e.g., epitope mapping methods, such as, x-ray analyses of crystals of antigen: antibody complexes which provides atomic resolution of the epitope and hydrogen/deuterium exchange mass spectrometry (HDX-MS), methods monitoring the binding of the antibody to antigen fragments or mutated variations of the antigen, where loss of binding due to a modification of an amino acid residue within the antigen sequence is often considered an indication of an epitope component, computational combinatorial methods for epitope mapping.

An anti-FAM19A5 antibody or antigen binding portion thereof that would be useful in the methods disclosed herewith can bind to at least one epitope of mature human FAM19A5, as determined, e.g., by binding of the antibodies to fragments of human FAM19A5. In some embodiments, anti-FAM19A5 antibodies or antigen binding portions thereof bind to a fragment located within the amino acid sequence of TLDRDSSQPRRTIARQTARC (SEQ ID NO: 6 or amino acid residues 42 to 61 of SEQ ID NO: 2), e.g., an epitope having at least 3, 4, 5, 6, 7, 8, 9, 10, 11, 12, 13, 14, 15, 16, 17, 18, 19, or 20 amino acids of SEQ ID NO: 6. In some embodiments, anti-FAM19A5 antibodies or antigen binding portion thereof bind to SEQ ID NO: 6 at one or more amino acids corresponding to amino acid residues 46 to 51 (i.e., DSSQPR), e.g., amino acid residues 46, 50, and 52 (i.e., D---P-R), e.g., amino acid residues 46, 47, 48, and 50 (i.e., DSS-P) of SEQ ID NO: 2. In some embodiments, anti-FAM19A5 antibodies or antigen binding portions thereof bind to a fragment located within the amino acid sequence of CDMLPCLEGEGCDLLINRSG (SEQ ID NO: 9 or amino acids 90 to 109 of SEQ ID NO: 2), e.g., an epitope having at least 3, 4, 5, 6, 7, 8, 9, 10, 11, 12, 13, 14, 15, 16, 17, 18, 19, or 20 amino acids of SEQ ID NO: 9. In certain embodiments, anti-FAM19A5 antibodies or antigen binding portion thereof bind to SEQ ID NO: 9 at one or more amino acids residues 99 to 107 (i.e., EGCDLLINR), e.g., amino acid residues 102, 103, 105, and 107 (i.e., DL-I-R), e.g., amino acid residues 99, 100, 102, 103, 105, and 107 (i.e., EG-DL-I-R), e.g., amino acid residues 99, 100, and 107 (i.e., EG------R) of SEQ ID NO: 4.

In some embodiments, the at least one epitope has the amino acid sequence that is at least 90%, at least about 95%, at least about 96%, at least about 97%, at least about 98%, at least about 99%, or about 100% identical to SEQ ID NO: 6. In some embodiments, the at least one epitope has the amino acid sequence that is at least 90%, at least about 95%, at least about 96%, at least about 97%, at least about 98%, at least about 99%, or about 100% identical to SEQ ID NO: 9.

In some embodiments, the anti-FAM19A5 antibody or antigen binding portion thereof binds to a human FAM19A5 epitope only, which is SEQ ID NO: 5, 6, 7, 8, 9, or 10, or a fragment located within the amino acid sequence of SEQ ID NO: 5, 6, 7, 8, 9, or 10, e.g., an epitope having 1, 2, 3, 4, 5, 6, 7, 8, 9, 10, 11, 12, 13, 14, 15, 16, 17, 18, 19, or 20 amino acids of SEQ ID NO: 5, 6, 7, 8, 9, or 10.

In some embodiments, the anti-FAM19A5 antibody or antigen binding portion thereof of the present disclosure binds to SEQ ID NO: 6 or a fragment thereof in its native conformation (i.e., un-denatured). In some embodiments, the anti-FAM19A5 antibody or antigen binding portion thereof of the present disclosure binds to SEQ ID NO: 9 or a fragment thereof in its native conformation (i.e., un-denatured). In other embodiments, the at least one epitope has the amino acid sequence that is at least 90%, at least about 95%, at least about 96%, at least about 97%, at least about 98%, at least about 99%, or about 100% identical to SEQ ID NO: 5. In some embodiments, the at least one epitope has the amino acid sequence that is at least 90%, at least about 95%, at least about 96%, at least about 97%, at least about 98%, at least about 99%, or about 100% identical to SEQ ID NO: 10. In some embodiments, the anti-FAM19A5 antibody or antigen binding portion thereof binds to both glycosylated and unglycosylated human FAM19A5.

In some embodiments, the anti-FAM19A5 antibody or antigen binding portion thereof further binds to one or more additional FAM19A5 epitopes. Therefore, certain anti-FAM19A5 antibodies or antigen binding portions thereof bind to an epitope of SEQ ID NO: 6 and an additional epitope or an epitope of SEQ ID NO: 9 and an additional epitope. Other anti-FAM19A5 antibodies or antigen binding portions thereof can bind to an epitope of SEQ ID NO: 5, SEQ ID NO: 9, and an additional epitope. In some embodiments, anti-FAM19A5 antibodies or antigen binding portions thereof bind to an epitope of SEQ ID NO: 6, an epitope of SEQ ID NO: 10, and an additional epitope. In some embodiments, the one or more additional FAM19A5 epitopes are selected from QLAAGTCEIVTLDR (SEQ ID NO: 5, epitope F1), TLDRDSSQPRRTIARQTARC (SEQ ID NO: 6, epitope F2), TARCACRKGQIAGTTRARPA (SEQ ID NO: 7, epitope F3), ARPACV-DARIIKTKQWCDML (SEQ ID NO: 8, epitope F4), CDMLPCLEGEGCDLLINRSG (SEQ ID NO: 9, epitope F5), or NRSGWTCTQPGGRIKTTTVS (SEQ ID NO: 10, epitope F6), or a fragment located within the amino acid sequence of SEQ ID NO: 5, SEQ ID NO: 6, SEQ ID NO: 7, SEQ ID NO: 8, SEQ ID NO: 9, or SEQ ID NO: 10, or any combination thereof. A fragment located within the amino acid sequence of SEQ ID NO: 5, SEQ ID NO: 6, SEQ ID NO: 7, SEQ ID NO: 8, SEQ ID NO: 9, or SEQ ID NO: 10, includes a fragment having 1, 2, 3, 4, 5, 6, 7, 8, 9, 10, 11, 12, 13, 14, 15, 16, 17, 18, 19, or 20 amino acids of any of SEQ ID NO: 5, SEQ ID NO: 6, SEQ ID NO: 7, SEQ ID NO: 8, SEQ ID NO: 9, or SEQ ID NO: 10. In some embodiments, the one or more additional FAM19A5 epitopes are selected from SEQ ID NO: 5, 6, 7, 8, 9, or 10, a fragment located within the amino acid sequence of SEQ ID NO: 5, 6, 7, 8, 9, or 10, e.g., a fragment having 1, 2, 3, 4, 5, 6, 7, 8, 9, 10, 11, 12, 13, 14, 15, 16, 17, 18, 19, or 20 amino acids of SEQ ID NO: 5, 6, 7, 8, 9, or 10, or any combination thereof. In some embodiments, the anti-FAM19A5 antibody or antigen binding portion thereof of the disclosure binds to any of the one or more additional epitopes in their native conformation (i.e., un-denatured). In some embodiments, the anti-FAM19A5 antibody or antigen binding portion thereof binds to both glycosylated and unglycosylated of the one or more additional FAM19A5 epitopes.

In some embodiments, anti-FAM19A5 antibodies or antigen binding portions thereof bind to at least one FAM19A5 epitope identified as EP2, EP4, and/or EP8, wherein EP2 comprises, consists essentially of, or consists of the amino acids DSSQP (SEQ ID NO: 66), wherein EP4 comprises, consists essentially of, or consists of the amino acids ARCACRK (SEQ ID NO: 68), and wherein EP8 comprises, consists essentially of, or consists of the amino acids TCTQPGGR (SEQ ID NO: 72). In some embodiments, the at least one epitope has the amino acid sequence that is at least 90%, at least about 95%, at least about 96%, at least about 97%, at least about 98%, at least about 99%, or about 100% identical to EP2, EP4, or EP8. In some embodiments, anti-FAM19A5 antibodies or antigen binding portion thereof only bind to EP2 In some embodiments, anti-FAM19A5 antibodies or antigen binding portion thereof bind to EP4 and EP8.

In some embodiments, the anti-FAM19A5 antibody, or antigen binding portion thereof, binds to at least one FAM19A5 epitope identified as EP6, EP7, or EP8, wherein EP6 comprises the amino acids KTKQWCDML (SEQ ID NO: 70), wherein EP7 comprises the amino acids GCDLLINR (SEQ ID NO: 71), and wherein EP8 comprises the amino acids TCTQPGGR (SEQ ID NO: 72). In some embodiments, the at least one epitope has the amino acid sequence that is at least 90%, at least about 95%, at least about 96%, at least about 97%, at least about 98%, at least about 99%, or about 100% identical to EP6, EP7, or EP8. In some embodiments, the anti-FAM19A5 antibody, or antigen binding portion thereof, only binds to EP6, EP7, or EP8. In some embodiments, the anti-FAM19A5 antibody, or antigen binding portion thereof, binds to EP6, EP7, and EP8. In some embodiments, the anti-FAM19A5 antibody, or antigen binding portion thereof, binds to EP7 and EP8. In some embodiments, the anti-FAM19A5 antibody, or antigen binding portion thereof, binds to EP7.

In some embodiments, anti-FAM19A5 antibodies or antigen binding portion thereof bind to one or more FAM19A5 epitopes selected from the group consisting of SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, and any combinations thereof.

In certain embodiments, provided herein is an antibody or antigen binding portion thereof that binds to FAM19A5 (e.g., human FAM19A5) with a 20%, 25%, 30%, 35%, 40%, 45%, 50%, 55%, 60%, 65%, 70%, 75%, 80%, 85%, 90%, 95% or higher affinity than to another protein in the FAM19A family as measured by, e.g., an immunoassay (e.g., ELISA), surface plasmon resonance, or kinetic exclusion assay. In a specific embodiment, provided herein is an antibody or antigen binding portion thereof that binds to FAM19A5 (e.g., human FAM19A5) with no cross reactivity with another protein in the FAM19A family as measured by, e.g., an immunoassay.

In certain embodiments, the anti-FAM19A5 antibodies are not native antibodies or are not naturally-occurring antibodies. For example, the anti-FAM19A5 antibodies have post-translational modifications that are different from those of antibodies that are naturally-occurring, such as by having more, less or a different type of post-translational modification.

IV. Exemplary Anti-FAM19A5 Antibodies

Particular antibodies that can be used in the methods disclosed herein are antibodies, e.g., monoclonal antibodies, having the CDR and/or variable region sequences disclosed herein, as well as antibodies having at least 80% identity (e.g., at least 85%, at least 90%, at least 95%, or at least 99% identity) to their variable region or CDR sequences. The amino acid sequences for the VH and VL CDRs for the different anti-FAM19A5 antibodies are provided in Tables 2 and 3, respectively. The CDRs for the following antibodies were identified using the Kabat numbering scheme (see supra): 1-65, 3-2, 2-13, 1-28, P2-C12, 13B4, 13F7, 15A9, P1-A03, P1-A08, P1-F02, P2-A01, P2-A03, P2-F07, P2-F11, SS01-13, SS01-13-s5, and S5-2.GKNG. The CDRs for the following antibodies were identified using the IMGT numbering system (see supra): 1-7A-IT, Low-PI, 1-30, 1-17, 1-32, 4-11, 6-10, 2-13D, 2-13D-37, 2-13D-37-1.5W-41, and 2-13D-37-3W-16. The VH and VL amino acid sequences of different anti-FAM19A5 antibodies of the present disclosure are provided in Tables 4 and 5, respectively.

TABLE 2

Variable heavy chain CDR amino acid sequences

| Antibody | VH-CDR1 | VH-CDR2 | VH-CDR3 |
|---|---|---|---|
| According to Kabat System | | | |
| Anti-FAM19A5 ("2-13") | SHGMF (SEQ ID NO: 11) | EITNDGSGTNYGSAVKG (SEQ ID NO: 12) | STYECPGGFSCWGDTGQIDA (SEQ ID NO: 13) |
| Anti-FAM19A5 ("3-2") | SFNMF (SEQ ID NO: 14) | QISSSGSSTNYAPAVRG (SEQ ID NO: 15) | SSYDCPYGHCSSGVDSAGEIDA (SEQ ID NO: 16) |
| Anti-FAM19A5 ("1-65") | SYQMG (SEQ ID NO: 17) | VINKSGSDTS (SEQ ID NO: 18) | GSASYITAATIDA (SEQ ID NO: 19) |
| Anti-FAM19A5 ("1-28") | GFDFSDYG (SEQ ID NO: 20) | IRSDGSNP (SEQ ID NO: 21) | AKDGNGYCALDAYRSGGYSCGVYPGSIDA (SEQ ID NO: 22) |
| Anti-FAM19A5 ("P2-C12") | TYAVT (SEQ ID NO: 89) | YINWRGGTSYANWAKG (SEQ ID NO: 90) | DASSGAAFGSYGMDP (SEQ ID NO: 91) |
| Anti-FAM19A5 ("13B4") | SSNWWS (SEQ ID NO: 95) | EIYHGGTTNYNPSLKG (SEQ ID NO: 96) | WQLVGGLDV (SEQ ID NO: 97) |
| Anti-FAM19A5 ("13F7") | GYSWT (SEQ ID NO: 101) | EISHFGSANYNPSLKS (SEQ ID NO: 102) | ALRGTYSRFYYGMDV (SEQ ID NO: 103) |
| Anti-FAM19A5 ("15A9") | SYYWS (SEQ ID NO: 107) | YIYPSGSTNYNPSLKS (SEQ ID NO: 108) | VNPFGYYYAMDV (SEQ ID NO: 109) |
| Anti-FAM19A5 ("P1-A03") | SDYMS (SEQ ID NO: 113) | IIYPSTTTYYASWAKG (SEQ ID NO: 114) | GSNWSSGMNL (SEQ ID NO: 115) |
| Anti-FAM19A5 ("P1-A08") | TYYMS (SEQ ID NO: 119) | IVYPSGTTYYANWAKG (SEQ ID NO: 120) | GDSFGYGL (SEQ ID NO: 121) |
| Anti-FAM19A5 ("P1-F02") | NYYMG (SEQ ID NO: 125) | IIYASGSTYYASWAKG (SEQ ID NO: 126) | IDIGVGDYGWAYDRLDL (SEQ ID NO: 127) |
| Anti-FAM19A5 ("P2-A01") | GYYMS (SEQ ID NO: 131) | IIYPSGSTDYASWAKG (SEQ ID NO: 132) | VAGYVGYGYETFFDI (SEQ ID NO: 133) |
| Anti-FAM19A5 ("P2-A03") | NYDMS (SEQ ID NO: 137) | FMDTDGSAYYATWAKG (SEQ ID NO: 138) | RGSSYYGGIDI (SEQ ID NO: 139) |
| Anti-FAM19A5 ("P2-F07") | SYYMN (SEQ ID NO: 143) | IIYPSGTTYYAGWAKG (SEQ ID NO: 144) | TVSGYFDI (SEQ ID NO: 145) |
| Anti-FAM19A5 ("P2-F11") | SYGVS (SEQ ID NO: 149) | YIANNYNPHYASWAKG (SEQ ID NO: 150) | DNYGMDP (SEQ ID NO: 151) |
| Anti-FAM19A5 ("SS01-13") | SYQMG (SEQ ID NO: 17) | VINKSGSDTS (SEQ ID NO: 18) | GSASYITAATIDA (SEQ ID NO: 19) |
| Anti-FAM19A5 ("SS01-13-s5") | SYQMG (SEQ ID NO: 17) | AINKSGSDTS (SEQ ID NO: 252) | GSASYITAATIDA (SEQ ID NO: 19) |
| Anti-FAM19A5 ("S5-2.GKNG") | SYQMG (SEQ ID NO: 17) | AINKGGSDTS (SEQ ID NO: 253) | GSASYITAATIDA (SEQ ID NO: 19) |
| According to IMGT system | | | |
| Anti-FAM19A5 ("1-7A-IT") | GFTFSSFNMF (SEQ ID NO: 218) | QISSSGSSTNYAPAVKG (SEQ ID NO: 219) | SSYDCPYGHCSSGVDSAGEIDA (SEQ ID NO: 16) |
| Anti-FAM19A5 ("Low-PI") | GFDFESFNMF (SEQ ID NO: 220) | QISSSEEDENYAPAVKG (SEQ ID NO: 221) | SSYDCPYGHCSSGVDSAGEIDA (SEQ ID NO: 16) |
| Anti-FAM19A5 ("1-30") | GFDFESFNMF (SEQ ID NO: 220) | QISSSEEDENYAPAVKG (SEQ ID NO: 221) | SSYDCPYGHCSSGVDSAGEIDA (SEQ ID NO: 16) |
| Anti-FAM19A5 ("1-17") | GFDFESFNMF (SEQ ID NO: 220) | QISSSEEDENYAPAVKG (SEQ ID NO: 221) | SSYDCPYGHCSSGVDSAGEIDA (SEQ ID NO: 16) |

TABLE 2-continued

Variable heavy chain CDR amino acid sequences

| Antibody | VH-CDR1 | VH-CDR2 | VH-CDR3 |
| --- | --- | --- | --- |
| Anti-FAM19A5 ("1-32") | GFDFESFNMF (SEQ ID NO: 220) | QISSSEEDENYAPAVKG (SEQ ID NO: 221) | SSYDCPYGHCSSGVDSAGEIDA (SEQ ID NO: 16) |
| Anti-FAM19A5 ("4-11") | GFDFESFNMF (SEQ ID NO: 220) | QISSSEEDENYAPAVKG (SEQ ID NO: 221) | SSYDCPYGHCSSGVDSAGEIDA (SEQ ID NO: 16) |
| Anti-FAM19A5 ("6-10") | GFDFESFNMF (SEQ ID NO: 220) | QISSSEEDENYAPAVKG (SEQ ID NO: 221) | SSYDCPYGHCSSGVDSAGEIDA (SEQ ID NO: 16) |
| Anti-FAM19A5 ("2-13D") | GFTFSSHGMF (SEQ ID NO: 222) | EITNDGSGTNYGSAVKG (SEQ ID NO: 12) | STYECPGGFSCWGDTGQIDA (SEQ ID NO: 13) |
| Anti-FAM19A5 ("2-13D-37") | GFDFSSHGMF (SEQ ID NO: 223) | EITNDGSGTNYGSAVKG (SEQ ID NO: 12) | STYECPGGFSCWGDTGQIDA (SEQ ID NO: 13) |
| Anti-FAM19A5 ("2-13D-37-1.5W-41") | GFDFSSHGMF (SEQ ID NO: 223) | EITNDGSGTNYGSAVKG (SEQ ID NO: 12) | SSYVCPGGFSCWGDTGQIDA (SEQ ID NO: 246) |
| Anti-FAM19A5 ("2-13D-37-3W-16") | GFDFSSHGMF (SEQ ID NO: 223) | EITNDGSGTNYGSAVKG (SEQ ID NO: 12) | SNYACPGGFSCWGDTGQIDA (SEQ ID NO: 247) |

TABLE 3

Variable light chain CDR amino acid sequences (according to Kabat system)

| Antibody | VL-CDR1 | VL-CDR2 | VL-CDR3 |
| --- | --- | --- | --- |
| According to Kabat System | | | |
| Anti-FAM19A5 ("2-13") | SGGSYSYG (SEQ ID NO: 23) | WDDERPS (SEQ ID NO: 24) | GTEDISGTAGV (SEQ ID NO: 25) |
| Anti-FAM19A5 ("3-2") | SGGGSYAGSYYYG (SEQ ID NO: 26) | ESNKRPS (SEQ ID NO: 27) | GSWDSSNGGI (SEQ ID NO: 28) |
| Anti-FAM19A5 ("1-65") | SGGGSSGYGYG (SEQ ID NO: 29) | WNDKRPS (SEQ ID NO: 30) | GNDDYSSDSGYVGV (SEQ ID NO: 31) |
| Anti-FAM19A5 ("1-28") | GYGYG (SEQ ID NO: 32) | QND (SEQ ID NO: 33) | GSEDSSTLAGI (SEQ ID NO: 34) |
| Anti-FAM19A5 ("P2-C12") | QASQSISSYLS (SEQ ID NO: 92) | EASKLAS (SEQ ID NO: 93) | QQGYSSTNVWNA (SEQ ID NO: 94) |
| Anti-FAM19A5 ("13B4") | SGDKLGNVYAS (SEQ ID NO: 98) | QDNKRPS (SEQ ID NO: 99) | QAWDSSTAV (SEQ ID NO: 100) |
| Anti-FAM19A5 ("13F7") | RSSQSLLHSNGYNYLD (SEQ ID NO: 104) | LGSNRAS (SEQ ID NO: 105) | MQARQTPLT (SEQ ID NO: 106) |
| Anti-FAM19A5 ("15A9") | RASQSISTSLN (SEQ ID NO: 110) | GASTLQS (SEQ ID NO: 111) | QESASIPRT (SEQ ID NO: 112) |
| Anti-FAM19A5 ("P1-A03") | LASEDIYSGIS (SEQ ID NO: 116) | GASNLES (SEQ ID NO: 117) | LGGYSYSSTGLT (SEQ ID NO: 118) |
| Anti-FAM19A5 ("P1-A08") | TADTLSRSYAS (SEQ ID NO: 122) | RDTSRPS (SEQ ID NO: 123) | ATSDGSGSNYQYV (SEQ ID NO: 124) |
| Anti-FAM19A5 ("P1-F02") | LASEDIYSGIS (SEQ ID NO: 128) | GASNLES (SEQ ID NO: 129) | LGGYSYSSIT (SEQ ID NO: 130) |
| Anti-FAM19A5 ("P2-A01") | LASEDIYSGIS (SEQ ID NO: 134) | GASNLES (SEQ ID NO: 135) | LGGVTYSSTGTHLT (SEQ ID NO: 136) |

TABLE 3-continued

Variable light chain CDR amino acid sequences (according to Kabat system)

| Antibody | VL-CDR1 | VL-CDR2 | VL-CDR3 |
|---|---|---|---|
| Anti-FAM19A5 ("P2-A03") | QASQSIGGNLA (SEQ ID NO: 140) | RASTLAS (SEQ ID NO: 141) | QSPAYDPAAYVGNA (SEQ ID NO: 142) |
| Anti-FAM19A5 ("P2-F07") | LASEDIYSALA (SEQ ID NO: 146) | GTSNLES (SEQ ID NO: 147) | QGYSSYPLT (SEQ ID NO: 148) |
| Anti-FAM19A5 ("P2-F11") | QASQSVYNNKNLA (SEQ ID NO: 152) | AASTLAS (SEQ ID NO: 153) | QGEFSCSSADCNA (SEQ ID NO: 154) |
| Anti-FAM19A5 ("SS01-13") | SGGASSGYGYG (SEQ ID NO: 208) | KDDERPS (SEQ ID NO: 209) | GNDDYSSDSGYVGV (SEQ ID NO: 31) |
| Anti-FAM19A5 ("SS01-13-S5") | SGGASSGYGYG (SEQ ID NO: 208) | KDSERPS (SEQ ID NO: 213) | GNDDYSSDSGYVGV (SEQ ID NO: 31) |
| Anti-FAM19A5 ("S5-2.GKNG") | SGGASSGYGYG (SEQ ID NO: 208) | KDSERPS (SEQ ID NO: 213) | GNDDYSSDSGYVGV (SEQ ID NO: 31) |

According to IMGT system

| Antibody | VL-CDR1 | VL-CDR2 | VL-CDR3 |
|---|---|---|---|
| Anti-FAM19A5 ("1-7A-IT") | SGGGSYAGSYYYG (SEQ ID NO: 26) | ENNKRPS (SEQ ID NO: 224) | GSWDSSNGGI (SEQ ID NO: 28) |
| Anti-FAM19A5 ("Low-PI") | SGGGSEEEQYYYG (SEQ ID NO: 225) | EDEERPS (SEQ ID NO: 226) | GSWDSEDEDH (SEQ ID NO: 227) |
| Anti-FAM19A5 ("1-30") | SGGGSEEEQYYYG (SEQ ID NO: 225) | QDEERPS (SEQ ID NO: 228) | GSWDSEDEDH (SEQ ID NO: 227) |
| Anti-FAM19A5 ("1-17") | SGGGSYAGSYYYG (SEQ ID NO: 26) | EDEQRPS (SEQ ID NO: 229) | GSWDSEDEDH (SEQ ID NO: 227) |
| Anti-FAM19A5 ("1-32") | SGGGSYAGSYYYG (SEQ ID NO: 26) | QDEERPS (SEQ ID NO: 228) | GSWDSEDEDH (SEQ ID NO: 227) |
| Anti-FAM19A5 ("4-11") | SGGGSYAGSYYYG (SEQ ID NO: 26) | EDHERPS (SEQ ID NO: 230) | GSWDSSDEDH (SEQ ID NO: 231) |
| Anti-FAM19A5 ("6-10") | SGGGSYAGSYYYG (SEQ ID NO: 26) | QDLLRPS (SEQ ID NO: 232) | GSWDSLSSSH (SEQ ID NO: 233) |
| Anti-FAM19A5 ("2-13D") | SGGVYSYG (SEQ ID NO: 248) | WDDERPS (SEQ ID NO: 24) | GTEDISGTAGV (SEQ ID NO: 25) |
| Anti-FAM19A5 ("2-13D-37") | SGGVYSYG (SEQ ID NO: 248) | WDDERPS (SEQ ID NO: 24) | GTEDISGTAGV (SEQ ID NO: 25) |
| Anti-FAM19A5 ("2-13D-37-1.5W-41") | SGGVYSYG (SEQ ID NO: 248) | WDDERPS (SEQ ID NO: 24) | GTEDISGTAGV (SEQ ID NO: 25) |
| Anti-FAM19A5 ("2-13D-37-3W-16") | SGGVYSYG (SEQ ID NO: 248) | WDDERPS (SEQ ID NO: 24) | GTEDISGTAGV (SEQ ID NO: 25) |

TABLE 4

Variable heavy chain amino acid sequence

| Antibody | VH Amino Acid Sequence (SEQ ID NO) |
|---|---|
| Anti-FAM19A5 ("2-13") | AVTLDESGGGLQTPGGALSLVCKASGFTFSSHGMFWVRQTPGKGLEYVAEITNDGSGTNYGSAVKGRATISRDNGQSTVRLQLNNLRAEDTGTYFCARSTYECPGGFSCWGDTGQIDAWGHGTEVIVSS (SEQ ID NO: 35) |
| Anti-FAM19A5 ("3-2") | AVTLDESGGGLQTPGGALSLVCKASGFTFSSFNMFWVRQAPGKGLEYVAQISSSGSSTNYAPAVRGRATISRDNGQSTVRLQLNNPGAEDTGTYYCAKSSYDCPYGHCSSGVDSAGEIDAWGHGTEVIVSS (SEQ ID NO: 36) |

TABLE 4-continued

Variable heavy chain amino acid sequence

| Antibody | VH Amino Acid Sequence (SEQ ID NO) |
|---|---|
| Anti-FAM19A5 ("1-65") | AVTLDESGGGLQTPGGALSLVCKASGFTFSSYQMGWVRQAPGKGLEWVGVINKSGSDTSY GSAVKGRATISRDNGQSTVRLQLNNLRAEDTGTYFCAKGSASYITAATIDAWGHGTEVIV SS (SEQ ID NO: 37) |
| Anti-FAM19A5 ("1-28") | AVTLDESGGGLQTPGGALSLVCKASGFDFSDYGMGWVRQAPGKGLEWVAAIRSDGSNPSYGSAV KGRATISKDNGRSTVRLQLNNLRAEDTATYYCAKDGNGYCALDAYRSGGYSCGVYPGSIDAWGHG TEVIVSS (SEQ ID NO:38) |
| Anti-FAM19A5 ("P2-C12") | QSLEESGGRLVTPGTPLTLTCTVSGFSLSTYAVTWVRQAPGKGLEWIGYINWRGGTSYAN WAKGRFTISKTSSTTVDLKMTSPTTEDTATYFCARDASSGAAFGSYGMDPWGPGTLVTVS S (SEQ ID NO: 155) |
| Anti-FAM19A5 ("13B4") | QVQLQESGPGLVKPSGTLSLNCAVSGGSISSSNWWSWVRQPPGKGLEWIGEIYHGGTTNY NPSLKGRVTMSVDKTKNQFSLRLSSVTAVDTAVYYCARWQLVGGLDVWGQGTTVTVSS (SEQ ID NO: 156) |
| Anti-FAM19A5 ("13F7") | QVQLQEWGAGLLKPSETLSLTCAINAESFNGYSWTWIRQTPGKGLEWIGEISHFGSANYN PSLKSRATISADKSKNQFSLKLTSVTAVDTAVYYCARALRGTYSRFYYGMDVWGQGTTVT VSS (SEQ ID NO: 157) |
| Anti-FAM19A5 ("15A9") | QVQLQESGPGLVKPSETLSLTCTVSGGSISSYYWSWIRQPPGKGLEWIGYIYPSGSTNYN PSLKSRVTISVDTSKNQFSLNLKSVTAVDTAVYYCARVNPFGYYYAMDVWGQGTTVTVSS (SEQ ID NO: 158) |
| Anti-FAM19A5 ("P1-A03") | QSVEESGGRLVTPGTPLTLTCTVSGFSLSSDYMSWVRQAPGEGLEWIGIIYPSTTTYYAS WAKGRFTISKTSSTTVELKMTSLTTEDTATYFCARGSNWSSGMNLWGPGTLVTVSS (SEQ ID NO: 159) |
| Anti-FAM19A5 ("P1-A08") | QSLEESGGRLVTPGTPLTLTCTASGFSLSTYYMSWVRQAPGKGLEWIGIVYPSGTTYYAN WAKGRFTISTASTTVDLMITSPTTEDTATYFCARGDSFGYGLWGPGTLVTVSS (SEQ ID NO: 160) |
| Anti-FAM19A5 ("P1-F02") | QSLEESGGRLVTPGTPLTLTCTASGFSLSNYYMGWVRQAPGEGLEWIGIIYASGSTYYAS WAKGRFTISKTSTTVDLKMTSLTTEDTATYFCARIDIGVGDYGWAYDRLDLWGQGTLVTV SS (SEQ ID NO: 161) |
| Anti-FAM19A5 ("P2-A01") | QEQLVESGGRLVTPGTPLTLSCTASGFFLSGYYMSWVRQAPGKGLEWIGIIYPSGSTDYA SWAKGRFTISKTSTTVDLKITTPTTEDTATYFCARVAGYVGYGYETFFDIWGPGTLVTVS L (SEQ ID NO: 162) |
| Anti-FAM19A5 ("P2-A03") | QSVEESGGRLVTPGTPLTLTCTVSGFSLNNYDMSWVRQAPGKGLEYIGFMDTDGSAYYAT WAKGRFTISRTSTTVDLKMTSPTTEDTATYFCARRGSSYYGGIDIWGPGTPVTVSL (SEQ ID NO: 163) |
| Anti-FAM19A5 ("P2-F07") | QSLEESGGRLVTPGTPLTLTCTASGFSLSSYYMNWVRQAPGKGLEWIGIIYPSGTTYYAG WAKGRFTISKTSTTVDLKITSPTSEDTATYFCARTVSGYFDIWGPGTLVTVSL (SEQ ID NO: 164) |
| Anti-FAM19A5 ("P2-F11") | QEQLVESGGRLVTPGTTLTLTCTVSGFSLSSYGVSWVRQAPGKGLEWIGYIANNYNPHYA SWAKGRFTISKTSSTTVDLKMTSLTTEDTATYFCARDNYGMDPWGPGTLVTVSS (SEQ ID NO: 165) |
| Anti-FAM19A5 ("SS01-13") | AVTLDESGGGLQTPGGALSLSCKASGFTFSSYQMGWVRQAPGKGLEWVGVINKSGSDTSY GSAVKGRATISRDNGQSTLYLQMNNLRAEDTAVYFCAKGSASYITAATIDAWGHGTEVIV SS (SEQ ID NO: 211) |
| Anti-FAM19A5 ("SS01-13-s5") | AVTLDESGGGLQTPGGALRLSCKASGFTFSSYQMGWVRQAPGKGLEWVSAINKSGSDTSY GSAVKGRATISRDNGQSTLYLQMNSLRAEDTAVYFCAKGSASYITAATIDAWGHGTEVIV SS (SEQ ID NO: 214) |
| Anti-FAM19A5 ("S5-2.GKNG") | AVTLDESGGGLQTPGGALRLSCKASGFTFSSYQMGWVRQAPGKGLEWVSAINKSGSDTSY GSAVKGRATISRDNGQSTLYLQMNSLRAEDTAVYFCAKGSASYITAATIDAWGHGTEVIV SS (SEQ ID NO: 249) |
| Anti-FAM19A5 ("1-7A-IT") | AVTLDESGGGLQTPGGALRLSCKASGFTFSSFNMFWVRQAPGKGLEYVSQISSSGSSTNY APAVKGRATISRDNGQSTLYLQMNSLRAEDTGTYYCAKSSYDCPYGHCSSGVDSAGEIDA WGHGTEVIVSS (SEQ ID NO: 234) |
| Anti-FAM19A5 ("Low-PI") | AVTLDESGGGLQTPGGALRLSCKASGFDFESFNMFWVRQAPGKGLEYVSQISSSEEDENY APAVKGRATISRDNGQSTLYLQMNSLRAEDTGTYYCAKSSYDCPYGHCSSGVDSAGEIDA WGHGTEVIVSS (SEQ ID NO: 235) |

TABLE 4-continued

Variable heavy chain amino acid sequence

| Antibody | VH Amino Acid Sequence (SEQ ID NO) |
|---|---|
| Anti-FAM19A5 ("1-30") | AVTLDESGGGLQTPGGALRLSCKASGFDFESFNMFWVRQAPGKGLEYVSQISSSEEDENY APAVKGRATISRDNGQSTLYLQMNSLRAEDTGTYYCAKSSYDCPYGHCSSGVDSAGEIDA WGHGTEVIVSS (SEQ ID NO: 235) |
| Anti-FAM19A5 ("1-17") | AVTLDESGGGLQTPGGALRLSCKASGFDFESFNMFWVRQAPGKGLEYVSQISSSEEDENY APAVKGRATISRDNGQSTLYLQMNSLRAEDTGTYYCAKSSYDCPYGHCSSGVDSAGEIDA WGHGTEVIVSS (SEQ ID NO: 235) |
| Anti-FAM19A5 ("1-32") | AVTLDESGGGLQTPGGALRLSCKASGFDFESFNMFWVRQAPGKGLEYVSQISSSEEDENY APAVKGRATISRDNGQSTLYLQMNSLRAEDTGTYYCAKSSYDCPYGHCSSGVDSAGEIDA WGHGTEVIVSS (SEQ ID NO: 235) |
| Anti-FAM19A5 ("4-11") | AVTLDESGGGLQTPGGALRLSCKASGFDFESFNMFWVRQAPGKGLEYVSQISSSEEDENY APAVKGRATISRDNGQSTLYLQMNSLRAEDTGTYYCAKSSYDCPYGHCSSGVDSAGEIDA WGHGTEVIVSS (SEQ ID NO: 235) |
| Anti-FAM19A5 ("6-10") | AVTLDESGGGLQTPGGALRLSCKASGFDFESFNMFWVRQAPGKGLEYVSQISSSEEDENY APAVKGRATISRDNGQSTLYLQMNSLRAEDTGTYYCAKSSYDCPYGHCSSGVDSAGEIDA WGHGTEVIVSS (SEQ ID NO: 235) |
| Anti-FAM19A5 ("2-13D") | AVTLDESGGGLQTPGGALRLSCSASGFTFSSHGMFWVRQAPGKGLEYVSEITNDGSGTNY GSAVKGRATISRDNGQSTLYLQMNSLRAEDTGTYFCARSTYECPGGFSCWGDTGQIDAWG HGTEVIVSS (SEQ ID NO: 236) |
| Anti-FAM19A5 ("2-13D-37") | AVTLDESGGGLQTPGGALRLSCSASGFDFSSHGMFWVRQAPGKGLEYVSEITNDGSGTNY GSAVKGRATISRDNGQSTLYLQMNSLRAEDTGTYFCARSTYECPGGFSCWGDTGQIDAWG HGTEVIVSS (SEQ ID NO: 250) |
| Anti-FAM19A5 ("2-13D-37-1.5W-41") | AVTLDESGGGLQTPGGALRLSCSASGFDFSSHGMFWVRQAPGKGLEYVSEITNDGSGTNY GSAVKGRATISRDNGQSTLYLQMNSLRAEDTGTYFCARSSYVCPGGFSCWGDTGQIDAWG HGTEVIVSS (SEQ ID NO: 237) |
| Anti-FAM19A5 ("2-13D-37-3W-16") | AVTLDESGGGLQTPGGALRLSCSASGFDFSSHGMFWVRQAPGKGLEYVSEITNDGSGTNY GSAVKGRATISRDNGQSTLYLQMNSLRAEDTGTYFCARSNYACPGGFSCWGDTGQIDAWG HGTEVIVSS (SEQ ID NO: 251) |

TABLE 5

Variable light chain amino acid sequence

| Antibody | VL Amino Acid Sequence (SEQ ID NO) |
|---|---|
| Anti-FAM19A5 ("2-13") | ALTQPSSVSANPGETVKITCSGGSYSYGWFQQKSPGSALVTVIYWDDERPSDIPSRFSGA LSGSTNTLTITGVQADDEAVYFCGTEDISGTAGVFGAGTTLTVL (SEQ ID NO: 39) |
| Anti-FAM19A5 ("3-2") | ALTQPSSVSANPGETVKITCSGGGSYAGSYYYGWYQQKAPGSAPVTLIYESNKRPSDIPS RFSGSTSGSTATLTITGVQADDEAIYYCGSWDSSNGGIFGAGTTLTVL (SEQ ID NO: 40) |
| Anti-FAM19A5 ("1-65") | ALTQPSSVSANPGETVKITCSGGGSSGYGYGWYQQKSPSSAPLTVIYWNDKRPSDIPSRF SGSKSGSTHTLTITGVQAEDEAVYFCGNDDYSSDSGYVGVFGAGTTLTVL (SEQ ID NO: 41) |
| Anti-FAM19A5 ("1-28") | ALTQPSSVSANLEGTVEITCSGSGYGYGWYQQKSPGSAPVTVIYQNDKRPSDIPSRFSGS KSGSTGTLTITGVQVEDEAVYYCGSEDSSTLAGIFGAGTTLTVL (SEQ ID NO: 42) |
| Anti-FAM19A5 ("P2-C12") | ELDMTQTPSSVSAAVGGTVTIKCQASQSISSYLSWYQQKPGQPPKLLIYEASKLASGVPS RFSGSGYGTEFTLTISDLECADAATYYCQQGYSSTNVWNAFGGGTNVEIK (SEQ ID NO: 166) |
| Anti-FAM19A5 ("13B4") | SYELTQPLSVSVSPGQTASITCSGDKLGNVYASWYQQKPGQSPTLVIYQDNKRPSGIPER FSGSNSGKTATLTISGTQALDEADYYCQAWDSSTAVFGGGTKLTVL (SEQ ID NO: 167) |
| Anti-FAM19A5 ("13F7") | DIVMTQTPLSLPVAPGEPASISCRSSQSLLHSNGYNYLDWYVQKPGQPPQLLIYLGSNRA SGVPDRFSGSGSGTDFTLKISRVEAEDVGVYYCMQARQTPLTFGGGTKVEIK (SEQ ID NO: 168) |

TABLE 5-continued

Variable light chain amino acid sequence

| Antibody | VL Amino Acid Sequence (SEQ ID NO) |
|---|---|
| Anti-FAM19A5 ("15A9") | DIQMTQSPSSLSASVGDRITISCRASQSISTSLNWYQQTPGKAPRLLIYGASTLQSGVPS RFSGGGSGTDFSLTITSLQPEDFATYYCQESASIPRTFGQGTKLDIK (SEQ ID NO: 169) |
| Anti-FAM19A5 ("P1-A03") | ELVMTQTPPSLSASVGETVRIRCLASEDIYSGISWYQQKPEKPPTLLISGASNLESGVPP RFSGSGSGTDYTLTIGGVQAEDAATYYCLGGYSYSSTGLTFGAGTNVEIK (SEQ ID NO: 170) |
| Anti-FAM19A5 ("P1-A08") | ELVLTQSPSVQVNLGQTVSLTCTADTLSRSYASWYQQKPGQAPVLLIYRDTSRPSGVPDR FSGSSSGNTATLTISGAQAGDEADYYCATSDGSGSNYQYVFGGGTQLTVT (SEQ ID NO: 171) |
| Anti-FAM19A5 ("P1-F02") | ELDMTQTPPSLSASVGETVRIRCLASEDIYSGISWYQQKPGKPPTLLIYGASNLESGVPP RFSGSGSGTDYTLTIGGVQAEDAATYYCLGGYSYSSITFGAGTNVEIK (SEQ ID NO: 172) |
| Anti-FAM19A5 ("P2-A01") | ELVMTQTPPSLSASVGETVRIRCLASEDIYSGISWYQQKPGKPPTLLIYGASNLESGVPP RFSGSGSGSDYTLTIGGVQAEDAATYYCLGGVTYSSTGTHLTFGAGTNVEIK (SEQ ID NO: 173) |
| Anti-FAM19A5 ("P2-A03") | ELDLTQTPASVSEPVGGTVTIKCQASQSIGGNLAWYQQKPGQPPKLLIYRASTLASGVPS RFKGSGSGTDFTLTISDLECADAATYYCQSPAYDPAAYVGNAFGGGTELEIL (SEQ ID NO: 174) |
| Anti-FAM19A5 ("P2-F07") | ELDLTQTPPSLSASVGGTVTINCLASEDIYSALAWYQQKPGKPPTLLISGTSNLESGVPP RFSGSGSGTDYTLTIGGVQAEDAATYFCQGYSSYPLTFGAGTNVEIK (SEQ ID NO: 175) |
| Anti-FAM19A5 ("P2-F11") | ELDLTQTPSSVSAAVGGTVTINCQASQSVYNNKNLAWYQQKPGQPPKLLIYAASTLASGV SSRFKGSGSGTQFTLTISDVQCDDAATYYCQGEFSCSSADCNAFGGGTELEIL (SEQ ID NO: 176) |
| Anti-FAM19A5 ("SS01-13") | ALTQPSSVSANPGETVRITCSGGASSGYGYGWYQQKPSSAPLTVIYKDDERPSDIPSRFS GSSSGSTHTLTITGVQAEDEAVYFCGNDDYSSDSGYVGVFGAGTTLTVL (SEQ ID NO: 212) |
| Anti-FAM19A5 ("SS01-13-s5") | ALTQPSSVSANPGETARITCSGGASSGYGYGWYQQKPSSAPLTVIYKDSERPSDIPSRFS GSSSGSTHTLTISGVQAEDEAVYFCGNDDYSSDSGYVGVFGAGTTLTVL (SEQ ID NO: 215) |
| Anti-FAM19A5 ("S5-2.GKNG") | ALTQPSSVSANPGETARITCSGGASSGYGYGWYQQKPSSAPLTVIYKDSERPSDIPSRFS GSSSGSTHTLTISGVQAEDEAVYFCGNDDYSSDSGYVGVFGAGTTLTVL (SEQ ID NO: 215) |
| Anti-FAM19A5 ("1-7A-IT") | ALTQPSSVSANPGETVKITCSGGGSYAGSYYYGWYQQKPGSAPVTLIYENNKRPSDIPSR FSGSTSGSTATLTITGVQAGDEADYYCGSWDSSNGGIFGAGTTLTVL (SEQ ID NO: 238) |
| Anti-FAM19A5 ("Low-PI") | ALTQPSSVSANPGETVKITCSGGGSEEEQYYYGWYQQKPGSAPVTLIYEDEERPSDIPSR FSGSTSGSTATLTITGVQAGDEADYYCGSWDSEDEDHFGAGTTLTVL (SEQ ID NO: 239) |
| Anti-FAM19A5 ("1-30") | ALTQPSSVSANPGETVKITCSGGGSEEEQYYYGWYQQKPGSAPVTLIYQDEERPSDIPSR FSGSTSGSTATLTITGVQAGDEADYYCGSWDSEDEDHFGAGTTLTVL (SEQ ID NO: 240) |
| Anti-FAM19A5 ("1-17") | ALTQPSSVSANPGETVKITCSGGGSYAGSYYYGWYQQKPGSAPVTLIYEDEQRPSDIPSR FSGSTSGSTATLTITGVQAGDEADYYCGSWDSEDEDHFGAGTTLTVL (SEQ ID NO: 241) |
| Anti-FAM19A5 ("1-32") | ALTQPSSVSANPGETVKITCSGGGSYAGSYYYGWYQQKPGSAPVTLIYQDEERPSDIPSR FSGSTSGSTATLTITGVQAGDEADYYCGSWDSEDEDHFGAGTTLTVL (SEQ ID NO: 242) |
| Anti-FAM19A5 ("4-11") | ALTQPSSVSANPGETVKITCSGGGSYAGSYYYGWYQQKPGSAPVTLIYEDHERPSDIPSR FSGSTSGSTATLTITGVQAGDEADYYCGSWDSSDEDHFGAGTTLTVL (SEQ ID NO: 243) |
| Anti-FAM19A5 ("6-10") | ALTQPSSVSANPGETVKITCSGGGSYAGSYYYGWYQQKPGSAPVTLIYQDLLRPSDIPSR FSGSTSGSTATLTITGVQAGDEADYYCGSWDSLSSSHFGAGTTLTVE (SEQ ID NO: 244) |

TABLE 5-continued

Variable light chain amino acid sequence

| Antibody | VL Amino Acid Sequence (SEQ ID NO) |
|---|---|
| Anti-FAM19A5 ("2-13D") | ALTQPSSVSANPGETAKITCSGGVYSYGWFQQKPGSALVTVIYWDDERPSDIPSRFSGAL SGSTNTLTITGVQAEDEADYYCGTEDISGTAGVFGAGTTLTVL (SEQ ID NO: 245) |
| Anti-FAM19A5 ("2-13D-37") | ALTQPSSVSANPGETAKITCSGGVYSYGWFQQKPGSALVTVIYWDDERPSDIPSRFSGAL SGSTNTLTITGVQAEDEADYYCGTEDISGTAGVFGAGTTLTVL (SEQ ID NO: 245) |
| Anti-FAM19A5 ("2-13D-37-1.5W-41") | ALTQPSSVSANPGETAKITCSGGVYSYGWFQQKPGSALVTVIYWDDERPSDIPSRFSGAL SGSTNTLTITGVQAEDEADYYCGTEDISGTAGVFGAGTTLTVL ((SEQ ID NO: 245) |
| Anti-FAM19A5 ("2-13D-37-3W-16") | ALTQPSSVSANPGETAKITCSGGVYSYGWFQQKPGSALVTVIYWDDERPSDIPSRFSGAL SGSTNTLTITGVQAEDEADYYCGTEDISGTAGVFGAGTTLTVL (SEQ ID NO: 245) |

Accordingly, provided herein is an anti-FAM19A5 antibody, or an antigen-binding portion thereof, comprising heavy and light chain variable regions, wherein the heavy chain variable region comprises the amino acid sequence of SEQ ID NOs: 35-38, 155-165, 211, 214, 234-237, or 249-251 (see Table 4). In other embodiments, the anti-FAM19A5 antibody, or an antigen binding portion thereof, comprises the CDRs of the heavy chain variable region selected from the group consisting of SEQ ID NOs: 35-38, 155-165, 211, 214, 234-237, or 249-251 (see Table 4).

Also provided is an anti-FAM19A5 antibody, or an antigen-binding portion thereof, comprising heavy and light chain variable regions, wherein the light chain variable region comprises the amino acid sequence of SEQ ID NOs: 39-42, 166-176, 212, 215, or 238-245 (see Table 5). In other embodiments, the anti-FAM19A5 antibody, or an antigen binding portion thereof, comprises the CDRs of the light chain variable region selected from the group consisting of SEQ ID NOs: 39-42, 166-176, 212, 215, or 238-245 (see Table 5).

In certain embodiments, the anti-FAM19A5 antibody, or an antigen binding portion thereof, comprises the CDRs of the heavy chain variable region selected from the group consisting of SEQ ID NOs: 35-38, 155-165, 211, 214, 234-237, or 249-251 and the CDRs of the light chain variable region selected from the group consisting of SEQ ID NOs: 39-42, 166-176, 212, 215, or 238-245.

Also provided is an anti-FAM19A5 antibody, or an antigen-binding portion thereof, comprising heavy and light chain variable regions, (i) wherein the heavy chain variable region comprises the amino acid sequence of SEQ ID NO: 35 and wherein the light chain variable region comprises the amino acid sequence of SEQ ID NO: 39; (ii) wherein the heavy chain variable region comprises the amino acid sequence of SEQ ID NO: 36 and wherein the light chain variable region comprises the amino acid sequence of SEQ ID NO: 40; (iii) wherein the heavy chain variable region comprises the amino acid sequence of SEQ ID NO: 37 and wherein the light chain variable region comprises the amino acid sequence of SEQ ID NO: 41; (iv) wherein the heavy chain variable region comprises the amino acid sequence of SEQ ID NO: 38 and wherein the light chain variable region comprises the amino acid sequence of SEQ ID NO: 42; (v) wherein the heavy chain variable region comprises the amino acid sequence of SEQ ID NO: 155 and wherein the light chain variable region comprises the amino acid sequence of SEQ ID NO: 166; (vi) wherein the heavy chain variable region comprises the amino acid sequence of SEQ ID NO: 156 and wherein the light chain variable region comprises the amino acid sequence of SEQ ID NO: 167; (vii) wherein the heavy chain variable region comprises the amino acid sequence of SEQ ID NO: 157 and wherein the light chain variable region comprises the amino acid sequence of SEQ ID NO: 168; (viii) wherein the heavy chain variable region comprises the amino acid sequence of SEQ ID NO: 158 and wherein the light chain variable region comprises the amino acid sequence of SEQ ID NO: 169; (ix) wherein the heavy chain variable region comprises the amino acid sequence of SEQ ID NO: 159 and wherein the light chain variable region comprises the amino acid sequence of SEQ ID NO: 170; (x) wherein the heavy chain variable region comprises the amino acid sequence of SEQ ID NO: 160 and wherein the light chain variable region comprises the amino acid sequence of SEQ ID NO: 171; (xi) wherein the heavy chain variable region comprises the amino acid sequence of SEQ ID NO: 161 and wherein the light chain variable region comprises the amino acid sequence of SEQ ID NO: 172; (xii) wherein the heavy chain variable region comprises the amino acid sequence of SEQ ID NO: 162 and wherein the light chain variable region comprises the amino acid sequence of SEQ ID NO: 173; (xiii) wherein the heavy chain variable region comprises the amino acid sequence of SEQ ID NO: 163 and wherein the light chain variable region comprises the amino acid sequence of SEQ ID NO: 174; (xiv) wherein the heavy chain variable region comprises the amino acid sequence of SEQ ID NO: 164 and wherein the light chain variable region comprises the amino acid sequence of SEQ ID NO: 175; (xv) wherein the heavy chain variable region comprises the amino acid sequence of SEQ ID NO: 165 and wherein the light chain variable region comprises the amino acid sequence of SEQ ID NO: 176; (xvi) wherein the heavy chain variable region comprises the amino acid sequence of SEQ ID NO: 211 and wherein the light chain variable region comprises the amino acid sequence of SEQ ID NO: 212; (xvii) wherein the heavy chain variable region comprises the amino acid sequence of SEQ ID NO: 214 and wherein the light chain variable region comprises the amino acid sequence of SEQ ID NO: 215; (xviii) wherein the heavy chain variable region comprises the amino acid sequence of SEQ ID NO: 249 and wherein the light chain variable region comprises the amino acid sequence of SEQ ID NO: 215; (xix) wherein the heavy chain variable region comprises the amino acid sequence of SEQ ID NO: 234 and wherein the light chain variable region comprises the amino acid sequence of SEQ ID NO: 238; (xx) wherein the heavy chain variable region comprises the amino acid sequence of SEQ ID NO: 235 and wherein the light chain variable region comprises the amino acid sequence of SEQ ID NO: 239; (xxi) wherein the heavy chain variable region comprises the amino acid sequence of SEQ ID NO: 235 and wherein the light chain variable region comprises the amino acid sequence of SEQ ID NO: 240; (xxii) wherein the heavy chain variable region comprises the amino acid sequence of SEQ ID NO: 235 and wherein the light chain variable region comprises the amino acid sequence of SEQ ID NO: 241; (xxiii) wherein the heavy chain variable region comprises the amino acid sequence of SEQ ID NO: 235 and wherein the light chain variable region comprises the amino acid sequence of SEQ ID NO: 242; (xxiv) wherein the heavy chain variable region comprises the amino acid sequence of SEQ ID NO: 235 and wherein the light chain variable region comprises the amino acid sequence of SEQ ID NO: 243; (xxv) wherein the heavy chain variable region comprises the amino acid sequence of SEQ ID NO: 235 and wherein the light chain variable region comprises the amino acid sequence of SEQ ID NO: 244; (xxvi) wherein the heavy chain variable region comprises the amino acid sequence of SEQ ID NO: 236 and wherein the light chain variable region comprises the amino acid sequence of SEQ ID NO: 245; (xxvii) wherein the heavy chain variable region comprises the amino acid sequence of SEQ ID NO: 250 and wherein the light chain variable region comprises the amino acid sequence of SEQ ID NO: 245; (xxviii) wherein the heavy chain variable region comprises the amino acid sequence of SEQ ID NO: 237 and wherein the light chain variable region comprises the amino acid sequence of SEQ ID NO: 245; or (xxix) wherein the heavy chain variable region comprises the amino acid sequence of SEQ ID NO: 251 and wherein the light chain variable region comprises the amino acid sequence of SEQ ID NO: 245.

Provided herein is an anti-FAM19A5 antibody, or an antigen-binding portion thereof, comprising a heavy chain variable region and a light chain variable region, wherein the heavy chain variable region comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NOs: 35-38, 155-165, 211, 214, 234-237, or 249-251 (see Table 4).

Also provided herein is an anti-FAM19A5 antibody, or an antigen-binding portion thereof, comprising a heavy chain variable region and a light chain variable region, wherein the light chain variable region comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NOs: 39-42, 166-176, 212, 215, or 238-245 (see Table 5).

Also provided is an anti-FAM19A5 antibody, or an antigen-binding portion thereof, comprising heavy and light chain variable regions, wherein the heavy chain variable region comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NOs: 35-38, 155-165, 211, 214, 234-237, or 249-251, and wherein the light chain variable region comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NOs: 39-42, 166-176, 212, 215, or 238-245.

In some embodiments, the disclosure provides an anti-FAM19A5 antibody, or an antigen-binding portion thereof, comprising:
  (a) heavy and light chain variable region sequences comprising SEQ ID NOs: 35 and 39, respectively;
  (b) heavy and light chain variable region sequences comprising SEQ ID NOs: 36 and 40, respectively;
  (c) heavy and light chain variable region sequences comprising SEQ ID NOs: 37 and 41, respectively;
  (d) heavy and light chain variable region sequences comprising SEQ ID NOs: 38 and 42, respectively;
  (e) heavy and light chain variable region sequences comprising SEQ ID NOs: 155 and 166, respectively;
heavy and light chain variable region sequences comprising SEQ ID NOs: 156 and 167, respectively;
  (g) heavy and light chain variable region sequences comprising SEQ ID NOs: 157 and 168, respectively;
  (h) heavy and light chain variable region sequences comprising SEQ ID NOs: 158 and 169, respectively;
  (i) heavy and light chain variable region sequences comprising SEQ ID NOs: 159 and 170, respectively;
  (j) heavy and light chain variable region sequences comprising SEQ ID NOs: 160 and 171, respectively;
  (k) heavy and light chain variable region sequences comprising SEQ ID NOs: 161 and 172, respectively;
  (l) heavy and light chain variable region sequences comprising SEQ ID NOs: 162 and 173, respectively;
  (m) heavy and light chain variable region sequences comprising SEQ ID NOs: 163 and 174, respectively;
  (n) heavy and light chain variable region sequences comprising SEQ ID NOs: 164 and 175, respectively;
  (o) heavy and light chain variable region sequences comprising SEQ ID NOs: 165 and 176, respectively;
  (p) heavy and light chain variable region sequences comprising SEQ ID NOs: 211 and 212, respectively;
  (q) heavy and light chain variable region sequences comprising SEQ ID NOs: 214 and 215, respectively;
  (r) heavy and light chain variable region sequences comprising SEQ ID NOs: 249 and 215, respectively;
  (s) heavy and light chain variable region sequences comprising SEQ ID NOs: 234 and 238, respectively;
  (t) heavy and light chain variable region sequences comprising SEQ ID NOs: 235 and 239, respectively;
  (u) heavy and light chain variable region sequences comprising SEQ ID NOs: 235 and 240, respectively;
  (v) heavy and light chain variable region sequences comprising SEQ ID NOs: 235 and 241, respectively;
  (w) heavy and light chain variable region sequences comprising SEQ ID NOs: 235 and 242, respectively;
  (x) heavy and light chain variable region sequences comprising SEQ ID NOs: 235 and 243, respectively;
  (y) heavy and light chain variable region sequences comprising SEQ ID NOs: 235 and 244, respectively
  (z) heavy and light chain variable region sequences comprising SEQ ID NOs: 236 and 245, respectively (aa) heavy and light chain variable region sequences comprising SEQ ID NOs: 250 and 245, respectively;
(bb) heavy and light chain variable region sequences comprising SEQ ID NOs: 237 and 245, respectively; or
(cc) heavy and light chain variable region sequences comprising SEQ ID NOs: 251 and 245, respectively.

In certain embodiments, the anti-FAM19A5 antibody or antigen-binding portion thereof of the present disclosure comprises (i) the heavy chain CDR1, CDR2 and CDR3 of 2-13, or combinations thereof, and/or the light chain CDR1, CDR2, and CDR3 of 2-13, or any combinations thereof; (ii) the heavy chain CDR1, CDR2 and CDR3 of 3-2, or combinations thereof, and/or the light chain CDR1, CDR2, and CDR3 of 3-2, or any combinations thereof; (iii) the heavy chain CDR1, CDR2 and CDR3 of 1-65, or combinations thereof, and/or the light chain CDR1, CDR2, and CDR3 of 1-65, or any combinations thereof; (iv) the heavy chain CDR1, CDR2 and CDR3 of 1-28, or combinations thereof, and/or the light chain CDR1, CDR2, and CDR3 of 1-28, or any combinations thereof; (v) the heavy chain CDR1, CDR2, and CDR3 of P2-C12, or combinations thereof, and/or the light chain CDR1, CDR2, and CDR3 of P2-C12, or any combinations thereof; (vi) the heavy chain CDR1, CDR2, and CDR3 of 13B4, or combinations thereof, and/or the light chain CDR1, CDR2, and CDR3 of 13B4, or any combinations thereof; (vii) the heavy chain CDR1, CDR2, and CDR3 of 13F7, or combinations thereof, and/or the light chain CDR1, CDR2, and CDR3 of 13F7, or any combinations thereof; (viii) the heavy chain CDR1, CDR2, and CDR3 of 15A9, or combinations thereof, and/or the light chain CDR1, CDR2, and CDR3 of 15A9, or any combinations thereof; (ix) the heavy chain CDR1, CDR2, and CDR3 of P1-A03, or combinations thereof, and/or the light chain CDR1, CDR2, and CDR3 of P1-A03, or any combinations thereof; (x) the heavy chain CDR1, CDR2, and CDR3 of P1-A08, or combinations thereof, and/or the light chain CDR1, CDR2, and CDR3 of P1-A08, or any combinations thereof; (xi) the heavy chain CDR1, CDR2, and CDR3 of P1-F02, or combinations thereof, and/or the light chain CDR1, CDR2, and CDR3 of P1-F02, or any combinations thereof; (xii) the heavy chain CDR1, CDR2, and CDR3 of P2-A01, or combinations thereof, and/or the light chain CDR1, CDR2, and CDR3 of P2-A01, or any combinations thereof; (xiii) the heavy chain CDR1, CDR2, and CDR3 of P2-A03, or combinations thereof, and/or the light chain CDR1, CDR2, and CDR3 of P2-A03, or any combinations thereof; (xiv) the heavy chain CDR1, CDR2, and CDR3 of P2-F07, or combinations thereof, and/or the light chain CDR1, CDR2, and CDR3 of P2-F07, or any combinations thereof; (xv) the heavy chain CDR1, CDR2, and CDR3 of P2-F11, or combinations thereof, and/or the light chain CDR1, CDR2, and CDR3 of F2-F11, or any combinations thereof; (xvi) the heavy chain CDR1, CDR2, and CDR3 of SS01-13, or combinations thereof, and/or the light chain CDR1, CDR2, and CDR3 of SS01-13, or any combinations thereof; (xvii) the heavy chain CDR1, CDR2, and CDR3 of SS01-13-s5, or combinations thereof, and/or the light chain CDR1, CDR2, and CDR3 of SS01-13-s5, or any combinations thereof; (xviii) the heavy chain CDR1, CDR2, and CDR3 of S5-2.GKNG, or combinations thereof, and/or the light chain CDR1, CDR2, and CDR3 of S5-2.GKNG, or any combinations thereof; (xix) the heavy chain CDR1, CDR2, and CDR3 of 1-7A-IT, or combinations thereof, and/or the light chain CDR1, CDR2, and CDR3 of 1-7A-IT, or any combinations thereof; (xx) the heavy chain CDR1, CDR2, and CDR3 of Low-PI, or combinations thereof, and/or the light chain CDR1, CDR2, and CDR3 of Low-PI, or any combinations thereof; (xxi) the heavy chain CDR1, CDR2, and CDR3 of 1-30, or combinations thereof, and/or the light chain CDR1, CDR2, and CDR3 of 1-30, or any combinations thereof; (xxii) the heavy chain CDR1, CDR2, and CDR3 of 1-17, or combinations thereof, and/or the light chain CDR1, CDR2, and CDR3 of 1-17, or any combinations thereof; (xxiii) the heavy chain CDR1, CDR2, and CDR3 of 1-32, or combinations thereof, and/or the light chain CDR1, CDR2, and CDR3 of 1-32, or any combinations thereof; (xxiv) the heavy chain CDR1, CDR2, and CDR3 of 4-11, or combinations thereof, and/or the light chain CDR1, CDR2, and CDR3 of 4-11, or any combinations thereof; (xxv) the heavy chain CDR1, CDR2, and CDR3 of 6-10, or combinations thereof, and/or the light chain CDR1, CDR2, and CDR3 of 6-10, or any combinations thereof; (xxvi) the heavy chain CDR1, CDR2, and CDR3 of 2-13D, or combinations thereof, and/or the light chain CDR1, CDR2, and CDR3 of 2-13D, or any combinations thereof; (xxvii) the heavy chain CDR1, CDR2, and CDR3 of 2-13D-37, or combinations thereof, and/or the light chain CDR1, CDR2, and CDR3 of 2-13D-37, or any combinations thereof; (xxviii) the heavy chain CDR1, CDR2, and CDR3 of 2-13D-37-1.5W-41, or combinations thereof, and/or the light chain CDR1, CDR2, and CDR3 of 2-13D-37-1.5W-41, or any combinations thereof; or (xxix) the heavy chain CDR1, CDR2, and CDR3 of 2-13D-37-3W-16, or combinations thereof, and/or the light chain CDR1, CDR2, and CDR3 of 2-13D-37-3W-16, or any combinations thereof. The amino acid sequences of the VH CDR1, CDR2, and CDR3 for the different anti-FAM19A5 antibodies disclosed herein are provided in Table 2. The amino acid sequences of the VL CDR1, CDR2, and CDR3 for the different anti-FAM19A5 antibodies disclosed herein are provided in Table 3.

In some embodiments, the anti-FAM19A5 antibody or antigen-binding portion thereof of the disclosure, which specifically binds to human FAM19A5, comprises:
 (a) a VH CDR1 comprising the amino acid sequence of SEQ ID NO: 11; and/or
 (b) a VH CDR2 comprising the amino acid sequence of SEQ ID NO: 12; and/or
 (c) a VH CDR3 comprising the amino acid sequence of SEQ ID NO: 13.

In specific embodiments, the antibody or antigen-binding portion thereof comprises one, two, or all three of the VH CDRs above.

In some embodiments, the anti-FAM19A5 antibody or antigen-binding portion thereof, which specifically binds to human FAM19A5, comprises:
 (a) a VL CDR1 comprising the amino acid sequence of SEQ ID NO: 23; and/or
 (b) a VL CDR2 comprising the amino acid sequence of SEQ ID NO: 24; and/or
 (c) a VL CDR3 comprising the amino acid sequence of SEQ ID NO: 25.

In specific embodiments, the antibody or antigen-binding portion thereof comprises one, two, or all three of the VL CDRs above.

In some embodiments, the anti-FAM19A5 antibody or antigen-binding portion thereof, which specifically binds to human FAM19A5, comprise:
 (a) a VH CDR1 comprising the amino acid sequence of SEQ ID NO: 11;
 (b) a VH CDR2 comprising the amino acid sequence of SEQ ID NO: 12;
 (c) a VH CDR3 comprising the amino acid sequence of SEQ ID NO: 13;

(d) a VL CDR1 comprising the amino acid sequence of SEQ ID NO: 23;
(e) a VL CDR2 comprising the amino acid sequence of SEQ ID NO: 24; and/or
(f) a VL CDR3 comprising the amino acid sequence of SEQ ID NO: 25.

In some embodiments, the anti-FAM19A5 antibody or antigen-binding portion thereof of the disclosure, which specifically binds to human FAM19A5, comprises:
(a) a VH CDR1 comprising the amino acid sequence of SEQ ID NO: 14; and/or
(b) a VH CDR2 comprising the amino acid sequence of SEQ ID NO: 15; and/or
(c) a VH CDR3 comprising the amino acid sequence of SEQ ID NO: 16.

In specific embodiments, the antibody or antigen-binding portion thereof comprises one, two, or all three of the VH CDRs above.

In some embodiments, the anti-FAM19A5 antibody or antigen-binding portion thereof, which specifically binds to human FAM19A5, comprises:
(a) a VL CDR1 comprising the amino acid sequence of SEQ ID NO: 26; and/or
(b) a VL CDR2 comprising the amino acid sequence of SEQ ID NO: 27; and/or
(c) a VL CDR3 comprising the amino acid sequence of SEQ ID NO: 28.

In specific embodiments, the antibody or antigen-binding portion thereof comprises one, two, or all three of the VL CDRs above.

In some embodiments, the anti-FAM19A5 antibody or antigen-binding portion thereof, which specifically binds to human FAM19A5, comprise:
(a) a VH CDR1 comprising the amino acid sequence of SEQ ID NO: 14;
(b) a VH CDR2 comprising the amino acid sequence of SEQ ID NO: 15;
(c) a VH CDR3 comprising the amino acid sequence of SEQ ID NO: 16;
(d) a VL CDR1 comprising the amino acid sequence of SEQ ID NO: 26;
(e) a VL CDR2 comprising the amino acid sequence of SEQ ID NO: 27; and/or
(f) a VL CDR3 comprising the amino acid sequence of SEQ ID NO: 28.

In some embodiments, the anti-FAM19A5 antibody or antigen-binding portion thereof of the disclosure, which specifically binds to human FAM19A5, comprises:
(a) a VH CDR1 comprising the amino acid sequence of SEQ ID NO: 17; and/or
(b) a VH CDR2 comprising the amino acid sequence of SEQ ID NO: 18; and/or
(c) a VH CDR3 comprising the amino acid sequence of SEQ ID NO: 19.

In specific embodiments, the antibody or antigen-binding portion thereof comprises one, two, or all three of the VH CDRs above.

In some embodiments, the anti-FAM19A5 antibody or antigen-binding portion thereof, which specifically binds to human FAM19A5, comprises:
(a) a VL CDR1 comprising the amino acid sequence of SEQ ID NO: 29; and/or
(b) a VL CDR2 comprising the amino acid sequence of SEQ ID NO: 30; and/or
(c) a VL CDR3 comprising the amino acid sequence of SEQ ID NO: 31.

In specific embodiments, the antibody or antigen-binding portion thereof comprises one, two, or all three of the VL CDRs above.

In some embodiments, the anti-FAM19A5 antibody or antigen-binding portion thereof, which specifically binds to human FAM19A5, comprise:
(a) a VH CDR1 comprising the amino acid sequence of SEQ ID NO: 17;
(b) a VH CDR2 comprising the amino acid sequence of SEQ ID NO: 18;
(c) a VH CDR3 comprising the amino acid sequence of SEQ ID NO: 19;
(d) a VL CDR1 comprising the amino acid sequence of SEQ ID NO: 29;
(e) a VL CDR2 comprising the amino acid sequence of SEQ ID NO: 30; and/or
(f) a VL CDR3 comprising the amino acid sequence of SEQ ID NO: 31.

In some embodiments, the anti-FAM19A5 antibody or antigen-binding portion thereof of the disclosure, which specifically binds to human FAM19A5, comprises:
(a) a VH CDR1 comprising the amino acid sequence of SEQ ID NO: 20; and/or
(b) a VH CDR2 comprising the amino acid sequence of SEQ ID NO: 21; and/or
(c) a VH CDR3 comprising the amino acid sequence of SEQ ID NO: 22.

In specific embodiments, the antibody or antigen-binding portion thereof comprises one, two, or all three of the VH CDRs above.

In some embodiments, the anti-FAM19A5 antibody or antigen-binding portion thereof, which specifically binds to human FAM19A5, comprises:
(a) a VL CDR1 comprising the amino acid sequence of SEQ ID NO: 32; and/or
(b) a VL CDR2 comprising the amino acid sequence of SEQ ID NO: 33; and/or
(c) a VL CDR3 comprising the amino acid sequence of SEQ ID NO: 34.

In specific embodiments, the antibody or antigen-binding portion thereof comprises one, two, or all three of the VL CDRs above.

In some embodiments, the anti-FAM19A5 antibody or antigen-binding portion thereof, which specifically binds to human FAM19A5, comprises:
(a) a VH CDR1 comprising the amino acid sequence of SEQ ID NO: 20;
(b) a VH CDR2 comprising the amino acid sequence of SEQ ID NO: 21;
(c) a VH CDR3 comprising the amino acid sequence of SEQ ID NO: 22;
(d) a VL CDR1 comprising the amino acid sequence of SEQ ID NO: 32;
(e) a VL CDR2 comprising the amino acid sequence of SEQ ID NO: 33; and/or
(f) a VL CDR3 comprising the amino acid sequence of SEQ ID NO: 34.

In specific embodiments, the anti-FAM19A5 antibody or antigen-binding portion thereof comprises one, two, three, four, five, or six of the CDRs above.

In some embodiments, the anti-FAM19A5 antibody or antigen-binding portion thereof of the disclosure, which specifically binds to human FAM19A5, comprises:
(a) a VH CDR1 comprising the amino acid sequence of SEQ ID NO: 220 and/or
(b) a VH CDR2 comprising the amino acid sequence of SEQ ID NO: 221; and/or (c) a VH CDR3 comprising the amino acid sequence of SEQ ID NO: 16.

In specific embodiments, the antibody or antigen-binding portion thereof comprises one, two, or all three of the VH CDRs above.

In some embodiments, the anti-FAM19A5 antibody or antigen-binding portion thereof, which specifically binds to human FAM19A5, comprises:
(a) a VL CDR1 comprising the amino acid sequence of SEQ ID NO: 225; and/or
(b) a VL CDR2 comprising the amino acid sequence of SEQ ID NO: 228; and/or
(c) a VL CDR3 comprising the amino acid sequence of SEQ ID NO: 227

In specific embodiments, the antibody or antigen-binding portion thereof comprises one, two, or all three of the VL CDRs above.

In some embodiments, the anti-FAM19A5 antibody or antigen-binding portion thereof, which specifically binds to human FAM19A5, comprises:
(a) a VH CDR1 comprising the amino acid sequence of SEQ ID NO: 220;
(b) a VH CDR2 comprising the amino acid sequence of SEQ ID NO: 221;
(c) a VH CDR3 comprising the amino acid sequence of SEQ ID NO: 16;
(d) a VL CDR1 comprising the amino acid sequence of SEQ ID NO: 225;
(e) a VL CDR2 comprising the amino acid sequence of SEQ ID NO: 228; and/or
(f) a VL CDR3 comprising the amino acid sequence of SEQ ID NO: 227.

In specific embodiments, the anti-FAM19A5 antibody or antigen-binding portion thereof comprises one, two, three, four, five, or six of the CDRs above.

A VH domain, or one or more CDRs thereof, described herein can be linked to a constant domain for forming a heavy chain, e.g., a full length heavy chain. Similarly, a VL domain, or one or more CDRs thereof, described herein can be linked to a constant domain for forming a light chain, e.g., a full length light chain. A full length heavy chain and full length light chain combine to form a full length antibody.

Accordingly, in specific embodiments, provided herein is an antibody comprising an antibody light chain and heavy chain, e.g., a separate light chain and heavy chain. With respect to the light chain, in a specific embodiment, the light chain of an antibody described herein is a kappa light chain. In another specific embodiment, the light chain of an antibody described herein is a lambda light chain. In yet another specific embodiment, the light chain of an antibody described herein is a human kappa light chain or a human lambda light chain. In a particular embodiment, an antibody described herein, which specifically binds to a FAM19A5 polypeptide (e.g., human FAM19A5) comprises a light chain which comprises any VL or VL CDR amino acid sequences described herein, and wherein the constant region of the light chain comprises the amino acid sequence of a human kappa light chain constant region. In a particular embodiment, an antibody described herein, which specifically binds to a FAM19A5 polypeptide (e.g., human FAM19A5) comprises a light chain which comprises a VL or VL CDR amino acid sequences described herein, and wherein the constant region of the light chain comprises the amino acid sequence of a human lambda light chain constant region. Non-limiting examples of human constant region sequences have been described in the art, e.g., see U.S. Pat. No. 5,693,780 and Kabat E A et al., (1991) supra.

With respect to the heavy chain, in some embodiments, the heavy chain of an antibody described herein can be an alpha (α), delta (δ), epsilon (ε), gamma (γ) or mu (μ) heavy chain. In another specific embodiment, the heavy chain of an antibody described can comprise a human alpha (α), delta (δ), epsilon (ε), gamma (γ) or mu (μ) heavy chain. In one embodiment, an antibody described herein, which specifically binds to FAM19A5 (e.g., human FAM19A5), comprises a heavy chain which comprises a VH or VH CDR amino acid sequence described herein, and wherein the constant region of the heavy chain comprises the amino acid sequence of a human gamma (γ) heavy chain constant region. In another embodiment, an antibody described herein, which specifically binds to FAM19A5 (e.g., human FAM19A5), comprises a heavy chain which comprises a VH or VH CDR amino acid sequence disclosed herein, and wherein the constant region of the heavy chain comprises the amino acid of a human heavy chain described herein or known in the art. Non-limiting examples of human constant region sequences have been described in the art, e.g., see U.S. Pat. No. 5,693,780 and Kabat E A et al., (1991) supra.

In some embodiments, an antibody described herein, which specifically binds to FAM19A5 (e.g., human FAM19A5) comprises a VL domain and a VH domain comprising the VH or VH CDRs and VL and VL CDRs described herein, and wherein the constant regions comprise the amino acid sequences of the constant regions of an IgG, IgE, IgM, IgD, IgA or IgY immunoglobulin molecule, or a human IgG, IgE, IgM, IgD, IgA or IgY immunoglobulin molecule. In another specific embodiment, an antibody described herein, which specifically binds to FAM19A5 (e.g., human FAM19A5) comprises a VL domain and a VH domain comprising any amino acid sequences described herein, and wherein the constant regions comprise the amino acid sequences of the constant regions of an IgG, IgE, IgM, IgD, IgA or IgY immunoglobulin molecule, any subclass (e.g., IgG1, IgG2, IgG3, IgG4, IgA1 and IgA2) of immunoglobulin molecule. In some embodiments, the constant regions comprise the amino acid sequences of the constant regions of a human IgG, which are naturally-occurring, including subclasses (e.g., IgG1, IgG2, IgG3 or IgG4), and allotypes (e.g., G1m, G2m, G3m, and nG4m) and variants thereof. See, e.g., Vidarsson G. et al. *Front Immunol.* 5:520 (published online Oct. 20, 2014) and Jefferis R. and Lefranc M P, *mAbs* 1:4, 1-7(2009). In some embodiments, the constant regions comprise the amino acid sequences of the constant regions of a human IgG1, IgG2, IgG3, or IgG4, or variants thereof.

In certain embodiments, the anti-FAM19A5 antibody or antigen-binding portion thereof disclosed herein does not have Fc effector functions, e.g., complement-dependent cytotoxicity (CDC) and/or antibody-dependent cellular phagocytosis (ADCP). Effector functions are mediated by the Fc region and the residues most proximal to the hinge region in the CH2 domain of the Fc region are responsible for effector functions of antibodies as it contains a largely overlapping binding site for C1q (complement) and IgG-Fc receptors (FcγR) on effector cells of the innate immune system. Also, IgG2 and IgG4 antibodies have lower levels of Fc effector functions than IgG1 and IgG3 antibodies. Effector functions of an antibody can be reduced or avoided by different approaches known in the art, including (1) using antibody fragments lacking the Fc region (e.g., such as a Fab, F(ab')2, single chain Fv (scFv), or a sdAb consisting of a monomeric VH or VL domain); (2) generating aglycosylated antibodies, which can be generated by, for example, deleting or altering the residue the sugar is attached to, removing the sugars enzymatically, producing the antibody in cells cultured in the presence of a glycosylation inhibitor, or by expressing the antibody in cells unable to glycosylate proteins (e.g., bacterial host cells, see, e.g., U.S. Pub. No. 20120100140); (3) employing Fc regions from an IgG subclass that have reduced effector function (e.g., a Fc region from IgG2 or IgG4 antibodies or a chimeric Fc region comprising a CH2 domain from IgG2 or IgG4 antibodies, see, e.g., U.S. Pub. No. 20120100140 and Lau C. et al. *J. Immunol.* 191:4769-4777 (2013)); and (4) generating a Fc region with mutations that result in reduced or no Fc functions. See e.g., U.S. Pub. No. 20120100140 and U.S. and PCT applications cited therein and An et al. *mAbs* 1:6, 572-579 (2009).

Thus, in some embodiments, the anti-FAM19A5 antibody or antigen-binding portion thereof disclosed herein is a Fab, a Fab', a F(ab')2, a Fv, a single chain Fv (scFv), or sdAb consisting of a monomeric VH or VL domain. Such antibody fragments are well known in the art and are described supra.

In some embodiments, the anti-FAM19A5 antibody or antigen-binding portion thereof disclosed herein comprises a Fc region with reduced or no Fc effector function. In some embodiments, the constant regions comprise the amino acid sequences of the Fc region of a human IgG2 or IgG4, in some embodiments, the anti-FAM19A5 antibody is of an IgG2/IgG4 isotype. In some embodiments, the anti-FAM19A5 antibody comprises a chimeric Fc region which comprises a CH2 domain from an IgG antibody of the IgG4 isotype and a CH3 domain from an IgG antibody of the IgG1 isotype, or a chimeric Fc region which comprises a hinge region from IgG2 and a CH2 region from IgG4, or a Fc region with mutations that result in reduced or no Fc functions. Fc regions with reduced or no Fc effector function include those known in the art. See e.g., Lau C. et al. *J. Immunol.* 191:4769-4777 (2013); An et al., *mAbs* 1:6, 572-579 (2009); and U.S. Pub. No. 20120100140 and the U.S. patents and publications and PCT publications cited therein. Also Fc regions with reduced or no Fc effector function can be readily made by a person of ordinary skill in the art.

V. Nucleic Acid Molecules

Another aspect described herein pertains to use of one or more nucleic acid molecules that encode any one of the antibodies or antigen-binding portions thereof described herein. The nucleic acids can be use as part of whole cells, a cell lysate, or a partially purified or substantially pure form. A nucleic acid is "isolated" or "rendered substantially pure" when purified away from other cellular components or other contaminants, e.g., other cellular nucleic acids (e.g., other chromosomal DNA, e.g., the chromosomal DNA that is linked to the isolated DNA in nature) or proteins, by standard techniques, including alkaline/SDS treatment, CsCl banding, column chromatography, restriction enzymes, agarose gel electrophoresis and others well known in the art. See, F. Ausubel, et al., ed. (1987) Current Protocols in Molecular Biology, Greene Publishing and Wiley Interscience, New York. A nucleic acid useful for the present methods can be, for example, DNA or RNA and can or cannot contain intronic sequences. In certain embodiments, the nucleic acid useful for the methods is a cDNA molecule.

Nucleic acids described herein can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Certain nucleic acids molecules useful for the present methods are those encoding the VH and VL sequences of the various anti-FAM19A5 antibodies of the present disclosure. Exemplary DNA sequences encoding the VH sequence of such antibodies are set forth in SEQ ID NOs: 43-46, and 177. Additional exemplary DNA sequences encoding the VH sequence of anti-FAM19A5 antibodies are provided in Table 6 (below). Exemplary DNA sequences encoding the VL sequences of such antibodies are set forth in SEQ ID NOs: 47-50 and 178. Additional exemplary DNA sequences encoding the VL sequence of anti-FAM19A5 antibodies are provided in Table 7 (below).

TABLE 6

| Variable heavy chain polynucleotide sequence | |
|---|---|
| Antibody | Variable Heavy Chain Polynucleotide Sequence (SEQ ID NO) |
| Anti-FAM19A5 (2-13) | GCCGTGACGTTGGACGAGTCCGGGGGGGGCCTCCAGACGCCCGGAGGAGCGCTCAGCCTC GTCTGCAAGGCCTCCGGGTTCACCTTCAGCAGCCATGGCATGTTCTGGGTGCGACAGACG CCCGGCAAGGGGTTGGAATATGTCGCTGAAATTACCAATGATGGTAGTGGCACAAACTAC GGGTCGGCGGTGAAGGGCCGTGCCACCATCTCGAGGGACAACGGGCAGAGCACAGTGAGG CTGCAGCTGAACAACCTCAGGGCTGAGGACACCGGCACCTACTTCTGCGCCAGATCTACT TATGAATGTCCTGGTGGTTTTAGTTGTTGGGGTGATACTGGTCAAATAGACGCATGGGGC CACGGGACCGAAGTCATCGTCTCCTCC (SEQ ID NO: 43) |
| Anti-FAM19A5 (3-2) | GCCGTGACGTTGGACGAGTCCGGGGGGGGCCTCCAGACGCCCGGAGGAGCGCTCAGCCTC GTCTGCAAGGCCTCCGGGTTCACCTTCAGCAGCTTCAACATGTTCTGGGTGCGACAGGCG CCCGGCAAGGGGCTGGAATACGTCGCTCAAATTAGCAGCAGTGGTAGTAGCACAAACTAC GCACCCGCGGTGAGGGGCCGTGCCACCATCTCGAGGGACAACGGGCAGAGCACAGTGAGG CTGCAGCTGAACAACCCCGGGGCTGAAGACACCGGCACCTACTACTGCGCCAAAAGTAGT TATGACTGTCCTTACGGTCATTGTAGTAGTGGTGTTGATAGTGCTGGTGAGATCGACGCA TGGGGCCACGGGACCGAAGTCATCGTCTCCTCC (SEQ ID NO: 44) |
| Anti-FAM19A5 (1-65) | GCCGTGACACTGGACGAATCTGGGGGAGGGCTGCAGACTCCAGGCGGAGCTCTGAGCCTG GTGTGCAAGGCATCCGGGTTCACCTTTAGCTCCTACCAGATGGGATGGGTGCGGCAGGCA CCAGGGAAGGGCCTGGAGTGGGTCGGAGTGATCAACAAATCTGGGAGTGACACAAGCTAC GGCAGCGCCGTGAAGGGAAGGGCCACCATCAGCAGGGACAATGGCCAGAGTACCGTGCGG CTGCAGCTGAACAATCTGCGCGCTGAGGACACTGGCACCTACTTCTGTGCTAAGGGATCA GCAAGCTATATCACAGCCGCTACTATTGATGCATGGGGACACGGGACAGAAGTCATCGTG TCTAGT (SEQ ID NO: 45) |

TABLE 6-continued

Variable heavy chain polynucleotide sequence

| Antibody | Variable Heavy Chain Polynucleotide Sequence (SEQ ID NO) |
|---|---|
| Anti-FAM19A5 (1-28) | GCCGTGACGTTGGACGAGTCCGGGGGGGGCCTCCAGACGCCCGGAGGAGCGCTCAGCCTC<br>GTCTGCAAGGCCTCCGGGTTCGACTTCAGCGATTATGGCATGGGTTGGGTGCGACAGGCT<br>CCAGGCAAGGGGCTGGAGTGGGTTGCTGCTATTAGAAGTGATGGTAGTAACCCATCATAC<br>GGGTCGGCGGTGAAGGGCCGTGCCACCATCTCGAAGGACAACGGGCGAAGCACAGTGAGG<br>CTGCAGCTGAACAACCTCAGGGCTGAGGACACCGCCACCTACTACTGCGCCAAGGATGGT<br>AATGGTTACTGTGCTCTCGATGCTTATCGTAGTGGTGGTTATAGTTGTGGTGTTTATCCT<br>GGTAGCATCGACGCATGGGGCCACGGGACCGAAGTCATCGTCTCCTCC (SEQ ID NO: 46) |
| Anti-FAM19A5 (P2-C12) | CAGTCGCTGGAGGAGTCCGGGGGTCGCCTGGTCACGCCTGGGACACCCCTGACACTCACC<br>TGCACCGTCTCTGGATTCTCCCTCAGTACCTATGCAGTGACCTGGGTCCGCCAGGCTCCA<br>GGGAAGGGGCTGGAATGGATCGGATACATTAATTGGCGTGGTGGGACATCCTACGCGAAC<br>TGGGCGAAAGGCCGATTCACCATCTCCAAAACCTCGTCGACCACGGTGGATCTGAAAATG<br>ACCAGTCCGACAACCGAGGACACGGCCACCTATTTCTGTGCCAGAGATGCTAGTAGTGGT<br>GCTGCTTTTGGGTCTTACGGCATGGACCCCTGGGGCCCAGGGACCCTCGTCACCGTCTCT<br>TCA (SEQ ID NO: 177) |
| Anti-FAM19A5 (SS01-13) | GCCGTGACGTTGGACGAGTCCGGGGGCGGCCTCCAGACGCCCGGAGGAGCGCTCTCTCTC<br>TCTTGCAAAGCCTCCGGGTTCACCTTCAGCAGCTATCAGATGGGCTGGGTGCGACAGGCG<br>CCCGGCAAGGGCTGGAATGGGTCGGTGTTATTAACAAGTCTGGTAGTGACACATCATAC<br>GGGTCGGCGGTGAAGGGCCGTGCCACCATCTCGAGGGACAACGGGCAGAGCACACTGTAC<br>CTGCAGATGAACAACCTCAGGGCTGAGGACACCGCTGTTTACTTCTGCGCCAAAGGTTCT<br>GCTAGTTACATAACTGCTGCTACCATCGACGCATGGGGCCACGGGACCGAAGTCATCGTC<br>TCCTCC (SEQ ID NO: 271) |
| Anti-FAM19A5 (SS01-13-S5) | GCCGTGACGTTGGACGAGTCCGGGGGCGGCCTCCAGACGCCCGGAGGAGCGCTCCGCCTC<br>TCTTGCAAGGCCTCCGGGTTCACCTTCAGCAGCTATCAGATGGGCTGGGTGCGACAGGCG<br>CCCGGCAAGGGGCTGGAATGGGTCAGCGCGATTAATAAGAGCGGTAGTGACACATCATAC<br>GGGTCGGCGGTGAAGGGCCGTGCCACCATCTCGAGGGACAACGGGCAGAGCACACTGTAC<br>CTGCAGATGAACAGCCTCAGGGCTGAGGACACCGCTGTTTACTTCTGCGCCAAAGGTTCT<br>GCTAGTTACATAACTGCTGCTACCATCGACGCATGGGGCCACGGGACCGAAGTCATCGTC<br>TCCTCC (SEQ ID NO: 216) |
| Anti-FAM19A5 ("S5-2.GKNG") | GCCGTGACGTTGGACGAGTCCGGGGGCGGCCTCCAGACGCCCGGAGGAGCGCTCCGCCTC<br>TCTTGCAAGGCCTCCGGGTTCACCTTCAGCAGCTATCAGATGGGCTGGGTGCGACAGGCG<br>CCCGGCAAGGGGCTGGAATGGGTCAGCGCGATTAATAAGGGCGGTAGTGACACATCATAC<br>GGGTCGGCGGTGAAGGGCCGTGCCACCATCTCGAGGGACAACGGGCAGAGCACACTGTAC<br>CTGCAGATGAACAGCCTCAGGGCTGAGGACACCGCTGTTTACTTCTGCGCCAAAGGTTCT<br>GCTAGTTACATAACTGCTGCTACCATCGACGCATGGGGCCACGGGACCGAAGTCATCGTC<br>TCCTCC (SEQ ID NO: 269) |
| Anti-FAM19A5 ("1-7A-IT") | GCCGTGACGTTGGATGAATCCGGGGGGGGCCTCCAGACGCCCGGAGGAGCGCTCCGCCTC<br>AGCTGCAAGGCCTCTGGGTTCACCTTCAGCAGCTTCAACATGTTCTGGGTGCGACAGGCG<br>CCCGGCAAGGGGCTGGAATACGTCTCGCAGATTAGCAGCAGTGGTAGTAGCACAAACTAC<br>GCACCCGCGGTGAAAGGCCGTGCCACCATCTCGAGGGACAACGGGCAGAGCACACTGTAT<br>CTGCAGATGAACAGCCTGCGCGCTGAAGACACCGGCACCTACTACTGCGCCAAAAGTAGT<br>TATGACTGTCCTTACGGTCATTGTAGTAGTGGTGTTGATAGTGCTGGTGAGATCGACGCA<br>TGGGGCCACGGGACCGAAGTCATCGTCTCCTCC (SEQ ID NO: 254) |
| Anti-FAM19A5 ("Low-PI") | GCCGTGACGTTGGATGAATCCGGGGGCGGCCTCCAGACGCCCGGAGGAGCGCTCCGCCTC<br>AGCTGCAAGGCCTCTGGGTTCACCTTCAGCAGCTTCAACATGTTCTGGGTGCGACAGGCG<br>CCCGGCAAGGGGCTGGAATACGTCTCGCAGATTAGCAGCAGTGGTAGTAGCACAAACTAC<br>GCACCCGCGGTGAAAGGCCGTGCCACCATCTCGAGGGACAACGGGCAGAGCACACTGTAT<br>CTGCAGATGAACAGCCTGCGCGCTGAAGACACCGGCACCTACTACTGCGCCAAAAGTAGT<br>TATGACTGTCCTTACGGTCATTGTAGTAGTGGTGTTGATAGTGCTGGTGAGATCGACGCA<br>TGGGGCCACGGGACCGAAGTCATCGTCTCCTCC (SEQ ID NO: 255) |
| Anti-FAM19A5 ("1-30") | GCCGTGACGTTGGATGAATCCGGGGGGGGCCTCCAGACGCCCGGAGGAGCGCTCCGCCTC<br>AGCTGCAAGGCCTCTGGCTTTGATTTTGAAAGCTTCAACATGTTCTGGGTGCGACAGGCG<br>CCCGGCAAGGGGCTGGAATACGTCTCGCAGATTAGCAGCAGTGAAGAAGATGAAAACTAC<br>GCACCCGCGGTGAAAGGCCGTGCCACCATCTCGAGGGACAACGGGCAGAGCACACTGTAT<br>CTGCAGATGAACAGCCTGCGCGCTGAAGACACCGGCACCTACTACTGCGCCAAAAGTAGT<br>TATGACTGTCCTTACGGTCATTGTAGTAGTGGTGTTGATAGTGCTGGTGAGATCGACGCA<br>TGGGGCCACGGGACCGAAGTCATCGTCTCCTCC (SEQ ID NO: 256) |
| Anti-FAM19A5 ("1-17") | GCCGTGACGTTGGATGAATCCGGGGGCGGCCTCCAGACGCCCGGAGGAGCGCTCCGCCTC<br>AGCTGCAAGGCCTCTGGCTTTGATTTTGAAAGCTTCAACATGTTCTGGGTGCGACAGGCG<br>CCCGGCAAGGGGCTGGAATACGTCTCGCAGATTAGCAGCAGTGAAGAAGATGAAAACTAC<br>GCACCCGCGGTGAAAGGCCGTGCCACCATCTCGAGGGACAACGGGCAGAGCACACTGTAT<br>CTGCAGATGAACAGCCTGCGCGCTGAAGACACCGGCACCTACTACTGCGCCAAAAGTAGT<br>TATGACTGTCCTTACGGTCATTGTAGTAGTGGTGTTGATAGTGCTGGTGAGATCGACGCA<br>TGGGGCCACGGGACCGAAGTCATCGTCTCCTCC (SEQ ID NO: 256) |

TABLE 6-continued

Variable heavy chain polynucleotide sequence

| Antibody | Variable Heavy Chain Polynucleotide Sequence (SEQ ID NO) |
|---|---|
| Anti-FAM19A5 ("1-32") | GCCGTGACGTTGGATGAATCCGGGGGGGGCCTCCAGACGCCCGGAGGAGCGCTCCGCCTC<br>AGCTGCAAGGCCTCTGGCTTTGATTTTGAAAGCTTCAACATGTTCTGGGTGCGACAGGCG<br>CCCGGCAAGGGGCTGGAATACGTCTCGCAGATTAGCAGCAGTGAAGGCAGTGAAGATTAC<br>GCACCCGCGGTGAAAGGCCGTGCCACCATCTCGAGGGACAACGGGCAGAGCACACTGTAT<br>CTGCAGATGAACAGCCTGCGCGCTGAAGACACCGGCACCTACTACTGCGCCAAAAGTAGT<br>TATGACTGTCCTTACGGTCATTGTAGTAGTGGTGTTGATAGTGCTGGTGAGATCGACGCA<br>TGGGGCCACGGGACCGAAGTCATCGTCTCCTCC (SEQ ID NO: 256) |
| Anti-FAM19A5 ("4-11") | GCCGTGACGTTGGATGAATCCGGGGGCGGCCTCCAGACGCCCGGAGGAGCGCTCCGCCTC<br>AGCTGCAAGGCCTCTGGCTTTGATTTTGAAAGCTTCAACATGTTCTGGGTGCGACAGGCG<br>CCCGGCAAGGGGCTGGAATACGTCTCGCAGATTAGCAGCAGTGAAGAAGATGAAAACTAC<br>GCACCCGCGGTGAAAGGCCGTGCCACCATCTCGAGGGACAACGGGCAGAGCACACTGTAT<br>CTGCAGATGAACAGCCTGCGCGCTGAAGACACCGGCACCTACTACTGCGCCAAAAGTAGT<br>TATGACTGTCCTTACGGTCATTGTAGTAGTGGTGTTGATAGTGCTGGTGAGATCGACGCA<br>TGGGGCCACGGGACCGAAGTCATCGTCTCCTCC (SEQ ID NO: 256) |
| Anti-FAM19A5 ("6-10") | GCCGTGACGTTGGATGAATCCGGGGGGGGCCTCCAGACGCCCGGAGGAGCGCTCCGCCTC<br>AGCTGCAAGGCCTCTGGCTTTGATTTTGAAAGCTTCAACATGTTCTGGGTGCGACAGGCG<br>CCCGGCAAGGGGCTGGAATACGTCTCGCAGATTAGCAGCAGTGAAGAAGATGAAAACTAC<br>GCACCCGCGGTGAAAGGCCGTGCCACCATCTCGAGGGACAACGGGCAGAGCACACTGTAT<br>CTGCAGATGAACAGCCTGCGCGCTGAAGACACCGGCACCTACTACTGCGCCAAAAGTAGT<br>TATGACTGTCCTTACGGTCATTGTAGTAGTGGTGTTGATAGTGCTGGTGAGATCGACGCA<br>TGGGGCCACGGGACCGAAGTCATCGTCTCCTCC (SEQ ID NO: 256) |
| Anti-FAM19A5 ("2-13D") | GCCGTGACGTTGGACGAGTCCGGGGGCGGCCTCCAGACGCCCGGAGGAGCGCTCCGCCTT<br>AGCTGCAGCGCCTCCGGGTTCACCTTCAGCAGCCATGGCATGTTCTGGGTGCGACAGGCG<br>CCCGGCAAGGGGTTGGAATATGTCTCGGAGATTACCAATGATGGTAGTGGCACAAACTAC<br>GGGTCGGCGGTGAAGGGCCGTGCCACCATCTCGAGGGACAACGGGCAGAGCACACTGTAT<br>CTGCAGATGAACAGCCTCAGGGCTGAGGACACCGGCACCTACTTCTGCGCCAGATCTACT<br>TATGAATGTCCTGGTGGTTTTAGTTGTTGGGGTGATACTGGTCAAATAGACGCATGGGGC<br>CACGGGACCGAAGTCATCGTCTCCTCC (SEQ ID NO: 257) |
| Anti-FAM19A5 ("2-13D-37") | GCCGTGACGTTGGACGAGTCCGGGGGGGGCCTCCAGACGCCCGGAGGAGCGCTCCGCCTT<br>AGCTGCAGCGCCTCCGGGTTCGATTTCAGCAGCCATGGCATGTTCTGGGTGCGACAGGCG<br>CCCGGCAAGGGGTTGGAATATGTCTCGGAGATTACCAATGATGGTAGTGGCACAAACTAC<br>GGGTCGGCGGTGAAGGGCCGTGCCACCATCTCGAGGGACAACGGGCAGAGCACACTGTAT<br>CTGCAGATGAACAGCCTCAGGGCTGAGGACACCGGCACCTACTTCTGCGCCAGATCTACT<br>TATGAATGTCCTGGTGGTTTTAGTTGTTGGGGTGATACTGGTCAAATAGACGCATGGGGC<br>CACGGGACCGAAGTCATCGTCTCCTCC (SEQ ID NO: 273) |
| Anti-FAM19A5 ("2-13D-37-1.5W-41") | GCCGTGACGTTGGACGAGTCCGGGGGGGGCCTCCAGACGCCCGGAGGAGCGCTCCGCCTT<br>AGCTGCAGCGCCTCCGGGTTCGATTTCAGCAGCCATGGCATGTTCTGGGTGCGACAGGCG<br>CCCGGCAAGGGGTTGGAATATGTCTCGGAGATTACCAATGATGGTAGTGGCACAAACTAC<br>GGGTCGGCGGTGAAGGGCCGTGCCACCATCTCGAGGGACAACGGGCAGAGCACACTGTAT<br>CTGCAGATGAACAGCCTCAGGGCTGAGGACACCGGCACCTACTTCTGCGCCAGATCTTCT<br>TATGTTTGTCCTGGTGGTTTTAGTTGTTGGGGTGATACTGGTCAAATAGACGCATGGGGC<br>CACGGGACCGAAGTCATCGTCTCCTCC (SEQ ID NO: 258) |
| Anti-FAM19A5 ("2-13D-37-3W-16") | GCCGTGACGTTGGACGAGTCCGGGGGCGGCCTCCAGACGCCCGGAGGAGCGCTCCGCCTT<br>AGCTGCAGCGCCTCCGGGTTCGATTTCAGCAGCCATGGCATGTTCTGGGTGCGACAGGCG<br>CCCGGCAAGGGGTTGGAATATGTCTCGGAGATTACCAATGATGGTAGTGGCACAAACTAC<br>GGGTCGGCGGTGAAGGGCCGTGCCACCATCTCGAGGGACAACGGGCAGAGCACACTGTAT<br>CTGCAGATGAACAGCCTCAGGGCTGAGGACACCGGCACCTACTTCTGCGCCAGATCTAAT<br>TATGCTTGTCCTGGTGGTTTTAGTTGTTGGGGTGATACTGGTCAAATAGACGCATGGGGC<br>CACGGGACCGAAGTCATCGTCTCCTCC (SEQ ID NO: 259) |

TABLE 7

Variable light chain polynucleotide sequence

| Antibody | Variable Light Chain Polynucleotide Sequence (SEQ ID NO) |
|---|---|
| Anti-FAM19A5 (2-13) | GCCCTGACTCAGCCGTCCTCGGTGTCAGCAAACCCAGGAGAAACCGTCAAGATAACCTGC<br>TCCGGGGGTAGCTATAGCTATGGCTGGTTCCAGCAGAAGTCTCCTGGCAGTGCCCTTGTC<br>ACTGTGATCTACTGGGATGATGAGAGACCCTCGGACATCCCTTCACGATTCTCCGGTGCC<br>CTATCCGGCTCCACAAACACATTAACCATCACTGGGGTCCAAGCCGACGACGAGGCTGTC<br>TATTTCTGTGGGACTGAAGACATCAGCGGCACTGCTGGTGTATTTGGGGCCGGGACAACC<br>CTGACCGTCCTG (SEQ ID NO: 47) |
| Anti-FAM19A5 (3-2) | GCCCTGACTCAGCCGTCCTCGGTGTCAGCAAACCCAGGAGAAACCGTCAAGATCACCTGC<br>TCCGGGGGTGGCAGCTATGCTGGAAGTTACTATTATGGCTGGTACCAGCAGAAGGCACCT<br>GGCAGTGCCCCTGTCACTCTGATCTATGAAAGCAACAAGAGACCCTCGGACATCCCTTCA |

TABLE 7-continued

Variable light chain polynucleotide sequence

| Antibody | Variable Light Chain Polynucleotide Sequence (SEQ ID NO) |
|---|---|
| | CGATTCTCCGGTTCCACATCTGGCTCCACAGCCACACTAACCATCACTGGGGTCCAAGCC<br>GATGACGAGGCTATCTATTACTGTGGGAGCTGGGACAGTAGCAATGGTGGTATATTTGGG<br>GCCGGGACAACCCTGACCGTCCTA (SEQ ID NO: 48) |
| Anti-FAM19A5<br>(1-65) | GCCCTGACTCAGCCCTCTTCCGTGTCAGCCAACCCTGGAGAAACTGTGAAGATCACCTGC<br>AGCGGAGGAGGGAGCTCCGGATACGGATATGGGTGGTATCAGCAGAAATCCCCATCTAGT<br>GCCCCCCTGACTGTGATCTATTGGAACGACAAGAGGCCTAGTGATATTCCATCAAGATTC<br>AGTGGATCAAAAAGCGGGTCCACTCACACCCTGACAATCACTGGCGTGCAGGCAGAGGAC<br>GAAGCCGTCTACTTCTGCGGAAATGACGATTACTCAAGCGATTCTGGCTATGTGGGCGTC<br>TTTGGCGCAGGAACCACACTGACAGTGCTG (SEQ ID NO: 49) |
| Anti-FAM19A5<br>(1-28) | GCCCTGACTCAGCCGTCCTCGGTGTCAGCAAACCTGGAAGGAACCGTCGAGATCACCTGC<br>TCCGGGAGTGGCTATGGTTATGGCTGGTATCAGCAGAAGTCTCCTGGCAGTGCCCCCTGTC<br>ACTGTGATCTATCAGAACGACAAGAGACCCTCGGACATCCCTTCACGATTCTCCGGTTCC<br>AAATCCGGCTCCACGGGCACATTAACCATCACTGGGGTCCAAGTCGAGGACGAGGCTGTC<br>TATTACTGTGGGAGTGAAGACAGCAGCACTCTTGCTGGTATATTTGGGGCCGGGACAACC<br>CTGACCGTCCTA (SEQ ID NO: 50) |
| Anti-FAM19A5<br>(P2-C12) | GAGCTCGATATGACCCAGACTCCATCCTCCGTGTCTGCAGCTGTGGGAGGCACAGTCACC<br>ATCAAGTGCCAGGCCAGTCAGAGCATTAGTAGCTACTTATCCTGGTATCAGCAGAAACCA<br>GGGCAGCCTCCCAAGCTCCTGATCTATGAAGCATCCAAACTGGCCTCTGGGGTCCCCATCG<br>CGGTTCAGCGGCAGTGGATATGGGACAGAGTTCACTCTCACCATCAGCGACCTGGAGTGT<br>GCCGATGCTGCCACTTACTACTGTCAACAGGGTTATAGTAGTACTAATGTTTGGAATGCT<br>TTCGGCGGAGGCACCAATGTGGAAATCAAA (SEQ ID NO: 178) |
| Anti-FAM19A5<br>(SS01-13) | GCCCTGACTCAGCCGTCCTCGGTGTCAGCAAACCCTGGGGAAACTGTTCGTATCACCTGC<br>TCCGGGGGTGCTAGCAGTGGCTATGGTTATGGCTGGTATCAGCAGAAGCCTAGCAGTGCC<br>CCTCTCACTGTGATCTACAAAGACGACGAAAGACCCTCGGACATCCCTTCACGATTCTCC<br>GGTTCCTCTTCCGGCTCCACACACACATTAACCATCACTGGGGTCCAAGCCGAGGACGAG<br>GCTGTATATTTCTGTGGGAATGATGACTACAGCAGTGATAGTGGATATGTCGGTGTATTT<br>GGGGCCGGGACAACCCTGACCGTCCTA (SEQ ID NO: 272) |
| Anti-FAM19A5<br>(SS01-13-S5) | GCCCTGACTCAGCCGTCCTCGGTGTCAGCAAACCCTGGGGAAACTGCGCGTATCACCTGC<br>TCCGGTGGTGCTAGCAGTGGCTATGGTTATGGCTGGTATCAGCAGAAGCCTAGCAGTGCC<br>CCTCTCACTGTGATCTACAAAGACTCTGAAAGACCCTCGGACATCCCTTCACGATTCTCC<br>GGTTCCTCTTCCGGCTCCACACACACATTAACCATCAGCGGGGTCCAAGCCGAGGACGAG<br>GCTGTATATTTCTGTGGGAATGATGACTACAGCAGTGATAGTGGATATGTCGGTGTATTT<br>GGGGCCGGGACAACCCTGACCGTCCTA (SEQ ID NO: 270) |
| Anti-FAM19A5<br>("S5-2.GKNG") | GCCCTGACTCAGCCGTCCTCGGTGTCAGCAAACCCTGGGGAAACTGCGCGTATCACCTGC<br>TCCGGTGGTGCTAGCAGTGGCTATGGTTATGGCTGGTATCAGCAGAAGCCTAGCAGTGCC<br>CCTCTCACTGTGATCTACAAAGACTCTGAAAGACCCTCGGACATCCCTTCACGATTCTCC<br>GGTTCCTCTTCCGGCTCCACACACACATTAACCATCAGCGGGGTCCAAGCCGAGGACGAG<br>GCTGTATATTTCTGTGGGAATGATGACTACAGCAGTGATAGTGGATATGTCGGTGTATTT<br>GGGGCCGGGACAACCCTGACCGTCCTA (SEQ ID NO: 270) |
| Anti-FAM19A5<br>("1-7A-IT") | GCCCTGACTCAGCCGTCCTCGGTGTCAGCAAACCCAGGAGAAACCGTCAAGATCACCTGC<br>TCCGGGGGTGGCAGCTATGCTGGAAGTTACTATTATGGCTGGTATCAGCAGAAGCCTGGC<br>AGTGCCCCTGTCACTCTGATCTATGAAACAACAAGAGACCCTCGGACATCCCTTCACGA<br>TTCTCCGGTTCCACATCTGGCTCCACAGCCACACTAACCATCACTGGGGTCCAAGCCGGC<br>GACGAGGCTGATTATTACTGTGGGAGCTGGGACAGTAGCAATGGTGGTATATTTGGGGCC<br>GGGACAACCCTGACCGTCCTA (SEQ ID NO: 261) |
| Anti-FAM19A5<br>("Low-PI") | GCCCTGACTCAGCCGTCCTCGGTGTCAGCAAACCCAGGAGAAACCGTCAAGATCACCTGC<br>TCCGGGGGTGGCAGCTATGCTGGAAGTTACTATTATGGCTGGTATCAGCAGAAGCCTGGC<br>AGTGCCCCTGTCACTCTGATCTATGAAACAACAAGAGACCCTCGGACATCCCTTCACGA<br>TTCTCCGGTTCCACATCTGGCTCCACAGCCACACTAACCATCACTGGGGTCCAAGCCGGC<br>GACGAGGCTGATTATTACTGTGGGAGCTGGGACAGTAGCAATGGTGGTATATTTGGGGCC<br>GGGACAACCCTGACCGTCCTA (SEQ ID NO: 262) |
| Anti-FAM19A5<br>("1-30") | GCCCTGACTCAGCCGTCCTCGGTGTCAGCAAACCCAGGAGAAACCGTCAAGATCACCTGC<br>TCCGGGGGTGGCAGCGAAGAAGAACAGTACTATTATGGCTGGTATCAGCAGAAGCCTGGC<br>AGTGCCCCTGTCACTCTGATCTATCAGGATGAAGAAAGACCCTCGGACATCCCTTCACGA<br>TTCTCCGGTTCCACATCTGGCTCCACAGCCACACTAACCATCACTGGGGTCCAAGCCGGC<br>GACGAGGCTGATTATTACTGTGGGAGCTGGGACAGTGAAGATGAAGATCATTTTGGGGCC<br>GGGACAACCCTGACCGTCCTA (SEQ ID NO: 263) |
| Anti-FAM19A5<br>("1-17") | GCCCTGACTCAGCCGTCCTCGGTGTCAGCAAACCCAGGAGAAACCGTCAAGATCACCTGC<br>TCCGGGGGTGGCAGCTATGCTGGAAGTTACTATTATGGCTGGTATCAGCAGAAGCCTGGC<br>AGTGCCCCTGTCACTCTGATCTATGAAGATGAACAGAGACCCTCGGACATCCCTTCACGA<br>TTCTCCGGTTCCACATCTGGCTCCACAGCCACACTAACCATCACTGGGGTCCAAGCCGGC<br>GACGAGGCTGATTATTACTGTGGGAGCTGGGACAGTGAAGATGAAGATCATTTTGGGGCC<br>GGGACAACCCTGACCGTCCTA (SEQ ID NO: 264) |

TABLE 7-continued

Variable light chain polynucleotide sequence

| Antibody | Variable Light Chain Polynucleotide Sequence (SEQ ID NO) |
|---|---|
| Anti-FAM19A5 ("1-32") | GCCCTGACTCAGCCGTCCTCGGTGTCAGCAAACCCAGGAGAAACCGTCAAGATCACCTGC<br>TCCGGGGGTGGCAGCTATGCTGGAAGTTACTATTATGGCTGGTATCAGCAGAAGCCTGGC<br>AGTGCCCCTGTCACTCTGATCTATCAGGATGAAGAAAGACCTCGGACATCCCTTCACGA<br>TTCTCCGGTTCCACATCTGGCTCCACAGCCACACTAACCATCACTGGGGTCCAAGCCGGC<br>GACGAGGCTGATTATTACTGTGGGAGCTGGGACAGTGAAGATGAAGATCATTTTGGGGCC<br>GGGACAACCCTGACCGTCCTA (SEQ ID NO: 265) |
| Anti-FAM19A5 ("4-11") | GCCCTGACTCAGCCGTCCTCGGTGTCAGCAAACCCAGGAGAAACCGTCAAGATCACCTGC<br>TCCGGGGGTGGCAGCTATGCTGGAAGTTACTATTATGGCTGGTATCAGCAGAAGCCTGGC<br>AGTGCCCCTGTCACTCTGATCTATGAAGACCACGAGAGACCCTCGGACATCCCTTCACGA<br>TTCTCCGGTTCCACATCTGGCTCCACAGCCACACTAACCATCACTGGGGTCCAAGCCGGC<br>GACGAGGCTGATTATTACTGTGGGAGCTGGGACAGTAGCGATGAAGATCATTTTGGGGCC<br>GGGACAACCCTGACCGTCCTA (SEQ ID NO: 266) |
| Anti-FAM19A5 ("6-10") | GCCCTGACTCAGCCGTCCTCGGTGTCAGCAAACCCAGGAGAAACCGTCAAGATCACCTGC<br>TCCGGGGGTGGCAGCTATGCTGGAAGTTACTATTATGGCTGGTATCAGCAGAAGCCTGGC<br>AGTGCCCCTGTCACTCTGATCTATCAGGATCTGCTGAGACCCTCGGACATCCCTTCACGA<br>TTCTCCGGTTCCACATCTGGCTCCACAGCCACACTAACCATCACTGGGGTCCAAGCCGGC<br>GACGAGGCTGATTATTACTGTGGGAGCTGGGACAGTCTGAGCAGCAGCCATTTTGGGGCC<br>GGGACAACCCTGACCGTCCTA (SEQ ID NO: 267) |
| Anti-FAM19A5 ("2-13D") | GCCCTGACTCAGCCGTCCTCGGTGTCAGCAAACCCAGGAGAAACCGCGAAGATAACCTGC<br>TCCGGGGGTGTGTATAGCTATGGCTGGTTCCAGCAGAAGCCTGGCAGTGCCCTTGTCACT<br>GTGATCTACTGGGATGATGAGAGACCCTCGGACATCCCTTCACGATTCTCCGGTGCCCTA<br>TCCGGCTCCACAAACACATTAACCATCACTGGGGTCCAAGCCGAAGACGAGGCTGATTAT<br>TATTGTGGGACTGAAGACATCAGCGGCACTGCTGGTGTATTTGGGGCCGGGACAACCCTG<br>ACCGTCCTG (SEQ ID NO: 268) |
| Anti-FAM19A5 ("2-13D-37") | GCCCTGACTCAGCCGTCCTCGGTGTCAGCAAACCCAGGAGAAACCGCGAAGATAACCTGC<br>TCCGGGGGTGTGTATAGCTATGGCTGGTTCCAGCAGAAGCCTGGCAGTGCCCTTGTCACT<br>GTGATCTACTGGGATGATGAGAGACCCTCGGACATCCCTTCACGATTCTCCGGTGCCCTA<br>TCCGGCTCCACAAACACATTAACCATCACTGGGGTCCAAGCCGAAGACGAGGCTGATTAT<br>TATTGTGGGACTGAAGACATCAGCGGCACTGCTGGTGTATTTGGGGCCGGGACAACCCTG<br>ACCGTCCTG (SEQ ID NO: 268) |
| Anti-FAM19A5 ("2-13D-37-1.5W-41") | GCCCTGACTCAGCCGTCCTCGGTGTCAGCAAACCCAGGAGAAACCGCGAAGATAACCTGC<br>TCCGGGGGTGTGTATAGCTATGGCTGGTTCCAGCAGAAGCCTGGCAGTGCCCTTGTCACT<br>GTGATCTACTGGGATGATGAGAGACCCTCGGACATCCCTTCACGATTCTCCGGTGCCCTA<br>TCCGGCTCCACAAACACATTAACCATCACTGGGGTCCAAGCCGAAGACGAGGCTGATTAT<br>TATTGTGGGACTGAAGACATCAGCGGCACTGCTGGTGTATTTGGGGCCGGGACAACCCTG<br>ACCGTCCTG (SEQ ID NO: 268) |
| Anti-FAM19A5 ("2-13D-37-3W-16") | GCCCTGACTCAGCCGTCCTCGGTGTCAGCAAACCCAGGAGAAACCGCGAAGATAACCTGC<br>TCCGGGGGTGTGTATAGCTATGGCTGGTTCCAGCAGAAGCCTGGCAGTGCCCTTGTCACT<br>GTGATCTACTGGGATGATGAGAGACCCTCGGACATCCCTTCACGATTCTCCGGTGCCCTA<br>TCCGGCTCCACAAACACATTAACCATCACTGGGGTCCAAGCCGAAGACGAGGCTGATTAT<br>TATTGTGGGACTGAAGACATCAGCGGCACTGCTGGTGTATTTGGGGCCGGGACAACCCTG<br>ACCGTCCTG (SEQ ID NO: 268) |

Once DNA fragments encoding VH and VL segments useful for the present methods are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region useful for the present methods can be converted to a full-length heavy chain gene by operatively linking the VH-encoding DNA to another DNA molecule encoding heavy chain constant regions (hinge, CH1, CH2 and/or CH3). The sequences of human heavy chain constant region genes are known in the art (see, e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, for example, an IgG2 and/or IgG 4 constant region. For a Fab fragment heavy chain gene, the VH-encoding DNA can be operatively linked to another DNA molecule encoding only the heavy chain CH1 constant region.

The isolated DNA encoding the VL region useful for the present methods can be converted to a full-length light chain gene (as well as a Fab light chain gene) by operatively linking the VL-encoding DNA to another DNA molecule encoding the light chain constant region, CL. The sequences of human light chain constant region genes are known in the art (see, e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region.

To create a scFv gene, the VH- and VL-encoding DNA fragments are operatively linked to another fragment encoding a flexible linker, e.g., encoding the amino acid sequence (Gly$_4$-Ser)$_3$, such that the VH and VL sequences can be expressed as a contiguous single-chain protein, with the VL and VH regions joined by the flexible linker (see, e.g., Bird et al. (1988) *Science* 242:423-426; Huston et al. (1988) *Proc. Natl. Acad. Sci. USA* 85:5879-5883; McCafferty et al., (1990) *Nature* 348:552-554).

In some embodiments, the present disclosure provides use of a vector comprising an isolated nucleic acid molecule comprising a nucleotide sequence encoding an antibody or antigen-binding portion thereof in the methods disclosed herein. In other embodiments, the vectors can be used for gene therapy.

Suitable vectors for the disclosed methods include expression vectors, viral vectors, and plasmid vectors. In one embodiment, the vector is a viral vector.

As used herein, an expression vector refers to any nucleic acid construct which contains the necessary elements for the transcription and translation of an inserted coding sequence, or in the case of an RNA viral vector, the necessary elements for replication and translation, when introduced into an appropriate host cell. Expression vectors can include plasmids, phagemids, viruses, and derivatives thereof.

Expression vectors for the disclosed methods can include polynucleotides encoding the antibody or antigen-binding portion thereof described herein. In one embodiment, the coding sequences for the antibody or antigen-binding portion thereof is operably linked to an expression control sequence. As used herein, two nucleic acid sequences are operably linked when they are covalently linked in such a way as to permit each component nucleic acid sequence to retain its functionality. A coding sequence and a gene expression control sequence are said to be operably linked when they are covalently linked in such a way as to place the expression or transcription and/or translation of the coding sequence under the influence or control of the gene expression control sequence. Two DNA sequences are said to be operably linked if induction of a promoter in the 5' gene expression sequence results in the transcription of the coding sequence and if the nature of the linkage between the two DNA sequences does not (1) result in the introduction of a frame-shift mutation, (2) interfere with the ability of the promoter region to direct the transcription of the coding sequence, or (3) interfere with the ability of the corresponding RNA transcript to be translated into a protein. Thus, a gene expression sequence would be operably linked to a coding nucleic acid sequence if the gene expression sequence were capable of effecting transcription of that coding nucleic acid sequence such that the resulting transcript is translated into the desired antibody or antigen-binding portion thereof.

Viral vectors useful for the present methods include, but are not limited to, nucleic acid sequences from the following viruses: retrovirus, such as Moloney murine leukemia virus, Harvey murine sarcoma virus, murine mammary tumor virus, and Rous sarcoma virus; lentivirus; adenovirus; adeno-associated virus; SV40-type viruses; polyomaviruses; Epstein-Barr viruses; papilloma viruses; herpes virus; vaccinia virus; polio virus; and RNA virus such as a retrovirus. One can readily employ other vectors well-known in the art. Certain viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Kriegler, M., Gene Transfer and Expression, A Laboratory Manual, W.H. Freeman Co., New York (1990) and Murry, E. J., Methods in Molecular Biology, Vol. 7, Humana Press, Inc., Cliffton, N.J. (1991).

In one embodiment, the virus useful for the present methods is an adeno-associated virus or a double-stranded DNA virus. The adeno-associated virus can be engineered to be replication-deficient and is capable of infecting a wide range of cell types and species. It further has advantages such as heat and lipid solvent stability; high transduction frequencies in cells of diverse lineages, including hematopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

In other embodiments, the vector useful for the present methods is derived from lentivirus. In certain embodiments, the vector is a vector of a recombinant lentivirus capable of infecting non-dividing cells.

The lentiviral genome and the proviral DNA typically have the three genes found in retroviruses: gag, pol and env, which are flanked by two long terminal repeat (LTR) sequences. The gag gene encodes the internal structural (matrix, capsid and nucleocapsid) proteins; the pol gene encodes the RNA-directed DNA polymerase (reverse transcriptase), a protease and an integrase; and the env gene encodes viral envelope glycoproteins. The 5' and 3' LTR's serve to promote transcription and polyadenylation of the virion RNA's. The LTR contains all other cis-acting sequences necessary for viral replication. Lentiviruses have additional genes including vif, vpr, tat, rev, vpu, nef and vpx (in HIV-1, HIV-2 and/or SIV).

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the cis defect prevents encapsidation of genomic RNA.

However, the resulting mutant remains capable of directing the synthesis of all virion proteins. Also useful for the disclosure is a recombinant lentivirus capable of infecting a non-dividing cell comprising transfecting a suitable host cell with two or more vectors carrying the packaging functions, namely gag, pol and env, as well as rev and tat. As will be disclosed herein below, vectors lacking a functional tat gene are desirable for certain applications. Thus, for example, a first vector can provide a nucleic acid encoding a viral gag and a viral pol and another vector can provide a nucleic acid encoding a viral env to produce a packaging cell. Introducing a vector providing a heterologous gene, herein identified as a transfer vector, into that packaging cell yields a producer cell which releases infectious viral particles carrying the foreign gene of interest.

According to the above-indicated configuration of vectors and foreign genes, the second vector can provide a nucleic acid encoding a viral envelope (env) gene. The env gene can be derived from nearly any suitable virus, including retroviruses. In some embodiments, the env protein is an amphotropic envelope protein which allows transduction of cells of human and other species.

Examples of retroviral-derived env genes include, but are not limited to: Moloney murine leukemia virus (MoMuLV or MMLV), Harvey murine sarcoma virus (HaMuSV or HSV), murine mammary tumor virus (MuMTV or MMTV), gibbon ape leukemia virus (GaLV or GALV), human immunodeficiency virus (HIV) and Rous sarcoma virus (RSV). Other env genes such as Vesicular stomatitis virus (VSV) protein G (VSV G), that of hepatitis viruses and of influenza also can be used.

The vector providing the viral env nucleic acid sequence is associated operably with regulatory sequences described elsewhere herein.

In certain embodiments, the vector useful for the methods includes a lentiviral vector in which the HIV virulence genes env, vif, vpr, vpu and nef were deleted without compromising the ability of the vector to transduce non-dividing cells.

In some embodiments, the vector includes a lentiviral vector which comprises a deletion of the U3 region of the 3' LTR. The deletion of the U3 region can be the complete deletion or a partial deletion.

In some embodiments, the lentiviral vector of the disclosure comprising the FVIII nucleotide sequence described herein can be transfected in a cell with (a) a first nucleotide sequence comprising a gag, a pol, or gag and pol genes and (b) a second nucleotide sequence comprising a heterologous env gene; wherein the lentiviral vector lacks a functional tat gene. In other embodiments, the cell is further transfected with a fourth nucleotide sequence comprising a rev gene. In certain embodiments, the lentiviral vector lacks functional genes selected from vif, vpr, vpu, vpx and nef, or a combination thereof.

In certain embodiments, a lentiviral vector comprises one or more nucleotide sequences encoding a gag protein, a Rev-response element, a central polypurine track (cPPT), or any combination thereof.

Examples of the lentiviral vectors are disclosed in WO9931251, WO9712622, WO9817815, WO9817816, and WO9818934, which are incorporated herein by reference in their entireties.

Other vectors useful for the present methods include plasmid vectors. Plasmid vectors have been extensively described in the art and are well-known to those of skill in the art. See, e.g., Sambrook et al., Molecular Cloning: A Laboratory Manual, Second Edition, Cold Spring Harbor Laboratory Press, 1989. In the last few years, plasmid vectors have been found to be particularly advantageous for delivering genes to cells in vivo because of their inability to replicate within and integrate into a host genome. These plasmids, however, having a promoter compatible with the host cell, can express a peptide from a gene operably encoded within the plasmid. Some commonly used plasmids available from commercial suppliers include pBR322, pUC18, pUC19, various pcDNA plasmids, pRC/CMV, various pCMV plasmids, pSV40, and pBlueScript. Additional examples of specific plasmids include pcDNA3.1, catalog number V79020; pcDNA3.1/hygro, catalog number V87020; pcDNA4/myc-His, catalog number V86320; and pBudCE4.1, catalog number V53220, all from Invitrogen (Carlsbad, Calif.). Other plasmids are well-known to those of ordinary skill in the art. Additionally, plasmids can be custom designed using standard molecular biology techniques to remove and/or add specific fragments of DNA.

VI. Antibody Production

Antibodies or fragments thereof that immunospecifically bind to FAM19A5 (e.g., human FAM19A5) can be produced by any method known in the art for the synthesis of antibodies, for example, by chemical synthesis or by recombinant expression techniques. The methods described herein employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis T et al., (1982) Molecular Cloning: A Laboratory Manual, Cold Spring Harbor Laboratory Press; Sambrook J et al., (1989), Molecular Cloning: A Laboratory Manual, Second Edition, Cold Spring Harbor Laboratory Press; Sambrook J et al., (2001) Molecular Cloning: A Laboratory Manual, Cold Spring Harbor Laboratory Press, Cold Spring Harbor, N.Y.; Ausubel F M et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press.

In a specific embodiment, an antibody described herein is an antibody (e.g., recombinant antibody) prepared, expressed, created or isolated by any means that involves creation, e.g., via synthesis, genetic engineering of DNA sequences. In certain embodiments, such antibody comprises sequences (e.g., DNA sequences or amino acid sequences) that do not naturally exist within the antibody germline repertoire of an animal or mammal (e.g., human) in vivo.

VII. Pharmaceutical Compositions

Provided herein are compositions comprising an antibody or antigen-binding portion thereof useful for the present methods having the desired degree of purity in a physiologically acceptable carrier, excipient, and/or stabilizer (Remington's Pharmaceutical Sciences (1990) Mack Publishing Co., Easton, Pa.). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In some embodiments, pharmaceutical compositions useful for the present methods comprise an antibody or antigen-binding portion thereof, a bispecific molecule, or a immunoconjugate described herein, and optionally one or more additional prophylactic or therapeutic agents, in a pharmaceutically acceptable carrier. In some embodiments, pharmaceutical compositions comprise an effective amount of an antibody or antigen-binding portion thereof described herein, and optionally one or more additional prophylactic of therapeutic agents, in a pharmaceutically acceptable carrier. In some embodiments, the antibody is the only active ingredient included in the pharmaceutical composition. Pharmaceutical compositions described herein can be useful in reducing a FAM19A5 activity and thereby treat a cardiovascular-related disease or disorder, such as atherosclerosis.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

A pharmaceutical composition useful for the present methods can be formulated for any route of administration to a subject. Parenteral administration, characterized by either subcutaneous, intramuscular, intraperitoneal, or intravenous injection, is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Preparations for parenteral administration of an antibody include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions can be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Topical mixtures comprising an antibody are prepared as described for the local and systemic administration. The resulting mixture can be a solution, suspension, emulsions or the like and can be formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

An antibody or antigen-binding portion thereof described herein can be formulated as an aerosol for topical application, such as by inhalation (see, e.g., U.S. Pat. Nos. 4,044,126, 4,414,209 and 4,364,923, which describe aerosols for delivery of a steroid useful for treatment of inflammatory diseases, particularly asthma). These formulations for administration to the respiratory tract can be in the form of an aerosol or solution for a nebulizer, or as a microtine powder for insufflations, alone or in combination with an inert carrier such as lactose. In such a case, the particles of the formulation will, in one embodiment, have diameters of less than 50 microns, in one embodiment less than 10 microns.

An antibody or antigen-binding portion thereof useful for the present methods can be formulated for local or topical application, such as for topical application to the skin and mucous membranes, in the form of gels, creams, and lotions. Topical administration is contemplated for transdermal delivery and also for administration to the mucosa or for inhalation therapies. Nasal solutions of the antibody alone or in combination with other pharmaceutically acceptable excipients can also be administered.

Transdermal patches, including iontophoretic and electrophoretic devices, are well known to those of skill in the art, and can be used to administer an antibody. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957.

In certain embodiments, a pharmaceutical composition comprising an antibody or antigen-binding portion thereof useful for the present methods is a lyophilized powder, which can be reconstituted for administration as solutions, emulsions and other mixtures. It can also be reconstituted and formulated as solids or gels. The lyophilized powder is prepared by dissolving an antibody or antigen-binding portion thereof described herein, or a pharmaceutically acceptable derivative thereof, in a suitable solvent. In some embodiments, the lyophilized powder is sterile. The solvent can contain an excipient which improves the stability or other pharmacological component of the powder or reconstituted solution, prepared from the powder. Excipients that can be used include, but are not limited to, dextrose, sorbitol, fructose, corn syrup, xylitol, glycerin, glucose, sucrose or other suitable agent. The solvent can also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

The antibodies or antigen-binding portions thereof, the bispecific molecule, or the immunoconjugate useful for the present methods and other compositions provided herein can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874. In a specific embodiment, the anti-FAM19A5 antibody or antigen-binding portion thereof useful for the present methods can be used to treat an atherosclerosis and/or reduce, ameliorate, or inhibit one or more symptoms related to atherosclerosis (e.g., increased total cholesterol, LDL, triglyceride levels, reduced HDL levels, and/or increased number and/or retention of oxo-LDL-induced foam cells within a plaque).

The compositions to be used for in vivo administration can be sterile. This is readily accomplished by filtration through, e.g., sterile filtration membranes.

VIII. Kits

Provided herein are kits comprising one or more antibodies useful for the present methods, or antigen-binding portions thereof, bispecific molecules, or immunoconjugates thereof. In a specific embodiment, provided herein is a pharmaceutical pack or kit comprising one or more containers filled with one or more of the ingredients of the pharmaceutical compositions useful for the present methods, such as one or more antibodies provided herein or an antigen-binding portion thereof, optional an instructing for use. In some embodiments, the kits contain a pharmaceutical composition useful for the present methods and any prophylactic or therapeutic agent, such as those described herein.

EXAMPLES

Example 1: Evaluation of Body Weight After In Vivo Administration of Anti-FAM19A5 Antibody in a Mouse Model of Atherosclerosis To begin assessing the effect of anti-FAM19A5 antibody treatment on atherosclerosis, atherosclerosis-prone C57BL/6 apolipoprotein E-deficient (Apoe −/−) mice (Jackson Laboratory, U.S.A.) were used. Briefly, the Apoe −/− mice were placed on a high-fat (hypercholesterolemic) diet (TD. 88137 Irradiated complete calories diet, 42% total fat, Halan Laboratories, Inc., U.S.A.) for 5 weeks to induce atherosclerosis. Then, either human IgG control antibody (10 mg/kg) or an anti-FAM19A5 antibody (clone "3-2") were intravenously administered once a week for a total of 6 weeks. The anti-FAM19A5 antibody was administered to the relevant mice at two different concentrations: (5 mg/kg) or (10 mg/kg). Normal (i.e., regular diet (+40 RMM-SP-10 Irradiated complete diet, 15.2% protein, SAFE Inc., France)) healthy mice were used a control. The normal and hypercholesterolemic mice remained on their respective diets for the entire duration of the experiment. Body weight and general clinical observations were monitored throughout the duration of the treatment. One week after the last antibody administration, the mice from the different treatment groups were sacrificed for further analysis. Table 8 provides the different treatment groups.

TABLE 8

| Treatment Groups | |
|---|---|
| Group | Treatment |
| Group 1 | Untreated; healthy animals |
| Group 2 | Anti-IgG control antibody (10 mg/kg) |
| Group 3 | Anti-FAM19A5 antibody (5 mg/kg) |
| Group 4 | Anti-FAM19A5 antibody (10 mg/kg) |

As shown in Table 9 (below) and FIG. 1, compared to animals placed on a regular diet (Group 1), animals that received the high-fat diet all gained weight during the course of the experiment. All the animals from Groups 1, 3, and 4 survived the entire duration of the experiment (i.e., 42 days). However, in Group 2 (hypercholesterolemic mice treated with the control human IgG antibody), 3/10 mice had died by the end of the experiment. Two of the dead mice exhibited abnormal symptoms prior to their death (e.g., spasms and gait disorders). There were no other significant abnormalities observed among the mice from the different treatment groups.

TABLE 9

| Mean Body Weight | | | | | | | |
|---|---|---|---|---|---|---|---|
| | Days | | | | | | |
| Groups | 0 | 7 | 14 | 21 | 28 | 35 | 42 |
| G1 | 27.1 ± 1.4 | 27.9 ± 1.3 | 28.7 ± 1.3 | 28.5 ± 1.8 | 28.9 ± 1.6 | 28.3 ± 1.2 | 30.1 ± 1.7 |
| G2 | 31.7 ± 2.2* | 33.1 ± 1.9* | 33.7 ± 1.6* | 34.8 ± 1.9* | 35.4 ± 2.1* | 34.9 ± 2.3 | 36.3 ± 2.1 |

TABLE 9-continued

| | Mean Body Weight | | | | | | |
|---|---|---|---|---|---|---|---|
| | Days | | | | | | |
| Groups | 0 | 7 | 14 | 21 | 28 | 35 | 42 |
| G3 | 30.5 ± 2.4* | 31.6 ± 2.1* | 32.2 ± 2.1* | 33.3 ± 2.6* | 33.9 ± 2.8* | 33.0 ± 4.1 | 34.1 ± 4.7 |
| G4 | 32.0 ± 1.2* | 33.1 ± 1.1* | 33.8 ± 1.1*# | 35.0 ± 1.4* | 35.3 ± 1.6* | 35.5 ± 1.6 | 36.1 ± 3.1 |

Significantly different from G1 vs G2~G4 (ANOVA, Fisher's PLSD post-hoc tests: *; $p < 0.05$)

The above results suggest that the administration of the anti-FAM19A5 antibody does not significantly affect body weight in hypercholesterolemic animals. However, anti-FAM19A5 treatment can promote survival as evidenced by the three mice that had died in the hypercholesterolemic group treated with the control anti-human IgG control antibody.

Example 2: Evaluation of the Effect of Anti-FAM19A5 Antibody Treatment on LDL Level To assess the effect of anti-FAM19A5 antibody treatment on the LDL level, hypercholesterolemic mice described in Example 1 were also used herein. Briefly, the mice from the different groups were sacrificed approximately a week after the last antibody administration (i.e., week 7 post-initial antibody administration). Blood (~1 mL) was collected from the abdominal vein, treated with EDTA-2K, and centrifuged (~3000 rpm for 10 minutes at room temperature) to remove the plasma. Then, the LDL levels of the mice were measured.

Figure 2:
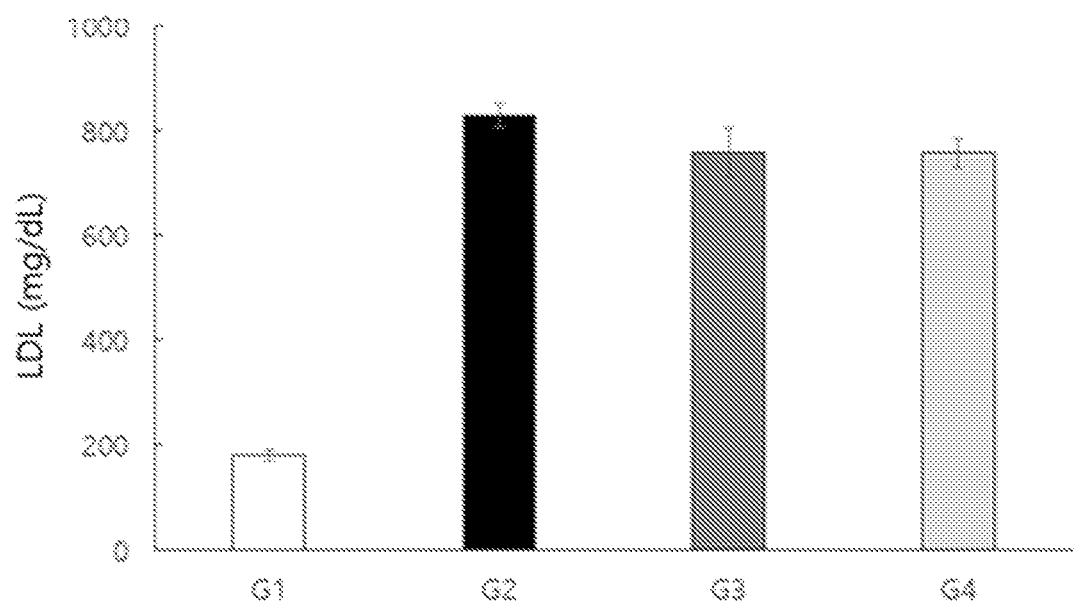
FIG. 2 shows the effect of anti-FAM19A5 antibody on LDL level in hypercholesterolemic mice. The mice were treated with either human IgG control antibody (G2) or anti-FAM19A5 antibody at two different concentrations, 5 mg/kg (G3) or 10 mg/kg (G4). Normal mice (i.e., regular diet; G1) were used as control. Data are shown as mean±S.D.
Figure 3A:
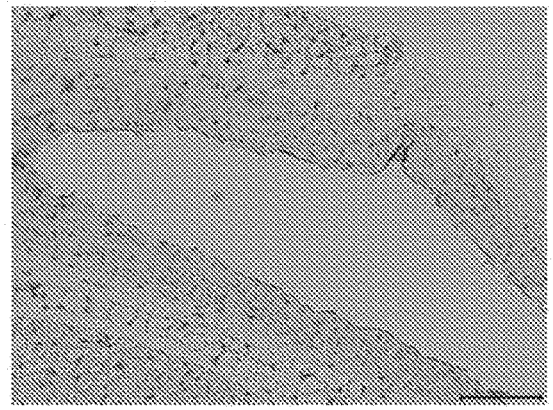
FIGS. 3A, 3B, 3C, and 3D show an immunohistochemistry analysis of CD68 (left panel) and CD146 (right panel) expression in the aorta of mice from the different treatment groups.
Figure 3A:
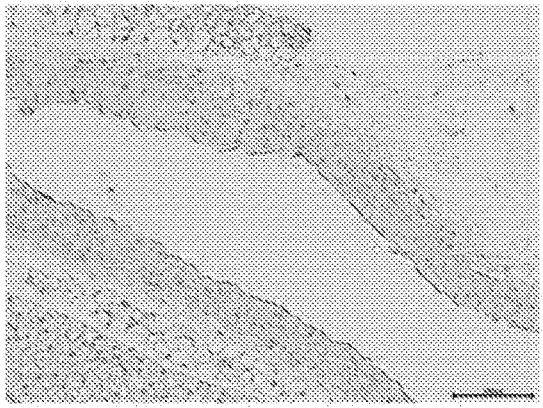
Figure 3B:
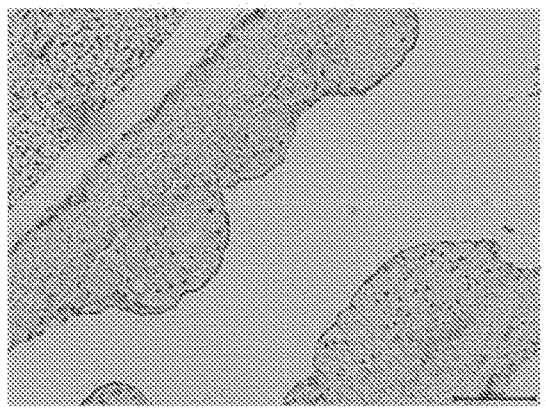
Figure 3B:
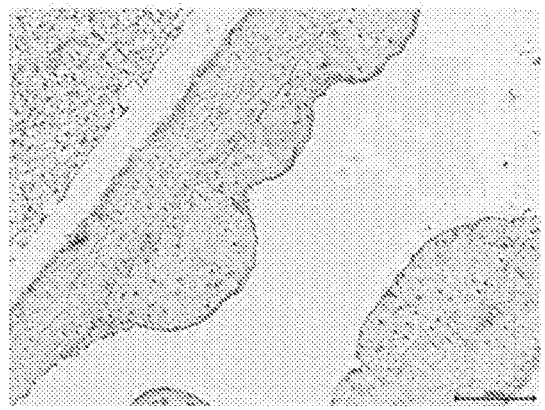
Figure 3C:
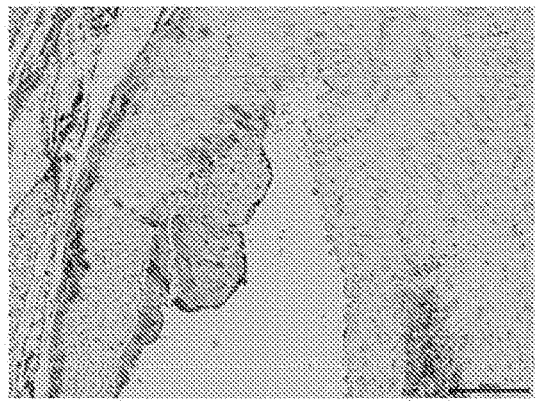
Figure 3C:
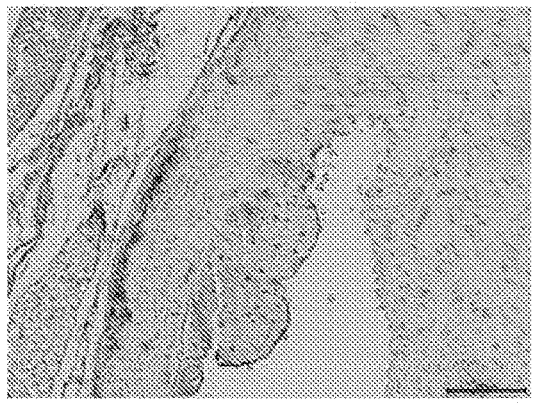
Figure 3D:
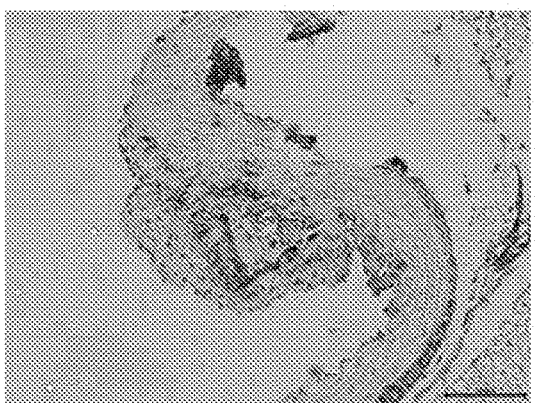
Figure 3D:
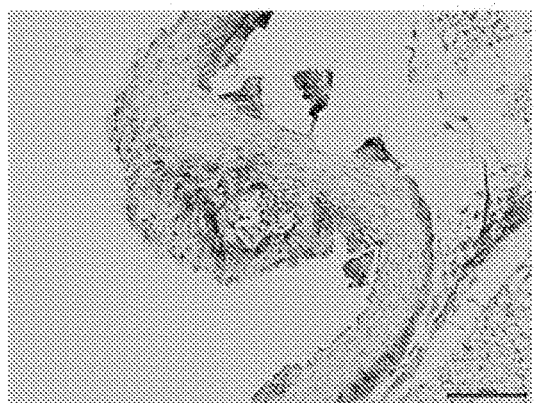

As shown in Table 10 (below), the LDL level was modestly reduced in hypercholesterolemic mice treated with anti-FAM19A5 antibody (both Groups 3 and 4) compared to mice treated with the human IgG control antibody (Group 2). (see also FIG. 2).

TABLE 10

| Plasma Levels of LDL | |
|---|---|
| Groups | LDL (mg/dL) |
| G1 | 179.2 ± 26.8 |
| G2 | 828.6 ± 66.7 |
| G3 | 757.4 ± 153.0 |
| G4 | 757.8 ± 100.1 |

The above results suggest that anti-FAM19A5 treatment can help treat atherosclerosis by lowering LDL levels in the blood of hypercholesterolemic animals. This decrease in LDL levels can translate to reduced total cholesterol level in the blood.

Example 3: Immunohistochemistry Analysis of the Effect of Anti-FAM19A5 Antibody Treatment on Migration of Macrophages to Atherosclerotic Lesion Sites on Aorta Phagocytosis by macrophage of dead cell and oxidized LDL is important for the clearance of atherosclerotic plaque. Therefore, to determine whether anti-FAM19A5 treatment has any effect on the accumulation and/or phagocytic properties of monocyte/macrophages in atherosclerotic lesion sites on blood vessels, the expression of CD68 and CD146 was assessed in the aorta of hypercholesterolemic mice described above in Example 1. CD68 and CD146 are markers commonly used to detect fat-laden macrophages (foam cells) within tissues.

Briefly, the mice from the different groups were sacrificed approximately a week after the last antibody administration (i.e., week 7 post-initial antibody administration). Prior to isolating the heart and aorta from the animals, cardiac perfusion was performed with PBS and then with 4% paraformaldehyde. The heart and aorta were collected and fixed in 10% neutral formalin. Then, the tissue samples were stained with CD68 and CD146, and the presence of foam cell or fat-laden macrophage of the total lesion area of the tissues samples was determined.

As shown in FIGS. 3A-3D, there was an increase in CD68 and CD146 expression in the aorta of hypercholesterolemic mice (Groups 2, 3, and 4) compared to normal healthy mice (Group 1). This increase was much more profound in hypercholesterolemic mice treated with anti-FAM19A5 antibody.

This result suggests that anti-FAM19A5 antibody can promote the migration and activation of CD68 and CD146 expressing fat-laden macrophages (foam cells) to atherosclerotic lesion sites within the aorta of hypercholesterolemic animals.

Example 4: Evaluation of the Effect of Anti-FAM19A5 Antibody Treatment on the Phagocytic Ability of BV2 Cells To assess whether anti-FAM19A5 antibody treatment has an effect on macrophage function, BV cells (an immortalized murine microglial cell line) was used. Briefly, the BV2 cells ($4 \times 10^3$/100 µL/well) were plated onto a 96 well plate and incubated at 37° C. 5% CO2 for 6 hours. Then, the BV2 cells were treated with human FAM19A5-Fc protein (0.25 µM, Lot #170815) alone or in combination with varying concentrations (25 µg/mL, 12.5 µg/mL, 6.25 µg/mL, or 3.125 µg/mL) of anti-FAM19A5 antibody (clone "1-30"; Lot #A5m180831). The treated cells were incubated for an additional 16 hours at 37° C. 5% CO2. After the incubation, PHRODO™ Green E. coli BioParticles (Thermofisher, P35366) were added to the cells (15 µg/100 µL/well). INCUCYTE® (Sartorius) was then used to observe the phagocytic uptake of the BioParticles by measuring green fluorescence intensity every 1 hour.

Figure 4A:
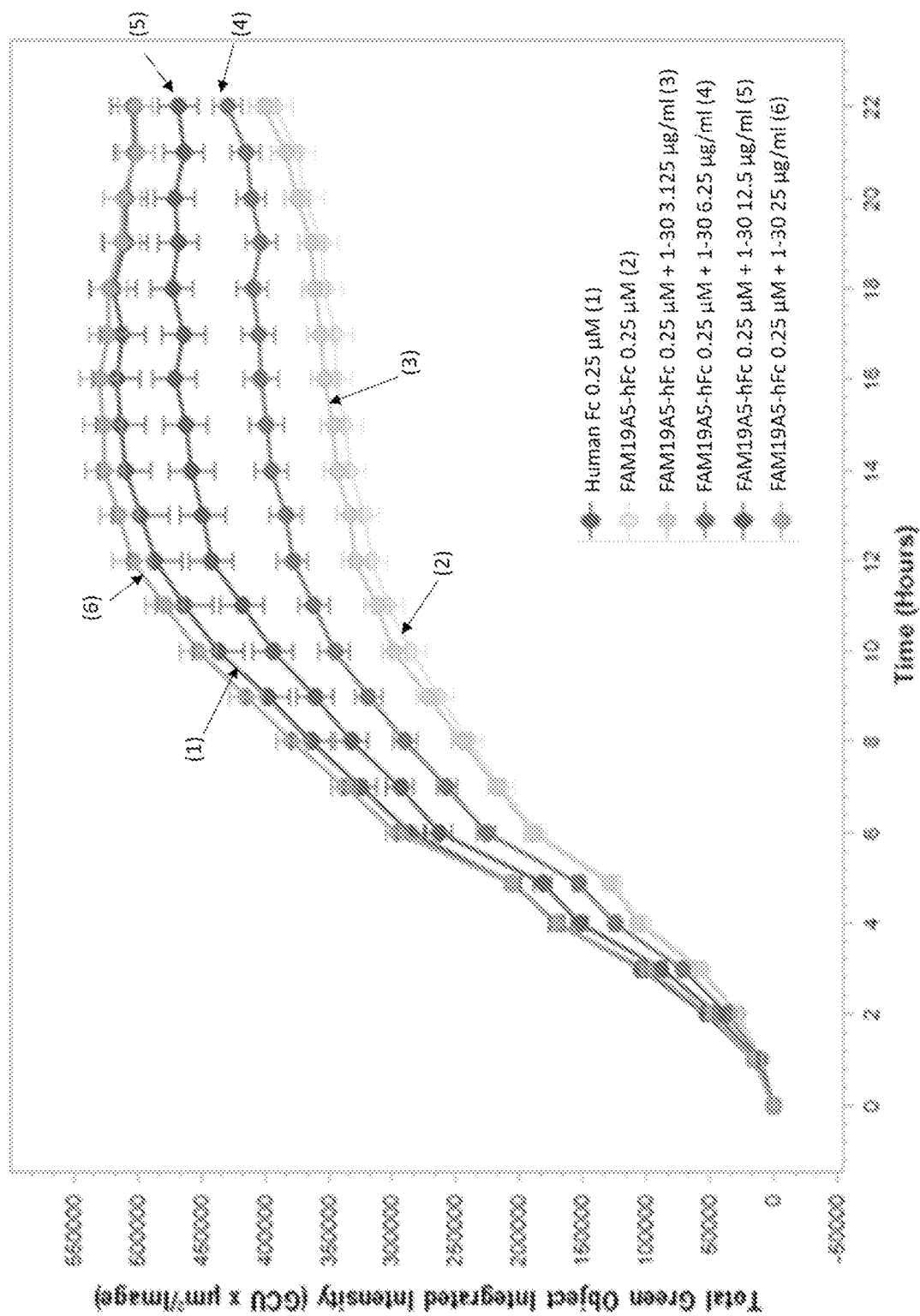
FIGS. 4A and 4B show the effect of anti-FAM19A5 antibody treatment on the phagocytic ability of BV2 cells.
Figure 4B:
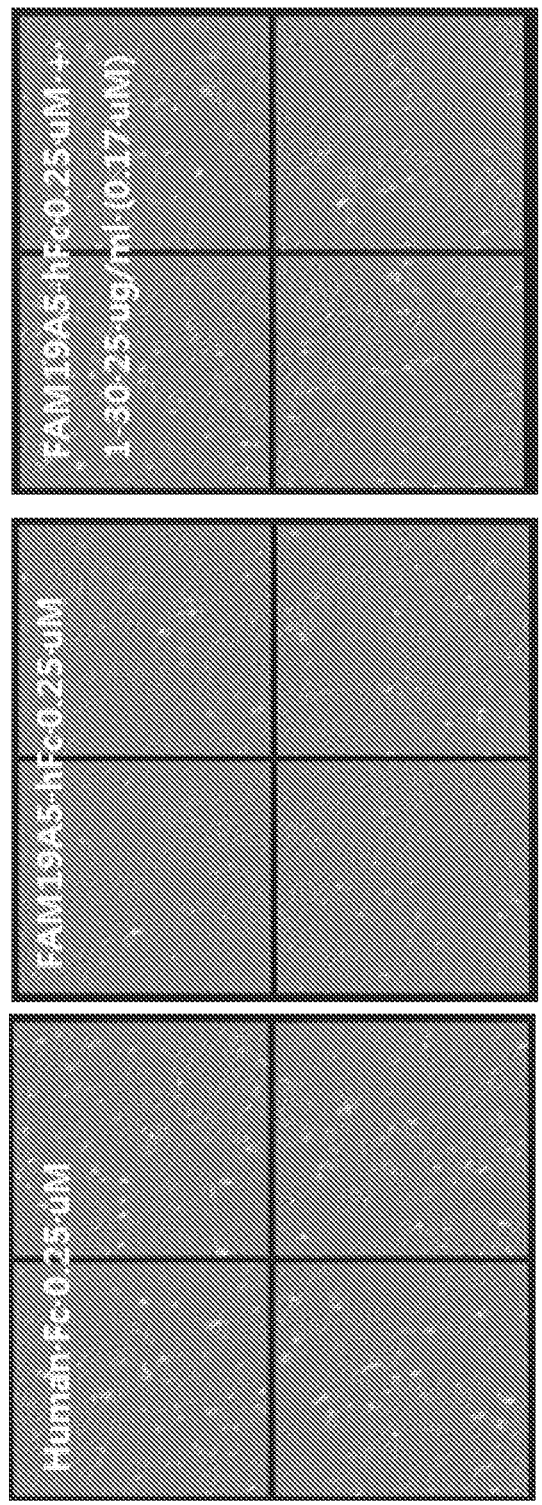

As shown in FIGS. 4A and 4B, treatment of BV2 cells with human FAM19A5-Fc protein inhibited the phagocytic ability of the BV2 cells. However, treatment of BV2 cells with the combination of human FAM19A5-Fc protein and anti-FAM19A5 antibody restored phagocytosis in a concentration-dependent manner. At approximately 9 hours post treatment with the BioParticles, compared to the control group (i.e., human FAM19A5-Fc protein alone), phagocytosis observed with 3.125, 6.25, 12.5, and 25 pg/mL anti-FAM19A5 antibody was 66%, 68%, 80%, 91%, and 104%, respectively.

The above results demonstrate that anti-FAM19A5 antibody can effectively restore the phagocytic ability of the BV2 cells after FAM19A5 protein treatment. Collectively, the above Examples suggest that anti-FAM19A5 antibody treatment can enhance both the migratory (e.g., to atherosclerotic lesion sites on blood vessel walls) and functional (e.g., phagocytosis) properties of lipid-laden macrophages in hypercholesterolemic animals. Not to be bound by any one theory, such macrophages can be important in the uptake of LDL from circulation and thereby, reduce the level of LDL in the blood.

Example 5: Evaluation of the Effect of Anti-FAM19A5 Antibody Treatment on the Phagocytosis of Oxidized LDL by BV2 Cells To further assess the effect of anti-FAM19A5 antibody on macrophage function, the ability of BV2 cells to phagocytose oxidized LDL after anti-FAM19A5 antibody treatment will be assessed. BV2 cells will be plated onto a 96 well plate and treated with human FAM19A5-Fc protein (0.25 µM, Lot #170815) alone or in combination with varying concentrations of anti-FAM19A5 antibody. The BV2 cells will be incubated at 37° C. 5% CO2. Then, Ox-LDL (purchased from AbD Serotec, Kidlington, Oxford, UK) will be added to the cells. The cellular content of Ox-LDL will be measured by using Oil Red O. INCUCYTE® (Sartorius) will be used to observe the phagocytic uptake of Ox-LDL by measuring Oil Red O intensity every 1 hour.

Example 6: Evaluation of the Effect of Anti-FAM19A5 Antibody Treatment on Plaque Formation To assess the effect that anti-FAM19A5 antibody has on plaque formation associated with atherosclerosis, atherosclerosis-prone C57BL/6 apolipoprotein E-deficient (Apoe −/−) mice (Jackson Laboratory, U.S.A.) will be used. As described in Example 1, atherosclerosis will be induced in the animals with a high-fat diet and then, treated with either human IgG control antibody or anti-FAM19A5 antibody. After the last treatment, the mice will be sacrificed and plaque build-up along blood vessel walls will be assessed using Oil Red O staining.

Example 7: Evaluation of the Effect of Anti-FAM19A5 Antibody Treatment on TNF-α Section by BV2 Cells To further understand the effect of anti-FAM19A5 antibody treatment on macrophages associated with atherosclerosis, BV2 cells were plated onto a 96 well plate ($5\times10^3$ cells/well) and incubated for 6 hours at 37° C. in 5% CO2 environment. The cells were then treated with the following: (i) 5 µL LPS (0.5 µg/mL) alone, (ii) 5 µL LPS (0.5 µg/mL)+5 µL FAM19A5-Fc protein (10 µg/mL), and (iii) 5 µL LPS (0.5 µg/mL)+5 µL FAM19A5-Fc protein (10 µg/mL)+varying concentrations of anti-FAM19A5 antibody (clone "1-30"). The final concentrations for the anti-FAM19A5 antibody were as follows: 100 µg/mL, 50 µg/mL, 25 µg/mL, 12.5 µg/mL, 6.25 µg/mL, 3.125 µg/mL, 1.5625 µg/mL, and 0.78125 µg/mL. The treated cells were incubated for an additional 16-18 hours at 37° C. in 5% CO2 environment. After the incubation, the cells were centrifuged at 3,000 rpm for 3 minutes. Then, supernatant from the different wells was collected and the concentration of TNF-α present in the sample was assessed using Quantikine ELISA mouse TNF-α immunoassay (R&D biosystems, cat #SMTA00B).

Figure 5:
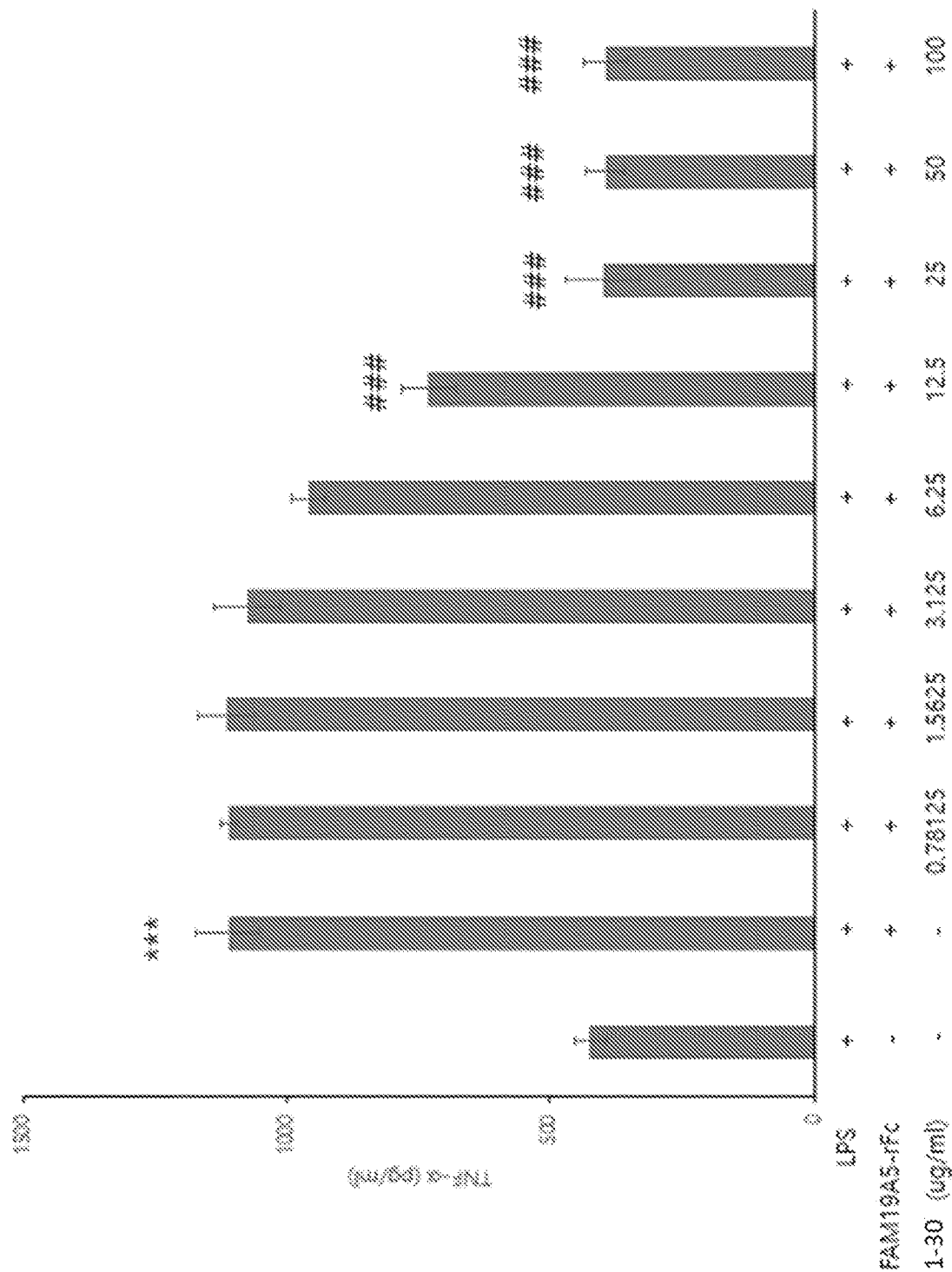
FIG. 5 shows the effect of anti-FAM19A5 antibody treatment on TNF-α production by BV2 cells. The different treatment groups shown include (from left to right): (1) LPS alone, (2) LPS+FAM19A5-Fc protein, (3) LPS+FAM19A5-Fc protein+0.78125 µg/mL of anti-FAM19A5 antibody, (4) LPS+FAM19A5-Fc protein+1.5625 µg/mL of anti-FAM19A5 antibody, (5) LPS+FAM19A5-Fc protein+3.125 µg/mL of anti-FAM19A5 antibody, (6) LPS+FAM19A5-Fc protein+6.25 µg/mL of anti-FAM19A5 antibody, (7) LPS+FAM19A5-Fc protein+12.5 µg/mL of anti-FAM19A5 antibody, (8) LPS+FAM19A5-Fc protein+25 µg/mL of anti-FAM19A5 antibody, (9) LPS+FAM19A5-Fc protein+50 µg/mL of anti-FAM19A5 antibody, and (10) LPS+FAM19A5-Fc protein+100 µg/mL of anti-FAM19A5 antibody. Data are shown as mean±S.D. "***" above the bars indicate a statistically significant difference ($p<0.005$) compared to LPS treated group. "###" above the bars indicate a statistically different difference ($p<0.005$) compared to LPS+FAM19A5-Fc protein treated group.

As shown in FIG. 5, FAM19A5-Fc protein greatly increased the amount of TNF-α produced by the BV2 cells after stimulation with LPS, compared to control cells (i.e., cells treated with LPS alone). This enhanced effect was inhibited when the anti-FAM19A5 antibody was added to the cells. The inhibitory effect was observed starting at a concentration of 12.5 µg/mL of the anti-FAM19A5 antibody ($IC_{50}$=11.5 µg/mL).

The above results demonstrate that an anti-FAM19A5 antibody disclosed herein can effectively neutralize FAM19A5 protein activity and thereby, inhibit and/or reduce the pro-inflammatory inducing effects that FAM19A5 protein can have on macrophages associated with atherosclerosis.

Example 8: Evaluation of the Effect of Anti-FAM19A5 Antibody Treatment on Peripheral Macrophages To assess the effect of anti-FAM19A5 antibody treatment on peripheral macrophages, the ability of mouse bone marrow-derived macrophages ("m-BMDMs") to phagocytize apoptotic cells was assessed.

To generate the apoptotic cells, thymocytes were isolated from mice and exposed 2 Gy of ionizing radiation with constant cell concentration of $1.0\times10^6$ thymocytes/mL. The apoptotic state of the cells was assessed using annexin V-positive and propidium iodide-negative staining or TUNEL staining by flow cytometry. When approximately 60-70% of the cells were apoptotic, the cells were labeled with PHRODO™ (Invitrogen) and used in the phagocytic assay as described below.

To measure phagocytosis, m-BMDMs were plated onto a 24-well plate ($2\times10^5$ cells/well) and incubated overnight. Then, the cells were starved for 30 min with DMEM/F12 containing 2% FBS and incubated with PHRODO™-labeled apoptotic thymocytes (described above) ($4.0\times10^6$ cells/well) in the presence of one of the following: (i) control Fc, (ii) FAM19A5-Fc protein, (iii) human IgG control antibody, (iv) 3-2 anti-FAM19A5 antibody, and (v) 1-65 anti-FAM19A5 antibody. The different treatment groups are shown in Table 11 (below). After the incubation, the cells were washed with PBS, trypsinized, resuspended in cold medium containing 1% NaN3, and analyzed by flow cytometry. Forward and side-scatter parameters were used to distinguish unengulfed targets from phagocytes. The data were analyzed using FlowJo software. Fluorescent signal-positive BMDMs were considered to be phagocytes engulfing targets.

TABLE 11

| Treatment Groups | |
|---|---|
| Group | Treatment |
| A1 | m-BMDMs only (negative control) |
| A2 | m-BMDMs + apoptotic thymocytes |
| A3 | m-BMDMs + apoptotic thymocytes + control Fc (0.4 µM) |
| A4 | m-BMDMs + apoptotic thymocytes + control Fc (0.8 µM) |
| A5 | m-BMDMs + apoptotic thymocytes + FAM19A5-Fc (0.4 µM) |
| A6 | m-BMDMs + apoptotic thymocytes + FAM19A5-Fc (0.8 µM) |
| B1 | m-BMDMs + apoptotic thymocytes + FAM19A5-Fc (0.8 µM) + hIgG1 control antibody (25 nM) |
| B2 | m-BMDMs + apoptotic thymocytes + FAM19A5-Fc (0.8 µM) + hIgG1 control antibody (50 nM) |
| B3 | m-BMDMs + apoptotic thymocytes + FAM19A5-Fc (0.8 µM) + "3-2" anti-FAM19A5 antibody (25 nM) |

TABLE 11-continued

Treatment Groups

| Group | Treatment |
|---|---|
| B4 | m-BMDMs + apoptotic thymocytes + FAM19A5-Fc (0.8 μM) + "3-2" anti-FAM19A5 antibody (50 nM) |
| B5 | m-BMDMs + apoptotic thymocytes + FAM19A5-Fc (0.8 μM) + "1-65" anti-FAM19A5 antibody (25 nM) |
| B6 | m-BMDMs + apoptotic thymocytes + FAM19A5-Fc (0.8 μM) + "1-65" anti-FAM19A5 antibody (50 nM) |

Figure 6A:
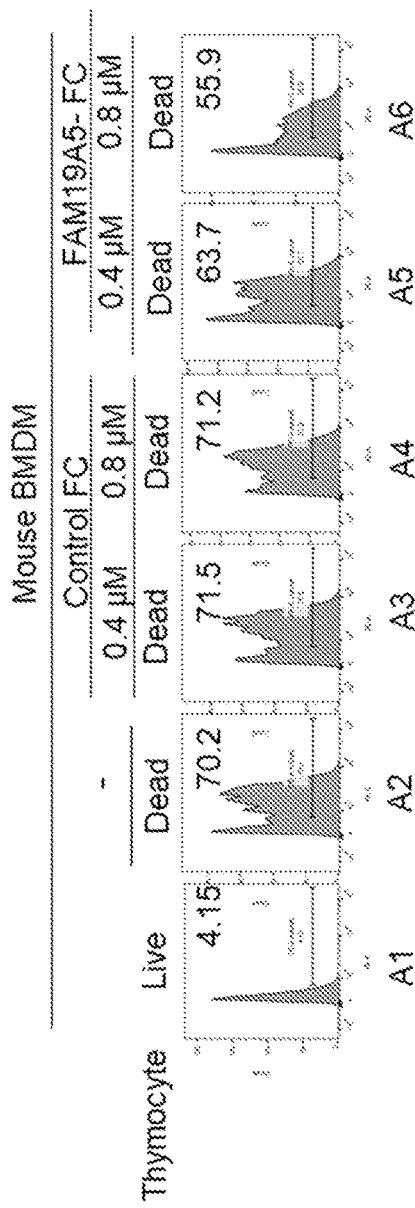
FIGS. 6A and 6B show the effect of FAM19A5 signaling on the phagocytic ability of mouse bone marrow-derived macrophages ("BMDM"). Phagocytic ability is measured using flow cytometry and represented by the percentage of mouse BMDMs that are positive for PHRODO™ expression.
Figure 6B:
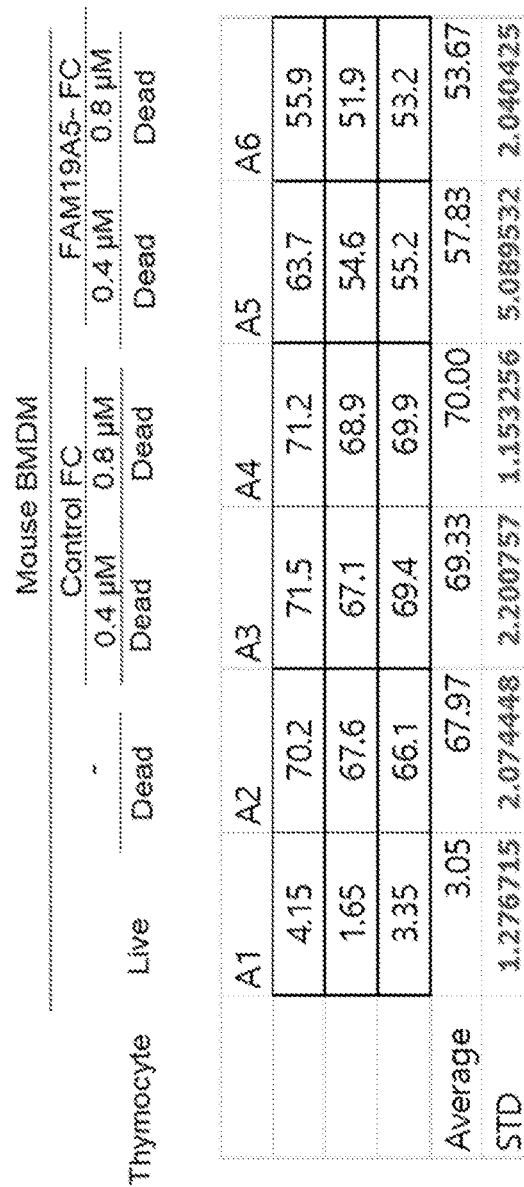
Figures 7A, 7B:
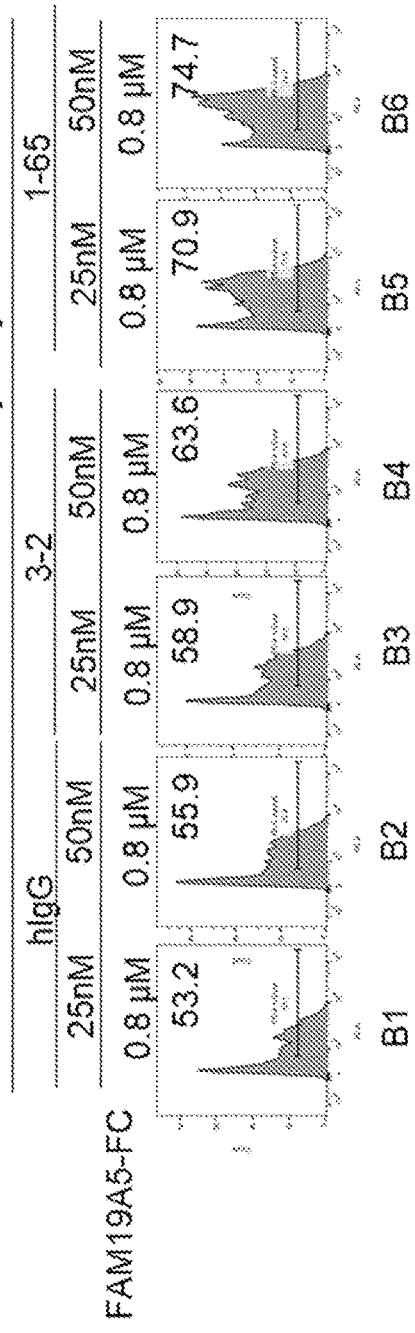
FIGS. 7A and 7B show the effect of anti-FAM19A5 antibody treatment on the phagocytic ability of mouse bone marrow-derived macrophages ("BMDM"). Phagocytic ability is measured using flow cytometry and represented by the percentage of mouse BMDMs that are positive for PHRODO™ expression.
Figure 8:
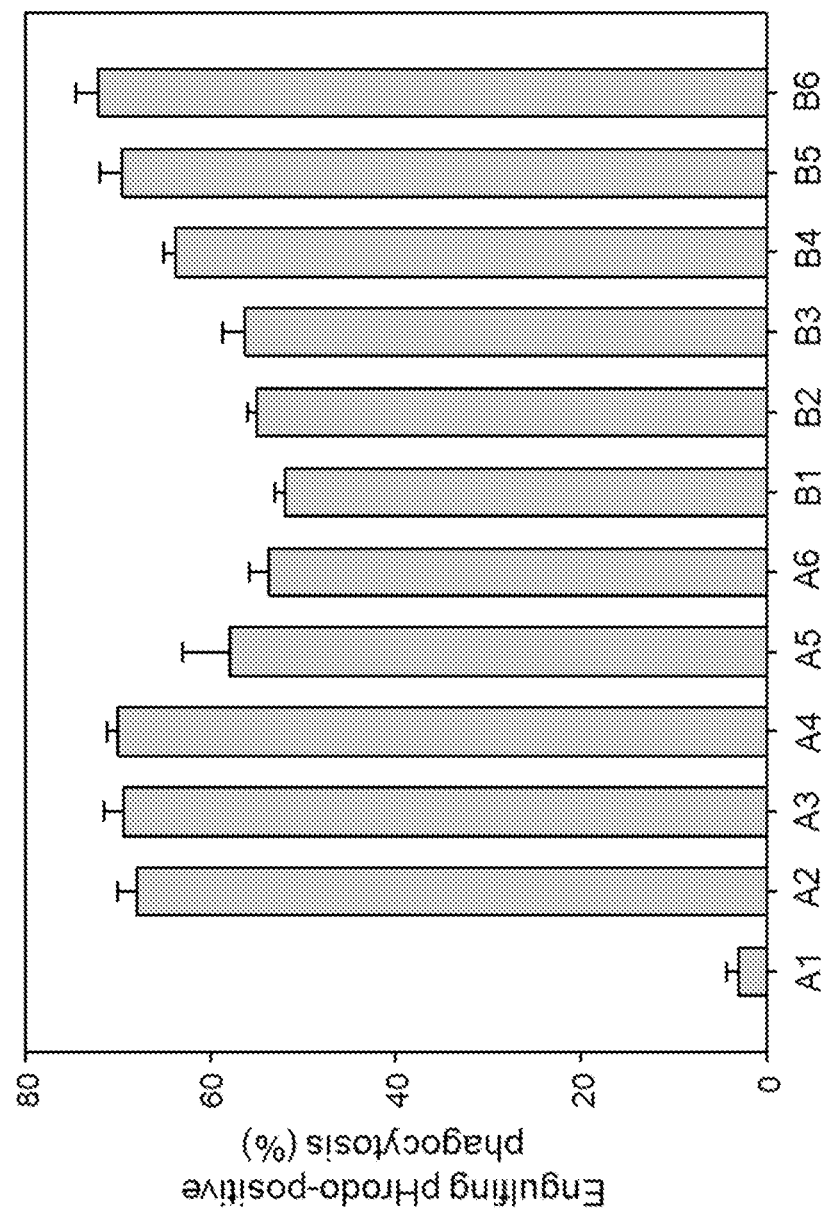
FIG. 8 provides a graphical comparison of the results shows in FIGS. 6A, 6B, 7A, and 7B. Data are shown as mean±S.D.

As shown in FIGS. 6A, 6B, and 8, FAM19A5-Fc protein inhibited the ability of the m-BMDMs to phagocytize the apoptotic thymocytes, compared to m-BMDMs that were not treated to FAM19A5-Fc protein (see, e.g., A3 and A4 vs. A5 and A6 in FIG. 6A). However, when the cells were also treated with the anti-FAM19A5 antibody (both the 3-2 and the 1-65 antibodies), the phagocytic ability of the m-BMDMs was comparable to the corresponding cells that were not treated with FAM19A5-Fc protein (see, e.g., B5 and B6 in FIG. 7A vs. A3 and A4 in FIG. 6A), suggesting that the anti-FAM19A5 antibodies (particularly at a concentration of 50 nM) effectively neutralized the activity of the FAM19A5-Fc protein.

The above results confirm the results observed earlier with the BV2 cells (see Example 4) and demonstrate that the administration of an anti-FAM19A5 antibody (such as those disclosed herein) can also improve the functional properties (e.g., phagocytosis) of peripheral macrophages, which could be useful in the treatment of atherosclerosis.

It is to be appreciated that the Detailed Description section, and not the Summary and Abstract sections, is intended to be used to interpret the claims. The Summary and Abstract sections can set forth one or more but not all exemplary embodiments of the present disclosure as contemplated by the inventor(s), and thus, are not intended to limit the present disclosure and the appended claims in any way.

The present disclosure has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

All publications, patents, patent applications, internet sites, and accession numbers/database sequences (including both polynucleotide and polypeptide sequences) cited herein are hereby incorporated by reference in their entirety for all purposes to the same extent as if each individual publication, patent, patent application, internet site, or accession number/database sequence were specifically and individually indicated to be so incorporated by reference.

What is claimed is:

1. A method of increasing a migration and/or accumulation of macrophages at an atherosclerotic lesion site in a subject in need thereof comprising administering to the subject an antagonist against a family with sequence similarity 19, member A5 ("FAM19A5") protein ("FAM19A5 antagonist"), wherein the FAM19A5 antagonist comprises an antibody, or an antigen-binding portion thereof, that specifically binds to the FAM19A5 protein ("anti-FAM19A5 antibody"), a polynucleotide encoding the anti-FAM19A5 antibody, a vector comprising the polynucleotide, or a combination thereof, wherein the anti-FAM19A5 antibody comprises a heavy chain CDR1, CDR2, and CDR3, and a light chain CDR1, CDR2, and CDR3, wherein:

(i) the heavy chain CDR1 comprises the amino acid sequence set forth in SEQ ID NO: 11, SEQ ID NO: 14, SEQ ID NO: 17, SEQ ID NO: 20, SEQ ID NO: 89, SEQ ID NO: 95, SEQ ID NO: 101, SEQ ID NO: 107, SEQ ID NO: 113, SEQ ID NO: 119, SEQ ID NO: 125, SEQ ID NO: 131, SEQ ID NO: 137, SEQ ID NO: 143, SEQ ID NO: 149, SEQ ID NO: 218, SEQ ID NO: 220, SEQ ID NO: 222, or SEQ ID NO: 223;

(ii) the heavy chain CDR2 comprises the amino acid sequence set forth in SEQ ID NO: 12, SEQ ID NO: 15, SEQ ID NO: 18, SEQ ID NO: 21, SEQ ID NO: 90, SEQ ID NO: 96, SEQ ID NO: 102, SEQ ID NO: 108, SEQ ID NO: 114, SEQ ID NO: 120, SEQ ID NO: 126, SEQ ID NO: 132, SEQ ID NO: 138, SEQ ID NO: 144, SEQ ID NO: 150, SEQ ID NO: 219, SEQ ID NO: 221, SEQ ID NO: 252, or SEQ ID NO: 253;

(iii) the heavy chain CDR3 comprises the amino acid sequence set forth in SEQ ID NO: 13, SEQ ID NO: 16, SEQ ID NO: 19, SEQ ID NO: 22, SEQ ID NO: 91, SEQ ID NO: 97, SEQ ID NO: 103, SEQ ID NO: 109, SEQ ID NO: 115, SEQ ID NO: 121, SEQ ID NO: 127, SEQ ID NO: 133, SEQ ID NO: 139, SEQ ID NO: 145, SEQ ID NO: 151, SEQ ID NO: 246, or SEQ ID NO: 247;

(iv) the light chain CDR1 comprises the amino acid sequence set forth in SEQ ID NO: 23, SEQ ID NO: 26, SEQ ID NO: 29, SEQ ID NO: 32, SEQ ID NO: 92, SEQ ID NO: 98, SEQ ID NO: 104, SEQ ID NO: 110, SEQ ID NO: 116, SEQ ID NO: 122, SEQ ID NO: 134, SEQ ID NO: 140, SEQ ID NO: 146, SEQ ID NO: 152, SEQ ID NO: 208, SEQ ID NO: 225, or SEQ ID NO: 248;

(v) the light chain CDR2 comprises the amino acid sequence set forth in SEQ ID NO: 24, SEQ ID NO: 27, SEQ ID NO: 30, SEQ ID NO: 33, SEQ ID NO: 93, SEQ ID NO: 99, SEQ ID NO: 105, SEQ ID NO: 111, SEQ ID NO: 117, SEQ ID NO: 123, SEQ ID NO: 129, SEQ ID NO: 135, SEQ ID NO: 141, SEQ ID NO: 147, SEQ ID NO: 153, SEQ ID NO: 209, SEQ ID NO: 213, SEQ ID NO: 224, SEQ ID NO: 226, SEQ ID NO: 228, SEQ ID NO: 229, SEQ ID NO: 230, or SEQ ID NO: 232; and (vi) the light chain CDR3 comprises the amino acid sequence set forth in SEQ ID NO: 25, SEQ ID NO: 28, SEQ ID NO: 31, SEQ ID NO: 34, SEQ ID NO: 94, SEQ ID NO: 100, SEQ ID NO: 106, SEQ ID NO: 112, SEQ ID NO: 118, SEQ ID NO: 124, SEQ ID NO: 130, SEQ ID NO: 136, SEQ ID NO: 142, SEQ ID NO: 148, SEQ ID NO: 154, SEQ ID NO: 227, SEQ ID NO: 231, or SEQ ID NO: 233.

2. The method of claim 1, wherein the increased migration and/or accumulation of macrophages at an atherosclerotic lesion site is associated with a decrease in a low density lipoprotein (LDL) level of the subject.

3. A method of reducing a low density lipoprotein (LDL) level in a subject in need thereof comprising administering to the subject an antagonist against a family with sequence similarity 19, member A5 ("FAM19A5") protein ("FAM19A5 antagonist"), wherein the FAM19A5 antagonist comprises an antibody, or an antigen-binding portion thereof, that specifically binds to the FAM19A5 protein ("anti-FAM19A5 antibody"), a polynucleotide encoding the anti-FAM19A5 antibody, a vector comprising the polynucleotide, or a combination thereof, wherein the anti-FAM19A5 antibody comprises a heavy chain CDR1, CDR2, and CDR3, and a light chain CDR1, CDR2, and CDR3, wherein:

(i) the heavy chain CDR1 comprises the amino acid sequence set forth in SEQ ID NO: 11, SEQ ID NO: 14, SEQ ID NO: 17, SEQ ID NO: 20, SEQ ID NO: 89, SEQ ID NO: 95, SEQ ID NO: 101, SEQ ID NO: 107, SEQ ID NO: 113, SEQ ID NO: 119, SEQ ID NO: 125, SEQ ID NO: 131, SEQ ID NO: 137, SEQ ID NO: 143, SEQ ID NO: 149, SEQ ID NO: 218, SEQ ID NO: 220, SEQ ID NO: 222, or SEQ ID NO: 223;

(ii) the heavy chain CDR2 comprises the amino acid sequence set forth in SEQ ID NO: 12, SEQ ID NO: 15, SEQ ID NO: 18, SEQ ID NO: 21, SEQ ID NO: 90, SEQ ID NO: 96, SEQ ID NO: 102, SEQ ID NO: 108, SEQ ID NO: 114, SEQ ID NO: 120, SEQ ID NO: 126, SEQ ID NO: 132, SEQ ID NO: 138, SEQ ID NO: 144, SEQ ID NO: 150, SEQ ID NO: 219, SEQ ID NO: 221, SEQ ID NO: 252, or SEQ ID NO: 253;

(iii) the heavy chain CDR3 comprises the amino acid sequence set forth in SEQ ID NO: 13, SEQ ID NO: 16, SEQ ID NO: 19, SEQ ID NO: 22, SEQ ID NO: 91, SEQ ID NO: 97, SEQ ID NO: 103, SEQ ID NO: 109, SEQ ID NO: 115, SEQ ID NO: 121, SEQ ID NO: 127, SEQ ID NO: 133, SEQ ID NO: 139, SEQ ID NO: 145, SEQ ID NO: 151, SEQ ID NO: 246, or SEQ ID NO: 247;

(iv) the light chain CDR1 comprises the amino acid sequence set forth in SEQ ID NO: 23, SEQ ID NO: 26, SEQ ID NO: 29, SEQ ID NO: 32, SEQ ID NO: 92, SEQ ID NO: 98, SEQ ID NO: 104, SEQ ID NO: 110, SEQ ID NO: 116, SEQ ID NO: 122, SEQ ID NO: 134, SEQ ID NO: 140, SEQ ID NO: 146, SEQ ID NO: 152, SEQ ID NO: 208, SEQ ID NO: 225, or SEQ ID NO: 248;

(v) the light chain CDR2 comprises the amino acid sequence set forth in SEQ ID NO: 24, SEQ ID NO: 27, SEQ ID NO: 30, SEQ ID NO: 33, SEQ ID NO: 93, SEQ ID NO: 99, SEQ ID NO: 105, SEQ ID NO: 111, SEQ ID NO: 117, SEQ ID NO: 123, SEQ ID NO: 129, SEQ ID NO: 135, SEQ ID NO: 141, SEQ ID NO: 147, SEQ ID NO: 153, SEQ ID NO: 209, SEQ ID NO: 213, SEQ ID NO: 224, SEQ ID NO: 226, SEQ ID NO: 228, SEQ ID NO: 229, SEQ ID NO: 230, or SEQ ID NO: 232; and (vi) the light chain CDR3 comprises the amino acid sequence set forth in SEQ ID NO: 25, SEQ ID NO: 28, SEQ ID NO: 31, SEQ ID NO: 34, SEQ ID NO: 94, SEQ ID NO: 100, SEQ ID NO: 106, SEQ ID NO: 112, SEQ ID NO: 118, SEQ ID NO: 124, SEQ ID NO: 130, SEQ ID NO: 136, SEQ ID NO: 142, SEQ ID NO: 148, SEQ ID NO: 154, SEQ ID NO: 227, SEQ ID NO: 231, or SEQ ID NO: 233.

4. A method of treating an atherosclerosis in a subject in need thereof comprising administering to the subject an antagonist against a family with sequence similarity 19, member A5 ("FAM19A5") protein ("FAM19A5 antagonist"), wherein the FAM19A5 antagonist comprises an antibody, or an antigen-binding portion thereof, that specifically binds to the FAM19A5 protein ("anti-FAM19A5 antibody"), a polynucleotide encoding the anti-FAM19A5 antibody, a vector comprising the polynucleotide, or a combination thereof, wherein the anti-FAM19A5 antibody comprises a heavy chain CDR1, CDR2, and CDR3, and a light chain CDR1, CDR2, and CDR3, wherein:

(i) the heavy chain CDR1 comprises the amino acid sequence set forth in SEQ ID NO: 11, SEQ ID NO: 14, SEQ ID NO: 17, SEQ ID NO: 20, SEQ ID NO: 89, SEQ ID NO: 95, SEQ ID NO: 101, SEQ ID NO: 107, SEQ ID NO: 113, SEQ ID NO: 119, SEQ ID NO: 125, SEQ ID NO: 131, SEQ ID NO: 137, SEQ ID NO: 143, SEQ ID NO: 149, SEQ ID NO: 218, SEQ ID NO: 220, SEQ ID NO: 222, or SEQ ID NO: 223;

(ii) the heavy chain CDR2 comprises the amino acid sequence set forth in SEQ ID NO: 12, SEQ ID NO: 15, SEQ ID NO: 18, SEQ ID NO: 21, SEQ ID NO: 90, SEQ ID NO: 96, SEQ ID NO: 102, SEQ ID NO: 108, SEQ ID NO: 114, SEQ ID NO: 120, SEQ ID NO: 126, SEQ ID NO: 132, SEQ ID NO: 138, SEQ ID NO: 144, SEQ ID NO: 150, SEQ ID NO: 219, SEQ ID NO: 221, SEQ ID NO: 252, or SEQ ID NO: 253;

(iii) the heavy chain CDR3 comprises the amino acid sequence set forth in SEQ ID NO: 13, SEQ ID NO: 16, SEQ ID NO: 19, SEQ ID NO: 22, SEQ ID NO: 91, SEQ ID NO: 97, SEQ ID NO: 103, SEQ ID NO: 109, SEQ ID NO: 115, SEQ ID NO: 121, SEQ ID NO: 127, SEQ ID NO: 133, SEQ ID NO: 139, SEQ ID NO: 145, SEQ ID NO: 151, SEQ ID NO: 246, or SEQ ID NO: 247;

(iv) the light chain CDR1 comprises the amino acid sequence set forth in SEQ ID NO: 23, SEQ ID NO: 26, SEQ ID NO: 29, SEQ ID NO: 32, SEQ ID NO: 92, SEQ ID NO: 98, SEQ ID NO: 104, SEQ ID NO: 110, SEQ ID NO: 116, SEQ ID NO: 122, SEQ ID NO: 134, SEQ ID NO: 140, SEQ ID NO: 146, SEQ ID NO: 152, SEQ ID NO: 208, SEQ ID NO: 225, or SEQ ID NO: 248;

(v) the light chain CDR2 comprises the amino acid sequence set forth in SEQ ID NO: 24, SEQ ID NO: 27, SEQ ID NO: 30, SEQ ID NO: 33, SEQ ID NO: 93, SEQ ID NO: 99, SEQ ID NO: 105, SEQ ID NO: 111, SEQ ID NO: 117, SEQ ID NO: 123, SEQ ID NO: 129, SEQ ID NO: 135, SEQ ID NO: 141, SEQ ID NO: 147, SEQ ID NO: 153, SEQ ID NO: 209, SEQ ID NO: 213, SEQ ID NO: 224, SEQ ID NO: 226, SEQ ID NO: 228, SEQ ID NO: 229, SEQ ID NO: 230, or SEQ ID NO: 232; and (vi) the light chain CDR3 comprises the amino acid sequence set forth in SEQ ID NO: 25, SEQ ID NO: 28, SEQ ID NO: 31, SEQ ID NO: 34, SEQ ID NO: 94, SEQ ID NO: 100, SEQ ID NO: 106, SEQ ID NO: 112, SEQ ID NO: 118, SEQ ID NO: 124, SEQ ID NO: 130, SEQ ID NO: 136, SEQ ID NO: 142, SEQ ID NO: 148, SEQ ID NO: 154, SEQ ID NO: 227, SEQ ID NO: 231, or SEQ ID NO: 233.

5. The method of claim 4, wherein the atherosclerosis is associated with: (i) a disease comprising a coronary heart disease (CHD), carotid artery disease, peripheral artery disease, chronic kidney disease, stroke, retinal artery occlusion, abdominal pain caused by intestinal damage, peritonitis, or combinations thereof; (ii) a high fat and/or high cholesterol (hypercholesterolemic) diet; (iii) an increased total cholesterol level, increased triglyceride level, increased LDL level, decreased HDL level, increased number and/or retention of oxo-LDL-induced foam cells within a plaque, or combinations thereof, compared to a subject without atherosclerosis; or (iv) a combination thereof.

6. The method of claim 4, wherein after the administration, the subject exhibits a decreased low density lipoprotein (LDL) level.

7. The method of claim 6, wherein after the administration, the subject exhibits: (i) an increased migration and/or accumulation of macrophages at an atherosclerotic lesion site of a blood vessel; (ii) an increased phagocytosis of LDL by macrophages at an atherosclerotic lesion site of a blood vessel; or (iii) both (i) and (ii).

8. The method of claim 7, wherein the blood vessel comprises an artery, vein, capillary, or combinations thereof.

9. The method of claim 8, wherein the artery is an aorta.

10. The method of claim 4, wherein the anti-FAM19A5 antibody comprises a heavy chain variable region (VH) and a light chain variable region (VL), wherein:

(i) the VH comprises the amino acid sequence set forth in SEQ ID NO: 35, SEQ ID NO: 36, SEQ ID NO: 37, SEQ ID NO: 38, SEQ ID NO: 155, SEQ ID NO: 156, SEQ ID NO: 157, SEO ID NO: 158, SEO ID NO: 159, SEO ID NO: 160, SEO ID NO: 161, SEQ ID NO: 162, SEQ ID NO: 163, SEQ ID NO: 164, SEQ ID NO: 165, SEQ ID NO: 211, SEQ ID NO: 214, SEQ ID NO: 249, SEQ ID NO: 234, SEQ ID NO: 235, SEQ ID NO: 236, SEQ ID NO: 237, SEQ ID NO: 250, or SEO ID NO: 251; and (ii) the VL comprises the amino acid sequence set forth in SEQ ID NO: 39, SEQ ID NO: 40, SEQ ID NO: 41, SEQ ID NO: 42, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 212, SEQ ID NO: 215, SEQ ID NO: 238, SEQ ID NO: 239, SEQ ID NO: 240, SEQ ID NO: 241, SEQ ID NO: 242, SEQ ID NO: 243, SEQ ID NO: 244, or SEQ ID NO: 245.

11. The method of claim 4, wherein the anti-FAM19A5 antibody comprises a Fab, Fab', F(ab')2, Fv, or single chain Fv (scFv).

12. The method of claim 4, wherein the anti-FAM19A5 antibody is a chimeric antibody, or a humanized antibody.

13. The method of claim 4, wherein the FAM19A5 antagonist is: (i) linked to a molecule having a second binding moiety, thereby forming a bispecific molecule; (ii) linked to an agent, thereby forming an immunoconjugate, or (iii) both (i) and (ii).

14. The method of claim 1, wherein:

(a) the heavy chain CDR1 comprises the amino acid sequence set forth in SEQ ID NO: 11, the heavy chain CDR2 comprises the amino acid sequence set forth in SEQ ID NO: 12, the heavy chain CDR3 comprises the amino acid sequence set forth in SEQ ID NO: 13, the light chain CDR1 comprises the amino acid sequence set forth in SEQ ID NO: 23, the light chain CDR2 comprises the amino acid sequence set forth in SEQ ID NO: 24, and the light chain CDR3 comprises the amino acid sequence set forth in SEQ ID NO: 25;

(b) the heavy chain CDR1 comprises the amino acid sequence set forth in SEQ ID NO: 14, the heavy chain CDR2 comprises the amino acid sequence set forth in SEQ ID NO: 15, the heavy chain CDR3 comprises the amino acid sequence set forth in SEQ ID NO: 16, the light chain CDR1 comprises the amino acid sequence set forth in SEQ ID NO: 26, the light chain CDR2 comprises the amino acid sequence set forth in SEQ ID NO: 27, and the light chain CDR3 comprises the amino acid sequence set forth in SEQ ID NO: 28;

(c) the heavy chain CDR1 comprises the amino acid sequence set forth in SEQ ID NO: 17, the heavy chain CDR2 comprises the amino acid sequence set forth in SEQ ID NO: 18, the heavy chain CDR3 comprises the amino acid sequence set forth in SEQ ID NO: 19, the light chain CDR1 comprises the amino acid sequence set forth in SEQ ID NO: 29, the light chain CDR2 comprises the amino acid sequence set forth in SEQ ID NO: 30, and the light chain CDR3 comprises the amino acid sequence set forth in SEQ ID NO: 31;

(d) the heavy chain CDR1 comprises the amino acid sequence set forth in SEQ ID NO: 20, the heavy chain CDR2 comprises the amino acid sequence set forth in SEQ ID NO: 21, the heavy chain CDR3 comprises the amino acid sequence set forth in SEQ ID NO: 22, the light chain CDR1 comprises the amino acid sequence set forth in SEQ ID NO: 32, the light chain CDR2 comprises the amino acid sequence set forth in SEQ ID NO: 33, and the light chain CDR3 comprises the amino acid sequence set forth in SEQ ID NO: 34;

(e) the heavy chain CDR1 comprises the amino acid sequence set forth in SEQ ID NO: 89, the heavy chain CDR2 comprises the amino acid sequence set forth in SEQ ID NO: 90, the heavy chain CDR3 comprises the amino acid sequence set forth in SEQ ID NO: 91, the light chain CDR1 comprises the amino acid sequence set forth in SEQ ID NO: 92, the light chain CDR2 comprises the amino acid sequence set forth in SEQ ID NO: 93, and the light chain CDR3 comprises the amino acid sequence set forth in SEQ ID NO: 94;

(f) the heavy chain CDR1 comprises the amino acid sequence set forth in SEQ ID NO: 95, the heavy chain CDR2 comprises the amino acid sequence set forth in SEQ ID NO: 96, the heavy chain CDR3 comprises the amino acid sequence set forth in SEQ ID NO: 97, the light chain CDR1 comprises the amino acid sequence set forth in SEQ ID NO: 98, the light chain CDR2 comprises the amino acid sequence set forth in SEQ ID NO: 99, and the light chain CDR3 comprises the amino acid sequence set forth in SEQ ID NO: 100;

(g) the heavy chain CDR1 comprises the amino acid sequence set forth in SEQ ID NO: 101, the heavy chain CDR2 comprises the amino acid sequence set forth in SEQ ID NO: 102, the heavy chain CDR3 comprises the amino acid sequence set forth in SEQ ID NO: 103, the light chain CDR1 comprises the amino acid sequence set forth in SEQ ID NO: 104, the light chain CDR2 comprises the amino acid sequence set forth in SEQ ID NO: 105, and the light chain CDR3 comprises the amino acid sequence set forth in SEQ ID NO: 106;

(h) the heavy chain CDR1 comprises the amino acid sequence set forth in SEQ ID NO: 107, the heavy chain CDR2 comprises the amino acid sequence set forth in SEQ ID NO: 108, the heavy chain CDR3 comprises the amino acid sequence set forth in SEQ ID NO: 109, the light chain CDR1 comprises the amino acid sequence set forth in SEQ ID NO: 110, the light chain CDR2 comprises the amino acid sequence set forth in SEQ ID NO: 111, and the light chain CDR3 comprises the amino acid sequence set forth in SEQ ID NO: 112;

(i) the heavy chain CDR1 comprises the amino acid sequence set forth in SEQ ID NO: 113, the heavy chain CDR2 comprises the amino acid sequence set forth in SEQ ID NO: 114, the heavy chain CDR3 comprises the amino acid sequence set forth in SEQ ID NO: 115, the light chain CDR1 comprises the amino acid sequence set forth in SEQ ID NO: 116, the light chain CDR2 comprises the amino acid sequence set forth in SEQ ID NO: 117, and the light chain CDR3 comprises the amino acid sequence set forth in SEQ ID NO: 118;

(j) the heavy chain CDR1 comprises the amino acid sequence set forth in SEQ ID NO: 119, the heavy chain CDR2 comprises the amino acid sequence set forth in SEQ ID NO: 120, the heavy chain CDR3 comprises the amino acid sequence set forth in SEQ ID NO: 121, the light chain CDR1 comprises the amino acid sequence set forth in SEQ ID NO: 122, the light chain CDR2 comprises the amino acid sequence set forth in SEQ ID NO: 123, and the light chain CDR3 comprises the amino acid sequence set forth in SEQ ID NO: 124;

(k) the heavy chain CDR1 comprises the amino acid sequence set forth in SEQ ID NO: 125, the heavy chain CDR2 comprises the amino acid sequence set forth in SEQ ID NO: 126, the heavy chain CDR3 comprises the amino acid sequence set forth in SEQ ID NO: 127, the light chain CDR1 comprises the amino acid sequence set forth in SEQ ID NO: 128, the light chain CDR2 comprises the amino acid sequence set forth in SEQ ID NO: 129, and the light chain CDR3 comprises the amino acid sequence set forth in SEQ ID NO: 130;

(l) the heavy chain CDR1 comprises the amino acid sequence set forth in SEQ ID NO: 131, the heavy chain CDR2 comprises the amino acid sequence set forth in SEQ ID NO: 132, the heavy chain CDR3 comprises the amino acid sequence set forth in SEQ ID NO: 133, the light chain CDR1 comprises the amino acid sequence set forth in SEQ ID NO: 134, the light chain CDR2 comprises the amino acid sequence set forth in SEQ ID NO: 135, and the light chain CDR3 comprises the amino acid sequence set forth in SEQ ID NO: 136;

(m) the heavy chain CDR1 comprises the amino acid sequence set forth in SEQ ID NO: 137, the heavy chain CDR2 comprises the amino acid sequence set forth in SEQ ID NO: 138, the heavy chain CDR3 comprises the amino acid sequence set forth in SEQ ID NO: 139, the light chain CDR1 comprises the amino acid sequence set forth in SEQ ID NO: 140, the light chain CDR2 comprises the amino acid sequence set forth in SEQ ID NO: 141, and the light chain CDR3 comprises the amino acid sequence set forth in SEQ ID NO: 142;

(n) the heavy chain CDR1 comprises the amino acid sequence set forth in SEQ ID NO: 143, the heavy chain CDR2 comprises the amino acid sequence set forth in SEQ ID NO: 144, the heavy chain CDR3 comprises the amino acid sequence set forth in SEQ ID NO: 145, the light chain CDR1 comprises the amino acid sequence set forth in SEQ ID NO: 146, the light chain CDR2 comprises the amino acid sequence set forth in SEQ ID NO: 147, and the light chain CDR3 comprises the amino acid sequence set forth in SEQ ID NO: 148;

(o) the heavy chain CDR1 comprises the amino acid sequence set forth in SEQ ID NO: 149, the heavy chain CDR2 comprises the amino acid sequence set forth in SEQ ID NO: 150, the heavy chain CDR3 comprises the amino acid sequence set forth in SEQ ID NO: 151, the light chain CDR1 comprises the amino acid sequence set forth in SEQ ID NO: 152, the light chain CDR2 comprises the amino acid sequence set forth in SEQ ID NO: 153, and the light chain CDR3 comprises the amino acid sequence set forth in SEQ ID NO: 154;

(p) the heavy chain CDR1 comprises the amino acid sequence set forth in SEQ ID NO: 17, the heavy chain CDR2 comprises the amino acid sequence set forth in SEQ ID NO: 18, the heavy chain CDR3 comprises the amino acid sequence set forth in SEQ ID NO: 19, the light chain CDR1 comprises the amino acid sequence set forth in SEQ ID NO: 208, the light chain CDR2 comprises the amino acid sequence set forth in SEQ ID NO: 209, and the light chain CDR3 comprises the amino acid sequence set forth in SEQ ID NO: 31;

(q) the heavy chain CDR1 comprises the amino acid sequence set forth in SEQ ID NO: 17, the heavy chain CDR2 comprises the amino acid sequence set forth in SEQ ID NO: 252, the heavy chain CDR3 comprises the amino acid sequence set forth in SEQ ID NO: 19, the light chain CDR1 comprises the amino acid sequence set forth in SEQ ID NO: 208, the light chain CDR2 comprises the amino acid sequence set forth in SEQ ID NO: 213, and the light chain CDR3 comprises the amino acid sequence set forth in SEQ ID NO: 31;

(r) the heavy chain CDR1 comprises the amino acid sequence set forth in SEQ ID NO: 17, the heavy chain CDR2 comprises the amino acid sequence set forth in SEQ ID NO: 253, the heavy chain CDR3 comprises the amino acid sequence set forth in SEQ ID NO: 19, the light chain CDR1 comprises the amino acid sequence set forth in SEQ ID NO: 208, the light chain CDR2 comprises the amino acid sequence set forth in SEQ ID NO: 213, and the light chain CDR3 comprises the amino acid sequence set forth in SEQ ID NO: 31;

(s) the heavy chain CDR1 comprises the amino acid sequence set forth in SEQ ID NO: 218, the heavy chain CDR2 comprises the amino acid sequence set forth in SEQ ID NO: 219, the heavy chain CDR3 comprises the amino acid sequence set forth in SEQ ID NO: 16, the light chain CDR1 comprises the amino acid sequence set forth in SEQ ID NO: 26, the light chain CDR2 comprises the amino acid sequence set forth in SEQ ID NO: 224, and the light chain CDR3 comprises the amino acid sequence set forth in SEQ ID NO: 28;

(t) the heavy chain CDR1 comprises the amino acid sequence set forth in SEQ ID NO: 220, the heavy chain CDR2 comprises the amino acid sequence set forth in SEQ ID NO: 221, the heavy chain CDR3 comprises the amino acid sequence set forth in SEQ ID NO: 16, the light chain CDR1 comprises the amino acid sequence set forth in SEQ ID NO: 225, the light chain CDR2 comprises the amino acid sequence set forth in SEQ ID NO: 226, and the light chain CDR3 comprises the amino acid sequence set forth in SEQ ID NO: 227;

(u) the heavy chain CDR1 comprises the amino acid sequence set forth in SEQ ID NO: 220, the heavy chain CDR2 comprises the amino acid sequence set forth in SEQ ID NO: 221, the heavy chain CDR3 comprises the amino acid sequence set forth in SEQ ID NO: 16, the light chain CDR1 comprises the amino acid sequence set forth in SEQ ID NO: 225, the light chain CDR2 comprises the amino acid sequence set forth in SEQ ID NO: 228, and the light chain CDR3 comprises the amino acid sequence set forth in SEQ ID NO: 227;

(v) the heavy chain CDR1 comprises the amino acid sequence set forth in SEQ ID NO: 220, the heavy chain CDR2 comprises the amino acid sequence set forth in SEQ ID NO: 221, the heavy chain CDR3 comprises the amino acid sequence set forth in SEQ ID NO: 16, the light chain CDR1 comprises the amino acid sequence set forth in SEQ ID NO: 26, the light chain CDR2 comprises the amino acid sequence set forth in SEQ ID NO: 229, and the light chain CDR3 comprises the amino acid sequence set forth in SEQ ID NO: 227;

(w) the heavy chain CDR1 comprises the amino acid sequence set forth in SEQ ID NO: 220, the heavy chain CDR2 comprises the amino acid sequence set forth in SEQ ID NO: 221, the heavy chain CDR3 comprises the amino acid sequence set forth in SEQ ID NO: 16, the light chain CDR1 comprises the amino acid sequence set forth in SEQ ID NO: 26, the light chain CDR2 comprises the amino acid sequence set forth in SEQ ID NO: 228, and the light chain CDR3 comprises the amino acid sequence set forth in SEQ ID NO: 227;

(x) the heavy chain CDR1 comprises the amino acid sequence set forth in SEQ ID NO: 220, the heavy chain CDR2 comprises the amino acid sequence set forth in SEQ ID NO: 221, the heavy chain CDR3 comprises the amino acid sequence set forth in SEQ ID NO: 16, the light chain CDR1 comprises the amino acid sequence set forth in SEQ ID NO: 26, the light chain CDR2 comprises the amino acid sequence set forth in SEQ ID NO: 230, and the light chain CDR3 comprises the amino acid sequence set forth in SEQ ID NO: 231;

(y) the heavy chain CDR1 comprises the amino acid sequence set forth in SEQ ID NO: 220, the heavy chain CDR2 comprises the amino acid sequence set forth in SEQ ID NO: 221, the heavy chain CDR3 comprises the amino acid sequence set forth in SEQ ID NO: 16, the light chain CDR1 comprises the amino acid sequence set forth in SEQ ID NO: 26, the light chain CDR2 comprises the amino acid sequence set forth in SEQ ID NO: 232, and the light chain CDR3 comprises the amino acid sequence set forth in SEQ ID NO: 233;

(z) the heavy chain CDR1 comprises the amino acid sequence set forth in SEQ ID NO: 222, the heavy chain CDR2 comprises the amino acid sequence set forth in SEQ ID NO: 12, the heavy chain CDR3 comprises the amino acid sequence set forth in SEQ ID NO: 13, the light chain CDR1 comprises the amino acid sequence set forth in SEQ ID NO: 248, the light chain CDR2 comprises the amino acid sequence set forth in SEQ ID NO: 24, and the light chain CDR3 comprises the amino acid sequence set forth in SEQ ID NO: 25;

(aa) the heavy chain CDR1 comprises the amino acid sequence set forth in SEQ ID NO: 223, the heavy chain CDR2 comprises the amino acid sequence set forth in SEQ ID NO: 12, the heavy chain CDR3 comprises the amino acid sequence set forth in SEQ ID NO: 13, the light chain CDR1 comprises the amino acid sequence set forth in SEQ ID NO: 248, the light chain CDR2 comprises the amino acid sequence set forth in SEQ ID NO: 24, and the light chain CDR3 comprises the amino acid sequence set forth in SEQ ID NO: 25;

(bb) the heavy chain CDR1 comprises the amino acid sequence set forth in SEQ ID NO: 223, the heavy chain CDR2 comprises the amino acid sequence set forth in SEQ ID NO: 12, the heavy chain CDR3 comprises the amino acid sequence set forth in SEQ ID NO: 246, the light chain CDR1 comprises the amino acid sequence set forth in SEQ ID NO: 248, the light chain CDR2 comprises the amino acid sequence set forth in SEQ ID NO: 24, and the light chain CDR3 comprises the amino acid sequence set forth in SEQ ID NO: 25; or (cc) the heavy chain CDR1 comprises the amino acid sequence set forth in SEQ ID NO: 223, the heavy chain CDR2 comprises the amino acid sequence set forth in SEQ ID NO: 12, the heavy chain CDR3 comprises the amino acid sequence set forth in SEQ ID NO: 247, the light chain CDR1 comprises the amino acid sequence set forth in SEQ ID NO: 248, the light chain CDR2 comprises the amino acid sequence set forth in SEQ ID NO: 24, and the light chain CDR3 comprises the amino acid sequence set forth in SEQ ID NO: 25.

15. The method of claim 3, wherein:

(a) the heavy chain CDR1 comprises the amino acid sequence set forth in SEQ ID NO: 11, the heavy chain CDR2 comprises the amino acid sequence set forth in SEQ ID NO: 12, the heavy chain CDR3 comprises the amino acid sequence set forth in SEQ ID NO: 13, the light chain CDR1 comprises the amino acid sequence set forth in SEQ ID NO: 23, the light chain CDR2 comprises the amino acid sequence set forth in SEQ ID NO: 24, and the light chain CDR3 comprises the amino acid sequence set forth in SEQ ID NO: 25;

(b) the heavy chain CDR1 comprises the amino acid sequence set forth in SEQ ID NO: 14, the heavy chain CDR2 comprises the amino acid sequence set forth in SEQ ID NO: 15, the heavy chain CDR3 comprises the amino acid sequence set forth in SEQ ID NO: 16, the light chain CDR1 comprises the amino acid sequence set forth in SEQ ID NO: 26, the light chain CDR2 comprises the amino acid sequence set forth in SEQ ID NO: 27, and the light chain CDR3 comprises the amino acid sequence set forth in SEQ ID NO: 28;

(c) the heavy chain CDR1 comprises the amino acid sequence set forth in SEQ ID NO: 17, the heavy chain CDR2 comprises the amino acid sequence set forth in SEQ ID NO: 18, the heavy chain CDR3 comprises the amino acid sequence set forth in SEQ ID NO: 19, the light chain CDR1 comprises the amino acid sequence set forth in SEQ ID NO: 29, the light chain CDR2 comprises the amino acid sequence set forth in SEQ ID NO: 30, and the light chain CDR3 comprises the amino acid sequence set forth in SEQ ID NO: 31;

(d) the heavy chain CDR1 comprises the amino acid sequence set forth in SEQ ID NO: 20, the heavy chain CDR2 comprises the amino acid sequence set forth in SEQ ID NO: 21, the heavy chain CDR3 comprises the amino acid sequence set forth in SEQ ID NO: 22, the light chain CDR1 comprises the amino acid sequence set forth in SEQ ID NO: 32, the light chain CDR2 comprises the amino acid sequence set forth in SEQ ID NO: 33, and the light chain CDR3 comprises the amino acid sequence set forth in SEQ ID NO: 34;

(e) the heavy chain CDR1 comprises the amino acid sequence set forth in SEQ ID NO: 89, the heavy chain CDR2 comprises the amino acid sequence set forth in SEQ ID NO: 90, the heavy chain CDR3 comprises the amino acid sequence set forth in SEQ ID NO: 91, the light chain CDR1 comprises the amino acid sequence set forth in SEQ ID NO: 92, the light chain CDR2 comprises the amino acid sequence set forth in SEQ ID NO: 93, and the light chain CDR3 comprises the amino acid sequence set forth in SEQ ID NO: 94;

(f) the heavy chain CDR1 comprises the amino acid sequence set forth in SEQ ID NO: 95, the heavy chain CDR2 comprises the amino acid sequence set forth in SEQ ID NO: 96, the heavy chain CDR3 comprises the amino acid sequence set forth in SEQ ID NO: 97, the light chain CDR1 comprises the amino acid sequence set forth in SEQ ID NO: 98, the light chain CDR2 comprises the amino acid sequence set forth in SEQ ID NO: 99, and the light chain CDR3 comprises the amino acid sequence set forth in SEQ ID NO: 100;

(g) the heavy chain CDR1 comprises the amino acid sequence set forth in SEQ ID NO: 101, the heavy chain CDR2 comprises the amino acid sequence set forth in SEQ ID NO: 102, the heavy chain CDR3 comprises the amino acid sequence set forth in SEQ ID NO: 103, the light chain CDR1 comprises the amino acid sequence set forth in SEQ ID NO: 104, the light chain CDR2 comprises the amino acid sequence set forth in SEQ ID NO: 105, and the light chain CDR3 comprises the amino acid sequence set forth in SEQ ID NO: 106;

(h) the heavy chain CDR1 comprises the amino acid sequence set forth in SEQ ID NO: 107, the heavy chain CDR2 comprises the amino acid sequence set forth in SEQ ID NO: 108, the heavy chain CDR3 comprises the amino acid sequence set forth in SEQ ID NO: 109, the light chain CDR1 comprises the amino acid sequence set forth in SEQ ID NO: 110, the light chain CDR2 comprises the amino acid sequence set forth in SEQ ID NO: 111, and the light chain CDR3 comprises the amino acid sequence set forth in SEQ ID NO: 112;

(i) the heavy chain CDR1 comprises the amino acid sequence set forth in SEQ ID NO: 113, the heavy chain CDR2 comprises the amino acid sequence set forth in SEQ ID NO: 114, the heavy chain CDR3 comprises the amino acid sequence set forth in SEQ ID NO: 115, the light chain CDR1 comprises the amino acid sequence set forth in SEQ ID NO: 116, the light chain CDR2 comprises the amino acid sequence set forth in SEQ ID NO: 117, and the light chain CDR3 comprises the amino acid sequence set forth in SEQ ID NO: 118;

(j) the heavy chain CDR1 comprises the amino acid sequence set forth in SEQ ID NO: 119, the heavy chain CDR2 comprises the amino acid sequence set forth in SEQ ID NO: 120, the heavy chain CDR3 comprises the amino acid sequence set forth in SEQ ID NO: 121, the light chain CDR1 comprises the amino acid sequence set forth in SEQ ID NO: 122, the light chain CDR2 comprises the amino acid sequence set forth in SEQ ID NO: 123, and the light chain CDR3 comprises the amino acid sequence set forth in SEQ ID NO: 124;

(k) the heavy chain CDR1 comprises the amino acid sequence set forth in SEQ ID NO: 125, the heavy chain CDR2 comprises the amino acid sequence set forth in SEQ ID NO: 126, the heavy chain CDR3 comprises the amino acid sequence set forth in SEQ ID NO: 127, the light chain CDR1 comprises the amino acid sequence set forth in SEQ ID NO: 128, the light chain CDR2 comprises the amino acid sequence set forth in SEQ ID NO: 129, and the light chain CDR3 comprises the amino acid sequence set forth in SEQ ID NO: 130;

(l) the heavy chain CDR1 comprises the amino acid sequence set forth in SEQ ID NO: 131, the heavy chain CDR2 comprises the amino acid sequence set forth in SEQ ID NO: 132, the heavy chain CDR3 comprises the amino acid sequence set forth in SEQ ID NO: 133, the light chain CDR1 comprises the amino acid sequence set forth in SEQ ID NO: 134, the light chain CDR2 comprises the amino acid sequence set forth in SEQ ID NO: 135, and the light chain CDR3 comprises the amino acid sequence set forth in SEQ ID NO: 136;

(m) the heavy chain CDR1 comprises the amino acid sequence set forth in SEQ ID NO: 137, the heavy chain CDR2 comprises the amino acid sequence set forth in SEQ ID NO: 138, the heavy chain CDR3 comprises the amino acid sequence set forth in SEQ ID NO: 139, the light chain CDR1 comprises the amino acid sequence set forth in SEQ ID NO: 140, the light chain CDR2 comprises the amino acid sequence set forth in SEQ ID NO: 141, and the light chain CDR3 comprises the amino acid sequence set forth in SEQ ID NO: 142;

(n) the heavy chain CDR1 comprises the amino acid sequence set forth in SEQ ID NO: 143, the heavy chain CDR2 comprises the amino acid sequence set forth in SEQ ID NO: 144, the heavy chain CDR3 comprises the amino acid sequence set forth in SEQ ID NO: 145, the light chain CDR1 comprises the amino acid sequence set forth in SEQ ID NO: 146, the light chain CDR2 comprises the amino acid sequence set forth in SEQ ID NO: 147, and the light chain CDR3 comprises the amino acid sequence set forth in SEQ ID NO: 148;

(o) the heavy chain CDR1 comprises the amino acid sequence set forth in SEQ ID NO: 149, the heavy chain CDR2 comprises the amino acid sequence set forth in SEQ ID NO: 150, the heavy chain CDR3 comprises the amino acid sequence set forth in SEQ ID NO: 151, the light chain CDR1 comprises the amino acid sequence set forth in SEQ ID NO: 152, the light chain CDR2 comprises the amino acid sequence set forth in SEQ ID NO: 153, and the light chain CDR3 comprises the amino acid sequence set forth in SEQ ID NO: 154;

(p) the heavy chain CDR1 comprises the amino acid sequence set forth in SEQ ID NO: 17, the heavy chain CDR2 comprises the amino acid sequence set forth in SEQ ID NO: 18, the heavy chain CDR3 comprises the amino acid sequence set forth in SEQ ID NO: 19, the light chain CDR1 comprises the amino acid sequence set forth in SEQ ID NO: 208, the light chain CDR2 comprises the amino acid sequence set forth in SEQ ID NO: 209, and the light chain CDR3 comprises the amino acid sequence set forth in SEQ ID NO: 31;

(q) the heavy chain CDR1 comprises the amino acid sequence set forth in SEQ ID NO: 17, the heavy chain CDR2 comprises the amino acid sequence set forth in SEQ ID NO: 252, the heavy chain CDR3 comprises the amino acid sequence set forth in SEQ ID NO: 19, the light chain CDR1 comprises the amino acid sequence set forth in SEQ ID NO: 208, the light chain CDR2 comprises the amino acid sequence set forth in SEQ ID NO: 213, and the light chain CDR3 comprises the amino acid sequence set forth in SEQ ID NO: 31;

(r) the heavy chain CDR1 comprises the amino acid sequence set forth in SEQ ID NO: 17, the heavy chain CDR2 comprises the amino acid sequence set forth in SEQ ID NO: 253, the heavy chain CDR3 comprises the amino acid sequence set forth in SEQ ID NO: 19, the light chain CDR1 comprises the amino acid sequence set forth in SEQ ID NO: 208, the light chain CDR2 comprises the amino acid sequence set forth in SEQ ID NO: 213, and the light chain CDR3 comprises the amino acid sequence set forth in SEQ ID NO: 31;

(s) the heavy chain CDR1 comprises the amino acid sequence set forth in SEQ ID NO: 218, the heavy chain CDR2 comprises the amino acid sequence set forth in SEQ ID NO: 219, the heavy chain CDR3 comprises the amino acid sequence set forth in SEQ ID NO: 16, the light chain CDR1 comprises the amino acid sequence set forth in SEQ ID NO: 26, the light chain CDR2 comprises the amino acid sequence set forth in SEQ ID NO: 224, and the light chain CDR3 comprises the amino acid sequence set forth in SEQ ID NO: 28;

(t) the heavy chain CDR1 comprises the amino acid sequence set forth in SEQ ID NO: 220, the heavy chain CDR2 comprises the amino acid sequence set forth in SEQ ID NO: 221, the heavy chain CDR3 comprises the amino acid sequence set forth in SEQ ID NO: 16, the light chain CDR1 comprises the amino acid sequence set forth in SEQ ID NO: 225, the light chain CDR2 comprises the amino acid sequence set forth in SEQ ID NO: 226, and the light chain CDR3 comprises the amino acid sequence set forth in SEQ ID NO: 227;

(u) the heavy chain CDR1 comprises the amino acid sequence set forth in SEQ ID NO: 220, the heavy chain CDR2 comprises the amino acid sequence set forth in SEQ ID NO: 221, the heavy chain CDR3 comprises the amino acid sequence set forth in SEQ ID NO: 16, the light chain CDR1 comprises the amino acid sequence set forth in SEQ ID NO: 225, the light chain CDR2 comprises the amino acid sequence set forth in SEQ ID NO: 228, and the light chain CDR3 comprises the amino acid sequence set forth in SEQ ID NO: 227;

(v) the heavy chain CDR1 comprises the amino acid sequence set forth in SEQ ID NO: 220, the heavy chain CDR2 comprises the amino acid sequence set forth in SEQ ID NO: 221, the heavy chain CDR3 comprises the amino acid sequence set forth in SEQ ID NO: 16, the light chain CDR1 comprises the amino acid sequence set forth in SEQ ID NO: 26, the light chain CDR2 comprises the amino acid sequence set forth in SEQ ID NO: 229, and the light chain CDR3 comprises the amino acid sequence set forth in SEQ ID NO: 227;

(w) the heavy chain CDR1 comprises the amino acid sequence set forth in SEQ ID NO: 220, the heavy chain CDR2 comprises the amino acid sequence set forth in SEQ ID NO: 221, the heavy chain CDR3 comprises the amino acid sequence set forth in SEQ ID NO: 16, the light chain CDR1 comprises the amino acid sequence set forth in SEQ ID NO: 26, the light chain CDR2 comprises the amino acid sequence set forth in SEQ ID NO: 228, and the light chain CDR3 comprises the amino acid sequence set forth in SEQ ID NO: 227;

(x) the heavy chain CDR1 comprises the amino acid sequence set forth in SEQ ID NO: 220, the heavy chain CDR2 comprises the amino acid sequence set forth in SEQ ID NO: 221, the heavy chain CDR3 comprises the amino acid sequence set forth in SEQ ID NO: 16, the light chain CDR1 comprises the amino acid sequence set forth in SEQ ID NO: 26, the light chain CDR2 comprises the amino acid sequence set forth in SEQ ID NO: 230, and the light chain CDR3 comprises the amino acid sequence set forth in SEQ ID NO: 231;

(y) the heavy chain CDR1 comprises the amino acid sequence set forth in SEQ ID NO: 220, the heavy chain CDR2 comprises the amino acid sequence set forth in SEQ ID NO: 221, the heavy chain CDR3 comprises the amino acid sequence set forth in SEQ ID NO: 16, the light chain CDR1 comprises the amino acid sequence set forth in SEQ ID NO: 26, the light chain CDR2 comprises the amino acid sequence set forth in SEQ ID NO: 232, and the light chain CDR3 comprises the amino acid sequence set forth in SEQ ID NO: 233;

(z) the heavy chain CDR1 comprises the amino acid sequence set forth in SEQ ID NO: 222, the heavy chain CDR2 comprises the amino acid sequence set forth in SEQ ID NO: 12, the heavy chain CDR3 comprises the amino acid sequence set forth in SEQ ID NO: 13, the light chain CDR1 comprises the amino acid sequence set forth in SEQ ID NO: 248, the light chain CDR2 comprises the amino acid sequence set forth in SEQ ID NO: 24, and the light chain CDR3 comprises the amino acid sequence set forth in SEQ ID NO: 25;

(aa) the heavy chain CDR1 comprises the amino acid sequence set forth in SEQ ID NO: 223, the heavy chain CDR2 comprises the amino acid sequence set forth in SEQ ID NO: 12, the heavy chain CDR3 comprises the amino acid sequence set forth in SEQ ID NO: 13, the light chain CDR1 comprises the amino acid sequence set forth in SEQ ID NO: 248, the light chain CDR2 comprises the amino acid sequence set forth in SEQ ID NO: 24, and the light chain CDR3 comprises the amino acid sequence set forth in SEQ ID NO: 25;

(bb) the heavy chain CDR1 comprises the amino acid sequence set forth in SEQ ID NO: 223, the heavy chain CDR2 comprises the amino acid sequence set forth in SEQ ID NO: 12, the heavy chain CDR3 comprises the amino acid sequence set forth in SEQ ID NO: 246, the light chain CDR1 comprises the amino acid sequence set forth in SEQ ID NO: 248, the light chain CDR2 comprises the amino acid sequence set forth in SEQ ID NO: 24, and the light chain CDR3 comprises the amino acid sequence set forth in SEQ ID NO: 25; or (cc) the heavy chain CDR1 comprises the amino acid sequence set forth in SEQ ID NO: 223, the heavy chain CDR2 comprises the amino acid sequence set forth in SEQ ID NO: 12, the heavy chain CDR3 comprises the amino acid sequence set forth in SEQ ID NO: 247, the light chain CDR1 comprises the amino acid sequence set forth in SEQ ID NO: 248, the light chain CDR2 comprises the amino acid sequence set forth in SEQ ID NO: 24, and the light chain CDR3 comprises the amino acid sequence set forth in SEQ ID NO: 25.

16. The method of claim 4, wherein:

(a) the heavy chain CDR1 comprises the amino acid sequence set forth in SEQ ID NO: 11, the heavy chain CDR2 comprises the amino acid sequence set forth in SEQ ID NO: 12, the heavy chain CDR3 comprises the amino acid sequence set forth in SEQ ID NO: 13, the light chain CDR1 comprises the amino acid sequence set forth in SEQ ID NO: 23, the light chain CDR2 comprises the amino acid sequence set forth in SEQ ID NO: 24, and the light chain CDR3 comprises the amino acid sequence set forth in SEQ ID NO: 25;

(b) the heavy chain CDR1 comprises the amino acid sequence set forth in SEQ ID NO: 14, the heavy chain CDR2 comprises the amino acid sequence set forth in SEQ ID NO: 15, the heavy chain CDR3 comprises the amino acid sequence set forth in SEQ ID NO: 16, the light chain CDR1 comprises the amino acid sequence set forth in SEQ ID NO: 26, the light chain CDR2 comprises the amino acid sequence set forth in SEQ ID NO: 27, and the light chain CDR3 comprises the amino acid sequence set forth in SEQ ID NO: 28;

(c) the heavy chain CDR1 comprises the amino acid sequence set forth in SEQ ID NO: 17, the heavy chain CDR2 comprises the amino acid sequence set forth in SEQ ID NO: 18, the heavy chain CDR3 comprises the amino acid sequence set forth in SEQ ID NO: 19, the light chain CDR1 comprises the amino acid sequence set forth in SEQ ID NO: 29, the light chain CDR2 comprises the amino acid sequence set forth in SEQ ID NO: 30, and the light chain CDR3 comprises the amino acid sequence set forth in SEQ ID NO: 31;

(d) the heavy chain CDR1 comprises the amino acid sequence set forth in SEQ ID NO: 20, the heavy chain CDR2 comprises the amino acid sequence set forth in SEQ ID NO: 21, the heavy chain CDR3 comprises the amino acid sequence set forth in SEQ ID NO: 22, the light chain CDR1 comprises the amino acid sequence set forth in SEQ ID NO: 32, the light chain CDR2 comprises the amino acid sequence set forth in SEQ ID NO: 33, and the light chain CDR3 comprises the amino acid sequence set forth in SEQ ID NO: 34;

(e) the heavy chain CDR1 comprises the amino acid sequence set forth in SEQ ID NO: 89, the heavy chain CDR2 comprises the amino acid sequence set forth in SEQ ID NO: 90, the heavy chain CDR3 comprises the amino acid sequence set forth in SEQ ID NO: 91, the light chain CDR1 comprises the amino acid sequence set forth in SEQ ID NO: 92, the light chain CDR2 comprises the amino acid sequence set forth in SEQ ID NO: 93, and the light chain CDR3 comprises the amino acid sequence set forth in SEQ ID NO: 94;

(f) the heavy chain CDR1 comprises the amino acid sequence set forth in SEQ ID NO: 95, the heavy chain CDR2 comprises the amino acid sequence set forth in SEQ ID NO: 96, the heavy chain CDR3 comprises the amino acid sequence set forth in SEQ ID NO: 97, the light chain CDR1 comprises the amino acid sequence set forth in SEQ ID NO: 98, the light chain CDR2 comprises the amino acid sequence set forth in SEQ ID NO: 99, and the light chain CDR3 comprises the amino acid sequence set forth in SEQ ID NO: 100;

(g) the heavy chain CDR1 comprises the amino acid sequence set forth in SEQ ID NO: 101, the heavy chain CDR2 comprises the amino acid sequence set forth in SEQ ID NO: 102, the heavy chain CDR3 comprises the amino acid sequence set forth in SEQ ID NO: 103, the light chain CDR1 comprises the amino acid sequence set forth in SEQ ID NO: 104, the light chain CDR2 comprises the amino acid sequence set forth in SEQ ID NO: 105, and the light chain CDR3 comprises the amino acid sequence set forth in SEQ ID NO: 106;

(h) the heavy chain CDR1 comprises the amino acid sequence set forth in SEQ ID NO: 107, the heavy chain CDR2 comprises the amino acid sequence set forth in SEQ ID NO: 108, the heavy chain CDR3 comprises the amino acid sequence set forth in SEQ ID NO: 109, the light chain CDR1 comprises the amino acid sequence set forth in SEQ ID NO: 110, the light chain CDR2 comprises the amino acid sequence set forth in SEQ ID NO: 111, and the light chain CDR3 comprises the amino acid sequence set forth in SEQ ID NO: 112;

(i) the heavy chain CDR1 comprises the amino acid sequence set forth in SEQ ID NO: 113, the heavy chain CDR2 comprises the amino acid sequence set forth in SEQ ID NO: 114, the heavy chain CDR3 comprises the amino acid sequence set forth in SEQ ID NO: 115, the light chain CDR1 comprises the amino acid sequence set forth in SEQ ID NO: 116, the light chain CDR2 comprises the amino acid sequence set forth in SEQ ID NO: 117, and the light chain CDR3 comprises the amino acid sequence set forth in SEQ ID NO: 118;

(j) the heavy chain CDR1 comprises the amino acid sequence set forth in SEQ ID NO: 119, the heavy chain CDR2 comprises the amino acid sequence set forth in SEQ ID NO: 120, the heavy chain CDR3 comprises the amino acid sequence set forth in SEQ ID NO: 121, the light chain CDR1 comprises the amino acid sequence set forth in SEQ ID NO: 122, the light chain CDR2 comprises the amino acid sequence set forth in SEQ ID NO: 123, and the light chain CDR3 comprises the amino acid sequence set forth in SEQ ID NO: 124;

(k) the heavy chain CDR1 comprises the amino acid sequence set forth in SEQ ID NO: 125, the heavy chain CDR2 comprises the amino acid sequence set forth in SEQ ID NO: 126, the heavy chain CDR3 comprises the amino acid sequence set forth in SEQ ID NO: 127, the light chain CDR1 comprises the amino acid sequence set forth in SEQ ID NO: 128, the light chain CDR2 comprises the amino acid sequence set forth in SEQ ID NO: 129, and the light chain CDR3 comprises the amino acid sequence set forth in SEQ ID NO: 130;

(l) the heavy chain CDR1 comprises the amino acid sequence set forth in SEQ ID NO: 131, the heavy chain CDR2 comprises the amino acid sequence set forth in SEQ ID NO: 132, the heavy chain CDR3 comprises the amino acid sequence set forth in SEQ ID NO: 133, the light chain CDR1 comprises the amino acid sequence set forth in SEQ ID NO: 134, the light chain CDR2 comprises the amino acid sequence set forth in SEQ ID NO: 135, and the light chain CDR3 comprises the amino acid sequence set forth in SEQ ID NO: 136;

(m) the heavy chain CDR1 comprises the amino acid sequence set forth in SEQ ID NO: 137, the heavy chain CDR2 comprises the amino acid sequence set forth in SEQ ID NO: 138, the heavy chain CDR3 comprises the amino acid sequence set forth in SEQ ID NO: 139, the light chain CDR1 comprises the amino acid sequence set forth in SEQ ID NO: 140, the light chain CDR2 comprises the amino acid sequence set forth in SEQ ID NO: 141, and the light chain CDR3 comprises the amino acid sequence set forth in SEQ ID NO: 142;

(n) the heavy chain CDR1 comprises the amino acid sequence set forth in SEQ ID NO: 143, the heavy chain CDR2 comprises the amino acid sequence set forth in SEQ ID NO: 144, the heavy chain CDR3 comprises the amino acid sequence set forth in SEQ ID NO: 145, the light chain CDR1 comprises the amino acid sequence set forth in SEQ ID NO: 146, the light chain CDR2 comprises the amino acid sequence set forth in SEQ ID NO: 147, and the light chain CDR3 comprises the amino acid sequence set forth in SEQ ID NO: 148;

(o) the heavy chain CDR1 comprises the amino acid sequence set forth in SEQ ID NO: 149, the heavy chain CDR2 comprises the amino acid sequence set forth in SEQ ID NO: 150, the heavy chain CDR3 comprises the amino acid sequence set forth in SEQ ID NO: 151, the light chain CDR1 comprises the amino acid sequence set forth in SEQ ID NO: 152, the light chain CDR2 comprises the amino acid sequence set forth in SEQ ID NO: 153, and the light chain CDR3 comprises the amino acid sequence set forth in SEQ ID NO: 154;

(p) the heavy chain CDR1 comprises the amino acid sequence set forth in SEQ ID NO: 17, the heavy chain CDR2 comprises the amino acid sequence set forth in SEQ ID NO: 18, the heavy chain CDR3 comprises the amino acid sequence set forth in SEQ ID NO: 19, the light chain CDR1 comprises the amino acid sequence set forth in SEQ ID NO: 208, the light chain CDR2 comprises the amino acid sequence set forth in SEQ ID NO: 209, and the light chain CDR3 comprises the amino acid sequence set forth in SEQ ID NO: 31;

(q) the heavy chain CDR1 comprises the amino acid sequence set forth in SEQ ID NO: 17, the heavy chain CDR2 comprises the amino acid sequence set forth in SEQ ID NO: 252, the heavy chain CDR3 comprises the amino acid sequence set forth in SEQ ID NO: 19, the light chain CDR1 comprises the amino acid sequence set forth in SEQ ID NO: 208, the light chain CDR2 comprises the amino acid sequence set forth in SEQ ID NO: 213, and the light chain CDR3 comprises the amino acid sequence set forth in SEQ ID NO: 31;

(r) the heavy chain CDR1 comprises the amino acid sequence set forth in SEQ ID NO: 17, the heavy chain CDR2 comprises the amino acid sequence set forth in SEQ ID NO: 253, the heavy chain CDR3 comprises the amino acid sequence set forth in SEQ ID NO: 19, the light chain CDR1 comprises the amino acid sequence set forth in SEQ ID NO: 208, the light chain CDR2 comprises the amino acid sequence set forth in SEQ ID NO: 213, and the light chain CDR3 comprises the amino acid sequence set forth in SEQ ID NO: 31;

(s) the heavy chain CDR1 comprises the amino acid sequence set forth in SEQ ID NO: 218, the heavy chain CDR2 comprises the amino acid sequence set forth in SEQ ID NO: 219, the heavy chain CDR3 comprises the amino acid sequence set forth in SEQ ID NO: 16, the light chain CDR1 comprises the amino acid sequence set forth in SEQ ID NO: 26, the light chain CDR2 comprises the amino acid sequence set forth in SEQ ID NO: 224, and the light chain CDR3 comprises the amino acid sequence set forth in SEQ ID NO: 28;

(t) the heavy chain CDR1 comprises the amino acid sequence set forth in SEQ ID NO: 220, the heavy chain CDR2 comprises the amino acid sequence set forth in SEQ ID NO: 221, the heavy chain CDR3 comprises the amino acid sequence set forth in SEQ ID NO: 16, the light chain CDR1 comprises the amino acid sequence set forth in SEQ ID NO: 225, the light chain CDR2 comprises the amino acid sequence set forth in SEQ ID NO: 226, and the light chain CDR3 comprises the amino acid sequence set forth in SEQ ID NO: 227;

(u) the heavy chain CDR1 comprises the amino acid sequence set forth in SEQ ID NO: 220, the heavy chain CDR2 comprises the amino acid sequence set forth in SEQ ID NO: 221, the heavy chain CDR3 comprises the amino acid sequence set forth in SEQ ID NO: 16, the light chain CDR1 comprises the amino acid sequence set forth in SEQ ID NO: 225, the light chain CDR2 comprises the amino acid sequence set forth in SEQ ID NO: 228, and the light chain CDR3 comprises the amino acid sequence set forth in SEQ ID NO: 227;

(v) the heavy chain CDR1 comprises the amino acid sequence set forth in SEQ ID NO: 220, the heavy chain CDR2 comprises the amino acid sequence set forth in SEQ ID NO: 221, the heavy chain CDR3 comprises the amino acid sequence set forth in SEQ ID NO: 16, the light chain CDR1 comprises the amino acid sequence set forth in SEQ ID NO: 26, the light chain CDR2 comprises the amino acid sequence set forth in SEQ ID NO: 229, and the light chain CDR3 comprises the amino acid sequence set forth in SEQ ID NO: 227;

(w) the heavy chain CDR1 comprises the amino acid sequence set forth in SEQ ID NO: 220, the heavy chain CDR2 comprises the amino acid sequence set forth in SEQ ID NO: 221, the heavy chain CDR3 comprises the amino acid sequence set forth in SEQ ID NO: 16, the light chain CDR1 comprises the amino acid sequence set forth in SEQ ID NO: 26, the light chain CDR2 comprises the amino acid sequence set forth in SEQ ID NO: 228, and the light chain CDR3 comprises the amino acid sequence set forth in SEQ ID NO: 227;

(x) the heavy chain CDR1 comprises the amino acid sequence set forth in SEQ ID NO: 220, the heavy chain CDR2 comprises the amino acid sequence set forth in SEQ ID NO: 221, the heavy chain CDR3 comprises the amino acid sequence set forth in SEQ ID NO: 16, the light chain CDR1 comprises the amino acid sequence set forth in SEQ ID NO: 26, the light chain CDR2 comprises the amino acid sequence set forth in SEQ ID NO: 230, and the light chain CDR3 comprises the amino acid sequence set forth in SEQ ID NO: 231;

(y) the heavy chain CDR1 comprises the amino acid sequence set forth in SEQ ID NO: 220, the heavy chain CDR2 comprises the amino acid sequence set forth in SEQ ID NO: 221, the heavy chain CDR3 comprises the amino acid sequence set forth in SEQ ID NO: 16, the light chain CDR1 comprises the amino acid sequence set forth in SEQ ID NO: 26, the light chain CDR2 comprises the amino acid sequence set forth in SEQ ID NO: 232, and the light chain CDR3 comprises the amino acid sequence set forth in SEQ ID NO: 233;

(z) the heavy chain CDR1 comprises the amino acid sequence set forth in SEQ ID NO: 222, the heavy chain CDR2 comprises the amino acid sequence set forth in SEQ ID NO: 12, the heavy chain CDR3 comprises the amino acid sequence set forth in SEQ ID NO: 13, the light chain CDR1 comprises the amino acid sequence set forth in SEQ ID NO: 248, the light chain CDR2 comprises the amino acid sequence set forth in SEQ ID NO: 24, and the light chain CDR3 comprises the amino acid sequence set forth in SEQ ID NO: 25;

(aa) the heavy chain CDR1 comprises the amino acid sequence set forth in SEQ ID NO: 223, the heavy chain CDR2 comprises the amino acid sequence set forth in SEQ ID NO: 12, the heavy chain CDR3 comprises the amino acid sequence set forth in SEQ ID NO: 13, the light chain CDR1 comprises the amino acid sequence set forth in SEQ ID NO: 248, the light chain CDR2 comprises the amino acid sequence set forth in SEQ ID NO: 24, and the light chain CDR3 comprises the amino acid sequence set forth in SEQ ID NO: 25;

(bb) the heavy chain CDR1 comprises the amino acid sequence set forth in SEQ ID NO: 223, the heavy chain CDR2 comprises the amino acid sequence set forth in SEQ ID NO: 12, the heavy chain CDR3 comprises the amino acid sequence set forth in SEQ ID NO: 246, the light chain CDR1 comprises the amino acid sequence set forth in SEQ ID NO: 248, the light chain CDR2 comprises the amino acid sequence set forth in SEQ ID NO: 24, and the light chain CDR3 comprises the amino acid sequence set forth in SEQ ID NO: 25; or (cc) the heavy chain CDR1 comprises the amino acid sequence set forth in SEQ ID NO: 223, the heavy chain CDR2 comprises the amino acid sequence set forth in SEQ ID NO: 12, the heavy chain CDR3 comprises the amino acid sequence set forth in SEQ ID NO: 247, the light chain CDR1 comprises the amino acid sequence set forth in SEQ ID NO: 248, the light chain CDR2 comprises the amino acid sequence set forth in SEQ ID NO: 24, and the light chain CDR3 comprises the amino acid sequence set forth in SEQ ID NO: 25.

17. The method of claim 1, wherein the anti-FAM19A5 antibody comprises a heavy chain variable region (VH) and a light chain variable region (VL), wherein:

(i) the VH comprises the amino acid sequence set forth in SEQ ID NO: 35, SEQ ID NO: 36, SEQ ID NO: 37, SEQ ID NO: 38, SEQ ID NO: 155, SEQ ID NO: 156, SEQ ID NO: 157, SEO ID NO: 158, SEO ID NO: 159, SEO ID NO: 160, SEO ID NO: 161, SEQ ID NO: 162, SEQ ID NO: 163, SEQ ID NO: 164, SEQ ID NO: 165, SEQ ID NO: 211, SEQ ID NO: 214, SEQ ID NO: 249, SEQ ID NO: 234, SEQ ID NO: 235, SEQ ID NO: 236, SEQ ID NO: 237, SEQ ID NO: 250, or SEO ID NO: 251; and (ii) the VL comprises the amino acid sequence set forth in SEQ ID NO: 39, SEQ ID NO: 40, SEQ ID NO: 41, SEQ ID NO: 42, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 212, SEQ ID NO: 215, SEQ ID NO: 238, SEQ ID NO: 239, SEQ ID NO: 240, SEQ ID NO: 241, SEQ ID NO: 242, SEQ ID NO: 243, SEQ ID NO: 244, or SEQ ID NO: 245.

18. The method of claim 3, wherein the anti-FAM19A5 antibody comprises a heavy chain variable region (VH) and a light chain variable region (VL), wherein:

(i) the VH comprises the amino acid sequence set forth in SEQ ID NO: 35, SEQ ID NO: 36, SEQ ID NO: 37, SEQ ID NO: 38, SEQ ID NO: 155, SEQ ID NO: 156, SEQ ID NO: 157, SEO ID NO: 158, SEO ID NO: 159, SEO ID NO: 160, SEO ID NO: 161, SEQ ID NO: 162, SEQ ID NO: 163, SEQ ID NO: 164, SEQ ID NO: 165, SEQ ID NO: 211, SEQ ID NO: 214, SEQ ID NO: 249, SEQ ID NO: 234, SEQ ID NO: 235, SEQ ID NO: 236, SEQ ID NO: 237, SEQ ID NO: 250, or SEO ID NO: 251; and (ii) the VL comprises the amino acid sequence set forth in SEQ ID NO: 39, SEQ ID NO: 40, SEQ ID NO: 41, SEQ ID NO: 42, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 212, SEQ ID NO: 215, SEQ ID NO: 238, SEQ ID NO: 239, SEQ ID NO: 240, SEQ ID NO: 241, SEQ ID NO: 242, SEQ ID NO: 243, SEQ ID NO: 244, or SEQ ID NO: 245.

19. The method of claim 10, wherein:

(a) the VH comprises the amino acid sequence set forth in SEQ ID NO: 35 and the VL comprises the amino acid sequence set forth in SEQ ID NO: 39;

(b) the VH comprises the amino acid sequence set forth in SEQ ID NO: 36 and the VL comprises the amino acid sequence set forth in SEQ ID NO: 40;

(c) the VH comprises the amino acid sequence set forth in SEQ ID NO: 37 and the VL comprises the amino acid sequence set forth in SEQ ID NO: 41;

(d) the VH comprises the amino acid sequence set forth in SEQ ID NO: 38 and the VL comprises the amino acid sequence set forth in SEQ ID NO: 42;

(e) the VH comprises the amino acid sequence set forth in SEQ ID NO: 155 and the VL comprises the amino acid sequence set forth in SEQ ID NO: 166;

(f) the VH comprises the amino acid sequence set forth in SEQ ID NO: 156 and the VL comprises the amino acid sequence set forth in SEQ ID NO: 167;

(g) the VH comprises the amino acid sequence set forth in SEQ ID NO: 157 and the VL comprises the amino acid sequence set forth in SEQ ID NO: 168;

(h) the VH comprises the amino acid sequence set forth in SEQ ID NO: 158 and the VL comprises the amino acid sequence set forth in SEQ ID NO: 169;

(i) the VH comprises the amino acid sequence set forth in SEQ ID NO: 159 and the VL comprises the amino acid sequence set forth in SEQ ID NO: 170;

(j) the VH comprises the amino acid sequence set forth in SEQ ID NO: 160 and the VL comprises the amino acid sequence set forth in SEQ ID NO: 171;

(k) the VH comprises the amino acid sequence set forth in SEQ ID NO: 161 and the VL comprises the amino acid sequence set forth in SEQ ID NO: 172;

(l) the VH comprises the amino acid sequence set forth in SEQ ID NO: 162 and the VL comprises the amino acid sequence set forth in SEQ ID NO: 173;

(m) the VH comprises the amino acid sequence set forth in SEQ ID NO: 163 and the VL comprises the amino acid sequence set forth in SEQ ID NO: 174;

(n) the VH comprises the amino acid sequence set forth in SEQ ID NO: 164 and the VL comprises the amino acid sequence set forth in SEQ ID NO: 175;

(o) the VH comprises the amino acid sequence set forth in SEQ ID NO: 165 and the VL comprises the amino acid sequence set forth in SEQ ID NO: 176;

(p) the VH comprises the amino acid sequence set forth in SEQ ID NO: 211 and the VL comprises the amino acid sequence set forth in SEQ ID NO: 212;

(q) the VH comprises the amino acid sequence set forth in SEQ ID NO: 214 and the VL comprises the amino acid sequence set forth in SEQ ID NO: 215;

(r) the VH comprises the amino acid sequence set forth in SEQ ID NO: 249 and the VL comprises the amino acid sequence set forth in SEQ ID NO: 215;
(s) the VH comprises the amino acid sequence set forth in SEQ ID NO: 234 and the VL comprises the amino acid sequence set forth in SEQ ID NO: 238;
(t) the VH comprises the amino acid sequence set forth in SEQ ID NO: 235 and the VL comprises the amino acid sequence set forth in SEQ ID NO: 239;
(u) the VH comprises the amino acid sequence set forth in SEQ ID NO: 235 and the VL comprises the amino acid sequence set forth in SEQ ID NO: 240;
(v) the VH comprises the amino acid sequence set forth in SEQ ID NO: 235 and the VL comprises the amino acid sequence set forth in SEQ ID NO: 241;
(w) the VH comprises the amino acid sequence set forth in SEQ ID NO: 235 and the VL comprises the amino acid sequence set forth in SEQ ID NO: 242;
(x) the VH comprises the amino acid sequence set forth in SEQ ID NO: 235 and the VL comprises the amino acid sequence set forth in SEQ ID NO: 243;
(y) the VH comprises the amino acid sequence set forth in SEQ ID NO: 235 and the VL comprises the amino acid sequence set forth in SEQ ID NO: 244;
(z) the VH comprises the amino acid sequence set forth in SEQ ID NO: 236 and the VL comprises the amino acid sequence set forth in SEQ ID NO: 245;
(aa) the VH comprises the amino acid sequence set forth in SEQ ID NO: 250 and the VL comprises the amino acid sequence set forth in SEQ ID NO: 245;
(bb) the VH comprises the amino acid sequence set forth in SEQ ID NO: 237 and the VL comprises the amino acid sequence set forth in SEQ ID NO: 245; or
(cc) the VH comprises the amino acid sequence set forth in SEQ ID NO: 251 and the VL comprises the amino acid sequence set forth in SEQ ID NO: 245.

20. The method of claim 17, wherein:
(a) the VH comprises the amino acid sequence set forth in SEQ ID NO: 35 and the VL comprises the amino acid sequence set forth in SEQ ID NO: 39;
(b) the VH comprises the amino acid sequence set forth in SEQ ID NO: 36 and the VL comprises the amino acid sequence set forth in SEQ ID NO: 40;
(c) the VH comprises the amino acid sequence set forth in SEQ ID NO: 37 and the VL comprises the amino acid sequence set forth in SEQ ID NO: 41;
(d) the VH comprises the amino acid sequence set forth in SEQ ID NO: 38 and the VL comprises the amino acid sequence set forth in SEQ ID NO: 42;
(e) the VH comprises the amino acid sequence set forth in SEQ ID NO: 155 and the VL comprises the amino acid sequence set forth in SEQ ID NO: 166;
(f) the VH comprises the amino acid sequence set forth in SEQ ID NO: 156 and the VL comprises the amino acid sequence set forth in SEQ ID NO: 167;
(g) the VH comprises the amino acid sequence set forth in SEQ ID NO: 157 and the VL comprises the amino acid sequence set forth in SEQ ID NO: 168;
(h) the VH comprises the amino acid sequence set forth in SEQ ID NO: 158 and the VL comprises the amino acid sequence set forth in SEQ ID NO: 169;
(i) the VH comprises the amino acid sequence set forth in SEQ ID NO: 159 and the VL comprises the amino acid sequence set forth in SEQ ID NO: 170;
(j) the VH comprises the amino acid sequence set forth in SEQ ID NO: 160 and the VL comprises the amino acid sequence set forth in SEQ ID NO: 171;
(k) the VH comprises the amino acid sequence set forth in SEQ ID NO: 161 and the VL comprises the amino acid sequence set forth in SEQ ID NO: 172;
(l) the VH comprises the amino acid sequence set forth in SEQ ID NO: 162 and the VL comprises the amino acid sequence set forth in SEQ ID NO: 173;
(m) the VH comprises the amino acid sequence set forth in SEQ ID NO: 163 and the VL comprises the amino acid sequence set forth in SEQ ID NO: 174;
(n) the VH comprises the amino acid sequence set forth in SEQ ID NO: 164 and the VL comprises the amino acid sequence set forth in SEQ ID NO: 175;
(o) the VH comprises the amino acid sequence set forth in SEQ ID NO: 165 and the VL comprises the amino acid sequence set forth in SEQ ID NO: 176;
(p) the VH comprises the amino acid sequence set forth in SEQ ID NO: 211 and the VL comprises the amino acid sequence set forth in SEQ ID NO: 212;
(q) the VH comprises the amino acid sequence set forth in SEQ ID NO: 214 and the VL comprises the amino acid sequence set forth in SEQ ID NO: 215;
(r) the VH comprises the amino acid sequence set forth in SEQ ID NO: 249 and the VL comprises the amino acid sequence set forth in SEQ ID NO: 215;
(s) the VH comprises the amino acid sequence set forth in SEQ ID NO: 234 and the VL comprises the amino acid sequence set forth in SEQ ID NO: 238;
(t) the VH comprises the amino acid sequence set forth in SEQ ID NO: 235 and the VL comprises the amino acid sequence set forth in SEQ ID NO: 239;
(u) the VH comprises the amino acid sequence set forth in SEQ ID NO: 235 and the VL comprises the amino acid sequence set forth in SEQ ID NO: 240;
(v) the VH comprises the amino acid sequence set forth in SEQ ID NO: 235 and the VL comprises the amino acid sequence set forth in SEQ ID NO: 241;
(w) the VH comprises the amino acid sequence set forth in SEQ ID NO: 235 and the VL comprises the amino acid sequence set forth in SEQ ID NO: 242;
(x) the VH comprises the amino acid sequence set forth in SEQ ID NO: 235 and the VL comprises the amino acid sequence set forth in SEQ ID NO: 243;
(y) the VH comprises the amino acid sequence set forth in SEQ ID NO: 235 and the VL comprises the amino acid sequence set forth in SEQ ID NO: 244;
(z) the VH comprises the amino acid sequence set forth in SEQ ID NO: 236 and the VL comprises the amino acid sequence set forth in SEQ ID NO: 245;
(aa) the VH comprises the amino acid sequence set forth in SEQ ID NO: 250 and the VL comprises the amino acid sequence set forth in SEQ ID NO: 245;
(bb) the VH comprises the amino acid sequence set forth in SEQ ID NO: 237 and the VL comprises the amino acid sequence set forth in SEQ ID NO: 245; or
(cc) the VH comprises the amino acid sequence set forth in SEQ ID NO: 251 and the VL comprises the amino acid sequence set forth in SEQ ID NO: 245.

* * * * *